US011192907B2

United States Patent
Balavoine et al.

(10) Patent No.: US 11,192,907 B2
(45) Date of Patent: Dec. 7, 2021

(54) AMINOPEPTIDASE A INHIBITORS AND PHARMACEUTICAL COMPOSITIONS COMPRISING THE SAME

(71) Applicants: QUANTUM GENOMICS, Paris (FR); INSTITUT NATIONAL DE LA SANTE ET DE LA RECHERCHE MEDICALE, Paris (FR); CENTRE NATIONAL DE LA RECHERCHE SCIENTIFIQUE, Paris (FR); COLLEGE DE FRANCE, Paris (FR)

(72) Inventors: Fabrice Balavoine, Paris (FR); Delphine Compere, Sceaux (FR); Catherine Llorens-Cortes, Bures sur Yvette (FR); Yannick Marc, Saint-Maur-des-Fosses (FR)

(73) Assignees: QUANTUM GENOMICS, Paris (FR); INSTITUT NATIONAL DE LA SANTÉ ET DE LA RECHERCHE MÉDICALE, Paris (FR); CENTRE NATIONAL DE LA RECHERCHE SCIENTIFIQUE, Paris (FR); COLLEGE DE FRANCE, Paris (FR)

( * ) Notice: Subject to any disclaimer, the term of this patent is extended or adjusted under 35 U.S.C. 154(b) by 0 days.

(21) Appl. No.: 17/288,516

(22) PCT Filed: Oct. 25, 2019

(86) PCT No.: PCT/EP2019/079229
§ 371 (c)(1),
(2) Date: Apr. 24, 2021

(87) PCT Pub. No.: WO2020/084131
PCT Pub. Date: Apr. 30, 2020

(65) Prior Publication Data
US 2021/0309678 A1   Oct. 7, 2021

(30) Foreign Application Priority Data

Oct. 26, 2018 (EP) ..................... 18306396

(51) Int. Cl.
C07F 9/58      (2006.01)
C07F 9/30      (2006.01)
C07F 9/653     (2006.01)
C07F 9/6539    (2006.01)

(52) U.S. Cl.
CPC ................ *C07F 9/58* (2013.01); *C07F 9/306* (2013.01); *C07F 9/6539* (2013.01); *C07F 9/65312* (2013.01)

(58) Field of Classification Search
CPC ........ C07F 9/58; C07F 9/306; C07F 9/65312; C07F 9/6539
USPC ......................................................... 514/89
See application file for complete search history.

(56) References Cited

FOREIGN PATENT DOCUMENTS

WO   WO 2020/084147   4/2020

OTHER PUBLICATIONS

Lejczak, B. et al. "Inhibition of Aminopeptidases by Phosphonic Acid and Phosphinic Acid Analogues of Aspartic and Glutamic Acids" *Journal of Enzyme Inhibition*, 1993, pp. 97-103, vol. 7.
Written Opinion in International Application No. PCT/EP2019/079229, dated Jan. 16, 2020, pp. 1-5.

*Primary Examiner* — Kristin A Vajda
(74) *Attorney, Agent, or Firm* — Saliwanchik, Lloyd & Eisenschenk

(57) ABSTRACT

The present invention relates to a novel compound, to a composition comprising the same, to methods for preparing the compound, and the use of this compound in therapy. In particular, the present invention relates to a compound that is useful in the treatment and prevention of primary and secondary arterial hypertension, ictus, myocardial ischaemia, cardiac and renal insufficiency, myocardial infarction, peripheral vascular disease, diabetic proteinuria, Syndrome X and glaucoma.

13 Claims, 2 Drawing Sheets

AMINOPEPTIDASE A INHIBITORS AND PHARMACEUTICAL COMPOSITIONS COMPRISING THE SAME

CROSS-REFERENCE TO RELATED APPLICATION

This application is the U.S. national stage application of International Patent Application No. PCT/EP2019/079229, filed Oct. 25, 2019.

FIELD OF THE INVENTION

The present invention relates to novel compounds, to a composition comprising the same, to methods for preparing the compounds, and the use of these compounds in therapy. In particular, the present invention relates to compounds that are useful in the treatment and prevention of primary and secondary arterial hypertension, ictus, myocardial ischemia, cardiac and renal insufficiency, myocardial infarction, peripheral vascular disease, diabetic proteinuria, Syndrome X and glaucoma.

BACKGROUND OF THE INVENTION

Essential Hypertension (HTN) and Heart Failure (HF) are two of the major pathologies in cardio-vascular disease. HTN affects approximately 1 billion individuals worldwide. It is a leading risk factor for coronary heart disease, HF, stroke and renal insufficiency. Despite the availability of effective and safe drugs, HTN and its concomitant risk factors remain uncontrolled in many patients. HF remains the leading cause of hospitalization for patients over 65 years old in western countries. HF affects one to five persons in a thousand in industrialized countries, all ages considered, with a prevalence of three to twenty in a thousand. In the US, HF healthcare expenses represented $21B in 2012, with the majority of costs related to hospitalizations. Despite the large number of drugs available HF has a poor prognosis as the one-year survival, all stages considered, is about 65%. HF remains one of the first causes of cardiovascular death, consequently, there is still an unmet medical need to develop new efficient and safe classes of drugs.

The systemic renin-angiotensin system (RAS) is known to play a central role in blood pressure (BP) regulation and sodium metabolism. Systemic drugs targeting the RAS such as angiotensin I converting enzyme (ACE) inhibitors and angiotensin-II receptor type 1 ($AT_1$) antagonists are clinically effective in lowering BP and in preventing cardiovascular and renal morbidity and mortality in patients. Furthermore, activity of the renin-angiotensin aldosterone system (RAAS) is increased in patients with HF, and its maladaptive mechanisms may lead to adverse effects such as cardiac remodelling and sympathetic activation. Current evidence based guideline IA recommended medicines for HF with reduced ejection fraction are mainly RAAS-acting molecules such ACE inhibitors or $AT_1$ receptor blockers and beta-adrenergic receptor blocking agents A functional RAS controlling cardiovascular functions and body fluid homeostasis is also present in the brain. Several studies suggest that increased activity of the brain RAS results in an increase in sympathetic neuron activity and vasopressin release and that hyperactivity of the brain RAS plays a critical role in mediating high BP in various animal models of HTN as well as cardiac remodeling and dysfunction in animals models of HF (Marc Y, Llorens-Cortes, C Progress in Neurobiology 2011, 95, pp 89-103; Westcott K V et al, Can. J. Physiol. Pharmacol. 2009, 87, pp 979-988). Because recent evidences support that angiotensin III (Ang III) through its action on $AT_1$ receptor may be the true peptide effector of the brain RAS for the central control of BP, the brain aminopeptidase A (APA) the enzyme generating Ang III from angiotensin II (Ang II) in the brain constitutes a promising therapeutic target for treatment of HTN and for the treatment of HF.

Aminopeptidase A (APA, EC 3.4.11.7) is a membrane-bound zinc metalloprotease, which has been characterized as the enzyme responsible for the conversion of AngII into AngIII in the brain (Zini S et al, Proc. Natl. Acad. Sci. USA 1996, 93, pp 11968-11973). Several APA inhibitors have been developed so far (Chauvel E N et al, J. Med. Chem. 1994, 37, pp 1339-1346; Chauvel E N et al, J. Med. Chem. 1994, 37, pp 2950-2957; David C et al, J. Med. Chem. 1999, 42, pp 5197-5211; Georgiadis D et al, Biochemistry 2000, 39, pp 1152-1155; Inguimbert N et al, J. Peptide Res. 2005, 65, pp 175-188). Among them, EC33 ((3S)-3-amino-4-thiol-butyl sulfonate) was reported as a specific and selective APA inhibitor. Central infusions of EC33 were found to inhibit brain APA activity, to block the pressor responses to intracerebro-ventricular (icv) infusion of Ang II, and to lower BP in several experimental models of hypertension (Fournid-Zaluski M C et al Proc. Natl. Acad. Sci. USA 2004, 101, pp 7775-7780).

It was also further demonstrated that acute oral administrations in conscious hypertensive DOCA-salt rats and SHR rats of RB150 (also known as Firibastat) (15 to 150 mg/kg), a brain penetrating prodrug of EC33, induce a dose-dependent decrease in BP (Bodineau L et al, Hypertension 2008, 51, pp 1318-1325; Marc Y et al, Hypertension 2012, 60, pp 411-418). Interestingly, RB150 was found to lower BP in DOCA-salt rats and SHRs first by decreasing vasopressin release, increasing aqueous diuresis and natriuresis, thereby decreasing blood volume and BP to control values, and secondly by lowering sympathetic tone, thereby reducing vascular resistances and consequently decreasing BP. It was also reported that chronic central infusions of RB150, and the $AT_1R$ blocker, losartan, are similarly effective in inhibiting sympathetic hyperactivity and cardiac dysfunction observed in rats with HF post myocardial infarction (MI) (Huang B S et al, Cardiovascular Res. 2013, 97, pp 424-431). Thus, RB150 is able to enter the brain after oral administration, block brain APA activity, normalize BP in hypertensive rats, and prevent cardiac dysfunction following MI in rats. Brain APA inhibitors represent a new class of centrally-acting agents for the treatment of HTN and HF.

The present inventors have now identified novel compounds which act as potent APA inhibitors and to that respect can be effective in reducing arterial hypertension and can have utility in treating arterial hypertension and the diseases to which it indirectly and directly contributes such as heart failure. Said compounds also present a satisfactory bioavailability and pharmacokinetics parameters, which makes them good candidates for oral or parenteral administration.

SUMMARY OF THE INVENTION

Accordingly, the invention provides a compound with the following formula (I):

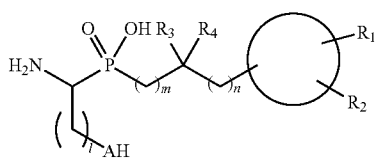

and more specifically having the following formula (II):

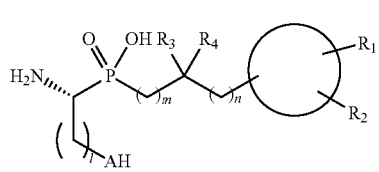

wherein:
AH represents —CO$_2$H, —SO$_3$H, —PO$_3$H$_2$;
l is 1, 2 or 3;
m and n are independently 0, 1 or 2;
R$_3$ and R$_4$ represent independently H, —OH, a halogen atom, an alkyl or a haloalkyl group; the ring (depicted by a circle in formulas) represents an aryl or a heterocycle;
with R$_1$ and R$_2$ representing independently a hydrogen atom, a halogen atom, a cyano group, an alkyl group, an alkoxy group, an alkylthio group, an alkylsulfoxide group, an alkylsulfonyl group, a haloalkyl group, a haloalkoxy group, a haloalkylthio group, an acyl group, an O-cycloalkyl group, a heteroalkyl group, an O-aryl group, an O-arylalkyl group, an aryl group, a heterocycle group or an arylalkyl group;
a pharmaceutical salt, solvate, zwitterionic form or prodrug thereof.

In another aspect, the present invention discloses a composition comprising said compound of formula (I) and more specifically of formula (II). The composition is more particularly a pharmaceutical composition. The present invention provides therefore a pharmaceutical composition comprising at least one compound of the invention, preferably in association with a pharmaceutically acceptable diluent or carrier.

According to another aspect, the invention relates to a method for prevention or treatment of arterial hypertension and indirectly and directly related diseases, comprising administration of a therapeutically effective amount of a compound of this invention. In another aspect, the present invention provides a compound of the invention for use in therapy or medicine as Active Pharmaceutical Ingredient, and in particular, in human medicine, and more specifically for the treatment of arterial hypertension or indirectly and directly related diseases or disorders.

In another aspect, the present invention provides the use of a compound of the invention for the preparation of a pharmaceutical composition for the treatment of arterial hypertension or indirectly and directly related diseases or disorders.

In another aspect, the present invention provides a method of treatment of a patient suffering from arterial hypertension or indirectly and directly related diseases comprising the administration of a therapeutically effective amount of a compound of the invention in a patient in need thereof.

DETAILED DESCRIPTION

Figure 1:
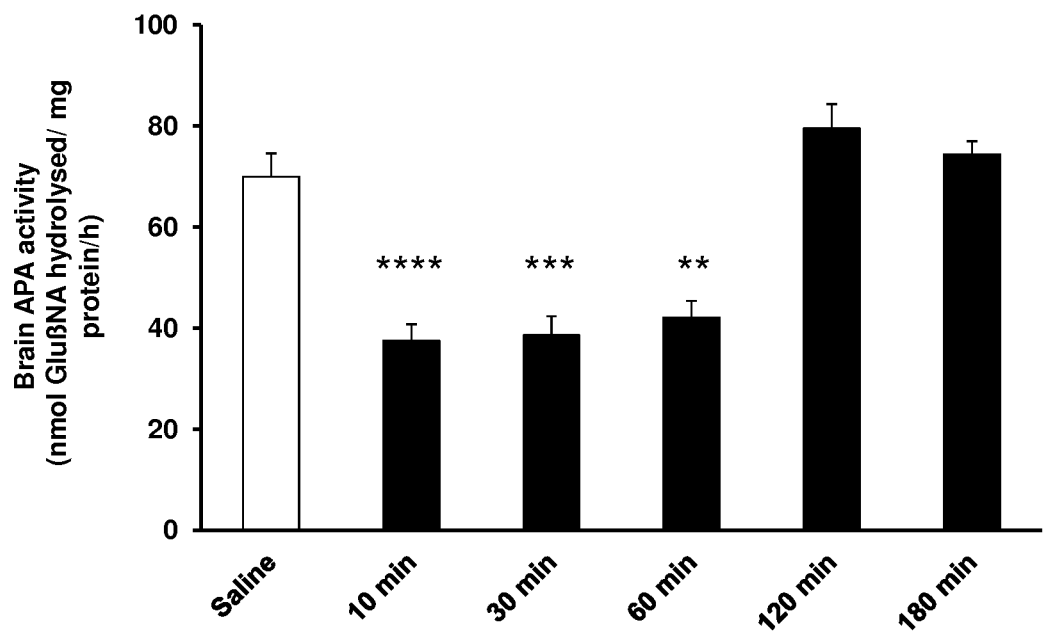
FIG. 1. describes the time course of inhibition of mouse brain APA ex vivo activity after intravenous (i.v.) administration of Example 22 (5 mg/kg).

The present invention thus relates to a compound having the following formula (I):

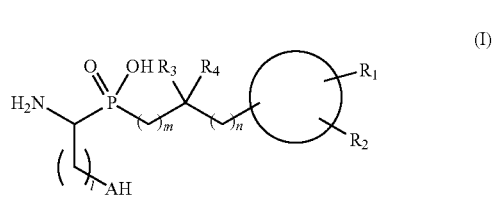

and more specifically having the following formula (II):

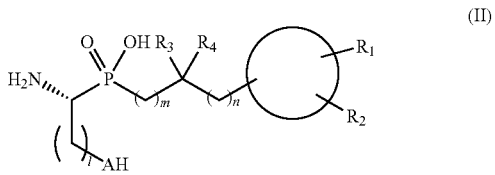

wherein:
AH represents —CO$_2$H, —SO$_3$H, —PO$_3$H$_2$;
l is 1, 2 or 3;
m and n are independently 0, 1 or 2;
R$_3$ and R$_4$ represent independently a hydrogen atom, a hydroxy group (OH), a halogen atom, an alkyl or a haloalkyl group;
the ring (depicted by a circle in formulas) represents an aryl or a heterocycle;
with R$_1$ and R$_2$ representing independently a hydrogen atom, a halogen atom, a cyano group, an alkyl group, an alkoxy group, an alkylthio group, an alkylsulfoxide group, an alkylsulfonyl group, a haloalkyl group, a haloalkoxy group, a haloalkylthio group, an acyl group, an O-cycloalkyl group, a heteroalkyl group, an O-aryl group, an O-arylalkyl group, an aryl group, a heterocycle group or an arylalkyl group.

The present invention provides compounds according to the invention for use or in methods of prevention or treatment of arterial hypertension and diseases to which arterial hypertension directly or indirectly contributes. Such diseases include diseases of the heart, the peripheral and cerebral vascular system, the brain, the eye and the kidney. In particular diseases include primary and secondary arterial hypertension, ictus, myocardial ischemia, cardiac and renal insufficiency, myocardial infarction, peripheral vascular disease, diabetic proteinuria, Syndrome X and glaucoma.

As used herein, "a compound of the invention" means a compound described above or a prodrug thereof or a pharmaceutically acceptable salt, solvate or any zwitterionic form thereof.

Within the context of the present invention:

The term "alkyl" or "Alk" means a monovalent or divalent, linear or branched, saturated hydrocarbon chain, having 1-8 carbon atoms (also named ($C_1$-$C_8$)alkyl), such as methyl, ethyl, propyl, isopropyl, n-butyl, iso-butyl, sec-butyl, tert-butyl, tert-butyl-methyl, n-pentyl, n-hexyl, n-heptyl, or n-octyl group.

The term "acyl" means a —C(O)R group, where R is an alkyl group as defined earlier or a phenyl group. An acyl group includes for example acetyl, ethylcarbonyl, or benzoyl group.

The term "alkoxy" or "alkyloxy" means a —OAlk group wherein Alk is an alkyl group as defined above. An alkoxy group includes for example methoxy, ethoxy, n-propyloxy, or tert-butyloxy group.

The term "aryl" means an aromatic monocyclic or bicyclic system having 4-10 carbon atoms (also named ($C_4$-$C_{10}$) aryl), it being understood that in the case of a bicyclic system, one of the cycles is aromatic and the other cycle is aromatic or unsaturated. Aryl groups include for example phenyl, naphthyl, indenyl, or benzocyclobutenyl groups.

The term "heterocycle" means a saturated, unsaturated or aromatic, fused, spiro-fused or bridged, monocyclic or bicyclic system with 3-12 members, having 1-4 heteroatoms, either identical or different, selected from oxygen, sulfur and nitrogen, and possibly containing 1 or 2 oxo (=O) or thioxo (=S) groups, it being understood that in the case of a bicyclic system, one of the cycles may be aromatic and the other cycle is aromatic, saturated or unsaturated. Heterocycle includes for example piperidyl, piperazyl, furyl, thienyl, pyrrolyl, pyrazolyl, imidazolyl, pyridyl, pyrimidyl, pyrazinyl, pyradizinyl, benzofuryl, benzothienyl, indolyl, quinolyl, isoquinolyl, benzodioxolyl, benzodioxinyl, benzo[1,2,5]thiadiazolyl, benzo[1,2,5]oxadiazolyl, [1,2,3]triazolyl, or [1,2,4]triazolyl groups.

The term "alkylthio" means a —SAlk group, wherein Alk is an alkyl group as defined earlier. Alkylthio for example includes methylthio, ethylthio, isopropylthio, or heptylthio.

The term "alkylsulfoxide" means a —S(O)Alk group, wherein Alk is an alkyl group as defined earlier. Alkylsulfoxide for example includes methylsulfoxide, ethylsulfoxide, or isopropylsulfoxide.

The term "alkylsulfonyl" means a —S(O)$_2$Alk group, wherein Alk is an alkyl group as defined earlier. Alkylsulfonyl for example includes methylsulfonyl, ethylsulfonyl, or isopropylsulfonyl.

The term "arylalkyl" means a -Alk-Ar group, wherein Alk represents an alkyl group as defined earlier, and Ar represents an aryl group as defined earlier.

The term "heteroalkyl" means a linear or branched saturated hydrocarbon chain, having from 1 to 5 carbon atoms and at least 1 or 2 heteroatoms, such as sulfur, nitrogen or oxygen atoms.

Heteroalkyl for example includes —O(CH$_2$)$_2$OCH$_3$ or —(CH$_2$)$_2$OCH$_3$ group.

The term "halogen atom" means fluorine, bromine, chlorine or iodine atom.

The term "cycloalkyl" means a saturated monocyclic or polycyclic system, such as a fused or bridged bicyclic system, having 3-12 carbon atoms (also named ($C_3$-$C_2$) cycloalkyl), such as the cyclopropyl, cyclobutyl, cyclopentyl, cyclohexyl, cycloheptyl, cyclooctyl, adamantly, decalinyl, or norbornyl groups.

The term "O-cycloalkyl" means a cycloalkyl group as defined earlier connected to the remainder of the molecule through an oxygen atom. O-cycloalkyl includes for example the O-cyclopentyl or O-cyclohexyl group.

The term "O-aryl" means an aryl group as defined earlier connected to the remainder of the molecule through an oxygen atom. O-aryl includes for example the O-phenyl group.

The term "O-arylalkyl" means an arylalkyl group as defined earlier connected to the remainder of the molecule through an oxygen atom. O-arylalkyl includes for example the O-benzyl group.

The "ester" means a —C(O)OR group with R representing an alkyl, aryl or arylalkyl group as defined above.

The term "haloalkyl" means a linear or branched saturated hydrocarbon chain, having 1-6 carbon atoms and substituted with one or more, and notably 1-6 halogen atoms, such as the trifluoromethyl or 2,2,2-trifluoroethyl groups.

The term "haloalkoxy" means a linear or branched saturated hydrocarbon chain, having 1-6 carbon atoms and substituted with one or more, and notably 1-6 halogen atoms, said chain being connected to the compound through an oxygen atom, such as the trifluoromethoxy or 2,2,2-trifluoroethoxy groups.

The term "haloalkylthio" means a linear or branched saturated hydrocarbon chain, comprising 1-6 carbon atoms and substituted with one or more, and notably 1-6 halogen atoms, said chain being connected to the compound through a sulfur atom, such as the trifluoromethylthio group.

The term "protective group" or "protection group" means the group which selectively blocks the reactive site in a multifunctional compound so that a chemical reaction may be selectively carried out at another non-protected reactive site, with the meaning conventionally associated with the latter in synthesis chemistry.

In the present invention, the term "pharmaceutically acceptable" refers to which can be used in the preparation of a pharmaceutical composition which is generally safe, non-toxic and not undesirable, biologically or otherwise, and which is commonly accepted for a veterinary or human pharmaceutical use.

The term "pharmaceutically acceptable salts" of the compounds of the invention include conventional salts formed from pharmaceutically acceptable inorganic or organic acids or bases as well as quaternary ammonium salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic etc. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. For example, preferred salt forms include chlorhydrate.

The term "pro-drug" means a chemical derivative of the compound, object of the invention, which generates in vivo said compound by one or more spontaneous chemical reactions with the physiological medium, notably by enzymatic reactions, photolysis and/or metabolic reactions. In the present case, pro-drugs of the compounds of the invention generate in vivo compounds identified as inhibitors of aminopeptidase A.

A pro-drug may be obtained by derivatizing functional group with specific labile moieties. The pro-drug with an acid function (such as phosphinic acid, carboxylic acid, sulfonic acid or phosphonic acid) notably comprises ester, the pro-drug with amine function notably comprises [(2- methylpropanoyl)oxy]ethoxycarbonyl via a carbamate group or comprises 2-oxo-[1,3-thiazolidine-4-yl]formamide via an amide group.

Other examples are described in T. Higuchi and V. Stella, "Pro-drugs as Novel Delivery system", Vol. 14, A.C.S Symposium Series, American Chemical Society (1975) and "Bioreversible Carriers in Grug Design: Theory and Application", edited by E. B. Roche, Pergamon Press: New York, 14-21 (1987).

According to the invention, the term "isomer" refers to compounds of the invention which have identical molecular formulae as identified herein but which differ by nature or in the binding sequence of their atoms or in the layout of their atoms in space. Isomers which differ in the layout of their atoms in space are designated by "stereoisomers". Stereosiomers which are not mirror images of each other, are designated as "diastereoisomers", and stereoisomers which are non-superposable mirror images of each other are designated as "enantiomers" or "optical isomers". "Stereoisomers" refer to racemates, enantiomers and diastereoisomers.

The person skilled in the art will recognize that stereocenters exist in the compounds of the invention. Any chiral center of a compound of the invention can be (R), (S) or racemate. Accordingly, the present invention includes all possible stereoisomers and geometric isomers of the compounds of formula (I) and includes not only racemic compounds but also the optically active isomers as well. According to a preferred embodiment, compounds of the invention is of formula (II). When a compound of formula (I) is desired as a single enantiomer, it may be obtained either by resolution of the final product or by stereospecific synthesis from either isomerically pure starting material or any suitable intermediate. Resolution of the final product, an intermediate or a starting material may be effected by any suitable method known in the art. See, for example, Stereochemistry of Carbon Compounds by E. L. Eliel (Mcgraw Hill, 1962) and Tables of Resolving Agents by S. H. Wilen.

The person skilled in the art will recognize that the compounds of the invention may contain at least one positive and one negative charge so that the compounds of the invention includes zwitterionic forms thereof. In chemistry, a zwitterion (also called an inner salt), is a molecule with two or more functional groups, of which at least one has a positive and one has a negative electrical charge and the charges on the different functional groups balance each other out, and the molecule as a whole is electrically neutral. The pH where this happens is known as the isoelectric point. Accordingly, any zwitterionic forms of the compounds of the invention including prodrugs thereof are within the scope of the present invention.

The specialist in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compounds of formula (I) or (II) are within the scope of the present invention.

It will also be appreciated by the specialist in organic chemistry that many organic compounds can exist in more than one crystalline form. For example, crystalline form may vary from solvate to solvate. Thus, all crystalline forms of the compounds of the invention or the pharmaceutically acceptable solvates thereof are within the scope of the present invention.

References herein to a compound according to the invention include both compounds of formula (I) or (II) and their pharmaceutically acceptable salts, solvates, zwitterionic forms or prodrugs.

According to preferred embodiments, the compounds of the present invention correspond to general formula (I) and more specifically formula (II), wherein:

l is 2 or 3; and/or m is 0 or 1; and/or n is 0 or 1; and/or

AH is $CO_2H$ or $SO_3H$ or $PO_3H_2$; and/or $R_3$ and $R_4$ are both H, or $R_3$ and $R_4$ are both methyl groups; and/or the ring is an aryl or a heterocycle group, and more specifically a phenyl, naphthyl, indol, aza-indol or isoxazol group.

According to a particular embodiment $R_1$ and $R_2$ are independently selected from the group consisting of: a hydrogen atom, a halogen atom, a cyano, an alkyl group, an alkoxy group, an alkylsulfonyl group, a haloalkyl group, a haloalkoxy group, an O-cycloalkyl group, a heteroalkyl group, an O-aryl group, an O-arylalkyl group and an aryl group.

According to more preferred embodiments, the compounds of the present invention correspond to general formula (I) and more specifically formula (II), wherein:

l is 2; and/or m+n=1; and/or

AH is $CO_2H$ or $SO_3H$; and/or $R_3$ and $R_4$ are H; and/or the ring is more specifically a phenyl, a naphthyl or indol group.

According to a more particular embodiment, $R_1$ and $R_2$ are independently selected from the group consisting of: a hydrogen atom, a halogen atom (preferably a chlorine or fluorine atom), a cyano, an alkyl group (preferably a methyl), an alkoxy group (preferably methoxy), an alkylsulfonyl group (preferably methanesulfonyl), a haloalkyl group (preferably trifluoromethyl), a haloalkoxy group (preferably trifluoromethoxy), an O-cycloalkyl group (preferably O-cyclopentyl or O-cyclohexyl), a heteroalkyl group (preferably methoxyethoxy), an O-aryl group (preferably O-phenyl), an O-arylalkyl group (preferably O-benzyl), and an aryl group (preferably phenyl).

References herein to a compound according to the invention include both compounds of formula (I) or (II) and their pharmaceutically acceptable salts, solvates, zwitterionic forms or pro-drugs.

According to a particular embodiment, a pro-drug of the compound according to the invention can be a product having the following formula (III):

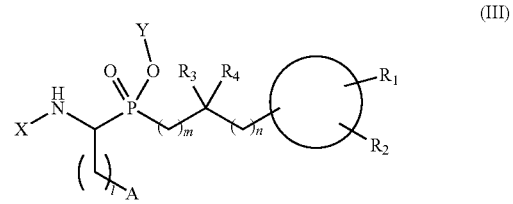

and more specifically, the following formula (IV):

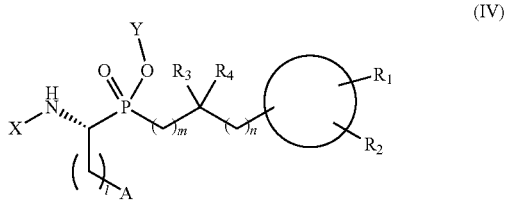

wherein:
l, m, n, R$_1$, R$_2$, R$_3$, R$_4$ are as defined above;

A represents —SO$_3$Z—CO$_2$Z or —P(O)(OZ)$_2$, with Z being selected from the group consisting of a hydrogen atom, an alkyl and arylalkyl group;

X represents a hydrogen atom, —(CO)-alkyl, —(CO)-alkoxy, —(CO)-benzyloxy,

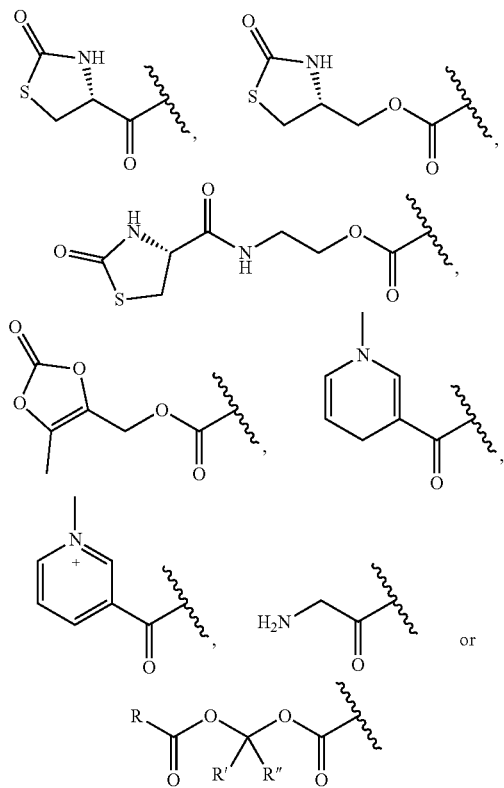

where R represents an alkyl group as defined above and, R' and R" represent independently a hydrogen atom or an alkyl group as defined above;

Y represents a hydrogen atom, an alkyl, aryl, arylalkyl group as defined above or

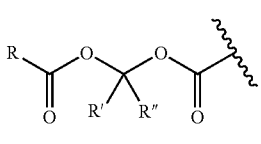

where R, R' and R", being identical or different, are as defined above, wherein at least one of Z, X and Y is different from hydrogen atom.

According to specific embodiments, the compound of the invention is selected from the group consisting of:
4-amino-4-[benzyl(hydroxy)phosphoryl]butanoic acid;
4-amino-4-{hydroxy[(2-methylphenyl)methyl] phosphoryl}butanoic acid;
4-amino-4-{hydroxy[(3-methylphenyl)methyl] phosphoryl}butanoic acid;
4-amino-4-{hydroxy[(4-methylphenyl)methyl] phosphoryl}butanoic acid;
4-amino-4-({[3,5-bis(trifluoromethyl)phenyl]methyl}(hydroxy)phosphoryl) butanoic acid;
4-amino-4-[({[1,1'-biphenyl]-2-yl}methyl)(hydroxy)phosphoryl] butanoic acid;
4-amino-4-[hydroxy({[3-(trifluoromethoxy)phenyl] methyl})phosphoryl]butanoic acid;
4-amino-4-[hydroxy({[4-(trifluoromethoxy)phenyl] methyl})phosphoryl]butanoic acid;
4-amino-4-{hydroxy[(4-methanesulfonylphenyl)methyl] phosphoryl}butanoic acid;
4-amino-4-{hydroxy[(2-methoxyphenyl)methyl]phosphoryl} butanoic acid;
4-amino-4-{hydroxy[(3-methoxyphenyl)methyl] phosphoryl}butanoic acid;
4-amino-4-{hydroxy[(4-methoxyphenyl)methyl] phosphoryl}butanoic acid;
4-amino-4-{[(3-cyanophenyl)methyl](hydroxy) phosphoryl}butanoic acid;
4-amino-4-{[(4-cyanophenyl)methyl](hydroxy) phosphoryl}butanoic acid;
4-amino-4-{hydroxy[(naphthalen-1-yl)methyl] phosphoryl}butanoic acid;
4-amino-4-{hydroxy[(2-phenoxyphenyl)methyl] phosphoryl}butanoic acid;
4-amino-4-{hydroxy[(3-phenoxyphenyl)methyl] phosphoryl}butanoic acid;
4-amino-4-{hydroxy[(4-phenoxyphenyl)methyl] phosphoryl}butanoic acid;
4-amino-4-[({[1,1'-biphenyl]-3-yl}methyl)(hydroxy)phosphoryl]butanoic acid;
4-amino-4-{hydroxy[(3-phenyl-1,2-oxazol-5-yl)methyl] phosphoryl}butanoic acid;
4-amino-4-{hydroxy[(5-phenyl-1,2-oxazol-3-yl)methyl] phosphoryl}butanoic acid;
4-amino-4-[hydroxy(2-phenylethyl)phosphoryl]butanoic acid;
4-amino-4-{hydroxy[2-(2-methylphenyl)ethyl] phosphoryl}butanoic acid;
4-amino-4-{hydroxy[2-(3-methylphenyl)ethyl] phosphoryl}butanoic acid;
4-amino-4-{hydroxy[2-(4-methylphenyl)ethyl] phosphoryl}butanoic acid;
4-amino-4-[hydroxy({2-[3-(trifluoromethyl)phenyl]ethyl}) phosphoryl]butanoic acid;
4-amino-4-[hydroxy(2-methyl-2-phenylpropyl)phosphoryl] butanoic acid;
4-amino-4-{[2-(2-chlorophenyl)ethyl](hydroxy) phosphoryl}butanoic acid;
4-amino-4-{[2-(3-chlorophenyl)ethyl](hydroxy) phosphoryl}butanoic acid;
4-amino-4-{hydroxy[2-(naphthalen-2-yl)ethyl] phosphoryl}butanoic acid;
4-amino-4-{hydroxy[2-(naphthalen-1-yl)ethyl] phosphoryl}butanoic acid;

4-amino-4-{hydroxy[2-(2-methoxyphenyl)ethyl]
  phosphoryl}butanoic acid;
4-amino-4-{hydroxy[2-(3-methoxyphenyl)ethyl]
  phosphoryl}butanoic acid;
4-amino-4-{hydroxy[2-(4-methoxyphenyl)ethyl]
  phosphoryl}butanoic acid;
4-amino-4-{hydroxy[2-(2-phenoxyphenyl)ethyl]
  phosphoryl}butanoic acid;
4-amino-4-({2-[2-(cyclopentyloxy)phenyl]ethyl}(hydroxy)
  phosphoryl) butanoic acid;
4-amino-4-[hydroxy(3-phenylpropyl)phosphoryl]butanoic
  acid;
4-amino-4-[hydroxy({2-[2-(trifluoromethoxy)phenyl]
  ethyl})phosphoryl] butanoic acid;
4-amino-4-[(2-{[1,1'-biphenyl]-2-yl}ethyl)(hydroxy)phosphoryl]butanoic acid;
4-amino-4-{[2-(2,3-dichlorophenyl)ethyl](hydroxy)
  phosphoryl}butanoic acid;
4-amino-4-{[2-(3-chloro-2-methoxyphenyl)ethyl](hydroxy)
  phosphoryl} butanoic acid;
3-carboxy-1-{hydroxy[2-(1-methyl-1H-indol-3-yl)ethyl]
  phosphoryl} propan-1-aminium chloride;
3-carboxy-1-({2-[2-(cyclohexyloxy)phenyl]ethyl}(hydroxy)phosphoryl) propan-1-aminium chloride;
3-carboxy-1-[hydroxy({2-[2-(2-methoxyethoxy)phenyl]
  ethyl})phosphoryl] propan-1-aminium chloride;
4-amino-4-{hydroxy[2-(3-phenyl-1,2-oxazol-5-yl)ethyl]
  phosphoryl}butanoic acid;
4-amino-4-{[2-(4-fluoro-2-methoxyphenyl)ethyl](hydroxy)
  phosphoryl}butanoic acid;
4-amino-4-{hydroxy[2-(1H-indazol-1-yl)ethyl]
  phosphoryl}butanoic acid;
1-({2-[2-(benzyloxy)phenyl]ethyl}(hydroxy)phosphoryl)-
  3-carboxy propan-1-aminium chloride;
5-amino-5-[hydroxy(2-phenylethyl)phosphoryl]pentanoic
  acid;
(1R)-3-carboxy-1-[hydroxy(2-phenylethyl)phosphoryl]propan-1-aminium chloride;
(1S)-3-carboxy-1-[hydroxy(2-phenylethyl)phosphoryl]propan-1-aminium chloride;
(1R)-3-carboxy-1-{hydroxy[2-(2-methoxyphenyl)ethyl]
  phosphoryl}propan-1-aminium chloride;
(4R)-4-amino-4-({2-[2-(cyclohexyloxy)phenyl]ethyl}(hydroxy)phosphoryl) butanoic acid;
(1-amino-4-methoxy-4-oxobutyl)(2-phenylethyl)phosphinic
  acid;
(1-amino-4-ethoxy-4-oxobutyl)(2-phenylethyl)phosphinic
  acid;
{4-ethoxy-1-[({1-[(2-methylpropanoyl)oxy]
  ethoxy}carbonyl)amino]-4-oxobutyl}(2-phenyl
ethyl)phosphinic acid;
1-[(benzyloxy)(2-phenylethyl)phosphoryl]-4-ethoxy-4-
  oxobutan-1-aminium chloride;
[1-amino-4-(benzyloxy)-4-oxobutyl](2-phenylethyl)phosphinic acid;
(4-ethoxy-4-oxo-1-{[(4R)-2-oxo-1,3-thiazolidin-4-yl]
  formamido}butyl)(2-phenylethyl) phosphinic acid;
3-amino-3-{hydroxy[(2-methoxyphenyl)methyl]
  phosphoryl}propane-1-sulfonic acid;
3-amino-3-[hydroxy(2-phenylethyl)phosphoryl]propane-1-
  sulfonic acid;
3-amino-3-{hydroxy[2-(2-methoxyphenyl)ethyl]
  phosphoryl}propane-1-sulfonic acid;
3-amino-3-[hydroxy(3-phenylpropyl)phosphoryl]propane-
  1-sulfonic acid;
3-amino-3-[({[1,1'-biphenyl]-3-yl}methyl)(hydroxy)phosphoryl]propane-1-sulfonic acid;
3-amino-3-{hydroxy[(3-phenyl-1,2-oxazol-5-yl)methyl]
  phosphoryl} propane-1-sulfonic acid;
3-amino-3-{hydroxy[(5-phenyl-1,2-oxazol-3-yl)methyl]
  phosphoryl}propane-1-sulfonic acid;
4-amino-4-[hydroxy(2-phenylethyl)phosphoryl]butane-1-
  sulfonic acid;
{3-amino-3-[hydroxy(2-phenylethyl)phosphoryl]
  propyl}phosphonic acid;
[4-ethoxy-1-({[(5-methyl-2-oxo-2H-1,3-dioxol-4-yl)
  methoxy]carbonyl}amino)-4-oxobutyl](2-phenylethyl)
  phosphinic acid;
ethyl 4-({[(5-methyl-2-oxo-2H-1,3-dioxol-4-yl)methoxy]
  carbonyl}amino)-4-({1-[(2-methyl propanoyl)oxy]
  ethoxy}(2-phenylethyl)phosphoryl)butanoate;
(1-{[(benzyloxy)carbonyl]amino}-4-ethoxy-4-oxobutyl)(2-
  phenylethyl)phosphinic acid;
3-({4-ethoxy-4-oxo-1-[(2-phenylethyl)phosphinato]
  butyl}carbamoyl)-1-methylpyridin-1-ium;
{4-ethoxy-4-oxo-1-[({[(4R)-2-oxo-1,3-thiazolidin-4-yl]
  methoxy}carbonyl)amino]butyl}(2-phenylethyl)phosphinic acid;
(4-ethoxy-4-oxo-1-{[(2-{[(4R)-2-oxo-1,3-thiazolidin-4-yl]
  formamido}ethoxy)carbonyl]amino}butyl)(2-phenylethyl)phosphinic acid; and
[1-(2-aminoacetamido)-4-ethoxy-4-oxobutyl](2-phenylethyl)phosphinic acid.

The compounds of the invention are conveniently administered in the form of pharmaceutical compositions. Such compositions may conveniently be presented for use in conventional manner in admixture with one or more physiologically acceptable carriers or excipients. The carrier(s) must be "acceptable" in the sense of being compatible with the other ingredients of the formulation and not deleterious to the subject receiving them.

While it is feasible that compounds of the present invention may be therapeutically administered as a raw chemical, it is also possible to present the active ingredient as a pharmaceutical formulation.

Accordingly, the present invention further provides a pharmaceutical composition comprising a compound of the present invention in association with one or more pharmaceutically acceptable carriers and, optionally, other active ingredients.

The pharmaceutical compositions include those suitable for oral, parenteral (including subcutaneous e.g. by injection or by depot tablet, intradermal, intrathecal, intraocular, intramuscular e.g. by depot and intravenous), ocular, rectal and topical (including dermal (i.e. on the skin), buccal and sublingual) or in a form suitable for administration by inhalation or insufflation, although the most suitable route may depend upon for example the condition and disorder of the recipient. The compositions may conveniently be presented in unit dosage form and may be prepared by any of the methods well known in the art of pharmacy. All methods include the step of associating the compounds of the invention, optionally with at least one other active ingredient, with the carrier which constitutes one or more accessory ingredients. In general, the formulations are prepared by uniformly and intimately associating the active ingredient with liquid carriers or finely divided solid carriers or both and then, if necessary, shaping the product into the desired formulation.

Pharmaceutical compositions suitable for oral administration may be presented as discrete units such as capsules, cachets or tablets (e.g. chewable tablets in particular for pediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a other conventional excipients such as binding agents (for example, syrup, gum arabic, gelatin, sorbitol, tragacanth, mucilage of starch, polyvinylpyrrolidone or hydroxymethyl cellulose), fillers (for example, lactose, sucrose, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycolate) or wetting agents, such as sodium lauryl sulfate. Molded tablets may be made by molding in a suitable machine a mixture of the powdered compound moistened with an inert liquid diluent. The tablets may optionally be coated or scored and may be formulated so as to provide slow or controlled release of the active ingredient therein. The tablets may be coated according to methods well-known in the art.

Alternatively, the compounds of the present invention may be incorporated into oral liquid preparations such as aqueous or oily suspensions, solutions, emulsions, and such as syrups or elixirs, for example. Moreover, pharmaceutical compositions (or formulations) containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or arabic gum; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. These preparations may also be formulated as suppositories, e.g., containing conventional suppository excipients such as cocoa butter or other glycerides.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of a sterile liquid carrier, for example, water-for-injection, immediately prior to use. Extemporaneous injection solutions and suspensions may be prepared from sterile powders, granules and tablets of the kind previously described.

Compositions for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavored excipient such as sucrose and arabic gum or tragacanth, and pastilles comprising the active ingredient in an excipient such as gelatin and glycerin or sucrose and arabic gum. For topical administration onto the skin, the compounds may be formulated as creams, gels, ointments or lotions or as a transdermal patch. For ocular administration, the compositions can be a liquid solution (such as eye-drop solution), a gel, a cream or any type of ophthalmic compositions.

The compounds may also be formulated as depot preparations. These long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For intranasal administration the compounds of the present invention may be used, for example as a liquid spray, as a powder or in the form of drops.

For administration by inhalation the compounds according to the present invention are conveniently delivered in the form of an aerosol spray presentation from a pressurised container or a nebuliser, with the use of a suitable propellant, e.g. 1,1,1,2-trifluoroethane (HFA 134A) and 1,1,1,2,3,3,3,-heptafluoropropane (HFA 227), carbon dioxide or other suitable gas. In the case of a pressurised aerosol the exact dosage may be determined by providing a valve adapted to deliver a metered amount. Capsules and cartridges of e.g. gelatin for use in an inhaler or insufflator may be formulated so as to contain a powder mix of a compound of the present invention and a suitable powder excipient such as lactose or starch. In addition to the ingredients particularly mentioned above, the formulations may include other agents conventional in the art having regard to the type of formulation in question, for example those suitable for oral administration may include flavoring agents.

It will be appreciated by the person skilled in the art that reference herein to treatment extends to prophylaxis as well as the treatment of established diseases or symptoms. Moreover, it will be appreciated that the amount of a compound of the present invention required for use in treatment will vary with the nature of the condition being treated and the age and the condition of the patient and will be ultimately at the discretion of the attendant physician or veterinarian.

The patient can be any mammal, including human or non-human mammal. The invention is more specifically addressed to human mammals, more specifically adults. In general, doses employed for adult human treatment will typically be in the range of 0.02-5000 mg per day, preferably 1-1500 mg per day. The desired dose may conveniently be presented in a single dose or as divided doses administered at appropriate intervals, for example as two, three, four or more sub-doses per day. The formulations according to the present invention may contain between 0.1-99% of the active ingredient, conveniently from 30-95% for tablets and capsules and 3-50% for liquid preparations.

The compounds of the present invention for use in the present invention may be used in association with one or more other therapeutic active agents, for example, beta-adrenergic receptor antagonists, calcium channel blocking agents, thiazide diuretics, angiotensin receptor antagonists and angiotensin converting enzyme inhibitors. The present invention thus provides in a further aspect the use of a combination comprising a compound of the invention with a further therapeutic agent in the treatment of arterial hypertension.

When the compounds of the present invention are used in association with other therapeutic agents, the compounds may be administered either sequentially or simultaneously by any suitable route.

The associations referred to above may suitably be presented for use in the form of a pharmaceutical formulation and thus pharmaceutical formulations comprising an association as defined above optimally together with a pharmaceutically acceptable carrier or excipient are a further aspect of the present invention. The individual components of such associations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any suitable formulation, suitably in a manner known for such compounds in the art.

When a compound of the present invention is used in association with a second therapeutic agent active against the same disease, the dose of each compound may differ from that administered when the compound is used alone. Appropriate doses will be readily determined by the person skilled in the art.

In another aspect, a subject of the present invention is a method for the prevention or treatment of arterial hypertension and of directly and indirectly related diseases, comprising the administration of a therapeutically effective amount of a compound of the present invention.

In another aspect, the present invention provides compounds of the present invention for use in therapeutics, and in particular in veterinary or human medicine.

The invention also relates to the use of a compound of formula (I) or (II), as a selective inhibitor with regard to aminopeptidase A.

In another aspect, the present invention provides the use of a compound of the present invention, for producing a medicinal product for use in the treatment of arterial hypertension and of directly and indirectly related diseases.

In another aspect, the present invention provides a method of treating a patient suffering from arterial hypertension and from directly and indirectly related diseases, comprising the administration to said patient of a therapeutically effective amount of a compound of the present invention.

The present invention provides methods for the prevention or treatment of arterial hypertension and of diseases to which arterial hypertension directly or indirectly contributes. These diseases comprise heart disease, heart failure, stroke, peripheral and/or cerebral vascular system diseases, brain, eye and kidney diseases. In particular, the diseases comprise primary and secondary arterial hypertension, an ictus, myocardial ischemia, cardiac insufficiency and renal insufficiency, myocardial infarction, a peripheral vascular disease, diabetic protinuria, syndrome X, glaucoma, neurodegenerative diseases and memory disorders.

The compounds of formula (I) or preferably (II) can be prepared by several methods. The starting products are commercial products or products prepared according to known synthesis from commercial compounds or known to one skilled in the art. More specifically, the method for preparing the compound of the invention comprises the following successive steps:

The compounds of formula (I), objects of the present invention, may be prepared according to the synthesis route described hereafter, by using precursors of the following formulae (V), (VI) and (VII),

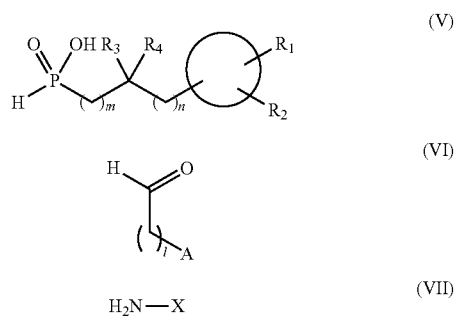

wherein l, m, n, $R_1$, $R_2$, $R_3$, $R_4$, A and X are defined above.

According to this synthesis route, a multi-component reaction is carried out between the compounds (V), (VI) and (VII) for example in the presence of acetic acid and acetyl chloride in organic solvent such as toluene in order to lead to the compound of formula (VIII):

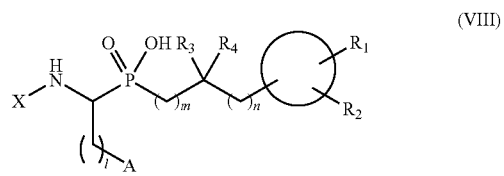

Next, simultaneously deprotection of the protecting group of function A and the protecting group X of amino function could occur by hydrogenolysis to lead to the formation of the compound of the present invention of formula (I).

In some cases, the group A of the compound of formula (VIII) is selectively de-protected by lithine for example to provide the intermediate compound of formula (IX),

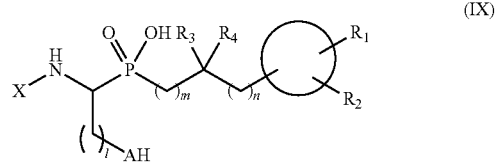

Next, the compound of formula (IX) is submitted to hydrogenolysis or to acidic conditions such as trifluoroacetic acid in organic solvent like anisole under heating to provide the compound of the present invention of formula (I).

The compounds of formula (I), objects of the present invention, may also be prepared according to the synthesis route described hereafter, by using precursors of the following formulae (Vbis) and (X),

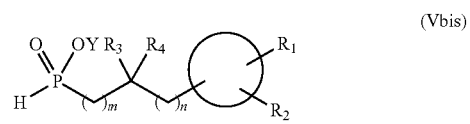

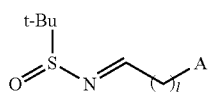

(X)

wherein l, m, n, Y, R$_1$, R$_2$, R$_3$, R$_4$ and A are defined above.

According to this synthesis route, a reaction is carried out between the compound (Vbis) and the sulfo-imine (X), obtained by well-known methods from the literature, in the presence for example of cesium carbonate in organic solvent such as dichloromethane in order to lead to the compound of formula (XI):

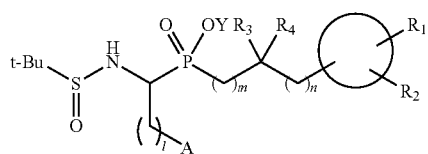

(XI)

wherein l, m, n, Y, R$_1$, R$_2$, R$_3$, R$_4$ and A are as defined above. It is worth noting that sulfo-imine intermediate (X) could be synthesized in chiral form by well-known methods of the literature. When chiral inductor protecting group is supported by sulfo-imine (X), this synthon could provide access to asymmetric synthesis of precursor of compound of formula (II).

Appropriate deprotection steps applied to intermediate (XI) in racemate form or chiral form provide access to compounds of the invention of formula (I) or (II) respectively.

The precursor of formula (V) may be obtained from the compound of the following formula (XII),

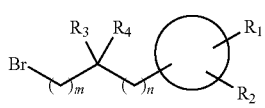

(XII)

wherein m, n, R$_1$, R$_2$, R$_3$, and R$_4$ are as defined above.

In the case where m=n=0, the compound of formula (V) may be obtained by reacting bis(trimethylsilyl)phosphonite in organic solvent like dichloromethane for example in cooled conditions such as 0° C. with the compound of formula (XII).

In the other cases, the compound of formula (V) may be obtained by reacting the corresponding Grignard reagent of the compound of formula (XII) with diethylchlorophosphite in organic solvent like diethyl ether or tetrahydrofuran in cooled conditions such as 0-10° C.

The precursor of formula (Vbis) may be obtained from the iodide analog of compound of the formula (XII) described previously submitted to dialkylphosphine-borane complex according to well-known methods of the literature leading to the compound of the following formula (XIII),

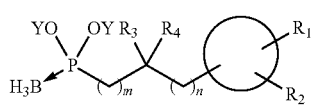

(XIII)

wherein m, n, Y, R$_1$, R$_2$, R$_3$ and R$_4$ are as defined earlier.

The compound of formula (XIII) is then submitted to acidic conditions such as tetrafluoroboric acid diethyl ether in organic solvent such as dichloromothane to provide the compound of formula (Vbis).

The following examples illustrate the invention but do not limit it by any means.

EXAMPLES

The starting products used are commercial products or products prepared according to known synthesis from commercial compounds or known to one skilled in the art. The different general procedures A, B, C, D, E and F lead to synthesis intermediates useful for preparing the compounds of the invention. Procedures G and H lead to synthesis of final compounds of the invention.

The structures of the compounds described in the examples were determined according to the usual spectrophotometric techniques (nuclear magnetic resonance (NMR), mass spectrometry including electrospray ionisation (ESI) . . . ) and purity was determined by high performance liquid chromatography (HPLC).

Synthesis intermediates and compounds of the invention are named according to the IUPAC (The International Union of Pure and Applied Chemistry) nomenclature and described in their neutral form.

The following abbreviations have been used:
AIBN: azobisisobutyronitrile
(Boc)$_2$O: di-tert-butyl dicarbonate
(n-Bu)$_4$NBr: tetra-n-butylammonium bromide
(n-Bu)$_4$NI: tetra-n-butylammonium iodide
AcCl: acetyl chloride
AcOH: acetic acid
BTSP: bis(trimethylsilyl)phosphonate
Cbz: carboxybenzyl
CH$_2$Cl$_2$ or DCM: dichloromethane
CHCl$_3$: chloroform
cHex: cyclohexane
CuSO$_4$: copper sulfate
DCC: N,N'-dicyclohexylcarbodiimide
DTAD: di-tert-butyl azodicarboxylate
EDCI: 1-ethyl-3-(3-dimethylaminopropyl)ethylcarbodiimide
Et$_2$O: diethyl ether
EtOAc: ethyl acetate
HBF$_4$.Et$_2$O: tetrafluoroboric acid diethyl ether complex
HCl: hydrochloric acid
HMDS: 1,1,1,3,3,3-Hexamethyldisilazane
I2: iodine
i-PrOH: isopropanol
K$_2$CO$_3$: potassium carbonate
KOtBu: potassium tert-botuxide
LiAlH$_4$: lithium aluminium hydride
LiHMDS: lithium bis(trimethylsilyl)amide
LiOH.H$_2$O: lithium hydroxide monohydrate (lithine)
MeOH: methanol
Mg: magnesium
Na$_2$S$_2$O$_3$: sodium thiosulfate
Na$_2$SO$_4$: sodium sulfate
NaBH$_4$: sodium borohydride
NaHCO$_3$: sodium bicarbonate
NEt$_3$: tritethylamine
NH$_2$Cbz: benzyl carbamate
NH$_4$Cl: ammonium chloride
Pd(PPh$_3$)$_4$: Tetrakis(triphenylphosphine)palladium(O)
TFA: trifluoroacetic acid Eq.: equivalent
ESI: Electrospray Ionisation
HPLC: High Performance Liquid Chromatography
NMR: Nuclear Magnetic Resonance
PTFE filter: polytetrafluoroethylene filter General Procedure for the Preparation of Intermediate (V) with m=n=0 (Procedure A)

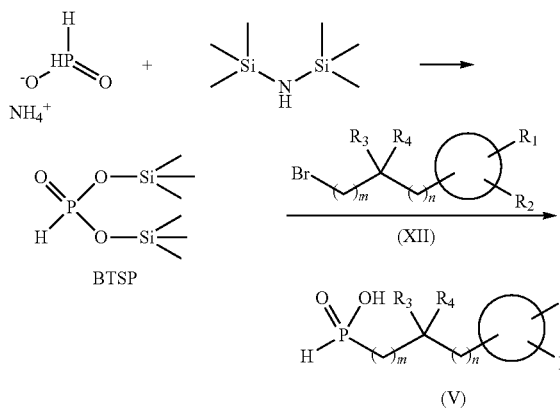

To a vial containing ammonium hypophosphite (5.0 or 10 eq.) was added HMDS (5.0 or 10 eq.) under argon. The white suspension was heated at 105° C. for 2 h in order to synthesize BTSP. The system was cooled to 0° C. then a solution of intermediate (XII) (1.0 eq.) in DCM (1.4-3.2 mL/mmol of intermediate (XII)) was added. The white suspension was stirred at room temperature overnight. MeOH was added to quench the excess of BTSP. The reaction mixture was filtered through a PTFE filter, and then concentrated in vacuo. The crude was stirred in 1 M HCl (pH=1) for 20 min and extracted with EtOAc (three times). The combined organic layer were dried over $Na_2SO_4$, filtered and concentrated in vacuo to obtain the desired intermediate (V).

General Procedure for the Preparation of Intermediate (V) with m or n≠0 (Procedure B)

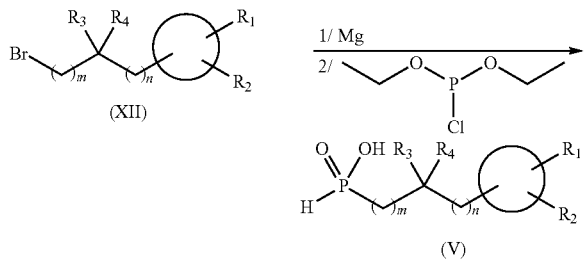

Intermediate (XII), transformed to the corresponding Grignard solution (0.5 to 1.0 M in anhydrous THF or $Et_2O$, 1.05 eq.), was added dropwise to a cooled solution (5° C.) of diethylchlorophosphite (1.0 eq.) in anhydrous $Et_2O$ (1.3 mL/mmol of diethylchlorophosphite), under argon atmosphere, maintaining the internal temperature between 0-10° C. during the addition. After 16 h of stirring at room temperature, the mixture was filtered through celite. The filtrate was concentrated under reduced pressure. The residue was dissolved in water and treated with concentrated aqueous HCl (pH=1). The resulting mixture was stirred at room temperature until a colorless transparent solution was obtained (15 min). This solution was extracted with EtOAc (three times) and the combined organic layers were washed with brine, dried over $Na_2SO_4$, filtered and concentrated in vacuo. The clear liquid was diluted in aqueous NaOH 2 M and the resulting solution was stirred for 1 h. The aqueous layer was washed with $Et_2O$, and then acidified with concentrated HCl (until pH=1). The resulting acid aqueous layer was extracted with DCM (three times). The combined organic layer was dried over $Na_2SO_4$, filtered, and concentrated under vacuum to afford the desired intermediate (V).

General Procedure for the Preparation of Phosphinate (Vbis) Via Phosphine-Borane Complex Intermediate (XIII) (Procedure C)

First Step:

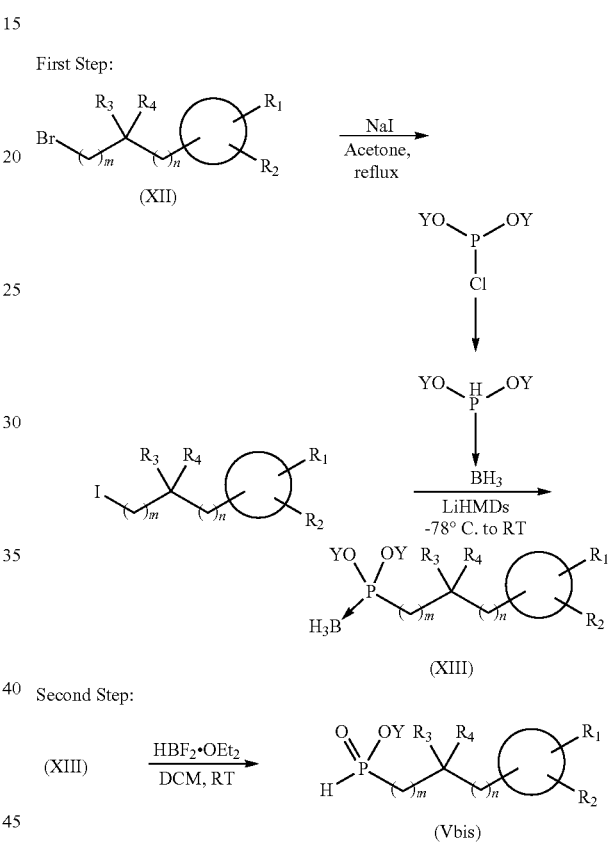

Second Step:

Dialkoxyphosphine-borane complex, $(BH_3)P(OY)_2H$, was prepared according to the reference Tetrahedron 2008, 64, 9181-9190.

In the case where Y=Et, $(BH_3)P(OEt)_2H$ (1.2 eq.) was solubilized in THF (3 mL/mmol of phosphine-borane complex) at −78° C. and the resulting solution was degassed. LiHMDS (1.0 M solution in THF, 1.2 eq.) was added dropwise and the resulting light yellow solution was stirred at −78° C. for 1 h. A solution of iodide derivative (1.0 eq.) in THF (1.5 mL/mmol of iodide derivative) resulting from transformation of its bromide analog (XII) was added and the mixture was allowed to warm-up to room temperature and stirred 2 h at room temperature. The reaction was quenched by addition of a 1/1 mixture of saturated solution of $NH_4Cl$/brine and EtOAc was added. The layers were separated and the aqueous phase was extracted with EtOAc. The combined organic extracts were washed with brine, dried over $Na_2SO_4$, filtered and concentrated under reduced pressure. The residue was purified by column chromatography to afford the intermediate (XIII).

Then, to a solution of intermediate (XIII) (1.0 eq.) in DCM (5 mL/mmol of intermediate (XIII)) at 0° C., was added dropwise HBF$_4$.Et$_2$O (5.0 eq.). The resulting solution was stirred at room temperature for 4 h. The reaction mixture concentrated under reduced pressure and aqueous solution of NaOH (2 M, 15 mL) was added. After stirring for 30 min, the aqueous mixture was washed twice with MTBE. The aqueous phase was acidified by dropwise addition of concentrated HCl to reach pH~1 and saturated with NaCl solution. EtOAc was added and the layers were separated. The aqueous phase was extracted with EtOAc (twice). The combined organic extracts were dried over Na$_2$SO$_4$, filtered and concentrated under reduced pressure to afford the desired intermediate (Vbis).

General Procedure for Multi-Component Reaction (Procedure D)

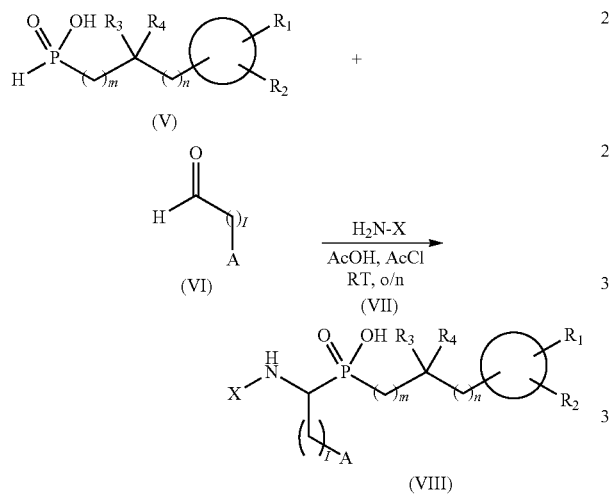

To a solution of intermediate (V) (1.0 eq.) and benzyl carbamate (VII) (H$_2$N—X with X=CBz) (1.1 eq.) in a mixture ~6:1 of AcOH (0.9-1.8 mL/mmol of intermediate (V)) and AcCl (0.09-0.52 mL/mmol of intermediate (V)) was added dropwise intermediate (VI) (1.2 eq.). After 18 h of stirring at room temperature, the reaction mixture was co-evaporated with toluene (three times). The residue was taken up in DCM, water was then added to quench the remaining AcCl and then the aqueous layer was extracted with DCM (three times). The combined organic layers were dried over Na$_2$SO$_4$, filtered and concentrated in vacuo. The crude material was triturated in Et$_2$O, filtered and the obtained solid was dried to afford the desired intermediate (VIII).

General Procedure for Alternative to Multi-Component Reaction (Procedure E)

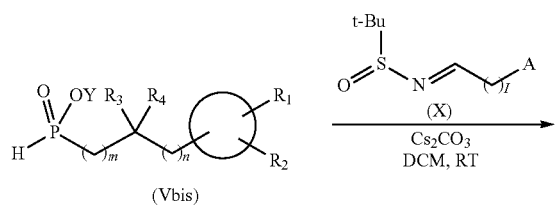

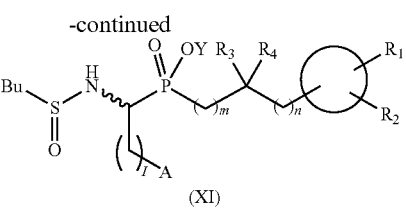

To cesium carbonate (2.5 eq.) in DCM (0.95 mL/mmol of cesium carbonate) was added the phosphinate (Vbis) (1.5 eq.). After 15 min, the racemic or chiral sulfo-imine of formula (X) (1.0 eq.) in DCM (2.4 mL/mmol of imine (X)) was added and the reaction mixture was stirred during 18 h. The reaction mixture was quenched with water. The aqueous layer was extracted with EtOAc (3 times). The organic extracts were washed with brine, dried over Na$_2$SO$_4$, filtered and concentrated in vacuo. The residue was purified by column chromatography (normal or reverse phase) to afford the desired intermediate (XI).

General Procedure for Selective Deprotection (Procedure F)

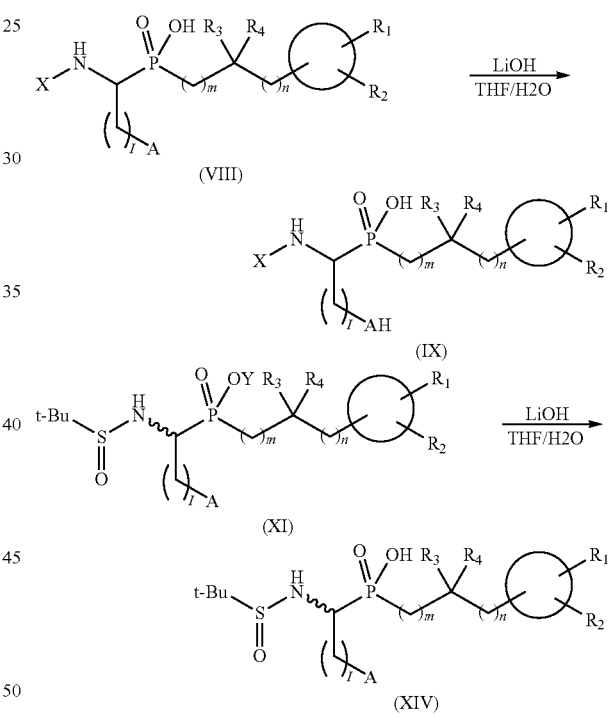

To intermediates (VIII) or (XI) (1.0 eq.) in a mixture of THF/water (4:1) was added LiOH.H$_2$O (3.0 eq.) in one portion. The mixture took instantaneously an orange coloration and was stirred at room temperature until completion of reaction. The mixture was concentrated to evaporate THF, then the aqueous layer was extracted with EtOAc (three times). The aqueous layer was then acidified to pH 1 with HCl aqueous solution while a precipitate appeared. Most of the time, the aqueous layer was extracted with DCM (five times) and the combined organic layers were dried over Na$_2$SO$_4$, filtered and concentrated in vacuo to afford the corresponding selectively deprotected intermediates (IX) and (XIV). In some cases, the precipitate obtained after acidic treatment was directly filtered and dried to afford these expected intermediates.

General Procedure for Final Deprotection in Acidic Conditions (Procedure G)

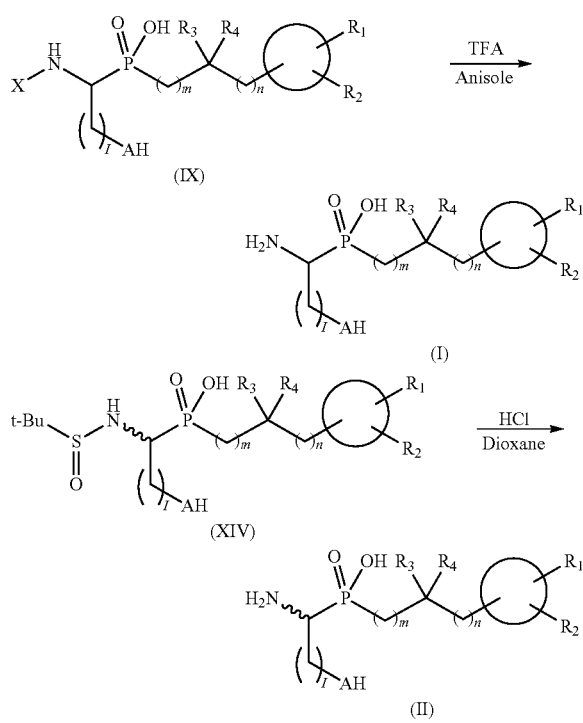

To intermediate (IX) or (XIV) selectively deprotected according to procedure F were added TFA/anisole or HCl/dioxane. The resulting solution was stirred at 75° C. for 2 to 6 h with TFA/anisole conditions then at room temperature if needed, otherwise at room temperature for HCl/dioxane conditions. After concentration and co-evaporation with toluene (three times), or direct filtration in the case where a precipitate appears, the crude was purified by trituration, preparative LCMS or reverse phase column to afford the desired compounds of the invention of formula (I) or (II).

General Procedure for Hydrogenolysis (Procedure H)

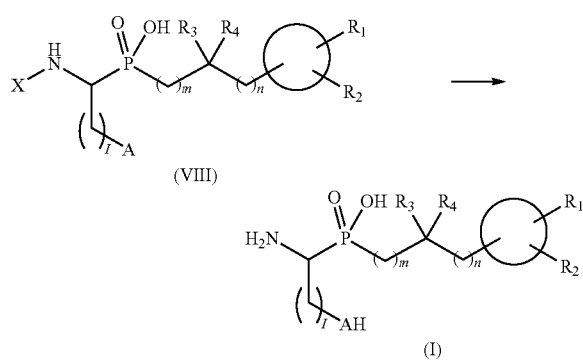

The intermediate (VIII) (1.0 eq.) was dissolved in a mixture of EtOH/AcOH or MeOH/AcOH (global volume: 17-34 mL/mmol of protected compound, depending on its solubility). The powder was sonicated to promote solubility and the clear solution was then submitted to H-Cube (catalyst=10% Pd/C, T=40° C., flow rate=0.6-0.8 mL/min, full $H_2$ mode or 10 bars). After concentration, the crude was purified by trituration or by reverse phase column to afford the desired compound of of the invention of formula (I).

Preparation of benzyl 4-oxobutanoate

Step 1: synthesis of benzyl 4-hydroxybutanoate

Gamma-butyrolactone (20 mL, 255 mmol, 1.0 eq.) and NaOH (10.2 g, 255 mmol, 1.0 eq.) were dissolved in water (170 mL) and the temperature was raised to 70° C. After 12 hours, water was evaporated and the white paste was included with the toluene evaporated (three times). The white solid was placed under vacuum and heated to 70° C. for 2 hours. The solid was taken up again with toluene to remove any trace of water. The obtained white solid was suspended in acetone (280 mL). Tetrabutylammonium iodide (4.72 g, 12.8 mmol, 0.05 eq.) and benzyl chloride (29.4 mL, 255 mmol, 1.0 eq.) were added to the suspension. The solution was refluxed for 6 h and then go back at room temperature overnight. The reactional mixture was then refluxed again during 6 h. At room temperature, the mixture was filtered and the filtrate was evaporated to give the crude which was purified by chromatography on silica gel. The fractions containing expected product were combined and concentrated in vacuo to afford the title product (36.5 g, 74%).

$^1$H NMR (CDCl$_3$, 500 MHz) δ (ppm): 7.39-7.31 (m, 5H); 5.13 (s, 2H); 3.69 (t, 2H, J=6.0 Hz); 2.50 (t, 2H, J=7.0 Hz); 1.93-1.88 (m, 2H)

Step 2: Synthesis of benzyl 4-oxobutanoate

Benzyl 4-hydroxybutanoate (10 g, 51.49 mmol, 1.0 eq.) was dissolved in dichloromethane (1.7 L) and cooled to 0° C. Dess-Martin periodinane (33 g, 77.23 mmol, 1.5 eq.) was added and the mixture was stirred at room temperature for 2 h30. The mixture was concentrated and the crude was purified by flash chromatography on silica gel. The fractions containing expected product were combined and concentrated in vacuo to afford the title compound (8.0 g, 81%) as a light yellow oil.

$^1$H NMR (CDCl$_3$, 500 MHz) δ (ppm): 9.82 (s, 11H); 7.39-7.31 (m, 5H); 5.14 (s, 2H); 2.82 (t, 2H, J=7.0 Hz); 2.71-2.67 (m, 2H) Preparation of methyl 4-oxobutanoate Step 1: methyl 4-hydroxybutanoate To a solution of γ-butyrolactone (10 mL, 127.7 mmol, 1.0 eq.) in MeOH (638 mL) was added Et$_3$N (104 mL, 766.6 mmol, 6.0 eq.), and the reaction was heated to 60° C. and stirred for 19 h. The reaction was then cooled to room temperature, diluted with toluene (200 mL) and concentrated in vacuo. The residual MeOH was removed azeotropically with toluene (2×40 mL). The crude (15 g) was purified by column chromatography. The fractions containing expected product were combined and concentrated in vacuo to afford the title compound (12.1 g, 80%) as a yellow oil.

$^1$H NMR (CDCl$_3$, 500 MHz) δ (ppm): 3.67 (m, 5H); 2.44 (m, 2H); 1.89 (m, 3H)

Step 2: methyl 4-oxobutanoate

Methyl 4-hydroxybutanoate (6 g, 50.79 mmol, 1.0 eq.) was dissolved in CH$_2$Cl$_2$ (1.7 L) and cooled to 0° C. Dess-Martin periodinane (32.3 g, 76.19 mmol, 1.5 eq.) was added and the yellow mixture was stirred at room temperature during 3 h. The mixture was concentrated and the crude (30 g) was purified by column chromatography. The fractions containing expected product were combined and concentrated in vacuo to afford the title compound (2.25 g, 380%) as a light yellow oil.

$^1$H NMR (CDCl$_3$, 500 MHz) δ (ppm): 9.81 (s, 1H), 3.69 (s, 3H); 2.80 (m, 2H); 2.63 (m, 2H)

Preparation of benzyl (4E)-4-[(2-methylpropane-2-sulfinyl)imino]butanoate

To a solution of benzyl 4-oxobutanoate (3.27 g, 17.0 mmol, 1.03 eq.) and racemic tert-butylsulfinamide (2.0 g, 16.5 mmol, 1.0 eq.) in DCM (32 mL) at room temperature, was added CuSO$_4$ (5.27 g, 33.0 mmol, 2.0 eq.). The resulting suspension was stirred at room temperature for 7 h before being filtered over Celite (EtOAc rinses) and the filtrate was concentrated under reduced pressure. The residue was purified by column chromatography to afford the title compound (4.0 g, 820%) as a pale yellow oil.

MS (ESI$^+$): [M+H]$^+$=296.2
$^1$H NMR (500 MHz, CDCl$_3$) δ (ppm): 8.16 (t, J=3.1 Hz, 1H); 7.48-7.31 (m, 4H); 5.28-5.04 (m, 2H); 2.99-2.76 (m, 3H); 2.76-2.63 (m, 1H); 1.18 (s, 9H)

Preparation of benzyl (4E)-4-{[(S)-2-methylpropane-2-sulfinyl]imino}butanoate

At room temperature, to a solution of (S)-2-methylpropane-2-sulfinamide (0.75 g, 6.19 mmol, 1.0 eq.) in DCM (12.0 mL), were successively added CuSO$_4$ (1.98 g, 12.38 mmol, 2.0 eq.) and benzyl 4-oxobutanoate (1.23 g, 6.37 mmol, 1.3 eq.). The reaction mixture was stirred at room temperature for 4 h. The solution was filtered on celite and the cake was washed with EtOAc. The filtrate was concentrated in vacuo. The obtained residue was purified by silica gel column chromatography to give the expected compound (1.3 g, 71%) as a colorless oil.

MS (ESI$^+$): [M+H]$^+$=296.2
$^1$H NMR (CDCl$_3$, 500 MHz) δ (ppm): 8.14 (t, 1H, J=3.0 Hz); 7.38-7.31 (m, 5H); 5.15-5.10 (m, 2H); 2.94-2.66 (m, 4H): 1.15 (s, 9H)

Preparation of benzyl (4E)-4-{[(R)-2-methylpropane-2-sulfinyl]imino}butanoate

At room temperature, to a solution of (R)-2-methylpropane-2-sulfinamide (0.2 g, 1.65 mmol, 1.0 eq.) in DCM (3.3 mL), were successively added CUSO$_4$ (527 mg, 3.3 mmol, 2.0 eq.) and benzyl 4-oxobutanoate (412 mg, 2.15 mmol, 1.3 eq.). The reaction mixture was stirred at room temperature for 3 h. The solution was filtered on celite and the cake was washed with EtOAc. The filtrate was concentrated in vacuo. The obtained residue was purified by silica gel column chromatography to give the expected compound (257 mg, 53%) as a light yellow oil.

MS (ESI$^+$): [M+H]$^+$=296.2
$^1$H NMR (CDCl$_3$, 500 MHz) δ (ppm): 8.13 (t, 1H, J=3.0 Hz); 7.38-7.31 (m, 5H); 5.15-5.09 (m, 2H); 2.94-2.66 (m, 4H): 1.15 (s, 9H)

Preparation of 2,2-dimethylpropyl 3-[(2-methylpropane-2-sulfinyl)imino]propane-1-sulfonate Step 1: 2,2-dimethylpropyl methanesulfonate To a cooled solution at 0° C. of 2,2-dimethylpropan-1-ol (10 g, 113.4 mmol, 1.0 eq.) and methane-sulfonyl chloride (8.2 mL, 323.3 mmol, 0.94 eq.) in DCM (200 mL) was added dropwise trimethylamine (45 mL, 106.6 mmol, 2.85 eq.). The internal reaction temperature was kept below 10° C. (internal thermometer). Addition was complete in 1 h30. The reaction mixture was stirred at 0° C. for an additional 2.5 h. The mixture was then washed with a saturated aqueous solution of NaHCO$_3$, dried over Na$_2$SO$_4$, filtered and concentrated in vacuo. The crude was purified by column chromatography to give the title compound (16.8 g, 89%) as a pale yellow oil.

$^1$H NMR (CDCl$_3$, 500 MHz) δ (ppm): 3.90 (s, 2H); 3.03 (s, 3H); 1.02 (s, 9H)

Step 2: 2,2-dimethylpropyl 3-hydroxypropane-1-sulfonate

Under Argon, a solution of n-butyllithium (2.5 M in hexane, 23 mL, 57.7 mmol, 1.2 eq.) was added dropwise to a cooled (−78° C. dry ice, acetone) solution of previous product (8.0 g, 48.1 mmol, 1.0 eq.) and tetramethylethylenediamine (7.9 mL, 96.2 mmol, 2.0 eq.) in dry THF (100 mL) over 15 min. The resulting solution was stirred for an additional 30 min at −78° C. then a solution of ethylene oxide (3.0 M in THF, 19.3 mL, 57.7 mmol, 1.2 eq.) was added dropwise over 15 min. The reaction mixture was stirred at room temperature for 16 h and was then diluted in Et$_2$O and washed with brine. The aqueous layer was extracted with Et$_2$O (3 x) and the combined organic layers were dried over Na$_2$SO$_4$, filtered and concentrated in vacuo. The resulting pale yellow oil was purified by column chromatography to provide the title compound (7.73 g, 76%) as a colorless oil.

$^1$H NMR (CDCl$_3$, 500 MHz) δ (ppm): 3.88 (s, 2H); 3.79 (t, J=5.5 Hz, 2H); 3.26 (t, J=8.0 Hz, 2H); 2.11 (tt, J=5.5 and 8.0 Hz, 2H); 0.99 (s, 9H)

Step 3: 2,2-dimethylpropyl 3-oxopropane-1-sulfonate

To a solution of the previous product (7.7 g, 17.6 mmol, 1.0 eq.) in DCM (810 mL) was added Dess Martin periodinane in one portion (23.3 g, 54.9 mmol, 1.5 eq.) at room temperature. After 1.5 h of stirring, the solution became milky and consumption of the starting material was complete. The reaction mixture was concentrated in vacuo and the residue (25 g) was purified by chromatography. The fractions containing expected product were combined and concentrated in vacuo to afford the expected compound (3.9 g, 590%) as a colorless oil which crystallized on standing.

$^1$H NMR (CDCl$_3$, 500 MHz) δ (ppm): 9.81 (s, 1H); 3.89 (s, 2H); 3.43 (t, J=7.5 Hz 2H); 3.07 (t, J=7.5 Hz 2H); 0.99 (s, 9H)

Step 4: 2,2-dimethylpropyl (3E)-3-[(2-methylpropane-2-sulfinyl)imino]propane-1-sulfonate To a solution of previous product (4.10 g, 19.7 mmol, 1.0 eq.) and racemic tert-butylsulfinamide (3.1 g, 25.6 mmol, 1.3 eq.) in DCM (33 mL) at room temperature, was added CuSO$_4$ (6.28 g, 39.4 mmol, 2.0 eq.). The resulting suspension was stirred at room temperature for 16 h before being filtered over Celite (EtOAc rinses) and the filtrate was concentrated under reduced pressure. The residue was purified by column chromatography to afford the title compound (5.2 g, 85%) as a white solid.

¹H NMR (500 MHz, CDCl₃) δ (ppm): 8.18 (t, J=3.1 Hz, 1H); 3.99-3.87 (m, 2H); 3.64-3.40 (m, 2H); 3.19-3.05 (m, 2H); 1.23 (s, 9H); 1.02 (s, 9H)

Example 1: 4-amino-4-[benzyl(hydroxy)phosphoryl] butanoic acid

Step 1: Benzylphosphinic acid

The title compound (252 mg, 55%) obtained as a colorless oil was prepared to the procedure A from benzyl bromide (317 µL, 2.92 mmol, 1.0 eq.) in DCM (1.5 mL) and freshly prepared BTSP (14.62 mmol, 5.0 eq.).

¹H NMR (CDCl₃, 500 MHz) δ (ppm): 7.34-7.31 (m, 2H); 7.29-7.21 (m, 3H); 6.98 (dt, 1H, J=560 and 1.8 Hz); 5.93 (bs, 1H); 3.12 (dd, 2H, J=18.3 and 1.8 Hz)

³¹P NMR (CDCl₃, 202 MHz) δ (ppm): 36.84

Step 2: Benzyl(1-{[(benzyloxy)carbonyl]amino}-4-methoxy-4-oxobutyl)phosphinic acid The title compound (522 mg, 80%) obtained as a white powder was prepared according to the procedure D for multi-component reaction from previous product (252 mg, 1.61 mmol, 1.0 eq.) and NH₂Cbz (268 mg, 1.78 mmol, 1.1 eq.) in AcOH (2.0 mL) and AcCl (0.4 mL) followed by addition of the methyl 4-oxobutanoate (90% purity, 208 µL, 1.78 mmol).

¹H NMR (DMSO-d6, 500 MHz) δ (ppm): 11.16 (bs, 1H); 7.49-7.17 (m, 11H); 5.07 (s, 2H); 3.72 (m, 1H); 3.56 (s, 3H); 2.98 (d, 2H, J=15.0 Hz); 2.43-2.30 (m, 2H); 2.05-1.91 (m, 1H); 1.78-1.69 (m, 1H)

Step 3: 4-[benzyl(hydroxy)phosphoryl]-4-{[(benzyloxy)carbonyl]amino}butanoic acid The title compound (304 mg, 60%) obtained as a white powder was prepared according to the procedure F from previous product (522 mg, 1.29 mmol) in a mixture of THF/water (4 mL/1 mL) with presence of LiOH.H₂O (92 mg, 3.86 mmol, 3.0 eq.).

MS (ESI⁺): [M+H]⁺=392.2

¹H NMR (DMSO-d6, 500 MHz) δ (ppm): 11.60 (bs, 2H); 7.47 (d, 1H, J=9.6 Hz); 7.42-7.10 (m, 9H); 5.07 (s, 2H); 3.76-3.69 (m, 1H); 2.98 (d, 2H, J=15.0 Hz); 2.36-2.20 (m, 2H); 2.03-1.97 (m, 1H); 1.73-1.66 (m, 1H)

³¹P NMR (DMSO-d6, 202 MHz) δ (ppm): 43.62

Step 4: 4-amino-4-[benzyl(hydroxy)phosphoryl] butanoic acid

The title compound (125 mg, 62%) obtained as a white powder was prepared according to the procedure H for hydrogenolysis from previous product (304 mg, 0.78 mmol) in a mixture EtOH/AcOH 9/1 (14 mL/1.5 mL).

Estimated purity: >95% (based on LCMS and NMR)

MS (ESI⁺): [(M−H₂O)+H]⁺=240.1; [M+H]⁺=258.1; [(M×2)+H]⁺=512.2; [(M×3)+H]⁺=772.4

¹H NMR (D20, 500 MHz) δ (ppm): 7.44-7.34 (m, 5H); 3.22 (td, 1H, J=8.5 and 5.0 Hz); 3.08 (dd, 2H, J=16.5 and 3.0 Hz); 2.57-2.42 (m, 2H); 2.11-2.04 (m, 1H); 1.94-1.85 (m, 1H)

³¹P NMR (D20, 202 MHz) δ (ppm): 30.41

Example 2: 4-amino-4-{hydroxy[(2-methylphenyl)methyl]phosphoryl}butanoic acid

Step 1: [(2-methylphenyl)methyl]phosphinic acid

The title compound (354 mg, 38%) obtained as a solid was prepared according to the procedure A from 1-(bromomethyl)-2-methylbenzene (1.0 g, 5.40 mmol, 1.0 eq.) in DCM (7.9 mL) and freshly prepared BTSP (27.02 mmol, 5.0 eq.).

MS (ESI⁺): [M+H]⁺=171.1

¹H NMR (CDCl₃, 500 MHz) δ (ppm): 8.91 (br s, 1H); 7.18-7.12 (m, 4H); 6.90 (dt, 1H, J=558.5 and 2.0 Hz); 3.11 (dd, 2H, J=18.5 and 2.0 Hz); 2.32 (s, 3H)

³¹P NMR (CDCl₃, 202 MHz) δ (ppm): 36.60

Step 2: [4-(benzyloxy)-1-{[(benzyloxy)carbonyl]amino}-4-oxobutyl][(2-methylphenyl) methyl]phosphinic acid The title compound (534 mg, 52%) obtained as a white powder was prepared according to the procedure D for multi-component reaction from previous product (354 mg, 2.08 mmol, 1.0 eq.) and NH₂Cbz (320 mg, 2.29 mmol, 1.1 eq.) in AcOH (2.0 mL) and AcCl (0.3 mL) followed by addition of the benzyl 4-oxobutanoate (443 mg, 2.50 mmol, 1.2 eq).

MS (ESI⁺): [M+H]⁺=496.1

¹H NMR (MeOD, 500 MHz) δ (ppm): 7.38-7.06 (m, 14H); 5.16-5.05 (m, 4H); 4.04-3.99 (m, 1H); 3.19-3.08 (m, 2H); 2.57-2.45 (m, 2H); 2.32 (s, 3H); 2.27-2.19 (m, 1H), 1.93-1.84 (m, 1H)

³¹P NMR (MeOD, 202 MHz) δ (ppm): 45.10

Step 3: 4-amino-4-{hydroxy[(2-methylphenyl)methyl]phosphoryl}butanoic acid

The title compound (92 mg, 56%) obtained as a white solid was prepared according to the procedure H for hydrogenolysis from previous product (300 mg, 0.60 mmol, 1.0 eq.) in a mixture EtOH/AcOH (1:1, 18 mL).

Estimated purity: >95% (estimated by LCMS and NMR)

MS (ESI⁺): [(M−H₂O)+H]⁺=254.1; [M+H]⁺=272.2; [(M×2)+H]⁺=543.2; [(M×3)+H]⁺=814.5

¹H NMR (MeOD, 500 MHz) δ (ppm): 7.31-7.28 (m, 1H); 7.15-7.05 (m, 3H); 3.17-3.13 (m, 1H); 3.07 (dd, 2H, J=16.0 and 1.5 Hz); 2.55 (t, 2H, J=7.5 Hz); 2.42 (s, 3H); 2.26-2.17 (m, 1H), 2.00-1.90 (m, 1H)

³¹P NMR (MeOD, 202 MHz) δ (ppm): 27.25

Example 3: 4-amino-4-{hydroxy[(3-methylphenyl)methyl]phosphoryl}butanoic acid

Step 1: [(3-methylphenyl)methyl]phosphinic acid

The title compound (518 mg, 56%, 80-85% purity) obtained as a solid was prepared according to the procedure A from 1-(bromomethyl)-3-methylbenzene (1.0 g, 5.40 mmol, 1.0 eq.) in DCM (7.9 mL) and freshly prepared BTSP (27.02 mmol, 5.0 eq.).

MS (ESI): [M+H]$^+$=171.1

$^1$H NMR (CDCl$_3$, 500 MHz) δ (ppm): 8.24 (br s, 1H); 7.22-7.17 (m, 1H); 7.08-7.01 (m, 3H); 6.94 (dt, 1H, J=560 and 2.0 Hz); 3.07 (dd, 2H, J=18.5 and 2.0 Hz); 2.32 (s, 3H)

$^{31}$P NMR (CDCl$_3$, 202 MHz) δ (ppm): 32.68

Step 2: [4-(benzyloxy)-1-{[(benzyloxy)carbonyl] amino}-4-oxobutyl][(3-methylphenyl) methyl]phosphinic acid The title compound (899 mg, 600%) obtained as a white powder was prepared according to the procedure D for multi-component reaction from previous product (518 mg, 3.04 mmol, 1.0 eq.) and NH$_2$Cbz (506 mg, 3.35 mmol, 1.1 eq.) in AcOH (3.0 mL) and AcCl (0.3 mL) followed by addition of the benzyl 4-oxobutanoate (702 mg, 3.65 mmol, 1.2 eq).

MS (ESI$^+$): [M+H]$^+$=496.1

$^1$H NMR (MeOD, 500 MHz) δ (ppm): 7.40-7.27 (m, 10H); 7.16 (t, 1H, J=7.5 Hz); 7.10 (br s, 1H); 7.05 (t, 2H, J=7.5 Hz); 5.12 (s, 2H); 5.11 (s, 2H); 4.00-3.95 (m, 1H); 3.10 (dd, 2H, J=16.0 and 6.0 Hz); 2.55-2.43 (m, 2H); 2.31 (s, 3H); 2.25-2.17 (m, 1H), 1.93-1.83 (m, 1H)

$^{31}$P NMR (MeOD, 202 MHz) δ (ppm): 45.01

Step 3: 4-amino-4-{hydroxy[(3-methylphenyl) methyl]phosphoryl}butanoic acid

The title compound (165 mg, 75%) obtained as a white solid was prepared according to the procedure H for hydrogenolysis from previous product (400 mg, 0.81 mmol, 1.0 eq.) in a mixture EtOH/AcOH (1:1, 22 mL).

Estimated purity: >95% (based on LCMS and NMR)

MS (ESI$^+$): [(M−H$_2$O)+H]$^+$=254.1; [M+H]$^+$=272.2; [(M×2)+H]$^+$=543.2; [(M×3)+H]$^+$=814.5

$^1$H NMR (MeOD, 500 MHz) δ (ppm): 7.18-7.11 (m, 3H); 7.00 (d, 1H, J=7.0 Hz); 3.08-3.04 (m, 1H); 3.00 (d, 2H, J=16.5 Hz); 2.49 (t, 2H, J=7.5 Hz); 2.31 (s, 3H); 2.19-2.10 (m, 1H), 1.95-1.85 (m, 1H)

$^{31}$P NMR (MeOD, 202 MHz) δ (ppm): 27.33

Example 4: 4-amino-4-{hydroxy[(4-methylphenyl) methyl]phosphoryl}butanoic acid

Step 1: [(4-methylphenyl)methyl]phosphinic acid

The title compound (574 mg, 62%) obtained as a light pink solid was prepared according to the procedure A from 1-(bromomethyl)-4-methylbenzene (1.0 g, 5.40 mmol, 1.0 eq.) in DCM (7.9 mL) and freshly prepared BTSP (27.02 mmol, 5.0 eq.).

MS (ESI$^+$): [M+H]$^+$=171.1

$^1$H NMR (CDCl$_3$, 500 MHz) δ (ppm): 9.51 (br s, 1H); 7.14-7.09 (m, 4H); 6.93 (dt, 1H, J=559.0 and 2.0 Hz); 3.07 (dd, 2H, J=18.5 and 2.0 Hz); 2.31 (s, 3H)

$^{31}$P NMR (CDCl$_3$, 202 MHz) δ (ppm): 36.50

Step 2: [4-(benzyloxy)-1-{[(benzyloxy)carbonyl] amino}-4-oxobutyl][(4-methylphenyl) methyl]phosphinic acid The title compound (940 mg, 56%) obtained as a white powder was prepared according to the procedure D for multi-component reaction from previous product (574 mg, 3.37 mmol, 1.0 eq.) and NH$_2$Cbz (561 mg, 3.71 mmol, 1.1 eq.) in AcOH (3.0 mL) and AcCl (0.3 mL) followed by addition of the benzyl 4-oxobutanoate (778 mg, 4.05 mmol, 1.2 eq).

MS (ESI$^+$): [M+H]$^+$=496.1

$^1$H NMR (MeOD, 500 MHz) δ (ppm): 7.38-7.26 (m, 10H); 7.14-7.06 (m, 4H); 5.10-5.09 (m, 4H); 3.97-3.92 (m, 1H); 3.06 (dd, 2H, J=15.5 and 5.0 Hz); 2.52-2.40 (m, 2H); 2.28 (s, 3H); 2.23-2.15 (m, 1H), 1.90-1.81 (m, 1H)

$^{31}$P NMR (MeOD, 202 MHz) δ (ppm): 44.83

Step 3: 4-amino-4-{hydroxy[(4-methylphenyl) methyl]phosphoryl}butanoic acid

The title compound (191 mg, 87%) obtained as a white solid was prepared according to the procedure H for hydrogenolysis from previous product (400 mg, 0.81 mmol, 1.0 eq.) in a mixture EtOH/AcOH (1:1, 21 mL).

Estimated purity: >95% (based on LCMS and NMR)

MS (ESI$^+$): [(M−H$_2$O)+H]$^+$=254.1; [M+H]$^+$=272.2; [(M×2)+H]$^+$=543.2; [(M×3)+H]$^+$=814.5

$^1$H NMR (MeOD, 500 MHz) δ (ppm): 7.22 (dd, 2H, J=8.0 and 2.0 Hz); 7.09 (d, 2H, J=7.5 Hz); 3.07-3.02 (m, 1H); 2.99 (d, 2H, J=16.0 Hz); 2.48 (t, 2H, J=7.5 Hz); 2.29 (s, 3H); 2.17-2.09 (m, 1H); 1.92-1.85 (m, 1H)

$^{31}$P NMR (MeOD, 202 MHz) δ (ppm): 27.44

Example 5: 4-amino-4-({[3,5-bis(trifluoromethyl) phenyl]methyl}(hydroxy)phosphoryl) butanoic acid Step 1: {[3,5-bis(trifluoromethyl)phenyl] methyl}phosphinic acid The title compound (160 mg, 17%) obtained as a white solid was prepared according to the procedure A from 1-(bromomethyl)-3,5-bis(trifluoromethyl)benzene (1 g, 3.26 mmol, 1.0 eq.) in DCM (5 mL) and freshly prepared BTSP (16.28 mmol, 5.0 eq.).

MS (ESI$^+$): [M+H]$^+$=293.0

$^1$H NMR (CDCl$_3$, 500 MHz) δ (ppm): 7.81 (s, 1H); 7.72-7.69 (m, 2H); 7.04 (d, 1H, J=569.0 Hz); 6.51 (br s, 1H); 3.25 (d, 2H, J=18.0 Hz)

$^{31}$P NMR (CDCl$_3$, 202 MHz) δ (ppm): 31.49

Step 2: [4-(benzyloxy)-1-{[(benzyloxy)carbonyl] amino}-4-oxobutyl]({[3,5-bis(trifluoro methyl)phenyl]methyl})phosphinic acid The title compound (149 mg, 44%) obtained as a white solid was prepared according to the procedure D for multi-component reaction from previous product (160 mg, 0.55 mmol, 1.0 eq.) and NH$_2$Cbz (91 mg, 0.60 mmol, 1.1 eq.) in AcOH (0.8 mL) and AcCl (0.1 mL) followed by addition of the benzyl 4-oxobutanoate (131 mg, 0.68 mmol, 1.2 eq).

$^1$H NMR (MeOD, 500 MHz) δ (ppm): 7.89-7.82 (m, 3H); 7.37-7.26 (m, 10H); 5.13-5.06 (m, 4H); 4.00-3.98 (m, 1H); 3.49 (dd, 2H, J=14.0 and 7.0 Hz); 2.53-2.44 (m, 2H); 2.27-2.19 (m, 1H); 1.93-1.83 (m, 1H)

Step 3: 4-amino-4-({[3,5-bis(trifluoromethyl)phenyl]methyl}(hydroxy)phosphoryl)butanoic acid The title compound (53 mg, 56%) obtained as a white powder was prepared according to the procedure H for hydrogenolysis from previous product (149 mg, 0.24 mmol, 1.0 eq.) in a mixture EtOH/AcOH (9:1, 4.3 mL).
Estimated purity: >95% (based on LCMS)
MS (ESI$^+$): [(M−H$_2$O)+H]$^+$=376.0; [M+H]$^+$=394.0; [(M× 2)+H]$^+$=787.2
$^1$H NMR (MeOD, 500 MHz) δ (ppm): 7.96 (s, 2H); 7.78 (s, 1H); 3.23-3.12 (m, 3H); 2.58 (t, 2H, J=7.5 Hz); 2.27-2.16 (m, 11H); 1.98-1.90 (m, 1H)
$^{31}$P NMR (MeOD, 202 MHz) δ (ppm): 24.89

Example 6: 4-amino-4-[({[1,1'-biphenyl]-2-yl}methyl)(hydroxy)phosphoryl]butanoic acid Step 1: ({[1,1'-biphenyl]-2-yl}methyl)phosphinic acid The title compound (498 mg, 53%) obtained as a white solid was prepared according to the procedure A from 2-(bromomethyl)-1,1'-biphenyl (1.0 g, 4.05 mmol, 1.0 eq.) in DCM (8.2 mL) and freshly prepared BTSP (20.23 mmol, 5.0 eq.).
MS (ESI$^+$): [M+H]$^+$=233.0
$^1$H NMR (CDCl$_3$, 500 MHz) δ (ppm): 7.41-7.25 (m, 9.5H); 6.28 (t, 0.5H, J=2.0 Hz); 4.16 (br s, 1H); 3.13 (dd, 2H, J=19.0 and 2.0 Hz)

Step 2: [4-(benzyloxy)-1-{[(benzyloxy)carbonyl]amino}-4-oxobutyl]({[1,1'-biphenyl]-2-yl}methyl)phosphinic acid The title compound (1.0 g, 85%) obtained as a white gum was prepared according to the procedure D for multi-component reaction from previous product (490 mg, 2.11 mmol, 1.0 eq.) and NH$_2$Cbz (351 mg, 2.32 mmol, 1.1 eq.) in AcOH (2.2 mL) and AcCl (0.4 mL) followed by addition of the benzyl 4-oxobutanoate (487 mg, 2.53 mmol, 1.2 eq).
$^1$H NMR (MeOD, 500 MHz) δ (ppm): 7.57-7.20 (m, 19H); 5.17-4.94 (m, 4H); 3.89-3.84 (m, 1H); 3.14 (dt, 2H, J=63.5 and 15.0 Hz); 2.47-2.35 (m, 2H); 2.15-2.05 (m, 1H); 1.83-1.70 (m, 1H)
$^{31}$P NMR (MeOD, 202 MHz) δ (ppm): 44.42

Step 3: 4-amino-4-[({[1,1'-biphenyl]-2-yl}methyl)(hydroxy)phosphoryl]butanoic acid The title compound (28 mg, 19%) obtained as a white solid was prepared according to the procedure H for hydrogenolysis from previous product (250 mg, 0.45 mmol, 1.0 eq.) in a mixture EtOH/AcOH (9:1, 8.0 mL).
Estimated purity: >95% (based on LCMS)
MS (ESI$^+$): [(M−H$_2$O)+H]$^+$=316.0; [M+H]$^+$=334.0; [(M× 2)+H]$^+$=667.3
$^1$H NMR (MeOD, 500 MHz) δ (ppm): 7.66 (d, 1H, J=8.0 Hz); 7.48-7.41 (m, 4H); 7.36-7.20 (m, 4H); 3.63-3.00 (m, 2H); 2.84-2.80 (m, 1H); 2.35 (td, 2H, J=7.5 and 2.5 Hz); 1.89-1.73 (m, 2H)
$^{31}$P NMR (MeOD, 202 MHz) δ (ppm): 29.11

Example 7: 4-amino-4-[hydroxy({[3-(trifluoromethoxy)phenyl]methyl})phosphoryl]butanoic acid Step 1: {[3-(trifluoromethoxy)phenyl]methyl}phosphinic acid The title compound (460 mg, 49%) obtained as a pale yellow oil was prepared according to the procedure A from 1-(bromomethyl)-3-(trifluoromethoxy)benzene (1.0 g, 3.92 mmol, 1.0 eq.) in DCM (7.9 mL) and freshly prepared BTSP (19.6 mmol, 5.0 eq.).
$^1$H NMR (CDCl$_3$, 500 MHz) δ (ppm): 8.05 (br s, 11H); 7.35 (t, 11H, J=8.0 Hz); 7.18-7.11 (m, 3H); 7.00 (d, 1H, J=569.0 Hz); 3.14 (d, 2H, J=18.5 Hz)
$^{31}$P NMR (CDCl$_3$, 202 MHz) δ (ppm): 34.25

Step 2: [4-(benzyloxy)-1-{[(benzyloxy)carbonyl]amino}-4-oxobutyl]({[3-(trifluoro methoxy)phenyl]methyl})phosphinic acid The title compound (741 mg, 68%) obtained as a white solid was prepared according to the procedure D for multi-component reaction from previous product (460 mg, 1.92 mmol, 1.0 eq.) and NH$_2$Cbz (318 mg, 2.11 mmol, 1.1 eq.) in AcOH (2.6 mL) and AcCl (0.9 mL) followed by addition of the benzyl 4-oxobutanoate (441 mg, 2.30 mmol, 1.2 eq).
MS (ESI$^+$): [M+H]$^+$=566.2
$^1$H NMR (MeOD, 500 MHz) δ (ppm): 7.38-7.12 (m, 14H); 5.10 (s, 2H); 5.09 (s, 2H) 3.99-3.94 (m, 11H); 3.17-3.13 (m, 2H); 2.53-2.42 (m, 2H); 2.26-2.17 (m, 1H); 1.91-1.82 (m, 1H)
$^{31}$P NMR (MeOD, 202 MHz) δ (ppm): 43.62

Step 3: 4-amino-4-[hydroxy({[3-(trifluoromethoxy)phenyl]methyl})phosphoryl]butanoic acid The title compound (23 mg, 19%) obtained as a white powder was prepared according to the procedure H for hydrogenolysis from previous product (200 mg, 0.35 mmol, 1.0 eq.) in a mixture EtOH/AcOH (1:1, 12 mL).
Estimated purity: >95% (based on LCMS and NMR)
MS (ESI$^+$): [(M−H$_2$O)+H]$^+$=324.0; [M+H]$^+$=342.0; [(M× 2)+H]$^+$=683.1
$^1$H NMR (MeOD, 500 MHz) δ (ppm): 7.38-7.30 (m, 3H); 7.11-7.09 (m, 1H); 3.12-3.02 (m, 3H); 2.54 (t, 2H, J=7.5 Hz); 2.23-2.14 (m, 1H); 1.99-1.87 (m, 1H) 20 $^{31}$P NMR (MeOD, 202 MHz) δ (ppm): 25.90

Example 8: 4-amino-4-[hydroxy({[4-(trifluoromethoxy)phenyl]methyl})phosphoryl]butanoic acid Step 1: {[4-(trifluoromethoxy)phenyl]methyl}phosphinic acid The title compound (750 mg, 80%) obtained as an oil was prepared according to the procedure A from 1-(bromomethyl)-4-(trifluoromethoxy)benzene (1.0 g, 3.92 mmol, 1.0 eq.) in DCM (7.9 mL) and freshly prepared BTSP (19.6 mmol, 5.0 eq.).
$^1$H NMR (CDCl$_3$, 500 MHz) δ (ppm): 7.97 (br s, 1H); 7.27-7.24 (m, 2H); 7.18 (d, 2H, J=8.5 Hz); 6.98 (dt, 1H, J=562 and 1.5 Hz); 3.12 (dd, 2H, J=18.0 and 1.5 Hz)
$^{31}$P NMR (CDCl$_3$, 202 MHz) δ (ppm): 35.03

Step 2: [4-(benzyloxy)-1-{[(benzyloxy)carbonyl]amino}-4-oxobutyl]({[4-(trifluoro methoxy)phenyl]methyl})phosphinic acid The title compound (498 mg, 70%) obtained as a white solid was prepared according to the procedure D for multi-component reaction from previous product (300 mg, 1.25 mmol, 1.0 eq.) and NH$_2$Cbz (207 mg, 1.37 mmol, 1.1 eq.) in AcOH (1.4 mL) and AcCl (0.245 mL) followed by addition of the benzyl 4-oxobutanoate (288 mg, 1.50 mmol, 1.2 eq). ¹H NMR (MeOD, 500 MHz) δ (ppm): 7.38-7.27 (m, 12H); 7.16 (d, 2H, J=8.5 Hz); 5.10 (s, 2H); 5.09 (s, 2H); 4.00-3.95 (m, 1H); 3.16 (dd, 2H, J=15.0 and 3.0 Hz); 2.54-2.42 (m, 2H); 2.24-2.19 (m, 1H); 1.90-1.85 (m, 1H)

Step 3: 4-amino-4-[hydroxy({[4-(trifluoromethoxy)phenyl]methyl})phosphoryl]butanoic acid The title compound (96 mg, 64%) obtained as a white powder was prepared according to the procedure H for hydrogenolysis from previous product (250 mg, 0.44 mmol, 1.0 eq.) in a mixture EtOH/AcOH (9:1, 8.0 mL).

Estimated purity: >95% (based on LCMS)

MS (ESI⁺): [(M−H₂O)+H]⁺=324.0; [M+H]⁺=342.0; [(M× 2)+H]⁺=683.2

¹H NMR (MeOD, 500 MHz) δ (ppm): 7.44-7.41 (dd, 2H, J=9.0 and 2.0 Hz); 7.19-7.17 (m, 2H); 3.12-3.03 (m, 3H); 2.55 (t, 2H, J=7.5 Hz); 2.22-2.16 (m, 1H); 1.99-1.90 (m, 1H)

³¹P NMR (MeOD, 202 MHz) δ (ppm): 26.32

Example 9: 4-amino-4-{hydroxy[(4-methanesulfonylphenyl)methyl]phosphoryl}butanoic acid

Step 1: [(4-methanesulfonylphenyl)methyl]phosphinic acid

The title compound (218 mg, 23%, 80% purity) obtained as a pale yellow solid was prepared according to the procedure A from 1-(bromomethyl)-4-(methylsulfonyl)benzene (1.0 g, 4.01 mmol, 1.0 eq.) in DCM (5.1 mL) and freshly prepared BTSP (20.07 mmol, 5.0 eq.).

MS (ESI⁺): [M+H]⁺=234.9

¹H NMR (MeOD, 500 MHz) δ (ppm): 7.94-7.92 (dd, 2H, J=8.5 and 1.0 Hz); 7.57-7.55 (dd, 2H, J=8.5 and 2.5 Hz); 7.06 (dt, 1H, J=555.0 and 1.5 Hz); 3.36-3.32 (m, 2H); 3.11 (s, 3H)

³¹P NMR (MeOD, 202 MHz) δ (ppm): 29.75

Step 2: [4-(benzyloxy)-1-{[(benzyloxy)carbonyl]amino}-4-oxobutyl][(4-methanesulfonyl phenyl)methyl]phosphinic acid The title compound was prepared according to the procedure D for multi-component reaction from previous product (218 mg, 0.93 mmol, 1.0 eq.) and NH₂Cbz (155 mg, 1.02 mmol, 1.1 eq.) in AcOH (1.0 mL) and AcCl (0.2 mL) followed by addition of the benzyl 4-oxobutanoate (214 mg, 1.12 mmol, 1.2 eq). The reaction mixture was stirred for 4 h (instead of 18 h) at room temperature to afford the expected product (450 mg, 87%) as a yellow oil.

MS (ESI⁺): [M+H]⁺=560.2

¹H NMR (MeOD, 500 MHz) δ (ppm): 7.84 (d, 2H, J=3.0 Hz); 7.51 (dd, 2H, J=8.5 and 2.5 Hz); 7.39-7.28 (m, 10H); 5.11 (s, 2H); 5.09 (s, 2H); 3.99-3.94 (m, 1H); 3.24 (dd, 2H, J=16.0 and 4.0 Hz); 3.07 (s, 3H), 2.54-2.39 (m, 2H); 2.25-2.17 (m, 1H); 1.91-1.82 (m, 1H)

³¹P NMR (MeOD, 202 MHz) δ (ppm): 43.19

Step 3: 4-amino-4-{hydroxy[(4-methanesulfonylphenyl)methyl]phosphoryl}butanoic acid The title compound (19 mg, 21%) obtained as a white solid was prepared according to the procedure H for hydrogenolysis from previous product (150 mg, 0.27 mmol, 1.0 eq.) in a mixture EtOH/AcOH (9:1, 4.8 mL).

Estimated purity: >95% (based on NMR)

MS (ESI⁺): [M+H]⁺=336.1

¹H NMR (DMSO-d6, 500 MHz) δ (ppm): 7.77 (d, 2H, J=8.0 Hz); 7.49 (dd, 2H, J=8.5 and 1.5 Hz); 3.16 (s, 3H); 3.01-2.98 (m, 2H); 2.78-2.74 (m, 11H); 2.39-2.33 (m, 1H from CH₂, the other H was under the DMSO signal); 1.97-1.88 (m, 1H), 1.85-1.75 (m, 1H)

³¹P NMR (DMSO-d6, 202 MHz) δ (ppm): 21.08

Example 10: 4-amino-4-{hydroxy[(2-methoxyphenyl)methyl]phosphoryl}butanoic acid

Step 1: 1-(bromomethyl)-2-methoxybenzene

Commercially available (2-methoxyphenyl) methanol (2.0 g, 14.5 mmol, 1.0 eq.) and carbon tetrabromide (7.68 g, 23.16 mmol, 1.6 eq.) were diluted in CH₂Cl₂ (70 mL). The solution was cooled at −5° C. (ice/salt bath) and triphenylphosphine (6.07 g, 23.16 mmol, 1.6 eq) was added in portions. When addition was completed, the yellow reaction media was stirred at room temperature overnight. The mixture was concentrated and purified by column chromatography to afford the title compound (2.13 g, 73%) as a light yellow oil.

¹H NMR (CDCl₃, 500 MHz) δ (ppm): 7.34-7.26 (m, 2H); 6.94-6.88 (m, 2H); 4.58 (s, 2H); 3.90 (s, 3H)

Step 2: [(2-methoxyphenyl)methyl]phosphinic acid

The title compound (1.54 g, 59%) obtained as a colorless oil was prepared according to the procedure A from 1-(bromomethyl)-2-methoxybenzene (2.1 g, 10.44 mmol, 1.0 eq.) in DCM (16.0 mL) and freshly prepared BTSP (104.4 mmol, 10 eq.).

MS (ESI⁺): [M+H]⁺=187.1

¹H NMR (CDCl₃, 500 MHz) δ (ppm): 9.18 (br s, 1H); 7.29-7.22 (m, 2H); 7.05 (dt, 1H, J=570.5 and 2.0 Hz); 6.96-6.93 (m, 1H); 6.89 (d, 1H, J=8.5 Hz); 3.85 (s, 3H); 3.24 (dd, 2H, J=19.5 and 2.0 Hz)

³¹P NMR (CDCl₃, 202 MHz) δ (ppm): 35.52

Step 3: [4-(benzyloxy)-1-{[(benzyloxy)carbonyl]amino}-4-oxobutyl][(2-methoxyphenyl) methyl]phosphinic acid The title compound (2.2 g, quantitative yield) obtained as a yellow solid was prepared according to the procedure D for multi-component reaction from previous product (800 mg, 4.30 mmol, 1.0 eq.) and NH₂Cbz (715 mg, 4.73 mmol, 1.1 eq.) in AcOH (7.8 mL) and AcCl (1.0 mL) followed by addition of the benzyl 4-oxobutanoate (991 mg, 5.16 mmol, 1.2 eq.).

MS (ESI⁺): [M+H]⁺=512.2

¹H NMR (MeOD, 500 MHz) δ (ppm): 7.36-7.18 (m, 12H); 6.94-6.84 (m, 2H); 5.17 (s, 4H); 4.01-3.96 (m, 1H); 3.79 (s, 3H); 3.27-3.15 (m, 2H); 2.51-2.36 (m, 2H); 2.23-2.14 (m, 1H); 1.87-1.77 (m, 11H)

³¹P NMR (MeOD, 202 MHz) δ (ppm): 45.42

Step 4: 4-amino-4-{hydroxy[(2-methoxyphenyl) methyl]phosphoryl}butanoic acid A pure fraction of the title compound (39 mg, 5%) obtained as a white solid was prepared according to the procedure H for hydrogenolysis from previous product (1.29 g, 2.52 mmol, 1.0 eq.) in a mixture of EtOH/AcOH (9:1, 50 mL).

Estimated purity: 93% (based on LCMS and NMR)

MS (ESI+): [(M−H$_2$O)+H]+=270.2; [M+H]+=288.2; [(M×2)+H]+=575.3, [(M×3)+H]+=862.6

$^1$H NMR (MeOD, 500 MHz) δ (ppm): 7.34 (dt, 1H, J=7.5 and 2.5 Hz); 7.19 (tt, 1H, J=8.0 and 2.0 Hz); 6.95 (d, 1H, J=8.0 Hz); 6.90 (tt, 1H, J=7.0 and 1.0 Hz); 3.86 (s, 3H); 3.19-3.12 (m, 1H); 3.04-2.98 (m, 2H); 2.46 (t, 2H, J=7.5 Hz); 2.20-2.11 (m, 1H); 1.96-1.85 (m, 1H)

$^{31}$P NMR (MeOD, 202 MHz) δ (ppm): 28.56

Example 11: 4-amino-4-{hydroxy[(3-methoxyphenyl)methyl]phosphoryl}butanoic acid Step 1: [(3-methoxyphenyl)methyl]phosphinic acid The title compound (393 mg, 42%, 70-80% purity) obtained as brown oil was prepared according to the procedure A from 1-(bromomethyl)-3-methoxybenzene (1.0 g, 4.97 mmol, 1.0 eq.) in DCM (10.6 mL) and freshly prepared BTSP (49.74 mmol, 10 eq.).

$^1$H NMR (CDCl$_3$, 500 MHz) δ (ppm): 7.23 (t, 1H, J=7.5 Hz); 6.96 (dt, 1H, J=562.0 and 2.0 Hz); 6.82-6.77 (m, 3H); 4.11 (br s, 1H); 3.78 (s, 3H); 3.08 (dd, 2H, J=18.5 and 2.0 Hz)

$^{31}$P NMR (CDCl$_3$, 202 MHz) δ (ppm): 33.26

Step 2: [4-(benzyloxy)-1-{[(benzyloxy)carbonyl]amino}-4-oxobutyl][(3-methoxyphenyl) methyl] phosphinic acid The title compound (930 mg, 66%) obtained as a white powder was prepared according to the procedure D for multi-component reaction from previous product (638 mg, 2.74 mmol, 1.0 eq.) and NH$_2$Cbz (455 mg, 3.02 mmol, 1.1 eq.) in AcOH (3.8 mL) and AcCl (0.3 mL) followed by addition of the benzyl 4-oxobutanoate (632 mg, 3.29 mmol, 1.2 eq).

MS (ESI+): [M+H]+=512.2

$^1$H NMR (MeOD, 500 MHz) δ (ppm): 7.37-7.25 (m, 10H); 7.16 (t, 1H, J=7.5 Hz); 6.86-6.76 (m, 3H); 5.094 (s, 2H); 5.088 (s, 2H); 4.00-3.95 (m, 1H); 3.76 (s, 3H); 3.15-3.04 (m, 2H); 2.53-2.41 (m, 2H); 2.24-2.15 (m, 1H); 1.91-1.81 (m, 1H)

$^{31}$P NMR (MeOD, 202 MHz) δ (ppm): 44.60

Step 3: 4-amino-4-{hydroxy[(3-methoxyphenyl)methyl]phosphoryl}butanoic acid

The title compound (135 mg, 58%) obtained as a white solid was prepared according to the procedure H for hydrogenolysis from previous product (414 mg, 0.81 mmol, 1.0 eq.) in a mixture EtOH/AcOH (1:1, 16 mL).

Estimated purity: >95% (based on LCMS and NMR)

MS (ESI+): [(M−H$_2$O)+H]+=270.2; [M+H]+=288.2; [(M×2)+H]+=575.3, [(M×3)+H]+=862.6

$^1$H NMR (MeOD, 500 MHz) δ (ppm): 7.17 (t, 1H, J=7.5 Hz); 6.95 (s, 1H); 6.91 (d, 1H, J=7.5 Hz); 6.75 (m, 1H); 3.78 (s, 3H); 3.09-3.05 (m, 1H); 3.01 (d, 2H, J=16.5 Hz); 2.50 (t, 2H, J=7.5 Hz); 2.20-2.11 (m, 1H), 1.95-1.86 (m, 1H)

$^{31}$P NMR (MeOD, 202 MHz) δ (ppm): 27.11

Example 12: 4-amino-4-{hydroxy[(4-methoxyphenyl)methyl]phosphoryl}butanoic acid Step 1: [(4-methoxyphenyl)methyl]phosphinic acid The title compound (399 mg, 43%) obtained as a brown oil was prepared according to the procedure A from 1-(bromomethyl)-4-methoxybenzene (1.0 g, 4.97 mmol, 1.0 eq.) in DCM (10.6 mL) and freshly prepared BTSP (49.74 mmol, 10 eq.).

MS (ESI+): [M+H]+=187.1

$^1$H NMR (CDCl$_3$, 500 MHz) δ (ppm): 7.14 (dd, 2H, J=8.5 and 2.5 Hz); 6.94 (d, 1H, J=557.5 Hz); 6.85 (d, 2H, J=8.5 Hz); 5.93 (br s, 1H); 3.77 (s, 3H); 3.05 (d, 2H, J=18.0 Hz)

$^{31}$P NMR (CDCl$_3$, 202 MHz) δ (ppm): 33.20

Step 2: [4-(benzyloxy)-1-{[(benzyloxy)carbonyl]amino}-4-oxobutyl][(4-methoxyphenyl) methyl] phosphinic acid The title compound (625 mg, 57%) obtained as a white powder was prepared according to the procedure D for multi-component reaction from previous product (399 mg, 2.14 mmol, 1.0 eq.) and NH$_2$Cbz (356 mg, 2.36 mmol, 1.1 eq.) in AcOH (3.5 mL) and AcCl (0.3 mL) followed by addition of the benzyl 4-oxobutanoate (494 mg, 2.57 mmol, 1.2 eq).

MS (ESI+): [M+H]+=512.2

$^1$H NMR (MeOD, 500 MHz) δ (ppm): 7.38-7.26 (m, 10H); 7.16 (dd, 2H, J=8.5 and 2.0 Hz); 6.81 (d, 2H, J=8.5 Hz); 5.09 (br s, 4H); 3.97-3.92 (m, 1H); 3.74 (s, 3H); 3.09-2.99 (m, 2H); 2.52-2.40 (m, 2H), 2.23-2.15 (m, 1H); 1.90-1.81 (m, 1H)

$^{31}$P NMR (MeOD, 202 MHz) δ (ppm): 45.05

Step 3: 4-amino-4-{hydroxy[(4-methoxyphenyl)methyl]phosphoryl}butanoic acid

The title compound (140 mg, 62%) obtained as a white solid was prepared according to the procedure H for hydrogenolysis from previous product (403 mg, 0.79 mmol, 1.0 eq.) in a mixture EtOH/AcOH (1:1, 16 mL).

Estimated purity: 92% (based on LCMS and NMR)

MS (ESI+): [(M−H$_2$O)+H]+=270.2; [M+H]+=288.1; [(M×2)+H]+=575.2, [(M×3)+H]+=862.5

$^1$H NMR (MeOD, 500 MHz) δ (ppm): 7.25 (dd, 2H, J=8.5 and 2.5 Hz); 6.84 (d, 2H, J=10.0 Hz); 3.76 (s, 3H); 3.07-3.02 (m, 1H); 2.96 (dd, 2H, J=16.5 and 2.0 Hz); 2.49 (t, 2H, J=7.5 Hz); 2.18-2.10 (m, 1H), 1.94-1.85 (m, 1H)

$^{31}$P NMR (MeOD, 202 MHz) δ (ppm): 27.61

Example 13: 4-amino-4-{[(3-cyanophenyl)methyl](hydroxy)phosphoryl}butanoic acid Step 1: [(3-cyanophenyl)methyl]phosphinic acid The title compound (487 mg, 26%, 70% purity) obtained as a white solid was prepared according to the procedure A from 3-(bromomethyl)benzonitrile (2.0 g, 10.2 mmol, 1.0 eq.) in DCM (16.2 mL) and freshly prepared BTSP (51.01 mmol, 5.0 eq.).

MS (ESI+): [M+H]+=182.1

$^1$H NMR (CDCl$_3$, 500 MHz) δ (ppm): 7.59-7.43 (m, 4.5H); 6.40 (s, 0.5H); 3.53 (br s, 1H); 3.12 (dd, 2H)

$^{31}$P NMR (CDCl$_3$, 202 MHz) δ (ppm): 33.70

Step 2: [4-(benzyloxy)-1-{[(benzyloxy)carbonyl]amino}-4-oxobutyl][(3-cyanophenyl) methyl]phosphinic acid The title compound (937 mg, 700%) obtained as a yellow oil was prepared according to the procedure D for multi-component reaction from previous product (478 mg, 2.64 mmol, 1.0 eq.) and NH$_2$Cbz (438 mg, 2.90 mmol, 1.1 eq.)

in AcOH (3.0 mL) and AcCl (0.3 mL) followed by addition of the benzyl 4-oxobutanoate (608 mg, 3.17 mmol, 1.2 eq). The crude was directly engaged in the next step.

Step 3: 4-{[(benzyloxy)carbonyl]amino}-4-{[(3-cyanophenyl)methyl](hydroxy)phosphoryl}butanoic acid The title compound (316 mg, 41%), directly engaged in the next step, was prepared according to the procedure F from previous product (937 mg, 1.85 mmol, 1.0 eq.) in a mixture of THF/water (15.8 mL/4.6 mL) with presence of LiOH.H$_2$O (233 mg, 5.55 mmol, 3.0 eq.).

Step 4: 4-amino-4-{[(3-cyanophenyl)methyl](hydroxy)phosphoryl}butanoic acid

The title compound (30 mg, 140%) obtained as a white solid was prepared according to the procedure G from previous product (316 mg, 759 µmol, 1.0 eq.) in TFA/anisole (2.6 mL/527 µL).
Estimated purity: >95% (based on LCMS and NMR)
MS (ESI$^+$): [(M−H$_2$O)+H]$^+$=265.1; [M+H]Y=283.1; [(M×2)+H]$^+$=565.1; [(M×3)+H]$^+$=847.3
$^1$H NMR (MeOD, 500 MHz) δ (ppm): 7.72 (q, 1H, J=2.0 Hz); 7.65 (dq, 1H, J=8.0 and 2.0 Hz); 7.56 (dq, 1H, J=8.0 and 2.0 Hz); 7.46 (t, 1H, J=8.0 Hz); 3.13-3.03 (m, 3H); 2.56 (t, 2H, J=7.5 Hz); 2.24-2.15 (m, 1H), 1.99-1.88 (m, 1H)
$^{31}$P NMR (MeOD, 202 MHz) δ (ppm): 25.56

Example 14: 4-amino-4-{[(4-cyanophenyl)methyl](hydroxy)phosphoryl}butanoic acid

Step 1: [(4-cyanophenyl)methyl]phosphinic acid

The title compound (700 mg, 38%) obtained as a solid was prepared according to the procedure A from 4-(bromomethyl)benzonitrile (2.0 g, 10.2 mmol, 1.0 eq.) in DCM (16.2 mL) and freshly prepared BTSP (51.01 mmol, 5.0 eq.).
MS (ESI$^+$): [M+H]$^+$=182.1
$^1$H NMR (CDCl$_3$, 500 MHz) δ (ppm): 7.64-7.62 (dd, 2H, J=8.5 and 1.0 Hz); 7.36-7.34 (m, 2H); 6.99 (dt, 1H, J=549.0 and 1.5 Hz); 4.18 (br s, 1H); 3.18 (dd, 2H, J=18.5 and 1.5 Hz)
$^{31}$P NMR (CDCl$_3$, 202 MHz) S (ppm): 33.82

Step 2: [4-(benzyloxy)-1-{[(benzyloxy)carbonyl]amino}-4-oxobutyl][(4-cyanophenyl) methyl]phosphinic acid The title compound (930 mg, 66%) obtained as a light yellow powder was prepared according to the procedure D for multi-component reaction from previous product (500 mg, 2.76 mmol, 1.0 eq.) and NH$_2$Cbz (459 mg, 3.04 mmol, 1.1 eq.) in AcOH (3.8 mL) and AcCl (0.3 mL) followed by addition of the benzyl 4-oxobutanoate (459 mg, 3.31 mmol, 1.2 eq).
MS (ESI$^+$): [M+H]$^+$=507.1
$^1$H NMR (MeOD, 500 MHz) δ (ppm): 7.67-7.26 (m, 14H); 5.09 (s, 4H); 3.99-3.94 (m, 1H); 3.26-3.15 (m, 2H); 2.54-2.39 (m, 2H); 2.25-2.16 (m, 1H), 1.91-1.82 (m, 1H)
$^{31}$P NMR (MeOD, 202 MHz) δ (ppm): 43.35

Step 3: 4-{[(benzyloxy)carbonyl]amino}-4-{[(4-cyanophenyl)methyl](hydroxy)phosphoryl}butanoic acid The title compound (343 mg, 83%) was prepared according to the procedure F from previous product (500 mg, 0.95 mmol, 1.0 eq.) in a mixture of THF/water (9.5 mL/2.4 mL) with presence of LiOH.H$_2$O (120 mg, 2.85 mmol, 3.0 eq.).
MS (ESI$^+$): [M+H]$^+$=417.0
$^1$H NMR (MeOD, 500 MHz) δ (ppm): 7.67-7.28 (m, 9H); 5.15-5.05 (m, 2H); 3.97-3.91 (m, 1H); 3.26-3.16 (m, 2H); 2.47-2.33 (m, 2H); 2.22-2.14 (m, 1H), 1.89-1.79 (m, 1H)
$^{31}$P NMR (MeOD, 202 MHz) δ (ppm): 43.04

Step 4: 4-amino-4-{[(4-cyanophenyl)methyl](hydroxy)phosphoryl}butanoic acid

The title compound (84 mg, 36%) obtained as a white solid was prepared according to the procedure G from previous product (343 mg, 824 µmol, 1.0 eq.) in TFA/anisole (3.8 mL/834 µL).
Estimated purity: >95% (based on LCMS and NMR)
MS (ESI$^+$): [(M−H$_2$O)+H]$^+$=265.1; [M+H]$^+$=283.1; [(M×2)+H]$^+$=565.1; [(M×3)+H]$^+$=847.3
$^1$H NMR (MeOD, 500 MHz) δ (ppm): 7.63 (d, 2H, J=7.5 Hz); 7.51 (d, 2H, J=7.5 Hz); 3.14-3.10 (m, 3H); 2.55 (t, 2H, J=6.5 Hz); 2.22-2.16 (m, 1H), 1.96-1.89 (m, 1H)
$^{31}$P NMR (MeOD, 202 MHz) δ (ppm): 25.36

Example 15: 4-amino-4-{hydroxy[(naphthalen-1-yl)methyl]phosphoryl}butanoic acid

Step 1: [(naphthalen-1-yl)methyl]phosphinic acid

The title compound (1.4 g, 75%) obtained as a white solid was prepared according to the procedure A from 1-(bromomethyl)naphthalene (2.0 g, 9.05 mmol, 1.0 eq.) in DCM (29.5 mL) and freshly prepared BTSP (45.23 mmol, 5.0 eq.).
MS (ESI$^+$): [M+H]$^+$=207.1
$^1$H NMR (CDCl$_3$, 500 MHz) δ (ppm): 7.93 (d, 1H, J=10.0 Hz); 7.84 (dd, 1H, J=5.0 Hz and 1.6 Hz); 7.77-7.75 (m, 1H); 7.54-7.44 (m, 2.5H); 7.40 (pseudo t, 1H, J=7.5 Hz); 7.35-7.33 (m, 1H); 6.77 (br s, 1H); 6.41 (s, 0.5H); 3.51 (d, 2H, J=20.0 Hz)
$^{31}$P NMR (CDCl$_3$, 202 MHz) δ (ppm): 35.44

Step 2: [4-(benzyloxy)-1-{[(benzyloxy)carbonyl]amino}-4-oxobutyl][(naphthalen-1-yl) methyl]phosphinic acid The title compound (1.07 g, 59%) obtained as a white powder was prepared according to the procedure D for multi-component reaction from previous product (700 mg, 3.40 mmol, 1.0 eq.) and NH$_2$Cbz (564 mg, 3.73 mmol, 1.1 eq.) in AcOH (5.6 mL) and AcCl (0.5 mL) followed by addition of the benzyl 4-oxobutanoate (783 mg, 4.07 mmol, 1.2 eq).
MS (ESI$^+$): [M+H]$^+$=532.2
$^1$H NMR (MeOD, 500 MHz) δ (ppm): 8.11 (d, 1H, J=8.0 Hz); 7.87-7.85 (m, 1H); 7.78 (d, 1H, J=8.0 Hz); 7.52-7.26 (m, 14H); 5.16-5.07 (m, 4H); 4.12-4.08 (m, 1H); 3.65-3.61 (m, 2H); 2.58-2.46 (m, 2H); 2.31-2.22 (m, 1H); 1.98-1.87 (m, 1H)

Step 3: 4-{[(benzyloxy)carbonyl]amino}-4-{hydroxy[(naphthalen-1-yl)methyl]phosphoryl}butanoic acid The title compound (384 mg, 88%) obtained as a white solid was prepared according to the procedure F from previous product (523 mg, 0.984 mmol, 1.0 eq.) in a mixture of THF/water (8.4 mL/2.5 mL) with presence of LiOH.H$_2$O (123 mg, 2.95 mmol, 3.0 eq.).

MS (ESI$^+$): [M+H]1=442.2

$^1$H NMR (MeOD, 500 MHz) δ (ppm): 8.11-8.09 (m, 1H); 7.85-7.83 (m, 1H); 7.76 (d, 1H, J=8.0 Hz); 7.50-7.26 (m, 9H); 5.13 (pseudo q, 2H, J=12.0 Hz); 4.12-4.05 (m, 1H); 3.67-3.57 (m, 2H); 2.50-2.36 (m, 2H); 2.28-2.19 (m, 1H); 1.94-1.84 (m, 1H)

$^{31}$P NMR (MeOD, 202 MHz) δ (ppm): 44.47

Step 4: 4-amino-4-{hydroxy[(naphthalen-1-yl)methyl]phosphoryl}butanoic acid

The title compound (56 mg, 21%) obtained as a white solid was prepared according to the procedure G from previous product (384 mg, 870 μmol, 1.0 eq.) in TFA/anisole (2.5 mL/605 μL).

Estimated purity: >95% (based on NMR & LCMS)

MS (ESI$^+$): [(M−H$_2$O)+H]$^+$=290.2; [M+H]$^+$=308.2; [(M×2)+H]$^+$=615.3; [(M×3)+H]$^+$=922.6

$^1$H NMR (MeOD, 500 MHz) δ (ppm): 8.25 (d, 1H, J=8.5 Hz); 7.84-7.83 (m, 1H); 7.73 (d, 1H, J=8.0 Hz); 7.54-7.51 (m, 2H); 7.48-7.45 (m, 1H); 7.41 (t, 1H, J=7.5 Hz); 3.53 (d, 2H, J=16.5 Hz); 3.15-3.11 (m, 1H); 2.45 (t, 2H, J=7.5 Hz); 2.248-2.14 (m, 1H); 1.97-1.89 (m, 1H)

$^{31}$P NMR (MeOD, 202 MHz) δ (ppm): 26.94

Example 16: 4-amino-4-{hydroxy[(2-phenoxyphenyl)methyl]phosphoryl}butanoic acid

Step 1: (2-phenoxyphenyl)methanol

At 0° C., a solution of 2-phenoxybenzoic acid (5.0 g, 23.34 mmol, 1.0 eq.) in anhydrous THF (12 mL) was added dropwise to a lithium aluminium hydride solution (2 M in THF, 23.3 mL, 46.68 mmol, 2.0 eq.) in anhydrous THF (13 mL) under Argon atmosphere. The reaction was exothermic and the mixture became yellow. The reaction mixture was stirred for 2 h at room temperature, cooled to 0° C. and then quenched slowly with 2 mL of H$_2$O. An aqueous solution of NaOH (4 mL, 15%) and H$_2$O (6 mL) were successively added and the mixture was stirred for 15 min. Anhydrous Na$_2$SO$_4$ was added and the mixture was stirred for 15 min. The yellow mixture was filtered over a pad of celite and the filtrate was concentrated under vacuum to give the title compound (4.7 g, quantitative yield).

MS (ESI$^+$): [M+H]$^+$=183.2

$^1$H NMR (CDCl$_3$, 500 MHz) δ (ppm): 7.46 (dd, 1H, J=7.5 and 1.5 Hz); 7.36-7.32 (m, 2H); 7.25 (dt, 1H, J=7.5 and 1.5 Hz); 7.15-7.09 (m, 2H); 6.99-6.97 (m, 2H); 6.88 (dd, 1H, J=8.0 and 1.5 Hz); 4.76 (d, 2H, J=5.5 Hz); 2.04 (t, 11H, J=6.0 Hz)

Step 2: 1-(bromomethyl)-2-phenoxybenzene (2-phenoxyphenyl)methanol previously obtained (2.1 g, 10.5 mmol, 1.0 eq.) and carbon tetrabromide (5.56 g, 16.78 mmol, 1.6 eq.) were diluted in CH$_2$C$_2$ (50 mL). The solution was cooled at −5° C. (ice/salt bath) and triphenylphosphine (4.40 g, 16.78 mmol, 1.6 eq) was added in portions. Once addition was completed, the yellow reaction media was stirred at room temperature for 3 h. The mixture was concentrated and purified by column chromatography to afford the title compound (2.8 g, quantitative yield) as a yellow oil.

$^1$H NMR (CDCl$_3$, 500 MHz) δ (ppm): 7.45 (dd, 1H, J=7.5 and 2.0 Hz); 7.37-7.33 (m, 2H); 7.27-7.23 (m, 1H); 7.14-7.02 (m, 4H); 6.84 (dd, 1H, J=7.5 and 1.0 Hz); 4.61 (s, 2H)

Step 3: [(2-phenoxyphenyl)methyl]phosphinic acid

The title compound (572 mg, 61%) obtained as a yellow oil was prepared according to the procedure A from 1-(bromomethyl)-2-phenoxybenzene (1.0 g, 4.97 mmol, 1.0 eq.) in DCM (7.6 mL) and freshly prepared BTSP (19.0 mmol, 5.0 eq.).

MS (ESI$^+$): [M+H]$^+$=249.2

$^1$H NMR (MeOD, 500 MHz) δ (ppm): 7.30-7.27 (m, 2H); 7.21-7.10 (m, 2H); 7.06-7.01 (m, 2H); 7.01 (dt, 1H, J=554.0 and 2.0 Hz); 6.92-6.89 (m, 2H); 6.77-6.75 (m, 1H); 3.18-3.13 (m, 2H)

$^{31}$P NMR (MeOD, 202 MHz) δ (ppm): 30.80

Step 4: [4-(benzyloxy)-1-{[(benzyloxy)carbonyl]amino}-4-oxobutyl][(2-phenoxyphenyl) methyl]phosphinic acid The title compound (1.0 g, 76%) obtained as a pale yellow solid was prepared according to the procedure D for multi-component reaction from previous product (572 mg, 2.30 mmol, 1.0 eq.) and NH$_2$Cbz (383 mg, 2.53 mmol, 1.1 eq.) in AcOH (4.0 mL) and AcCl (0.5 mL) followed by addition of the benzyl 4-oxobutanoate (531 mg, 2.77 mmol, 1.2 eq).

MS (ESI$^+$): [M+H]$^+$=574.3

$^1$H NMR (MeOD, 500 MHz) δ (ppm): 7.45-7.43 (m, 11H); 7.37-7.24 (m, 13H); 7.20-7.16 (m, 11H); 7.10-7.04 (m, 2H); 6.99 (dd, 11H, J=8.5 and 1.0 Hz); 6.79 (d, 1H, J=8.5 Hz); 5.08-5.04 (m, 4H); 4.04-3.99 (m, 1H); 3.25-3.16 (m, 2H); 2.52-2.39 (m, 2H); 2.24-2.17 (m, 1H); 1.89-1.80 (m, 1H)

$^{31}$P NMR (MeOD, 202 MHz) δ (ppm): 44.73

Step 5: 4-amino-4-{hydroxy[(2-phenoxyphenyl)methyl]phosphoryl}butanoic acid The title compound (75 mg, 41%) obtained as a white solid was prepared according to the procedure H for hydrogenolysis from previous product (300 mg, 0.52 mmol, 1.0 eq.) in a mixture of EtOH/AcOH (1:1, 9.0 mL).

Estimated purity: >95% (based on LCMS and NMR)

MS (ESI$^+$): [(M−H$_2$O)+H]$^+$=332.2; [M+H]$^+$=350.2; [(M×2)+H]$^+$=699.4

$^1$H NMR (MeOD, 500 MHz) δ (ppm): 7.53 (dt, 1H, J=7.5 and 2.0 Hz); 7.36-7.33 (m, 2H); 7.18 (dt, 1H, J=7.5 and 2.0 Hz); 7.11-7.08 (m, 2H); 7.01-6.99 (m, 2H); 6.82 (d, 1H, J=8.0 Hz); 3.17-3.05 (m, 3H); 2.48 (dt, 2H, J=8.0 and 2.5 Hz); 2.22-2.13 (m, 1H); 1.99-1.88 (m, 1H)

$^{31}$P NMR (MeOD, 202 MHz) δ (ppm): 27.49

Example 17: 4-amino-4-{hydroxy[(3-phenoxyphenyl)methyl]phosphoryl}butanoic acid

Step 1: [(3-phenoxyphenyl)methyl]phosphinic acid

The title compound (208 mg, 44%) obtained as a colorless oil was prepared according to the procedure A from 1-(bromomethyl)-3-phenoxybenzene (1 g, 3.26 mmol, 1.0 eq.) in DCM (1.5 mL) and freshly prepared BTSP (16.28 mmol, 5.0 eq.).

$^1$H NMR (CDCl$_3$, 500 MHz) δ (ppm): 7.34-7.30 (m, 2H); 7.28-7.25 (m, 1H); 7.10 (m, 1H); 7.01-6.95 (m, 3H); 6.99

(dt, 1H, J=560 and 1.8 Hz); 6.91-6.88 (m, 2H); 5.18 (bs, 1H); 3.09 (dd, 2H, J=18.3 and 1.8 Hz)

$^{31}$P NMR (CDCl$_3$, 202 MHz) δ (ppm): 36.25

Step 2: (1-{[(benzyloxy)carbonyl]amino}-4-methoxy-4-oxobutyl)[(3-phenoxyphenyl) methyl] phosphinic acid The title compound (351 mg, 84%) obtained as a white powder was prepared according to the procedure D for multi-component reaction from previous product (208 mg, 0.84 mmol, 1 eq.) and NH$_2$Cbz (140 mg, 0.92 mmol, 1.1 eq.) in AcOH (1.0 mL) and AcCl (0.2 mL) followed by addition of the methyl 4-oxobutanoate (90% purity, 98 μL, 0.93 mmol).

$^1$H NMR (CDCl$_3$, 500 MHz) δ (ppm): 7.36-7.27 (m, 7H); 7.18 (t, 1H, J=7.9 Hz); 7.08-7.05 (m, 1H); 6.98-6.91 (m, 4H); 6.83 (d, 1H, J=8.4 Hz); 5.15-5.07 (m, 3H); 4.40 (bs, 1H); 3.95 (m, 1H); 3.59 (s, 3H); 3.00 (dd, 2H, J=15.9 and 3.3 Hz); 2.36 (t, 2H, J=7.2 Hz); 2.09-2.03 (m, 11H); 1.81-1.72 (m, 1H)

Step 3: 4-{[(benzyloxy)carbonyl]amino}-4-{hydroxy[(3-phenoxyphenyl)methyl] phosphoryl}butanoic acid The title compound (310 mg, 91%), obtained as a white solid, was prepared according to the procedure F from previous product (351 mg, 0.71 mmol, 1.0 eq.) in a mixture of THF/water (3 mL/1 mL) with presence of LiOH.H$_2$O (51 mg, 2.12 mmol, 3.0 eq.).

MS (ESI$^+$): [M+H]$^+$=484.2

$^1$H NMR (DMSO-d6, 500 MHz) δ (ppm): 11.62 (bs, 2H); 7.46 (dd, 1H, J=9.6 Hz); 7.39-7.20 (m, 8H); 7.12 (td, 1H, J=7.4 and 1.2 Hz); 7.07-6.96 (m, 3H); 6.95-6.93 (m, 1H); 6.82 (d, 1H, J=8.3 Hz); 5.05 (s, 2H); 3.71 (qd, 1H, J=10.0 and 3.7 Hz); 2.99 (d, 2H, J=15.0 Hz); 2.35-2.18 (m, 2H); 2.03-1.94 (m, 1H); 1.73-1.63 (m, 1H)

Step 4: 4-amino-4-{hydroxy[(3-phenoxyphenyl) methyl]phosphoryl}butanoic acid

The title compound (173 mg, 770%) obtained as a white powder was prepared according to the procedure H for hydrogenolysis from previous product (310 mg, 0.64 mmol, 1.0 eq.) in a mixture of EtOH/AcOH (9/1, 15.5 mL).

Estimated purity: >95% (based on LCMS and NMR)

MS (ESI$^+$): [(M-H$_2$O)+H]$^+$=332.1; [M+H]$^+$=350.1; [(M×2)+H]$^+$=699.4

$^1$H NMR (DMSO-d6/D20, 500 MHz) δ (ppm): 7.33 (t, 2H, J=7.8 Hz); 7.22 (t, 1H, J=7.9 Hz); 7.08 (t, 1H, J=7.4 Hz); 7.02 (d, 1H, J=7.7 Hz); 6.95-6.91 (m, 3H); 6.72 (d, 1H, J=8.2 Hz); 2.88-2.84 (m, 3H); 2.37-2.24 (m, 2H); 1.92-1.85 (m, 1H); 1.74-1.65 (m, 1H)

Example 18: 4-amino-4-{hydroxy[(4-phenoxyphenyl)methyl]phosphoryl}butanoic acid

Step 1: [(4-phenoxyphenyl)methyl]phosphinic acid

The title compound (559 mg, 65%, 80% purity contaminated with product of double addition) obtained as an oil was prepared according to the procedure A from 1-(bromomethyl)-4-phenoxybenzene (917 mg, 3.48 mmol, 1.0 eq.) in DCM (7.0 mL) and freshly prepared BTSP (17.42 mmol, 5.0 eq.).

MS (ESI$^+$): [M+H]$^+$=249.0

$^1$H NMR (MeOD, 500 MHz) δ (ppm): 7.36-7.32 (m, 2H); 7.28-7.26 (m, 2H); 7.12-7.09 (m, 1H); 6.99 (dt, 1H, J=553.5 and 2.0 Hz); 6.98 (m, 4H); 3.17 (dd, 2H, J=18.5 and 2.0 Hz)

$^{31}$P NMR (MeOD, 202 MHz) δ (ppm): 32.43

Step 2: [4-(benzyloxy)-1-{[(benzyloxy)carbonyl] amino}-4-oxobutyl][(4-phenoxyphenyl) methyl] phosphinic acid The title compound (670 mg, 52%) obtained as a white solid was prepared according to the procedure D for multi-component reaction from previous product (559 mg, 2.25 mmol, 1.0 eq.) and NH$_2$Cbz (374 mg, 2.48 mmol, 1.1 eq.) in AcOH (2.4 mL) and AcCl (0.5 mL) followed by addition of the benzyl 4-oxobutanoate (519 mg, 2.70 mmol, 1.2 eq).

MS (ESI$^+$): [M+H]$^+$=574.2

$^1$H NMR (MeOD, 500 MHz) δ (ppm): 7.37-7.17 (m, 14H); 7.09 (t, 1H, J=7.5 Hz); 6.96 (m, 2H); 6.87 (d, 2H, J=8.5 Hz); 5.09 (s, 4H); 3.98-3.92 (m, 1H); 3.12-3.08 (m, 2H); 2.54-2.42 (m, 2H); 2.24-2.16 (m, 1H); 1.92-1.82 (m, 1H)

$^{31}$P NMR (MeOD, 202 MHz) δ (ppm): 44.66

Step 3: 4-amino-4-{hydroxy[(4-phenoxyphenyl) methyl]phosphoryl}butanoic acid

The title compound (21 mg, 14%) obtained as a white solid was prepared according to the procedure H for hydrogenolysis from previous product (250 mg, 0.44 mmol, 1.0 eq.) in a mixture EtOH/AcOH (1:1, 12 mL).

Estimated purity: >95% (based on LCMS and NMR)

MS (ESI$^+$): [(M-H$_2$O)+H]$^+$=332.1; [M+H]$^+$=350.1; [(M×2)+H]$^+$=399.3

$^1$H NMR (MeOD, 500 MHz) δ (ppm): 7.34-7.30 (m, 4H); 7.08 (tt, 1H, J=7.5 and 1.0 Hz); 6.96 (m, 2H); 6.91 (d, 2H, J=8.5 Hz); 3.11-3.06 (in, 11H); 3.02 (dd, 2H, J=16.0 and 3.5 Hz); 2.52 (t, 2H, J=7.5 Hz); 2.21-2.12 (m, 1H); 1.96-1.86 (m, 1H)

$^{31}$P NMR (MeOD, 202 MHz) δ (ppm): 27.03

Example 19: 4-amino-4-[({[1,1'-biphenyl]-3-yl}methyl)(hydroxy)phosphoryl]butanoic acid Step 1: {[1,1'-biphenyl]-3-yl}methanol A solution of ethyl [1,1'-biphenyl]-3-carboxylate (2.50 g, 11.0 mmol, 1.0 eq.) in anhydrous THF (5.5 mL) was added dropwise to a solution of commercial solution of lithium aluminium hydride (2.0 M in THF, 11.0 mL, 22 mmol, 2.0 eq.) under argon atmosphere at 0° C. The mixture was stirred at room temperature for 1 h. After cooling down to 0° C., water (0.9 mL), aqueous solution of 15% NaOH (0.9 mL) and water again (2.7 mL) were added. After stirring for 15 min, Na$_2$SO$_4$ was added and the suspension was filtered over celite (MTBE rinses). The filtrate was concentrated under reduced pressure to afford the title compound (2.0 g, 98%) as a white solid.

MS (ESI$^+$): [(M-H$_2$O)+H]$^+$=167.2

$^1$H NMR (CDCl$_3$, 500 MHz) δ (ppm): 7.68-7.60 (m, 3H); 7.56 (dt, J=7.8, 1.6 Hz, 1H); 7.47 (t, J=7.6 Hz, 3H); 7.44-7.34 (m, 2H); 4.80 (d, J=5.9 Hz, 2H); 1.71 (t, J=6.0 Hz, 1H)

Step 2: 3-(iodomethyl)-1,1'-biphenyl

To a solution of triphenylphosphine (3.7 g, 14 mmol, 1.3 eq.) in DCM (60 mL) at 0° C., was added 12 (3.58 g, 14.1 mmol, 1.3 eq.). After stirring at 0° C. during 15 min, imidazole (961 mg, 14.1 mmol, 1.3 eq.) and the compound obtained in the previous step (2.0 g, 10.9 mmol, 1.0 eq.) were added to this solution. The resulting mixture was stirred at room temperature for 1 h. The reaction mixture was partitioned between EtOAc and a saturated solution of $Na_2S_2O_3$, triggering a decoloration. The layers were separated and the organic phase was washed (brine), dried over $Na_2SO_4$, filtered and concentrated under reduced pressure. The residue was purified by column chromatography to afford the title compound (2.9 g, 910%) as a pale yellow solid.

$^1$H NMR (CDCl$_3$, 500 MHz) δ (ppm): δ 7.67-7.56 (m, 3H); 7.55-7.44 (m, 3H); 7.44-7.34 (m, 3H); 4.55 (s, 2H)

Step 3: phosphine-borane complex intermediate

The title compound (2.90 g, 100%) obtained as a colorless oil was prepared according to the first step of the procedure C from the product obtained previously (2.70 g, 9.20 mmol, 1.0 eq.) in THF (4 mL) with presence of $(BH_3)P(OEt)_2H$ (1.50 g, 11.0 mmol, 1.2 eq.) in THF (25 mL) and LiHMDS (1.0 M solution in THF, 11.0 mL, 11.0 mmol, 1.2 eq.)

MS (ESI$^+$): [(M−H$_2$)—H]$^-$=299

$^1$H NMR (CD$_3$OD, 500 MHz) δ (ppm): δ 7.46-7.39 (m, 2H); 7.33 (q, J=2.1 Hz, 1H); 7.31 (br d, J=7.7 Hz, 11H); 7.28-7.21 (m, 2H); 7.21-7.11 (m, 2H); 7.09-7.01 (m, 11H); 3.90-3.79 (m, 4H), 3.08 (d, J=11.7 Hz, 2H), 1.04 (t, J=7.1 Hz, 6H), 0.67-0.14 (m, 3H)

Step 4: ({[1,1'-biphenyl]-3-yl}methyl)phosphinic acid

The title compound (862 mg, 74%) obtained as a pale pink solid was prepared according to a variant of the second step of the procedure C from the product obtained previously (1.5 g, 5.0 mmol, 1.0 eq.) in DCM (25 mL) with presence of HBF$_4$.Et$_2$O (3.38 mL, 24.8 mmol, 5.0 eq.).

MS (ESI$^+$): [M+H]$^+$=233.1; [(M×2)+H]$^+$=465.0

$^1$H NMR (CD$_3$OD, 500 MHz) δ (ppm): 7.66-7.62 (m, 2H); 7.59-7.50 (m, 2H); 7.49-7.41 (m, 3H); 7.39-7.32 (m, 1H); 7.32-7.24 (m, 1H); 7.06 (dm, J$^1$$_{P-H}$=500 Hz, 1H); 3.29 (dd, J=18.4, 2.0 Hz, 2H)

$^{31}$P NMR (CD$_3$OD, 202 MHz) δ (ppm): 32.5

Step 5: [4-(benzyloxy)-1-{[(benzyloxy)carbonyl]amino}-4-oxobutyl]({[1,1'-biphenyl]-3-yl}methyl)phosphinic acid The title compound (1.2 g, considered quantitative yield) was prepared according to the procedure D for multicomponent reaction from previous product (0.43 g, 1.8 mmol, 1.0 eq.) and NH$_2$Cbz (308 mg, 2.04 mmol, 1.1 eq.) in AcOH (2.6 mL) and AcCl (0.3 mL) followed by addition of the benzyl 4-oxobutanoate (427 mg, 2.22 mmol, 1.2 eq.).

MS (ESI$^+$): [M+H]$^+$=558.2

Step 6: 4-{[(benzyloxy)carbonyl]amino}-4-[({[1,1'-biphenyl]-3-yl}methyl)(hydroxy) phosphoryl]butanoic acid The title compound (390 mg, 45% for two steps), obtained as a white solid, was prepared according to the procedure F from previous product (1.2 g, 2.15 mmol, 1.0 eq.) in a mixture of THF/water (4/1, 11 mL) with presence of LiOH.H$_2$O (270 mg, 6.46 mmol, 3.0 eq.).

MS (ESI$^-$): [M+H]$^+$=468.0; [(M×2)+H]$^-$=935.4

$^1$H NMR (CD$_3$OD, 500 MHz) δ (ppm): 7.70-7.59 (m, 3H); 7.59-7.47 (m, 1H); 7.47-7.41 (m, 2H); 7.41-7.21 (m, 8H); 5.16-5.04 (m, 2H); 4.02 (td, J=10.0, 3.5 Hz, 1H); 3.30-3.14 (m, 2H); 2.57-2.34 (m, 2H); 2.29-2.13 (m, 1H); 1.95-1.80 (m, 1H)

$^{31}$P NMR (CD$_3$OD, 202 MHz) δ (ppm): 45.0

Step 7: 4-amino-4-[({[1,1'-biphenyl]-3-yl}methyl)(hydroxy)phosphoryl]butanoic acid The title compound (81 mg, 29%) obtained as a white solid was prepared according to the procedure G from previous product (390 mg, 834 µmol, 1.0 eq.) in TFA/anisole (1.7 mL/2.7 mL).

Estimated purity: 95% (based on LCMS and NMR)

MS (ESI$^-$): [M−H]$^-$=332.1; [(M×2)-H]$^-$=665.3

$^1$H NMR (CD$_3$OD, 500 MHz) δ (ppm): δ 7.70-7.59 (m, 3H); 7.51-7.40 (m, 3H); 7.40-7.30 (m, 3H); 3.18-3.08 (m, 3H); 2.54 (t, J=7.3 Hz, 2H); 2.28-2.18 (m, 1H); 2.03-1.87 (m, 1H)

$^{31}$P NMR (CD$_3$OD, 202 MHz) δ (ppm): 27.0

Example 20: 4-amino-4-{hydroxy[(3-phenyl-1,2-oxazol-5-yl)methyl]phosphoryl}butanoic acid Step 1: 5-methyl-3-phenyl-1,2-oxazole To a solution of (Z)—N-hydroxybenzimidoyl chloride (2.0 g, 12.9 ol, 1.0 eq.) in DCM (26 mL), were added propyne (1 M solution in THF, 25.7 mL, 25.7 mmol, 2.0 eq.) and Et$_3$N (2.33 mL, 16.7 mmol, 1.3 eq.). The resulting reaction mixture was stirred at room temperature for 16 h. The reaction mixture was partitioned between EtOAc and saturated solution of NH$_4$Cl. The layers were separated and the aqueous phase was extracted with EtOAc. The combined organic extracts were washed with brine, dried over Na$_2$SO$_4$, filtered and concentrated under reduced pressure. The residue was purified by column chromatography to afford the title compound (1.57 g, 77%) as a white solid.

MS (ESI$^+$): [M+H]$^+$=160.2

$^1$H NMR (CDCl$_3$, 500 MHz) δ (ppm): 7.88-7.71 (m, 2H); 7.53-7.42 (m, 3H); 6.32 (q, J=0.9 Hz, 1H); 2.50 (d, J=0.9 Hz, 3H)

Step 2: [(3-phenyl-1,2-oxazol-5-yl)methyl]phosphinic acid

To a solution of previous compound (2.94 g, 18.5 mmol, 1.0 eq.) in THF (30 mL) at −78° C., was added a freshly prepared LDA solution (0.5 M solution in THF, 44.3 mL, 22.2 mmol, 1.2 eq.). After stirring at −78° C. for 1 h, chlorodiethylphosphite (3.18 mL, 22.2 mmol, 1.2 equiv) was added dropwise. Stirring was maintained at −78° C. for 1 h and then at room temperature for 3 h. Water (20 mL) was added, followed by concentrated solution of aqueous of HCl (2 mL). The suspension was extracted with EtOAc (3×) and the combined organic extracts were washed with brine, dried over Na$_2$SO$_4$, filtered and concentrated under reduced pressure. The yellow liquid was treated with 2 N NaOH solution (10 mL) and the mixture was stirred at room temperature for 30 min. The aqueous phase was washed with Et$_2$O, acidified with concentrated HCl and extracted with DCM (3×). The combined organic extracts were dried over Na$_2$SO$_4$, filtered and concentrated under reduced pressure to afford the title compound (2.6 g, 63%) as a light yellow oil.

MS (ESI$^+$): [M+H]$^+$=224.1; [(M×2)+H]$^+$=447.0

$^{1}$H NMR (500 MHz, CDCl$_3$) δ (ppm): 7.83-7.74 (m, 2H); 7.56-7.36 (m, 3H); 7.28 (dm, J$^{1}_{P\text{-}H}$=583 Hz, 1H); 6.60 (d, J=2.8 Hz, 1H); 3.45 (d, J=18.3 Hz, 2H)

$^{31}$P NMR (CDCl$_3$, 202 MHz) δ (ppm): 27.6

Step 3: [4-(benzyloxy)-1-{[(benzyloxy)carbonyl]amino}-4-oxobutyl][(3-phenyl-1,2-oxazol-5-yl)methyl]phosphinic acid The title compound (1.1 g, estimated quantitative yield) was prepared according to the procedure D for multi-component reaction from previous product (450 mg, 2.0 mmol, 1.0 eq.) and NH$_2$Cbz (335 mg, 2.22 mmol, 1.1 eq.) in AcOH (3.5 mL) and AcCl (0.4 mL) followed by addition of the benzyl 4-oxobutanoate (465 mg, 2.42 mmol, 1.2 eq.).

MS (ESI): [M+H]$^+$=549.1

Step 4: 4-{[(benzyloxy)carbonyl]amino}-4-[hydroxy[(3-phenyl-1,2-oxazol-5-yl)methyl]phosphoryl] butanoic acid The title compound (717 mg, 78% for two steps) obtained as a white solid was prepared according to the procedure F from previous product (1.1 g, 2.0 mmol) in a mixture of THF/water (4/1, 10 mL) and LiOH.H$_2$O (252 mg, 6.02 mmol, 3.0 eq.).

MS (ESI$^+$): [M+H]$^+$=459.0; [(M×2)+H]$^+$=917.3

$^{1}$H NMR (CD$_3$OD, 500 MHz) δ (ppm): 7.96-7.67 (m, 2H); 7.57-7.42 (m, 3H); 7.41-7.17 (m, 5H); 6.77 (d, J=2.5 Hz, 1H); 5.24-5.03 (m, 2H); 4.23-4.00 (m, 1H); 3.53-3.38 (m, 2H); 2.55-2.37 (m, 2H); 2.32-2.15 (m, 1H); 1.99-1.80 (m, 1H)

$^{31}$P NMR (CD$_3$OD, 202 MHz) δ (ppm): 40.4

Step 5: 4-amino-4-{hydroxy[(3-phenyl-1,2-oxazol-5-yl)methyl]phosphoryl}butanoic acid The title compound (37 mg, 7%) obtained as a white solid was prepared according to the procedure G from previous product (717 mg, 1.56 mmol, 1.0 eq.) in TFA/anisole (6 mL/8.5 mL).

Estimated purity: >100% (based on LCMS) and >95% (based on NMR)

MS (ESI$^+$): [M+H]$^+$=325.1; [(M×2)+H]$^+$=649.2
MS (ESI$^-$): [M-H]$^-$=323.1; [(M×2)-H]$^-$=647.2

$^{1}$H NMR (CD$_3$OD, 500 MHz) δ (ppm): 7.96-7.64 (m, 2H); 7.56-7.31 (m, 3H); 6.78 (d, J=2.5 Hz, 1H); 3.36 (s, 2H); 3.28 (td, J=8.1, 5.4 Hz, 1H); 2.63 (t, J=7.3 Hz, 2H); 2.39-2.18 (m, 1H); 2.10-1.86 (m, 1H)

$^{31}$P NMR (CD$_3$OD, 202 MHz) δ (ppm): 22.6

Example 21: 4-amino-4-{hydroxy[(5-phenyl-1,2-oxazol-3-yl)methyl]phosphoryl}butanoic acid Step 1: 3-methyl-5-phenyl-1,2-oxazole To a solution of 1-phenylbutane-1,3-dione (4.87 g, 30.0 mmol, 1.0 eq.) in THF/EtOH (1/1, 150 mL), was added hydroxylamine hydrochloride (2.08 g, 30.0 mmol, 1.0 eq.). The resulting reaction mixture was stirred at reflux for 24 h. After cooling down to room temperature, the volatiles were removed under reduced pressure and the residue was partitioned between EtOAc and water. The layers were separated and the aqueous phase was extracted with EtOAc. The combined organic extracts were washed with brine, dried over Na$_2$SO$_4$, filtered and concentrated under reduced pressure. The residue was purified by column chromatography to afford the title compound (3.78 g, 79%) as a white solid.

MS (ESI$^+$): [M+H]$^+$=160.2

$^{1}$H NMR (CDCl$_3$, 500 MHz) δ (ppm): 7.86-7.70 (m, 2H), 7.55-7.39 (m, 3H), 6.39 (s, 1H), 2.38 (s, 3H)

Step 2: benzyl [(5-phenyl-1,2-oxazol-3-yl)methyl]phosphinate

To a solution of previous compound (5.26 g, 33.0 mmol, 1 eq.) in THF (5 3 mL) at −78° C., was added a freshly prepared LDA solution (0.5 M solution in THF, 79.3 mL, 39.6 mmol, 1.2 eq.). After stirring at −78° C. for 1 h, chlorodiethylphosphite (5.69 mL, 39.6 mmol, 1.2 eq.) was added dropwise. Stirring was maintained at −78° C. for 1 h and then at room temperature for 16 h. Water (20 mL) was added, followed by concentrated aqueous solution of HCl (2 mL). The suspension was extracted with EtOAc (3×) and the combined organic extracts were washed with brine, dried over Na$_2$SO$_4$, filtered and concentrated under reduced pressure. The yellow liquid was treated with 2 N NaOH solution (20 mL) and the mixture was stirred at room temperature for 30 min. The aqueous phase was washed with Et$_2$O, acidified with concentrated aqueous solution of HCl and extracted with DCM (3×). The combined organic extracts were dried over Na$_2$SO$_4$, filtered and concentrated under reduced pressure to afford 4.1 g of a yellow oil. The residue was dissolved in DCM (100 mL), benzyl alcohol (2.48 mL; 23.9 mmol) and EDCI (5.28 g, 27.6 mmol) were added. The mixture was stirred at room temperature for 16 h. The reaction mixture was partitioned between EtOAc and aqueous solution HCl 1 N. The layers were separated and the organic phase was washed with aqueous solution HCl 1 N and brine, dried over Na$_2$SO$_4$, filtered and concentrated under reduced pressure. The residue was purified to afford the title compound (1.16 g, 20% over two steps) as a yellow oil.

MS (ESI$^+$): [M+H]$^+$=314.1

$^{1}$H NMR (500 MHz, CD$_3$OD) δ (ppm): 7.89-7.81 (m, 2H); 7.57-7.48 (m, 3H); 7.40-7.31 (m, 4H); 7.31-7.20 (m, 1H); 6.82 (d, J=1.0 Hz, 1H); 4.62 (s, 2H); 3.56-3.41 (m, 2H)

Step 3: benzyl 4-[(benzyloxy)[(5-phenyl-1,2-oxazol-3-yl)methyl]phosphoryl]-4-[(2-methylpropane-2-sulfinyl)amino]butanoate The title compound (213 mg, 19%) obtained as a mixture of 4 diastereoisomers as a yellow oil was prepared according to the procedure E from previous product (580 mg, 1.9 mmol, 1.0 eq.) and cesium carbonate (905 mg, 2.78 mmol, 1.5 eq.) in CH$_2$Cl$_2$ (5 mL) followed by addition of a solution of the racemic benzyl (4E)-4-[(2-methylpropane-2-sulfinyl)imino]butanoate (711 mg, 2.41 mmol, 1.3 eq.) in CH$_2$Cl$_2$ (2.3 mL).

MS (ESI$^+$): [M+H]$^+$=609.3

$^{1}$H NMR (CD$_3$OD, 500 MHz) δ (ppm): δ 7.87-7.73 (m, 2H); 7.60-7.47 (m, 3H); 7.45-7.25 (m, 10H); 6.75-6.61 (m, 1H); 5.24-5.02 (m, 4H); 4.00-3.82 (m, 1H); 3.76-3.58 (m, 1H); 3.58-3.43 (m, 1H); 2.87-2.53 (m, 2H); 2.47-2.20 (m, 1H); 2.12-1.93 (m, 1H); 1.30-1.22 (m, 9H)

$^{31}$P NMR (CD$_3$OD, 202 MHz) δ (ppm): 49.64; 49.32; 48.78; 48.31

Step 4: 4-{hydroxy[(5-phenyl-1,2-oxazol-3-yl)methyl]phosphoryl}-4-[(2-methylpropane-2-sulfinyl)amino]butanoic acid The title compound (178 mg, quantitative yield) obtained as a colorless oil was prepared according to the procedure F from previous product (213 mg, 0.35 mmol, 1.0 eq.) in a mixture of THF/water (4/1, 2 mL) with presence of LiOH.H$_2$O (44 mg, 1.1 mmol, 3.0 eq.).

MS (ESI$^+$): [M+H]$^+$=429.1; [(M×2)+H]$^+$=857.3

Step 5: 4-amino-4-{hydroxy[(5-phenyl-1,2-oxazol-3-yl)methyl]phosphoryl}butanoic acid The title compound (40 mg, 27%) obtained as a white solid was prepared according to the procedure G from previous product (178 mg, 0.416 mmol, 1.0 eq.) with 4.0 M HCl solution in dioxane (2.31 mL, 9.24 mmol, 22 eq.).

Estimated purity: >95% (based on LCMS and NMR)

MS (ESI$^+$): [M+H]$^+$=325.0; [(M×2)+H]$^+$=649.1

MS (ESI$^-$): [M−H]$^-$=323.0; [(M×2)-H]$^-$=647.1

$^1$H NMR (CD$_3$OD, 500 MHz) δ (ppm): 7.93-7.76 (m, 2H); 7.61-7.42 (m, 3H); 6.85 (d, J=0.9 Hz, 1H); 3.32-3.25 (m, 1H); 3.25-3.08 (m, 2H); 2.62 (t, J=7.3 Hz, 2H); 2.38-2.21 (m, 1H); 2.09-1.89 (m, 1H)

$^{31}$P NMR (CD$_3$OD, 202 MHz) δ (ppm): 24.4

Example 22: 4-amino-4-[hydroxy(2-phenylethyl)phosphoryl]butanoic acid

Step 1: (2-phenylethyl)phosphinic acid

The title compound (700 mg, 65%) obtained as a pale yellow oil was prepared according to the procedure B from diethylchlorophosphite (1 mL, 6.26 mmol, 1.0 eq.) in anhydrous Et$_2$O (10 mL) followed by addition of a phenylpropylmagnesium chloride solution (1.0 M in THF, 6.6 mL, 6.56 mmol, 1.05 eq.).

$^1$H NMR (CDCl$_3$, 500 MHz) δ (ppm): 7.94 (bs); 7.12 (dt, 1H, J=547.0 and 1.9 Hz); 7.32-7.21 (m, 5H); 2.97-2.91 (m, 2H); 2.14-2.07 (m, 2H)

Step 2: (1-{[(benzyloxy)carbonyl]amino}-4-methoxy-4-oxobutyl)(2-phenylethyl)phosphinic acid The title compound (356 mg, 72%) obtained as a pale yellow powder was prepared according to the procedure D for multi-component reaction from previous product (200 mg, 1.18 mmol, 1.0 eq.) and NH$_2$Cbz (195 mg, 1.29 mmol, 1.1 eq.) in AcOH (2.0 mL) and AcCl (0.4 mL) followed by addition of the methyl 4-oxobutanoate (90% purity, 165 µL, 1.41 mmol, 1.2 eq).

$^1$H NMR (CDCl$_3$, 500 MHz) δ (ppm): 8.53 (bs, 1H); 7.31-7.14 (m, 10H); 5.35 (d, 1H, J=10.3 Hz); 5.10 (d, 2H, J=15.0 Hz); 4.05 (tdd, 1H, J=11.1, 8.1 and 3.5 Hz); 3.60 (s, 3H); 3.00-2.82 (m, 2H); 2.48-2.39 (m, 2H); 2.25 (ddt, 1H, J=10.8, 7.3 and 3.5 Hz); 2.11-1.99 (m, 2H); 1.97-1.88 (m, 1H)

$^{31}$P NMR (CDCl$_3$, 202 MHz) δ (ppm): 53.56

Step 3: 4-{[(benzyloxy)carbonyl]amino}-4-[hydroxy(2-phenylethyl)phosphoryl]butanoic acid The title compound (184 mg, 95%) obtained as a white solid was prepared according to the procedure F from previous product (200 mg, 0.47 mmol, 1.0 eq.) in a mixture of THF/water (4 mL/1 mL) with presence of LiOH.H$_2$O (60 mg, 1.43 mmol, 3.0 eq.).

$^1$H NMR (DMSO-d6, 500 MHz) δ (ppm): 11.94 (bs, 2H); 7.50 (d, 1H, J=9.7 Hz); 7.37-7.20 (m, 7H); 7.21-7.12 (m, 3H); 5.09 (d, 11H, J=12.8 Hz); 5.01 (d, 1H, J=12.7 Hz); 3.73 (ddt, 11H, J=13.5, 9.6 and 4.7 Hz); 2.83-2.68 (m, 2H); 2.39-2.33 (m, 1H); 2.29-2.23 (m, 1H); 2.08-2.00 (m, 1H); 1.83-1.69 (m, 2H)

$^{31}$P NMR (DMSO-d6, 202 MHz) δ (ppm): 43.44

Step 4: 4-amino-4-[hydroxy(2-phenylethyl)phosphoryl]butanoic acid

The title compound (62 mg, 47%) obtained as a white powder was prepared according to the procedure H for hydrogenolysis from previous product (184 mg, 0.45 mmol, 1.0 eq.) in a mixture EtOH/AcOH (9 mL/1 mL).

Estimated purity: >95% (based on LCMS and NMR)

MS (ESI$^+$): [(M−H$_2$O)+H]$^+$=254.2; [M+H]$^+$=272.2; [(M×2)+H]$^+$=543.3; [(M×3)+H]$^+$=814.6

$^1$H NMR (D20, 500 MHz) δ (ppm): 7.44-7.37 (m, 4H); 7.34-7.31 (m, 1H); 3.14 (td, 1H, J=8.8 and 4.8 Hz); 2.95-2.89 (m, 2H); 2.67-2.55 (m, 2H); 2.26-2.17 (m, 1H); 2.05-1.93 (m, 3H)

$^{31}$P NMR (D20, 202 MHz) δ (ppm): 34.54

Example 23: 4-amino-4-{hydroxy[2-(2-methylphenyl)ethyl]phosphoryl}butanoic acid

Step 1: [2-(2-methylphenyl)ethyl]phosphinic acid

The title compound (856 mg, 62%) obtained as a light yellow oil was prepared according to the procedure B from diethylchlorophosphite (1 mL, 6.90 mmol, 1.0 eq.) in anhydrous Et$_2$O (9 mL) followed by addition of the freshly prepared Grignard reagent from 1-(2-bromoethyl)-2-methylbenzene in anhydrous Et$_2$O.

MS (ESI$^+$): [M+H]$^+$=185.2

$^1$H NMR (CDCl$_3$, 500 MHz) δ (ppm): 9.32 (br s, 1H); 7.17-7.13 (m, 4H); 7.16 (dt, 1H, J=546.0 and 2.0 Hz); 2.95-2.89 (m, 2H); 2.33 (s, 3H); 2.09-2.02 (m, 2H)

$^{31}$P NMR (CDCl$_3$, 202 MHz) δ (ppm): 36.48

Step 2: [4-(benzyloxy)-1-{[(benzyloxy)carbonyl]amino}-4-oxobutyl][2-(2-methylphenyl)ethyl]phosphinic acid The title compound (866 mg, 63%) obtained as a white solid was prepared according to the procedure D for the multi-component reaction from previous product (500 mg, 2.71 mmol, 1.0 eq.) and NH$_2$Cbz (420 mg, 2.78 mmol, 1.02 eq.) in AcOH (4.7 mL) and AcCl (0.6 mL) followed by addition of the benzyl 4-oxobutanoate (582 mg, 3.03 mmol, 1.12 eq.).

MS (ESI$^+$): [M+H]$^+$=510.2

$^1$H NMR (MeOD, 500 MHz) δ (ppm): 7.37-7.23 (m, 10H); 7.13-7.07 (m, 4H); 5.15-5.03 (m, 4H); 4.06-4.01 (m, 1H); 2.93-2.79 (m, 2H); 2.58-2.45 (m, 2H); 2.33-2.22 (m, 1H); 2.26 (s, 3H); 1.98-1.82 (m, 3H)

$^{31}$P NMR (MeOD, 202 MHz) δ (ppm): 48.97

Step 3: 4-amino-4-{hydroxy[2-(2-methylphenyl)ethyl]phosphoryl}butanoic acid

The title compound (220 mg, 87%) obtained as a white powder was prepared according to the procedure H for hydrogenolysis from previous product (450 mg, 0.88 mmol, 1.0 eq.) in a mixture EtOH/AcOH (1:2, 20 mL).

Expected purity: >95% (based on LCMS and NMR)

MS (ESI$^+$): [(M−H$_2$O)+H]$^+$=268.2; [M+H]$^+$=286.2; [(M×2)+H]$^+$=571.2

¹H NMR (MeOD, 500 MHz) δ (ppm): 7.19 (dd, 1H, J=7.5 and 2.0 Hz); 7.12-7.04 (m, 3H); 3.13-3.08 (m, 1H); 2.90 (q, 2H, J=8.0 Hz); 2.60 (dt, 2H, J=7.5 and 1.5 Hz); 2.34 (s, 3H); 2.28-2.19 (m, 1H); 1.99-1.79 (m, 3H)
³¹P NMR (MeOD, 202 MHz) δ (ppm): 31.36

Example 24: 4-amino-4-{hydroxy[2-(3-methylphenyl)ethyl]phosphoryl}butanoic acid

Step 1: [2-(3-methylphenyl)ethyl]phosphinic acid

The title compound (908 mg, 71%) obtained as a light white oil was prepared according to the procedure B from diethylchlorophosphite (1 mL, 6.90 mmol, 1.0 eq.) in anhydrous Et₂O (9 mL) followed by addition of the freshly prepared Grignard reagent from 1-(2-bromoethyl)-3-methylbenzene in anhydrous Et₂O.
MS (ESI⁺): [M+H]⁺=185.2
¹H NMR (CDCl₃, 500 MHz) δ (ppm): 7.18 (t, 1H, J=8.0 Hz); 7.11 (dt, 1H, J=543.0 and 2.0 Hz); 7.03-6.99 (m, 3H); 6.57 (br s, 1H); 2.91-2.85 (m, 2H); 2.32 (s, 3H); 2.10-2.03 (m, 2H)
³¹P NMR (CDCl₃, 202 MHz) δ (ppm): 36.61

Step 2: [4-(benzyloxy)-1-{[(benzyloxy)carbonyl]amino}-4-oxobutyl][2-(3-methylphenyl) ethyl]phosphinic acid The title compound (961 mg, 69%) obtained as a white solid was prepared according to the procedure D for multicomponent reaction from previous product (500 mg, 2.71 mmol, 1.0 eq.) and NH₂Cbz (451 mg, 2.99 mmol, 1.1 eq.) in AcOH (5.0 mL) and AcCl (0.6 mL) followed by addition of the benzyl 4-oxobutanoate (626 mg, 3.26 mmol, 1.2 eq.).
MS (ESI⁺): [M+H]⁺=510.2
¹H NMR (MeOD, 500 MHz) δ (ppm): 7.37-7.28 (m, 7H); 7.27-7.23 (m, 3H); 7.14 (t, 1H, J=7.5 Hz); 7.01-6.99 (m, 2H); 6.94 (d, 1H, J=7.5 Hz); 5.17-5.04 (m, 4H); 4.05-4.00 (m, 1H); 2.89-2.73 (m, 2H); 2.66-2.44 (m, 2H); 2.31-2.20 (m, 1H); 2.29 (s, 3H); 2.02-1.84 (m, 3H)
³¹P NMR (MeOD, 202 MHz) δ (ppm): 49.31

Step 3: 4-amino-4-{hydroxy[2-(3-methylphenyl)ethyl]phosphoryl}butanoic acid The title compound (123 mg, 440%) obtained as a white powder was prepared according to the procedure H for hydrogenolysis from previous compound (500 mg, 0.98 mmol, 1.0 eq.) in a mixture EtOH/AcOH (1:1, 20 mL).
Expected purity: >95% (based on LCMS and NMR)
MS (ESI⁺): [(M−H₂O)+H]⁺=268.2; [M+H]⁺=286.2; [(M×2)+H]⁺=571.2
¹H NMR (MeOD, 500 MHz) δ (ppm): 7.14 (t, 1H, J=7.5 Hz); 7.08 (s, 1H); 7.04 (d, 1H, J=8.0 Hz); 6.99 (d, 1H, J=7.5 Hz); 3.07-3.02 (m, 1H); 2.88-2.83 (m, 2H); 2.59-2.56 (m, 2H); 2.30 (s, 3H); 2.26-2.17 (m, 1H); 1.97-1.85 (m, 3H)
³¹P NMR (MeOD, 202 MHz) δ (ppm): 31.34

Example 25: 4-amino-4-{hydroxy[2-(4-methylphenyl)ethyl]phosphoryl}butanoic acid

Step 1: [2-(4-methylphenyl)ethyl]phosphinic acid

The title compound (858 mg, 68%) obtained as an oil was prepared according to the procedure B from diethylchlorophosphite (1 mL, 6.90 mmol, 1.0 eq.) in anhydrous Et₂O (9 mL) followed by addition of the freshly prepared Grignard reagent from 1-(2-bromoethyl)-4-methylbenzene in anhydrous Et₂O.
MS (ESI⁺): [M+H]⁺=185.2
¹H NMR (MeOD, 500 MHz) δ (ppm): 7.34-7.29 (m, 5H); 7.19 (dt, 1H, J=540.5 and 2.0 Hz); 3.07-3.01 (m, 2H); 2.49 (s, 3H); 2.26-2.19 (m, 2H)
³¹P NMR (MeOD, 202 MHz) δ (ppm): 33.97

Step 2: [4-(benzyloxy)-1-{[(benzyloxy)carbonyl]amino}-4-oxobutyl][2-(4-methylphenyl) ethyl]phosphinic acid The title compound (1.16 g, 900%) obtained as a white solid was prepared according to the procedure D for multicomponent reaction from previous product (500 mg, 2.71 mmol, 1.0 eq.) and NH₂Cbz (420 mg, 2.78 mmol, 1.02 eq.) in AcOH (4.5 mL) and AcCl (0.6 mL) followed by addition of the benzyl 4-oxobutanoate (582 mg, 3.03 mmol, 1.2 eq.).
MS (ESI⁺): [M+H]⁺=510.2
¹H NMR (MeOD, 500 MHz) δ (ppm): 7.40-7.25 (m, 10H); 7.12-6.97 (m, 4H); 5.17-5.03 (m, 4H); 4.04-4.00 (m, 1H); 2.88-2.72 (m, 2H); 2.66-2.41 (m, 2H); 2.29 (s, 3H); 2.29-2.21 (m, 1H); 2.04-1.83 (m, 3H)
³¹P NMR (MeOD, 202 MHz) δ (ppm): 49.32

Step 3: 4-amino-4-{hydroxy[2-(4-methylphenyl)ethyl]phosphoryl}butanoic acid Compound obtained in previous step (500 mg, 0.981 mmol, 1.0 eq.) in a mixture H₂O/AcOH (1:1, 16 mL) was added over 5% Pd(OH)₂/C (137 mg, 0.05 eq.) under argon. The reactional mixture was stirred overnight under hydrogen atmosphere (1 atm). When the reaction was completed, the reactional mixture was put under argon atmosphere, filtered through a PTFE filter and concentrated. The crude was co-evaporated with toluene (three times), triturated in hot EtOH and dried to afford the title compound (40 mg, 14%) as a white solid.
Expected purity: >95% (based on LCMS and NMR)
MS (ESI⁺): [(M−H₂O)+H]⁺=268.2; [M+H]⁺=286.2; [(M×2)+H]⁺=571.2
¹H NMR (MeOD, 500 MHz) δ (ppm): 7.13 (d, 2H, J=8.0 Hz); 7.08 (d, 2H, J=8.0 Hz); 3.06-3.02 (m, 1H); 2.88-2.83 (m, 2H); 2.59-2.56 (m, 2H); 2.28 (s, 3H); 2.26-2.15 (m, 1H); 1.97-1.85 (m, 3H)
³¹P NMR (MeOD, 202 MHz) δ (ppm): 31.51

Example 26: 4-amino-4-[hydroxy({2-[3-(trifluoromethyl)phenyl]ethyl})phosphoryl]butanoic acid

Step 1: {2-[3-(trifluoromethyl)phenyl]ethyl}phosphinic acid

The title compound (953 mg, 58%) obtained as a light yellow oil was prepared according to the procedure B from diethylchlorophosphite (1 mL, 6.90 mmol, 1.0 eq.) in anhydrous Et₂O (9 mL) followed by addition of the freshly prepared Grignard reagent from 1-(2-bromoethyl)-3-trifluoromethylbenzene in anhydrous Et₂O.
MS (ESI⁺): [M+H]⁺=239.0
¹H NMR (CDCl₃, 500 MHz) δ (ppm): 7.51-7.39 (m, 4H); 7.15 (dt, 1H, J=550.0 and 1.5 Hz); 6.13 (br s, 1H); 3.03-2.97 (m, 2H); 2.15-2.09 (m, 2H)
³¹P NMR (CDCl₃, 202 MHz) δ (ppm): 36.39

Step 2: [4-(benzyloxy)-1-{[(benzyloxy)carbonyl]amino}-4-oxobutyl]({2-[3-(trifluoro methyl)phenyl]ethyl})phosphinic acid The title compound (350 mg, 37%) obtained as a white solid was prepared according to the procedure D for multi-component reaction from previous product (400 mg, 1.68 mmol, 1.0 eq.) and NH₂Cbz (387 mg, 2.02 mmol, 1.1 eq.) in AcOH (2.4 mL) and AcCl (0.5 mL) followed by addition of the benzyl 4-oxobutanoate (387 mg, 2.02 mmol, 1.2 eq.).

MS (ESI⁺): [M+H]⁺=564.1

¹H NMR (MeOD, 500 MHz) δ (ppm): 7.57-7.22 (m, 14H); 5.16-5.05 (m, 4H); 4.06-4.01 (m, 1H); 3.02-2.84 (m, 2H); 2.58-2.45 (m, 2H); 2.30-2.21 (m, 1H); 2.02-1.83 (m, 3H)

³¹P NMR (MeOD, 202 MHz) δ (ppm): 48.36

Step 3: 4-amino-4-{hydroxy([2-[3-(trifluoromethyl)phenyl]ethyl})phosphoryl]butanoic acid The title compound (30 mg, 25%) obtained as a white powder was prepared according to the procedure H for hydrogenolysis from compound obtained in previous step (200 mg, 0.35 mmol, 1.0 eq.) in a mixture EtOH/AcOH (1:1, 12 mL).

Estimated purity: >95% (based on LCMS and NMR)

MS (ESI⁺): [(M–H₂O)+H]⁺=322.0; [M+H]⁺=340.1; [(M×2)+H]⁺=697.2

¹H NMR (MeOD, 500 MHz) δ (ppm): 7.59 (s, 1H); 7.54-7.53 (m, 1H); 7.49-7.47 (m, 2H); 3.15-3.11 (m, 1H); 3.01-2.96 (m, 2H); 2.62 (t, 2H, J=7.5 Hz); 2.29-2.20 (m, 1H); 1.99-1.86 (m, 3H)

³¹P NMR (MeOD, 202 MHz) δ (ppm): 30.53

Example 27: 4-amino-4-[hydroxy(2-methyl-2-phenylpropyl)phosphoryl]butanoic acid

Step 1: (2-methyl-2-phenylpropyl)phosphinic acid

The title compound (349 mg, 26%) obtained as a light yellow oil was prepared according to the procedure B from diethylchlorophosphite (1 mL, 6.90 mmol, 1.0 eq.) in anhydrous Et₂O (9 mL) followed by addition of a (2-methyl-2-phenylpropyl)magnesium chloride solution (0.5 M in THF, 14.5 mL, 7.24 mmol, 1.05 eq.).

MS (ESI⁺): [M+H]⁺=199.1

¹H NMR (MeOD, 500 MHz) δ (ppm): 7.46-7.44 (m, 2H); 7.35-7.31 (m, 2H); 7.22-7.19 (m, 1H); 6.59 (dt, 1H); 2.19 (dd, 2H); 1.53 (s, 3H); 1.52 (s, 3H)

³¹P NMR (MeOD, 202 MHz) δ (ppm): 31.97

Step 2: [4-(benzyloxy)-1-{[(benzyloxy)carbonyl]amino}-4-oxobutyl](2-methyl-2-phenyl propyl)phosphinic acid The title compound (393 mg, 43%) obtained as a white solid was prepared according to the procedure D for multi-component reaction from previous product (349 mg, 1.76 mmol, 1 eq.) and NH₂Cbz (293 mg, 1.94 mmol, 1.1 eq.) in AcOH (1.8 mL) and AcCl (0.5 mL) followed by addition of the benzyl 4-oxobutanoate (406 mg, 2.11 mmol, 1.2 eq).

MS (ESI⁺): [M+H]⁺=524.2

¹H NMR (MeOD, 500 MHz) δ (ppm): 7.38-7.13 (m, 15H); 5.16-5.02 (m, 4H); 3.74-3.69 (m, 1H); 2.47-2.41 (m, 1H); 2.38-2.32 (m, 1H); 2.16-2.07 (m, 3H); 1.81-1.69 (m, 1H); 1.524 (s, 3H), 1.518 (s, 3H)

³¹P NMR (MeOD, 202 MHz) δ (ppm): 47.23

Step 3: 4-amino-4-[hydroxy(2-methyl-2-phenylpropyl)phosphoryl]butanoic acid

The title compound (30 mg, 27%) obtained as a white powder was prepared according to the procedure H for hydrogenolysis from previous compound (193 mg, 0.37 mmol, 1.0 eq.) in a mixture EtOH/AcOH (1:1, 12 mL).

Estimated purity: >95% (based on LCMS and NMR)

MS (ESI⁺): [(M–H₂O)+H]⁺=282.1; [M+H]⁺=300.1; [(M×2)+H]⁺=599.2; [(M×3)+H]⁺=898.5

¹H NMR (MeOD, 500 MHz) δ (ppm): 7.49-7.46 (m, 2H); 7.32-7.29 (m, 2H); 7.19-7.16 (m, 1H); 2.38-2.30 (m, 2H); 2.20-2.16 (m, 1H); 2.08-1.98 (m, 3H); 1.76-1.68 (m, 11H); 1.58 (s, 3H); 1.57 (s, 3H)

³¹P NMR (MeOD, 202 MHz) δ (ppm): 29.13

Example 28: 4-amino-4-{[2-(2-chlorophenyl)ethyl](hydroxy)phosphoryl}butanoic acid Step 1: [2-(2-chlorophenyl)ethyl]phosphinic acid The title compound (734 mg, 52%) was prepared according to the procedure B from diethylchlorophosphite (1 mL, 6.90 mmol, 1.0 eq.) in anhydrous Et₂O (9 mL) followed by addition of a (2-chlorophenethyl)magnesium bromide solution (0.5 M in THF, 14.5 mL, 7.24 mmol, 1.05 eq.).

MS (ESI⁺): [M+H]⁺=205.0 and 207.0

¹H NMR (CDCl₃, 500 MHz) δ (ppm): 10.18 (br s, 1H); 7.35 (dd, 1H, J=7.0 and 2.0 Hz); 7.28-7.26 (m, 2H); 7.22-7.16 (m, 1H); 7.16 (dt, 1H, J=549 and 2.0 Hz); 3.07-3.01 (m, 2H); 2.16-2.09 (m, 2H)

³¹P NMR (CDCl₃, 202 MHz) δ (ppm): 36.58

Step 2: [4-(benzyloxy)-1-{[(benzyloxy)carbonyl]amino}-4-oxobutyl][2-(2-chlorophenyl) ethyl]phosphinic acid The title compound (740 mg, 82%) obtained as a solid was prepared according to the procedure D for multi-component reaction from previous product (350 mg, 1.71 mmol, 1 eq.) and NH₂Cbz (305 mg, 2.02 mmol, 1.1 eq.) in AcOH (2.5 mL) and AcCl (0.9 mL) followed by addition of the benzyl 4-oxobutanoate (424 mg, 2.20 mmol, 1.2 eq).

MS (ESI⁺): [M+H]⁺=530.2 and 532.1

¹H NMR (MeOD, 500 MHz) δ (ppm): 7.37-7.20 (m, 14H); 5.17-5.07 (m, 4H); 4.08-4.04 (m, 1H); 3.03-2.98 (m, 2H); 2.60-2.48 (m, 2H); 2.31-2.22 (m, 1H); 2.03-1.88 (m, 3H)

³¹P NMR (MeOD, 202 MHz) δ (ppm): 48.54

Step 3: 4-{[(benzyloxy)carbonyl]amino}-4-{[2-(2-chlorophenyl)ethyl](hydroxy) phosphoryl}butanoic acid The title compound (191 mg, 73%) obtained as a white solid was prepared according to the procedure F from previous product (316 mg, 0.596 mmol, 1.0 eq.) in a mixture of THF/water (6 mL/1.5 mL) with presence of LiOH.H₂O (75 mg, 1.79 mmol, 3 eq.).

MS (ESI⁺): [M+H]⁺=440.0 and 442.0

¹H NMR (MeOD, 500 MHz) δ (ppm): 7.36-7.19 (m, 9H); 5.11 (dd, 2H, J=47.0 and 12.5 Hz); 4.05-4.01 (m, 1H);

3.03-2.93 (m, 2H); 2.52-2.35 (m, 2H); 2.27-2.19 (m, 1H); 2.02-1.95 (m, 2H); 1.92-1.82 (m, 1H)

$^{31}$P NMR (MeOD, 202 MHz) δ (ppm): 48.76

Step 4: 4-amino-4-{[2-(2-chlorophenyl)ethyl](hydroxy)phosphoryl}butanoic acid The title compound (73 mg, 55%) obtained as a white solid was prepared according to the procedure G from previous product (191 mg, 434 µmol, 1.0 eq.) in TFA/anisole (3.0 mL/454 µL).

Estimated purity: >95% (based on LCMS and NMR)
MS (ESI$^+$): [(M−H$_2$O)+H]$^+$=288.1 and 290.1; [M+H]$^+$=306.1 and 308.1; [(M×2)+H]$^+$=611.1, 613.1 and 615.1

$^1$H NMR (MeOD, 500 MHz) δ (ppm): 7.37-7.34 (m, 2H); 7.23 (td, 1H, J=7.5 and 1.5 Hz); 7.18 (td, 1H, J=7.5 and 2.0 Hz); 3.16-3.12 (m, 1H); 3.05-3.00 (m, 2H); 2.61 (t, 2H, J=7.5 Hz); 2.29-2.00 (m, 1H); 2.01-1.83 (m, 3H)

$^{31}$P NMR (MeOD, 202 MHz) δ (ppm): 30.65

Example 29: 4-amino-4-{[2-(3-chlorophenyl)ethyl](hydroxy)phosphoryl}butanoic acid

Step 1: [2-(3-chlorophenyl)ethyl]phosphinic acid

The title compound (1.0 g, 71%) was prepared according to the procedure B from diethylchlorophosphite (1 mL, 6.90 mmol, 1.0 eq.) in anhydrous Et$_2$O (9 mL) followed by addition of the freshly prepared Grignard reagent from 1-(2-bromoethyl)-3-chlorobenzene in anhydrous Et$_2$O.

MS (ESI$^+$): [M+H]$^+$=205.0 and 207.0
$^1$H NMR (CDCl$_3$, 500 MHz) δ (ppm): 10.26 (br s, 1H); 7.28-7.21 (m, 3H); 7.16 (dt, 1H, J=549.0 and 2.0 Hz); 7.13 (dt, 1H, J=7.5 and 1.5 Hz); 2.97-2.91 (m, 2H); 2.15-2.08 (m, 2H)

$^{31}$P NMR (CDCl$_3$, 202 MHz) δ (ppm): 36.0

Step 2: [4-(benzyloxy)-1-{[(benzyloxy)carbonyl]amino}-4-oxobutyl][2-(3-chlorophenyl) ethyl]phosphinic acid The title compound (748 mg, 58%) obtained as a white solid was prepared according to the procedure D for multi-component reaction from previous product (500 mg, 2.44 mmol, 1.0 eq.) and NH$_2$Cbz (406 mg, 2.93 mmol, 1.1 eq.) in AcOH (3.0 mL) and AcCl (0.3 mL) followed by addition of the benzyl 4-oxobutanoate (564 mg, 2.93 mmol, 1.2 eq).

MS (ESI$^+$): [M+H]$^+$=530.1 and 532.0
$^1$H NMR (MeOD, 500 MHz) δ (ppm): 7.37-7.19 (m, 13H); 7.08 (d, 1H, J=7.5 Hz); 5.18-5.05 (m, 4H); 4.05-4.00 (m, 1H); 2.92-2.76 (m, 2H); 2.58-2.46 (m, 2H); 2.29-2.21 (m, 1H); 1.99-1.84 (m, 3H)

$^{31}$P NMR (MeOD, 202 MHz) δ (ppm): 48.70

Step 3: 4-{[(benzyloxy)carbonyl]amino}-4-{[2-(3-chlorophenyl)ethyl](hydroxy) phosphoryl}butanoic acid The title compound (157 mg, 95%) obtained as a white solid was prepared according to the procedure F from previous product (200 mg, 0.38 mmol, 1.0 eq.) in a mixture of THF/water (4 mL/1 mL) with presence of LiOH.H$_2$O (47 mg, 1.13 mmol, 3.0 eq.).

$^1$H NMR (MeOD, 500 MHz) δ (ppm): 7.35-7.21 (m, 8H); 7.09 (d, 1H, J=7.5 Hz); 5.13 (dd, 2H, J=64.5 and 12.5 Hz); 4.04-3.99 (m, 1H); 2.95-2.76 (m, 2H); 2.52-2.36 (m, 2H); 2.27-2.17 (m, 1H); 1.99-1.81 (m, 3H)

Step 4: 4-amino-4-{[2-(3-chlorophenyl)ethyl](hydroxy)phosphoryl}butanoic acid The title compound (60 mg, 33%) obtained as a white solid was prepared according to the procedure G from previous product (265 mg, 602 µmol, 1.0 eq.) in TFA/anisole (9.0 mL/1.8 mL).

Estimated purity: >95% (based on LCMS and NMR)
MS (ESI$^+$): [(M−H$_2$O)+H]$^+$=288.1 and 290.1; [M+H]$^+$=306.1 and 308.1; [(M×2)+H]$^+$=611.2, 613.1 and 615.1

$^1$H NMR (MeOD, 500 MHz) δ (ppm): 7.30 (t, 1H, J=2.0 Hz); 7.25 (t, 1H, J=8.0 Hz); 7.20-7.17 (m, 2H); 3.13-3.08 (m, 1H); 2.91-2.86 (m, 2H); 2.61 (t, 2H, J=7.5 Hz); 2.28-2.19 (m, 1H); 1.99-1.82 (m, 3H)

$^{31}$P NMR (MeOD, 202 MHz) δ (ppm): 30.72

Example 30: 4-amino-4-{hydroxy[2-(naphthalen-2-yl)ethyl]phosphoryl}butanoic acid

Step 1: 2-(naphthalen-2-yl)ethan-1-ol

At 0° C., a solution of 2-naphthylacetic acid (5.0 g, 26.85 mol, 1.0 eq.) in anhydrous THF (13 mL) was added dropwise to a lithium aluminium hydride solution (2 M solution in THF, 27 mL, 53.70 mmol, 2.0 eq.) in anhydrous THF (13 mL) under argon atmosphere. The reaction was exothermic and the mixture became yellow. The reaction mixture was stirred for 2 h at room temperature, cooled to 0° C. and then quenched slowly with 2 mL of H$_2$O. An aqueous solution of NaOH (4 mL, 15%) and H$_2$O (6 mL) were successively added and the mixture was stirred for 15 min. Anhydrous Na$_2$SO$_4$ was added and the mixture was stirred for 15 min. The yellow mixture was filtered over a pad of celite and the filtrate was concentrated under vacuum to give the expected compound (4.5 g, 97%) as a yellow powder.

$^1$H NMR (CDCl$_3$, 500 MHz) δ (ppm): 7.83-7.79 (m, 3H); 7.69 (t, 1H, J=1.0 Hz); 7.49-7.43 (m, 2H); 7.37 (dd, 1H, J=8.0 and 1.5 Hz); 3.96 (t, 2H, J=6.5 Hz); 3.04 (t, 2H, J=6.5 Hz)

Step 2: 2-(2-bromoethyl)naphthalene

A solution of triphenylphosphine (4.72 g, 18 mmol, 1.3 eq.) and N-bromosuccinimide (3.2 g, 18 mmol, 1.3 eq.) in anhydrous DCM (45 mL) was stirred for 10 minutes. The product obtained in the previous step (2.33 g, 13.5 mmol, 1.0 eq.) was added, followed immediately by imidazole (919 mg, 13.5 mmol, 1.0 eq.) and the mixture was stirred at room temperature for 24 hours. The reaction mixture was partitioned between H$_2$O and DCM and the aqueous layer was extracted with DCM (three times). The combined organic extracts was dried over Na$_2$SO$_4$, filtered and evaporated to dryness. The crude residue was purified by column chromatography to give the expected compound (2.3 g, 72%) as a white solid.

$^1$H NMR (CDCl$_3$, 500 MHz) δ (ppm): 7.83-7.80 (m, 3H); 7.67 (br s, 1H); 7.50-7.44 (m, 2H); 7.34 (dd, 1H, J=8.0 and 1.5 Hz); 3.66 (t, 2H, J=7.5 Hz); 3.34 (t, 2H, J=7.5 Hz)

Step 3: [2-(naphthalen-2-yl)ethyl]phosphinic acid

The title compound (1.24 g, 82%) obtained as a white solid was prepared according to the procedure B from diethylchlorophosphite (1 mL, 6.90 mmol, 1.0 eq.) in anhydrous Et$_2$O (9 mL) followed by addition of the freshly prepared Grignard reagent from 2-(2-bromoethyl)naphthalene in anhydrous THF.

MS (ESI$^+$): [M+H]$^+$=221.1

$^1$H NMR (CDCl$_3$, 500 MHz) δ (ppm): 7.81-7.76 (m, 3H); 7.66 (br s, 1H); 7.48-7.42 (m, 2H); 7.34 (dd, 1H, J=8.5 and 1.5 Hz); 7.16 (dt, 1H, J=550.0 and 2.0 Hz); 3.13-3.08 (m, 2H); 2.23-2.16 (m, 2H)

$^{31}$P NMR (CDCl$_3$, 202 MHz) δ (ppm): 37.46

Step 4: [4-(benzyloxy)-1-{[(benzyloxy)carbonyl] amino}-4-oxobutyl][2-(naphthalen-2-yl) ethyl]phosphinic acid The title compound (880 mg, 89%) obtained as a white solid was prepared according to the procedure D for multi-component reaction from previous product (400 mg, 1.82 mmol, 1.0 eq.) and NH$_2$Cbz (302 mg, 2.00 mmol, 1.1 eq.) in AcOH (2.9 mL) and AcCl (0.4 mL) followed by addition of the benzyl 4-oxobutanoate (418 mg, 2.18 mmol, 1.2 eq.).

MS (ESI$^+$): [M+H]$^+$=546.1

$^1$H NMR (MeOD, 500 MHz) δ (ppm): 7.81 (dd, 1H, J=7.5 and 2.0 Hz); 7.77 (dd, 2H, J=7.5 and 2.5 Hz); 7.63 (br s, 11H); 7.46-7.41 (m, 2H); 7.37-7.28 (m, 8H); 7.20-7.13 (m, 3H); 5.18-5.03 (m, 4H); 4.09-4.04 (m, 1H); 3.10-2.95 (m, 2H); 2.58-2.46 (m, 2H); 2.31-2.24 (m, 1H); 2.12-1.99 (m, 2H); 1.95-1.86 (m, 1H)

$^{31}$P NMR (MeOD, 202 MHz) δ (ppm): 49.01

Step 5: 4-{[(benzyloxy)carbonyl]amino}-4-{hydroxyl[2-(naphthalen-2-yl)ethyl] phosphoryl}butanoic acid The title compound (250 mg, 68%) obtained as a white solid was prepared according to the procedure F from previous product (440 mg, 0.81 mmol, 1.0 eq.) in a mixture of THF/water (7 mL/2 mL) with presence of LiOH.H$_2$O (102 mg, 2.42 mmol, 3.0 eq.).

MS (ESI$^+$): [M+H]$^+$=456.2

$^1$H NMR (MeOD, 500 MHz) δ (ppm): 7.82-7.80 (m, 1H); 7.78-7.76 (m, 2H); 7.64 (br s, 1H); 7.46-7.41 (m, 2H); 7.33-7.30 (m, 3H); 7.21-7.14 (m, 3H); 5.13 (dd, 2H, J=71.5 and 12.5 Hz); 4.08-4.04 (m, 1H); 3.12-2.96 (m, 2H); 2.52-2.38 (m, 2H); 2.29-2.21 (m, 1H); 2.13-2.01 (m, 2H); 1.93-1.84 (m, 1H)

$^{31}$P NMR (MeOD, 202 MHz) δ (ppm): 49.01

Step 6: 4-amino-4-{hydroxy[2-(naphthalen-2-yl) ethyl]phosphoryl}butanoic acid

The title compound (84 mg, 480%) obtained as a white solid was prepared according to the procedure G from previous product (250 mg, 549 μmol, 1.0 eq.) in TFA/anisole (1.6 mL/380 μL).

Estimated purity: >95% (based on HPLC & NMR)

MS (ESI$^+$): [(M−H$_2$O)+H]$^+$=304.1; [M+H]$^+$=322.2; [(M×2)+H]$^+$=643.3

$^1$H NMR (MeOD, 500 MHz) δ (ppm): 7.81-7.78 (m, 3H); 7.71 (s, 1H); 7.45-7.39 (m, 3H); 3.10-3.05 (m, 3H); 2.57 (t, 2H, J=7.0 Hz); 2.28-2.19 (m, 1H); 2.04-1.89 (m, 3H)

$^{31}$P NMR (D$_2$O, 202 MHz) δ (ppm): 34.98

Example 31: 4-amino-4-{hydroxy[2-(naphthalen-1-yl)ethyl]phosphoryl}butanoic acid Step 1: (2-(naphthalen-1-yl)ethyl)phosphinic acid The title compound (777 mg, 51%) obtained as a white solid was prepared according to the procedure B from diethylchlorophosphite (1 mL, 6.90 mmol, 1.0 eq.) in anhydrous Et$_2$O (9 mL) followed by addition of the freshly prepared Grignard reagent from 1-(2-bromoethyl)naphthalene in anhydrous Et$_2$O.

MS (ESI$^+$): [M+H]$^+$=221.1

$^1$H NMR (MeOD, 500 MHz) δ (ppm): 8.07 (dq, 1H, J=8.5 and 1.0 Hz); 7.89-7.87 (m, 1H); 7.77-7.74 (m, 1H); 7.57-7.53 (m, 1H); 7.51-7.47 (m, 1H); 7.43-7.39 (m, 1H); 7.10 (dt, 1H, J=541.5 and 2.0 Hz); 3.40-3.34 (m, 2H); 2.20-2.13 (m, 2H)

$^{31}$P NMR (MeOD, 202 MHz) δ (ppm): 37.79

Step 2: [4-(benzyloxy)-1-{[(benzyloxy)carbonyl] amino}-4-oxobutyl][2-(naphthalen-1-yl)ethyl]phosphinic acid The title compound (520 mg, 27%) obtained as a white solid was prepared according to the procedure D for multi-component reaction from previous product (777 mg, 3.53 mmol, 1.0 eq.) and NH$_2$Cbz (587 mg, 3.88 mmol, 1.1 eq.) in AcOH (5.0 mL) and AcCl (0.6 mL) followed by addition of the benzyl 4-oxobutanoate (813 mg, 4.23 mmol, 1.2 eq.).

MS (ESI$^+$): [M+H]$^+$=546.3

$^1$H NMR (MeOD, 500 MHz) δ (ppm): 8.05 (d, 1H, J=8.0 Hz); 7.88-7.87 (m, 1H); 7.75 (d, 1H, J=8.0 Hz); 7.51-7.46 (m, 2H); 7.40-7.27 (m, 10H); 7.18-7.17 (m, 2H); 5.15-5.04 (m, 4H); 4.12-4.07 (m, 1H); 2.61-2.47 (m, 2H); 2.33-2.25 (m, 1H); 2.16-1.99 (m, 2H); 1.96-1.86 (m, 1H)—2 protons were under the MeOD peak $^{31}$P NMR (MeOD, 202 MHz) δ (ppm): 49.08

Step 3: 4-{[(benzyloxy)carbonyl]amino}-4-{hydroxyl[2-(naphthalen-1-yl)ethyl] phosphoryl}butanoic acid The title compound (340 mg, 78%) obtained as a white solid was prepared according to the procedure F from previous product (520 mg, 0.90 mmol, 1.0 eq.) in a mixture of THF/water (7 mL/2 mL) with presence of LiOH.H$_2$O (120 mg, 2.86 mmol, 3.0 eq.).

MS (ESI$^+$): [M+H]$^+$=456.2

$^1$H NMR (MeOD, 500 MHz) δ (ppm): 8.06 (d, 1H, J=7.5 Hz); 7.88-7.87 (m, 1H); 7.75 (d, 1H, J=8.0 Hz); 7.52-7.46 (m, 2H); 7.40-7.29 (m, 5H); 7.20-7.19 (m, 2H); 5.11 (dd, 2H, J=51.0 and 12.5 Hz); 4.12-4.07 (m, 1H); 2.53-2.34 (m, 2H); 2.31-2.22 (m, 1H); 2.15-2.02 (m, 2H); 1.94-1.84 (m, 1H)—2 protons were under the MeOD peak $^{31}$P NMR (MeOD, 202 MHz) δ (ppm): 49.31

Step 4: 4-amino-4-{hydroxy[2-(naphthalen-1-yl) ethyl]phosphoryl}butanoic acid

The title compound (37 mg, 15%) obtained as a white solid was prepared according to the procedure G from previous product (340 mg, 623 μmol, 1.0 eq.) in TFA/anisole (1.8 mL/435 μL).

Estimated purity: >95% (based on HPLC & NMR)

MS (ESI$^+$): [(M−H$_2$O)+H]$^+$=304.2; [M+H]$^+$=322.2; [(M×2)+H]$^+$=643.5

$^1$H NMR (MeOD, 500 MHz) δ (ppm): 8.18 (d, 1H, J=8.5 Hz); 7.85 (d, 1H, J=8.0 Hz); 7.72 (d, 1H, J=8.0 Hz); 7.55-7.51 (m, 1H); 7.48-7.45 (m, 1H); 7.43-7.37 (m, 2H); 3.38 (q, 2H, J=8.0 Hz); 3.14-3.10 (m, 1H); 2.59 (t, 2H, J=7.5 Hz); 2.28-2.19 (m, 1H); 2.07-1.89 (m, 3H)

$^{31}$P NMR (MeOD, 202 MHz) δ (ppm): 31.27

Example 32: 4-amino-4-{hydroxy[2-(2-methoxyphenyl)ethyl]phosphoryl}butanoic acid

Step 1: [2-(2-methoxyphenyl)ethyl]phosphinic acid

The title compound (620 mg, 60%) obtained as a light yellow oil was prepared according to the procedure B from diethylchlorophosphite (0.75 mL, 5.17 mmol, 1.0 eq.) in anhydrous Et$_2$O (9 mL) followed by addition of a (2-methoxyphenethyl)magnesium bromide solution (0.5 M in THF, 10.9 mL, 5.43 mmol, 1.05 eq.).

MS (ESI$^+$): [M+H]$^+$=201.1

$^1$H NMR (MeOD, 500 MHz) δ (ppm): 7.22-7.15 (m, 2H); 6.99 (dt, 1H, J=538.5 and 2.0 Hz); 6.93 (dd, 1H, J=8.5 and 1.5 Hz); 6.87 (dt, 1H, J=7.5 and 1.0 Hz); 3.84 (s, 3H); 2.90-2.84 (m, 2H); 2.05-1.98 (m, 2H)

$^{31}$P NMR (MeOD, 202 MHz) δ (ppm): 34.83

Step 2: [4-(benzyloxy)-1-{[(benzyloxy)carbonyl]amino}-4-oxobutyl][2-(2-methoxyphenyl) ethyl] phosphinic acid The title compound (605 mg, 69%) obtained as a white solid was prepared according to the procedure D for multicomponent reaction from previous product (334 mg, 1.67 mmol, 1.0 eq.) and NH$_2$Cbz (277 mg, 1.84 mmol, 1.1 eq.) in AcOH (1.8 mL) and AcCl (0.3 mL) followed by addition of the benzyl 4-oxobutanoate (384 mg, 2.00 mmol, 1.2 eq).

MS (ESI$^+$): [M+H]$^+$=526.2

$^1$H NMR (MeOD, 500 MHz) δ (ppm): 7.37-7.21 (m, 10H); 7.18 (dt, 1H, J=7.5 and 1.5 Hz); 7.08 (dd, 1H, 7.5 and 1.5 Hz); 6.90 (d, 1H, J=8.0 Hz); 6.86-6.83 (m, 1H); 5.15-5.05 (m, 4H); 4.02-3.98 (m, 1H); 3.78 (s, 3H); 2.88-2.83 (m, 2H); 2.56-2.43 (m, 2H); 2.28-2.19 (m, 1H); 1.99-1.83 (m, 3H).

Step 3: 4-amino-4-{hydroxy[2-(2-methoxyphenyl)ethyl]phosphoryl}butanoic acid The title compound (23 mg, 20%) obtained as a white powder was prepared according to the procedure H for hydrogenolysis from previous product (200 mg, 0.38 mmol, 1.0 eq.) in a mixture EtOH/AcOH (1:2, 12 mL).

Expected purity: >95% (based on LCMS and NMR)

MS (ESI$^+$): [(M−H$_2$O)+H]$^+$=284.1; [M+H]$^+$=302.1; [(M×2)+H]$^+$=603.2

$^1$H NMR (MeOD, 500 MHz) δ (ppm): 7.19-7.15 (m, 2H); 6.91 (d, 1H, J=8.0 Hz); 6.85 dt, 1H, J=7.5 and 1.0 Hz); 3.83 (s, 3H); 3.09-3.05 (m, 1H); 2.90-2.85 (m, 2H); 2.57 (dt, 2H, J=7.5 and 1.0 Hz); 2.27-2.18 (m. 1H): 2.00-1.79 (m, 3H)

$^{31}$P NMR (MeOD, 202 MHz) δ (ppm): 31.92

Example 33: 4-amino-4-{hydroxy[2-(3-methoxyphenyl)ethyl]phosphoryl} butanoic acid

Step 1: [2-(3-methoxyphenyl)ethyl]phosphinic acid

The title compound (657 mg, 480%) obtained as a light yellow oil was prepared according to the procedure B from diethylchlorophosphite (1 mL, 6.90 mmol, 1.0 eq.) in anhydrous Et$_2$O (9 mL) followed by addition of the freshly prepared Grignard reagent from 1-(2-bromoethyl)-3-methoxybenzene in anhydrous Et$_2$O.

MS (ESI$^+$): [M+H]$^+$=201.1

$^1$H NMR (CDCl$_3$, 500 MHz) δ (ppm): 7.23-7.20 (m, 1H); 7.13 (dt, 1H, J=547.5 and 2.0 Hz); 6.81-6.76 (m, 3H); 6.30 (br s, 1H); 3.79 (s, 3H); 2.94-2.88 (m, 2H); 2.13-2.07 (m, 2H)

$^{31}$P NMR (CDCl$_3$, 202 MHz) δ (ppm): 33.45

Step 2: [4-(benzyloxy)-1-{[(benzyloxy)carbonyl]amino}-4-oxobutyl][2-(3-methoxy phenyl) ethyl] phosphinic acid The title compound (1.3 g, 75%) obtained as a white solid was prepared according to the procedure D for multicomponent reaction from previous product (657 mg, 3.28 mmol, 1.0 eq.) and NH$_2$Cbz (546 mg, 3.61 mmol, 1.1 eq.) in AcOH (6.0 mL) and AcCl (0.8 mL) followed by addition of the benzyl 4-oxobutanoate (757 mg, 3.94 mmol, 1.2 eq.).

MS (ESI$^+$): [M+H]$^+$=526.2

$^1$H NMR (MeOD, 500 MHz) δ (ppm): 7.37-7.23 (m, 10H); 7.17 (t, 1H, J=8.0 Hz); 6.76-6.73 (m, 3H); 5.20-5.04 (m, 4H); 4.05-4.00 (m, 1H); 3.76 (s, 3H); 2.91-2.75 (m, 2H); 2.58-2.45 (m, 2H); 2.29-2.20 (m, 1H); 2.03-1.84 (m, 3H)

$^{31}$P NMR (MeOD, 202 MHz) δ (ppm): 49.23

Step 3: 4-amino-4-{hydroxy[2-(3-methoxyphenyl)ethyl]phosphoryl} butanoic acid The title compound (151 mg, 53%) obtained as a white powder was prepared according to the procedure H for hydrogenolysis from previous product (500 mg, 0.98 mmol, 1.0 eq.) in a mixture EtOH/AcOH (1:1, 20 mL).

Expected purity: >95% (based on LCMS and NMR)

MS (ESI$^+$): [(M−H$_2$O)+H]$^+$=284.2; [M+H]$^+$=302.2; [(M×2)+H]$^+$=603.3

$^1$H NMR (MeOD, 500 MHz) δ (ppm): 7.17 (t, 1H, J=8.0 Hz); 6.84-6.82 (m, 2H); 6.74-6.72 (m, 1H); 3.77 (s, 3H); 3.08-3.03 (m, 1H); 2.87 (q, 2H, J=8.5 Hz); 2.62-2.55 (m, 2H); 2.26-2.18 (m, 1H); 1.99-1.86 (m, 3H)

$^{31}$P NMR (MeOD, 202 MHz) δ (ppm): 31.22

Example 34: 4-amino-4-{hydroxy[2-(4-methoxyphenyl)ethyl]phosphoryl}butanoic acid

Step 1: [2-(4-methoxyphenyl)ethyl]phosphinic acid

The title compound (553 mg, 40%) obtained as a colorless oil was prepared according to the procedure B from diethylchlorophosphite (1 mL, 6.90 mmol, 1.0 eq.) in anhydrous Et$_2$O (9 mL) followed by addition of the freshly prepared Grignard reagent from 1-(2-bromoethyl)-4-methoxybenzene in anhydrous Et$_2$O.

MS (ESI$^+$): [M+H]$^+$=201.2

$^1$H NMR (MeOD, 500 MHz) δ (ppm): 7.17-7.15 (m, 2H); 6.99 (dt, 1H, J=538.5 and 2.0 Hz); 6.86-6.83 (m, 2H); 3.76 (s, 3H); 2.86-2.80 (m, 2H); 2.05-1.98 (m, 2H)

$^{31}$P NMR (MeOD, 202 MHz) δ (ppm): 33.82

Step 2: [4-(benzyloxy)-1-{[(benzyloxy)carbonyl]amino}-4-oxobutyl][2-(4-methoxyphenyl) ethyl] phosphinic acid The title compound (1.2 g, 830%) obtained as a white solid was prepared according to the procedure D for multicomponent reaction from previous product (553 mg, 2.76 mmol, 1.0 eq.) and NH$_2$Cbz (460 mg, 3.04 mmol, 1.1 eq.)

in AcOH (4.0 mL) and AcCl (0.4 mL) followed by addition of the benzyl 4-oxobutanoate (637 mg, 3.32 mmol, 1.2 eq.).

MS (ESI$^+$): [M+H]$^+$=526.2

$^1$H NMR (MeOD, 500 MHz) δ (ppm): 7.37-7.24 (m, 10H); 7.06 (d, 2H, J=8.5 Hz); 6.81 (d, 2H, J=8.5 Hz); 5.17-5.03 (m, 4H); 4.04-3.99 (m, 1H); 3.76 (s, 3H); 2.87-2.71 (m, 2H); 2.57-2.44 (m, 2H); 2.28-2.20 (m, 1H); 2.00-1.83 (m, 3H)

$^{31}$P NMR (MeOD, 202 MHz) δ (ppm): 49.36

Step 3: 4-amino-4-{hydroxy[2-(4-methoxyphenyl) ethyl]phosphoryl}butanoic acid The title compound (220 mg, 77%) obtained as a white powder was prepared according to the procedure H for hydrogenolysis from previous product (500 mg, 0.95 mmol, 1.0 eq.) in a mixture EtOH/AcOH (1:1, 20 mL).

Estimated purity: >94% (based on LCMS and NMR)

MS (ESI$^+$): [(M−H$_2$O)+H]$^+$=284.2; [M+H]$^+$=302.2; [(M×2)+H]$^+$=603.3

$^1$H NMR (MeOD, 500 MHz) δ (ppm): 7.16 (d, 2H, J=8.5 Hz); 6.83 (d, 2H, J=9.0 Hz); 3.76 (s, 3H); 3.06-3.01 (m, 1H); 2.86-2.81 (m, 2H); 2.58 (dt, 2H, J=7.5 and 2.0 Hz); 2.26-2.16 (m, 1H); 1.99-1.84 (m, 3H)

$^{31}$P NMR (MeOD, 202 MHz) δ (ppm): 31.37

Example 35: 4-amino-4-{hydroxy[2-(2-phenoxyphenyl)ethyl]phosphoryl}butanoic acid

Step 1: 2-(2-phenoxyphenyl)ethan-1-ol

At 0° C., a solution of 2-(2-phenoxyphenyl)acetic acid (2.5 g, 10.95 mmol, 1.0 eq.) in anhydrous THF (5.5 mL) was added dropwise to a lithium aluminium hydride solution (2 M in THF, 10.95 mL, 21.91 mmol, 2.0 eq.) in anhydrous THF (5.5 mL) under argon atmosphere. The reaction was exothermic and the mixture became yellow. The reaction mixture was stirred for 2 h at room temperature, cooled to 0° C. and then quenched slowly with 1 mL of H$_2$O. An aqueous solution of NaOH (2 mL, 15%) and H$_2$O (3 mL) were successively added and the mixture was stirred for 15 min. Anhydrous Na$_2$SO$_4$ was added and the mixture was stirred for 15 min. The yellow mixture was filtered over a pad of celite and the filtrate was concentrated under vacuum to give the title compound (1.9 g, 81%) as a yellow oil.

MS (ESI$^+$): [M+H]$^+$=197.2

$^1$H NMR (CDCl$_3$, 500 MHz) δ (ppm): 7.34-7.30 (m, 3H); 7.20 (dt, 1H, J=7.5 and 2.0 Hz); 7.11-7.06 (m, 2H); 6.96-6.93 (m, 2H); 6.89 (dd, 1H, J=8.5 and 1.5 Hz); 3.87 (t, 2H, J=6.5 Hz); 2.93 (t, 2H, J=6.5 Hz)

Step 2: 1-(2-bromoethyl)-2-phenoxybenzene 2-(2-phenoxyphenyl)ethan-1-ol obtained in the previous step (1.9 g, 8.87 mmol, 1.0 eq.) and carbon tetrabromide (4.71 g, 14.19 mmol, 1.6 eq.) were diluted in CH$_2$Cl$_2$ (45 mL). The solution was cooled at −5° C. (an ice/salt bath) and triphenylphosphine (3.72 g, 14.19 mmol, 1.6 eq.) was added in portions. Once the addition was completed, the yellow reaction was stirred at room temperature during 2 h. The mixture was concentrated and purified by column chromatography to afford the title compound (1.9 g, 77%) as a colorless oil.

$^1$H NMR (CDCl$_3$, 500 MHz) δ (ppm): 7.35-7.31 (m, 2H); 7.29 (dd, 1H, J=7.5 and 1.5 Hz); 7.22 (dt, 1H, J=7.5 and 1.5 Hz); 7.11-7.07 (m, 2H); 6.97-6.95 (m, 2H); 6.87 (dd, 1H, J=8.0 and 1.0 Hz); 3.62 (t, 2H, J=7.5 Hz); 3.23 (t, 2H, J=7.5 Hz)

Step 3: [2-(2-phenoxyphenyl)ethyl]phosphinic acid

The title compound (950 mg, 55%) was prepared according to the procedure B from diethylchlorophosphite (0.95 mL, 6.55 mmol, 1.0 eq.) in anhydrous Et$_2$O (9 mL) followed by addition of the freshly prepared Grignard reagent from 1-(2-bromoethyl)-2-phenoxybenzene in anhydrous Et$_2$O.

MS (ESI$^+$): [M+H]$^+$=263.2

$^1$H NMR (MeOD, 500 MHz) δ (ppm): 7.36-7.31 (m, 3H); 7.22 (dt, 1H, J=8.0 and 1.5 Hz); 7.12-7.07 (m, 2H); 6.98 (dt, 1H, J=540.0 and 2.0 Hz); 6.95-6.92 (m, 2H); 6.85 (dd, 1H, J=8.0 and 1.5 Hz); 2.94-2.88 (m, 2H); 2.09-2.02 (m, 2H)

$^{31}$P NMR (MeOD, 202 MHz) δ (ppm): 34.02

Step 4: [4-(benzyloxy)-1-{[(benzyloxy)carbonyl] amino}-4-oxobutyl][2-(2-phenoxyphenyl) ethyl] phosphinic acid The title compound (622 mg, 56%) obtained as a white solid was prepared according to the procedure D for multi-component reaction from previous product (500 mg, 1.91 mmol, 1.0 eq.) and NH$_2$Cbz (317 mg, 2.10 mmol, 1.1 eq.) in AcOH (4.0 mL) and AcCl (0.5 mL) followed by addition of the benzyl 4-oxobutanoate (440 mg, 2.29 mmol, 1.2 eq.).

MS (ESI$^+$): [M+H]$^+$=588.3

$^1$H NMR (MeOD, 500 MHz) δ (ppm): 7.36-7.18 (m, 14H); 7.08-7.04 (m, 2H); 6.91 (dd, 2H, J=8.5 and 1.5 Hz); 6.80 (dd, 1H, J=8.0 and 1.5 Hz); 5.17-4.97 (m, 4H); 4.02-3.98 (m, 1H); 2.94-2.89 (m, 2H); 2.54-2.41 (m, 2H); 2.24-2.15 (m, 1H); 2.04-1.98 (m, 2H); 1.89-1.81 (m, 1H)

$^{31}$P NMR (MeOD, 202 MHz) δ (ppm): 49.20

Step 5: 4-amino-4-{hydroxy[2-(2-phenoxyphenyl) ethyl]phosphoryl}butanoic acid The title compound (85 mg, 46%) obtained as a white powder was prepared according to the procedure H for hydrogenolysis from previous compound (300 mg, 0.51 mmol, 1.0 eq.) in a mixture EtOH/AcOH (1:1, 9.0 mL).

Estimated purity: >95% (based on LCMS and NMR)

MS (ESI$^+$): [(M−H$_2$O)+H]$^+$=346.2; [M+H]$^+$=364.2; [(M×2)+H]$^+$=727.5

$^1$H NMR (MeOD, 500 MHz) δ (ppm): 7.37 (dd, 1H, J=8.0 and 2.0 Hz); 7.33-7.30 (m, 2H); 7.18 (dt, 1H, J=8.0 and 2.0 Hz); 7.11-7.04 (m, 2H); 6.93 (dd, 2H, J=8.5 and 1.5 Hz); 6.82 (dd, 1H, J=8.0 and 1.5 Hz); 3.07-3.03 (m, 1H); 2.93 (pseudo q, 2H, J=8.0 Hz); 2.52 (t, 2H, J=7.5 Hz); 2.19-2.10 (m, 1H); 1.97-1.85 (m, 3H)

$^{31}$P NMR (MeOD, 202 MHz) δ (ppm): 31.14

Example 36: 4-amino-4-({2-[2-(cyclopentyloxy) phenyl]ethyl}(hydroxy)phosphoryl) butanoic acid

Step 1: methyl 2-[2-(cyclopentyloxy)phenyl]acetate

To a solution of methyl 2-(2-hydroxyphenyl)acetate (1.5 g, 9.03 mmol, 1.0 eq.) in DMF (9 mL) at 0° C. was added Cs$_2$CO$_3$ (4.41 g, 13.54 mmol, 1.5 eq.). After 10 min, iodocyclopentane (1.57 mL, 13.54 mmol, 1.5 eq) was added. The reaction mixture was stirred at room temperature for 19 h. Water was then added and the aqueous layer was extracted with Et$_2$O (twice). The combined organic layers was washed with brine, dried over Na$_2$SO$_4$, filtered and concentrated.

The crude was purified by column chromatography to afford the title compound (1.4 g, 66%) as a yellow oil.

MS (ESI$^+$): [M+H]$^+$=235.2

$^1$H NMR (CDCl$_3$, 500 MHz) δ (ppm): 7.21 (dt, 1H, J=8.0 and 2.0 Hz); 7.16 (dd, 1H, J=7.5 and 2.0 Hz); 6.89-6.84 (m, 2H); 4.80-4.77 (m, 1H); 3.67 (s, 3H); 3.58 (s, 2H); 1.89-1.72 (m, 6H); 1.65-1.59 (m, 2H)

Step 2: 2-[2-(cyclopentyloxy)phenyl]ethan-1-ol

A solution of the compound obtained in the previous step (1.6 g, 6.83 mmol, 1.0 eq.) in anhydrous THF (3.4 mL) under argon atmosphere at 0° C. was added dropwise to a lithium aluminium hydride solution (2 M solution in THF, 6.8 mL, 13.66 mmol, 2.0 eq.). The reaction mixture was stirred for 1 h at room temperature, cooled to 0° C. and then quenched slowly with 0.6 mL of H$_2$O. An aqueous solution of NaOH (0.6 mL, 15%) and H$_2$O (1.5 mL) were successively added and the mixture was stirred for 15 min. Anhydrous Na$_2$SO$_4$ was added and the mixture was stirred for further 15 min. The yellow mixture was filtered over a pad of celite and the filtrate was concentrated. The crude was purified by column chromatography to afford the title compound (1.3 g, 92%) as an oil.

MS (ESI$^+$): [M+H]$^+$=207.2

$^1$H NMR (CDCl$_3$, 500 MHz) δ (ppm): 7.20-7.14 (m, 2H); 6.89-6.85 (m, 2H); 4.82-4.74 (m, 1H); 3.82 (t, 2H, J=6.5 Hz); 2.88 (t, 2H, J=6.5 Hz); 1.95-1.76 (m, 6H); 1.68-1.54 (m, 3H)

Step 3: 1-(2-bromoethyl)-2-(cyclopentyloxy)benzene

The compound obtained in the previous step (1.3 g, 6.30 mmol, 1.0 eq.) and carbon tetrabromide (3.34 g, 10.08 mmol, 1.6 eq.) were diluted in CH$_2$Cl$_2$ (30 mL). The solution was cooled at −5° C. (ice/salt bath) and triphenylphosphine (2.64 g, 10.08 mmol, 1.6 eq) was added in portions. Once addition was completed, the yellow reaction media was stirred at room temperature during 2 h. The mixture was concentrated and purified by column chromatography to afford the title compound (1.3 g, 77%).

$^1$H NMR (CDCl$_3$, 500 MHz) δ (ppm): 7.20-7.14 (dt, 1H, J=7.5 and 1.5 Hz); 7.13 (dd, 1H, J=7.5 and 1.5 Hz); 6.88-6.84 (m, 2H); 4.81-4.78 (m, 1H); 3.56 (t, 2H, J=7.5 Hz); 3.14 (t, 2H, J=7.5 Hz); 1.94-1.76 (m, 6H); 1.69-1.61 (m, 2H)

Step 4: {2-[2-(cyclopentyloxy)phenyl]ethyl}phosphinic acid

The title compound (622 mg, 53%) was prepared according to the procedure B from diethylchlorophosphite (0.67 mL, 4.62 mmol, 1.0 eq.) in anhydrous Et$_2$O (4 mL) followed by addition of the freshly prepared Grignard reagent from 1-(2-bromoethyl)-2-(cyclopentyloxy)benzene in anhydrous Et$_2$O.

MS (ESI$^+$): [M+H]$^+$=255.2

$^1$H NMR (CDCl$_3$, 500 MHz) δ (ppm): 7.19-7.13 (m, 2H); 7.10 (dt, 1H, J=544.0 and 2.0 Hz); 6.85-6.81 (m, 2H); 6.04 (br s, 1H); 4.80-4.77 (m, 1H); 2.90-2.84 (m, 2H); 2.11-2.01 (m, 2H), 1.93-1.75 (m, 6H); 1.68-1.57 (m, 2H)

$^{31}$P NMR (CDCl$_3$, 202 MHz) δ (ppm): 39.24

Step 5: [4-(benzyloxy)-1-{[(benzyloxy)carbonyl]amino}-4-oxobutyl]({2-[2-(cyclopentyloxy) phenyl]ethyl})phosphinic acid The title compound (620 mg, 44%) obtained as a white solid was prepared according to the procedure D for multi-component reaction from previous product (622 mg, 2.45 mmol, 1.0 eq.) and NH$_2$Cbz (407 mg, 2.69 mmol, 1.1 eq.) in AcOH (5.3 mL) and AcCl (0.8 mL) followed by addition of the benzyl 4-oxobutanoate (564 mg, 2.94 mmol, 1.2 eq.).

MS (ESI$^+$): [M+H]$^+$=580.3

$^1$H NMR (MeOD, 500 MHz) δ (ppm): 7.39-7.29 (m, 10H); 7.26-7.21 (m, 1H); 7.17-7.13 (m, 1H); 7.08-7.06 (m, 1H); 6.88 (d, 1H, J=8.0 Hz); 6.81 (t, 1H, J=7.5 Hz); 5.13-5.04 (m, 4H); 4.01-3.96 (m, 1H); 2.87-2.79 (m, 2H); 2.56-2.43 (m, 2H), 2.27-2.19 (m, 1H); 2.04-1.76 (m, 9H); 1.67-1.60 (m, 2H)

$^{31}$P NMR (MeOD, 202 MHz) δ (ppm): 49.82

Step 6: 4-amino-4-({2-[2-(cyclopentyloxy)phenyl]ethyl}(hydroxy)phosphoryl) butanoic acid The title compound (50 mg, 260%) obtained as a white powder was prepared according to the procedure H for hydrogenolysis from previous compound (310 mg, 0.53 mmol, 1.0 eq.) in a mixture EtOH/AcOH (1:1, 9.0 mL).

Estimated purity: >95% (based on LCMS and NMR)

MS (ESI$^+$): [(M−H$_2$O)+H]$^+$=338.2; [M+H]$^+$=356.2; [(M×2)+H]$^+$=711.5

$^1$H NMR (D20, 500 MHz) δ (ppm): 6.66-6.62 (m, 2H); 6.40 (d, 11H, J=8.0 Hz); 6.32 (t, 1H, J=7.5 Hz); 4.28-4.23 (m, 1H); 2.76-2.72 (m, 1H); 2.32-2.22 (m, 2H); 2.04-1.88 (m, 2H); 1.68-1.51 (m, 3H); 1.46-1.37 (m, 1H); 1.34-1.25 (m, 2H); 1.20-0.97 (m, 6H)

$^{31}$P NMR (MeOD, 202 MHz) δ (ppm): 31.97

Example 37: 4-amino-4-[hydroxy(3-phenylpropyl)phosphoryl]butanoic acid

Step 1: (3-phenylpropyl)phosphinic acid

The preparation of (3-phenylpropyl)phosphinic acid is described originally by Smid, P. et al, PCT Int. Appl., 2008071738, 2008.

Under argon, to a previously degassed solution of hypophosphorous acid (50 wt % in water, 2.47 mL, 22.6 mmol) in EtOH (15 mL) were added allyl benzene (1 mL, 7.6 mmol) and AIBN (100 mg, 1.2 mmol). The mixture was refluxed for 6 h and LCMS revealed an uncomplete conversion. Another portion of AIBN (100 mg, 1.2 mmol) was then added and the mixture was subsequently refluxed for 18 h. The mixture is constantly colorless and transparent during the reaction. The mixture was then concentrated in vacuo and the resulting oil was cooled to 0° C. and 15 mL of 2 N NaOH solution was added to reach pH 14. The solution was transferred into a separatory funnel and this aqueous layer was washed with Et$_2$O (3×20 mL). The aqueous layer was acidified with 2 N HCl to reach pH 1 and then extracted with AcOEt (4×30 mL). The combined organic layers were washed with brine (100 mL), dried on Na$_2$SO$_4$ and concentrated in vacuo to provide the title compound (1.2 g, 86%) as a colorless oil contaminated by 8% of the di-addition by-product.

MS (ESI$^+$): [M+H]$^+$=185

$^1$H NMR (CDCl$_3$, 500 MHz) δ (ppm): 7.08 (dt, 1H, J=545.0 and 5.0 Hz); 7.30-7.27 (m, 2H); 7.22-7.18 (m, 1H); 7.18-7.13 (m, 2H); 2.72 (t, 2H, J=10.0 Hz); 1.97-1.88 (m, 2H); 1.78-1.72 (m, 2H)

$^{31}$P NMR (CDCl$_3$, 202 MHz) δ (ppm): 39.53

Step 2: (1-{[(benzyloxy)carbonyl]amino}-4-methoxy-4-oxobutyl)(3-phenylpropyl) phosphinic acid The title compound (389 mg, 83%) obtained as a fine white powder was prepared according to the procedure D for multi-component reaction from previous product (200 mg, 1.09 mmol, 1.0 eq.) and NH$_2$Cbz (181 mg, 1.19 mmol, 1.1 eq.) in AcOH (2 mL) and AcCl (0.4 mL) followed by addition of the methyl 4-oxobutanoate (90% purity, 150 µL, 1.3 mmol).

MS (ESI$^+$): [M+H]$^+$=434

$^1$H NMR (CDCl$_3$, 500 MHz) δ (ppm): 7.48-7.30 (m, 5H); 7.28-7.23 (m, 2H); 7.83-7.17 (m, 1H); 7.16-7.13 (m, 1H); 6.30-6.20 (brs, 1H); 5.28-5.18 (m, 1H); 5.14-5.08 (m, 1H); 3.67 (ddt, J=2.0, 9.5 and 10.0 Hz, 1H); 3.63 (s, 3H); 2.65 (t, J=8.0 Hz, 2H); 2.42 (t, J=8.0 Hz, 2H); 2.25-2.16 (m, 1H); 1.99-1.81 (m. 3H); 1.76-1.64 (m, 2H)

$^{13}$C NMR (CDCl$_3$, 125 MHz) δ (ppm): 173.5; 156.5 (d, J=5.0 Hz); 141.1; 136.4; 128.8 (2C); 128.7 (2C); 128.6 (2C); 128.5; 128.3; 126.4; 67.5; 51.9; 49.2 (d, J=102.0 Hz); 36.7 (d, J=15.0 Hz); 30.5 (d, J=11.9 Hz); 26.5; 25.8; 23.6; 22.9 (d, J=3.1 Hz)

$^{31}$P NMR (CDCl$_3$, 202 MHz) δ (ppm): 55.29

Step 3: 4-(((benzyloxy)carbonyl)amino)-4-(hydroxy (3phenylpropyl)phosphoryl)butanoic acid The title compound (473 mg, 96%) obtained as an oily residue which crystallised on standing was prepared according to the procedure F from previous product (510 mg, 1.18 mmol, 1.0 eq.) in a mixture of THF/water (4 mL/1 mL) with presence of LiOH.H$_2$O (85 mg, 3.53 mmol, 3.0 eq.).

MS (ESI$^-$): [M−H]$^-$=418

$^1$H NMR (DMSO-d6, 500 MHz) δ (ppm): 11.5 (brs, 1H); 7.43 (d, J=9.5 Hz, 1H); 7.39-7.30 (m, 5H); 7.28 (t, J=7.5 Hz, 2H); 7.22-7.12 (m, 3H); 5.07 (d, J=12.0 Hz, 1H); 5.03 (d, J=12.0 Hz, 1H); 3.69 (m, 1H); 2.58 (d, J=7.5 Hz, 2H); 2.38-2.30 (m, 1H); 2.26-2.20 (m, 1H); 2.04-1.96 (m, 1H); 1.85-1.62 (m, 3H); 1.52 (ddd, J=7.5, 9.0 and 13.5 Hz, 2H)

$^{31}$P NMR (DMSO-d6, 202 MHz) δ (ppm): 46.42

Step 4: 4-amino-4-[hydroxy(3-phenylpropyl)phosphoryl]butanoic acid

The title compound (71 mg, 60%) obtained as a white powder was prepared according to the procedure H for hydrogenolysis from previous product (473 mg, 1.13 mmol, 1.0 eq.) in a mixture EtOH/AcOH (9:1, c=50 mM).

Estimated purity: 90% (based on HPLC)

MS (ESI$^+$): [(M−H$_2$O)+H]$^+$=268.2; [M+H]$^+$=286.2; [(M×2)+H]$^+$=571.5

$^1$H NMR (D20, 500 MHz) δ (ppm): 7.41 (t, J=7.0 Hz, 2H); 7.34 (d, J=7.0 Hz, 2H); 7.30 (t, J=7.0 Hz, 1H); 3.22 (td, J=7.5 and 5.0 Hz, 1H); 2.76 (t, J=7.5 Hz, 2H); 2.59 (td, J=7.5 and 3.5 Hz, 2H); 2.20-2.09 (m, 1H); 1.99-1.82 (m, 3H); 1.71-1.60 (m, 2H)

$^{31}$P NMR (D20, 202 MHz) δ (ppm): 35.79

Example 38: 4-amino-4-[hydroxy({2-[2-(trifluoromethoxy)phenyl]ethyl})phosphoryl]butanoic acid Step 1: 2-[2-(trifluoromethoxy)phenyl]ethan-1-ol A solution of 2-[2-(trifluoromethoxy)phenyl]acetic acid (2.5 g, 11 mmol, 1.0 eq) in anhydrous THF (6 mL) at 0° C. was added dropwise to a lithium aluminium hydride solution (2 M solution in THF, 23 mmol, 11 mL) under argon atmosphere. The reaction was exothermic and the mixture became yellow. The reaction mixture was stirred for 40 min at room temperature, cooled to 0° C. and then quenched slowly with 0.86 mL of H$_2$O. A 15% aqueous solution of NaOH (0.86 mL) and H$_2$O (2.6 mL) were successively added and the mixture was stirred for 15 min. Anhydrous Na$_2$SO$_4$ was added and the mixture was stirred for 15 min. The yellow mixture was filtered over a pad of celite and the filtrate was concentrated under vacuum. The mixture was concentrated and purified by column chromatography to afford the desired intermediate (2 g, 85%) as a clear oil.

MS (ESI$^+$): [M+H]$^+$=207.2

$^1$H NMR (CDCl$_3$, 500 MHz) δ (ppm): 7.35-7.31 (m, 1H); 7.29-7.21 (m, 3H); 3.87 (t, J=6.8 Hz, 2H); 2.96 (t, J=6.7 Hz, 2H); 1.46 (s, 1H)

Step 2: 1-(2-bromoethyl)-2-(trifluoromethoxy)benzene

The product obtained in the previous step (2.0 g, 9.7 mmol, 1.0 eq.) and carbon tetrabromide (5.2 g, 15 mmol, 1.6 eq.) were diluted in CH$_2$Cl$_2$ (50 mL). The solution was cooled at −5° C. and triphenylphosphine (4.1 g, 15 mmol, 1.6 eq) was added in portions. Once the addition was completed, the reaction was stirred at room temperature during 1 h. The mixture was concentrated and purified by column chromatography to afford the expected intermediate (2.27 g, 87%) as a pale yellow oil.

$^1$H NMR (CDCl$_3$, 500 MHz) δ (ppm): 7.33-7.29 (m, 2H); 7.27-7.23 (m, 2H); 3.57 (t, J=7.5 Hz, 2H); 3.24 (t, J=7.5 Hz, 2H)

Step 3: {2-[2-(trifluoromethoxy)phenyl] ethyl}phosphinic acid

The title compound (740 mg, 48%) was prepared according to the procedure B from diethylchlorophosphite (0.87 mL, 6.0 mmol, 1.0 eq.) in anhydrous Et$_2$O (5 mL) followed by addition of the freshly prepared Grignard reagent from 1-(2-bromoethyl)-2-(trifluoromethoxy)benzene in anhydrous Et$_2$O.

MS (ESI$^+$): [M+H]$^+$=255.1; [(M×2)+H]$^+$=509.0

$^1$H NMR (CD$_3$OD, 500 MHz) δ (ppm): 7.69 (t, J=2.0 Hz, 0.5H); 7.35-7.17 (m, 4H); 6.59 (t, J=1.9 Hz, 0.5H); 3.04-2.88 (m, 2H); 2.08 (m, 2H)

$^{31}$P NMR (CD$_3$OD, 202 MHz) δ (ppm): 36.48

Step 4: [4-(benzyloxy)-1-{[(benzyloxy)carbonyl]amino}-4-oxobutyl]([2-[2-(trifluoro methoxy)phenyl] ethyl])phosphinic acid The title compound (800 mg, 47%) obtained as a white solid was prepared according to the procedure D for multi-component reaction from previous product (740 mg, 3.1 mmol, 1 eq.) and NH$_2$Cbz (481 mg, 3.19 mmol, 1.1 eq.) in AcOH (5.2 mL) and AcCl (0.6 mL) followed by addition of the benzyl 4-oxobutanoate (707 mg, 3.48 mmol, 1.2 eq.).

MS (ESI$^+$): [M+H]$^+$=580.2

$^1$H NMR (CD$_3$OD, 500 MHz) δ (ppm): 7.43-7.19 (m, 14H); 5.18-5.00 (m, 4H); 4.08-3.96 (m, 1H); 3.00-2.89 (m, 2H); 2.59-2.44 (m, 2H); 2.30-2.20 (m, 1H); 1.99-1.81 (m, 3H)

$^{31}$P NMR (CD$_3$OD, 202 MHz) δ (ppm): 48.45

Step 5: 4-amino-4-[hydroxy({2-[2-(trifluoromethoxy)phenyl]ethyl})phosphoryl]butanoic acid The title compound (100 mg, 46%) obtained as a white powder was prepared according to the procedure H for hydrogenolysis from previous compound (350 mg, 0.6 mmol, 1.0 eq.) in a mixture EtOH/AcOH (1:1, 10 mL).

Estimated purity: >95% (based on HPLC and NMR)

MS (ESI+): [(M−H$_2$O)+H]+=338.1; [M+H]+=356.1; [(M×2)+H]+=711.3

$^1$H NMR (CD$_3$OD, 500 MHz) δ (ppm): 7.48-7.39 (m, 1H); 7.31-7.21 (m, 3H); 3.12 (td, J=8.4, 5.2 Hz, 1H); 2.98 (q, J=8.4 Hz, 2H); 2.60 (t, J=7.5 Hz, 2H); 2.30-2.16 (m, 1H); 2.01-1.75 (m, 3H)

$^{31}$P NMR (CD$_3$OD, 202 MHz) δ (ppm): 30.36

Example 39: 4-amino-4-[(2-{[1,1'-biphenyl]-2-yl}ethyl)(hydroxy)phosphoryl]butanoic acid

Step 1: ethyl 2-{[1,1'-biphenyl]-2-yl}acetate

Ethyl 2-(2-bromophenyl)acetate (2.5 g, 10 mmol, 1.0 eq.), phenylboronic acid (1.5 g, 12 mmol, 1.2 eq.), potassium carbonate (7.1 g, 51 mmol, 5.0 eq.) and Pd(PPh$_3$)$_4$ (1.2 g, 1.03 mmol, 0.1 eq.) were added in a flask and the atmosphere was purged with argon for 10 min. An argon-degassed 4/1 mixture of dioxane/water (0.2 M, 50 mL) was added. Once the addition was completed, the reaction was stirred at 80° C. during 24 h. The reaction mixture was then cooled to room temperature. Water and CH$_2$Cl$_2$ were added. The aqueous layer was extracted with CH$_2$Cl$_2$ (three times). The combined organic layer was dried over Na$_2$SO$_4$, filtered, and concentrated under vacuum. The mixture was concentrated and purified by column chromatography to afford the title compound (2.39 g, 97%) as a clear oil.

MS (ESI+): [M+H]+=241

$^1$H NMR (CDCl$_3$, 500 MHz) δ (ppm): 7.45-7.20 (m, 9H); 4.08 (q, J=7.1 Hz, 2H); 3.59 (s, 2H); 1.19 (t, J=7.1 Hz, 3H)

Step 2: 2-{[1,1'-biphenyl]-2-yl}ethan-1-ol

A solution of the compound obtained in the previous step (2.4 g, 9.3 mmol, 1.0 eq.) in anhydrous THF (5 mL) at 0° C. was added dropwise to a lithium aluminium hydride solution (2 M solution in THF, 9.9 mL, 20 mmol) under argon atmosphere. The reaction was exothermic and the mixture became yellow. The reaction mixture was stirred for 45 min at room temperature, cooled to 0° C. and then quenched slowly with 0.7 mL of H$_2$O. An aqueous 15% solution of NaOH (0.7 mL) and H$_2$O (2.1 mL) were successively added and the mixture was stirred for 15 min. Anhydrous Na$_2$SO$_4$ was added and the mixture was stirred for 15 min. The yellow mixture was filtered over a pad of celite and the filtrate was concentrated under vacuum to afford the title compound (1.17 g, 590%) as a yellow powder.

MS (ESI+): [(M−H$_2$O)+H]+=181.2

$^1$H NMR (CDCl$_3$, 500 MHz) δ (ppm): 7.49-7.19 (m, 9H); 3.71 (td, J=6.8, 5.7 Hz, 2H); 2.91 (t, J=6.9 Hz, 2H)

Step 3: 2-(2-bromoethyl)-1,1'-biphenyl

The compound obtained in the previous step (1.17 g, 5.90 mmol, 1.0 eq.) and carbon tetrabromide (3.13 g, 9.44 mmol, 1.6 eq.) were diluted in CH$_2$C$_2$ (30 mL). The solution was cooled at −5° C. and triphenylphosphine (2.48 g, 9.44 mmol, 1.6 eq.) was added in portions. Once the addition was completed, the yellow reaction was stirred at room temperature during 1 h. The mixture was concentrated and purified by column chromatography to afford the title compound (1.4 g, 90%).

$^1$H NMR (CDCl$_3$, 500 MHz) δ (ppm): 7.48-7.17 (m, 9H); 3.40-3.29 (m, 2H); 3.17 (dd, J=8.4, 7.2 Hz, 2H)

Step 4: (2-{[1,1'-biphenyl]-2-yl}ethyl)phosphinic acid

The title compound (460 mg, 37%) was prepared according to the procedure B from diethylchlorophosphite (0.74 mL, 5.1 mmol, 1.0 eq.) in anhydrous Et$_2$O (4 mL) followed by addition of the freshly prepared Grignard reagent from 2-(2-bromoethyl)-1,1'-biphenyl in anhydrous Et$_2$O.

MS (ESI+): [M+H]+=247

Step 5: [4-(benzyloxy)-1-{[(benzyloxy)carbonyl]amino}-4-oxobutyl](2-{[1,1'-biphenyl]-2-yl}ethyl)phosphinic acid The title compound (245 mg, 23%) obtained as a white solid was prepared according to the procedure D for multicomponent reaction from previous product (460 mg, 1.9 mmol, 1.0 eq.) and NH$_2$Cbz (313 mg, 2.07 mmol, 1.1 eq.) in AcOH (2.3 mL) and AcCl (0.3 mL) followed by addition of the benzyl 4-oxobutanoate (434 mg, 2.26 mmol, 1.2 eq.).

MS (ESI+): [M+H]+=572.2

$^1$H NMR (CD$_3$OD, 500 MHz) δ (ppm): 7.43-7.09 (m, 19H); 5.28-4.94 (m, 4H); 3.88 (m, 1H); 2.86 (m, 2H); 2.62-2.29 (m, 2H); 2.15-1.99 (m, 1H); 1.87-1.66 (m, 3H)

$^{31}$P NMR (CD$_3$OD, 202 MHz) δ (ppm): 48.47

Step 6: 4-amino-4-[(2-{[1,1'-biphenyl]-2-yl}ethyl)(hydroxy)phosphoryl]butanoic acid The title compound (76 mg, 510%) obtained as a white powder was prepared according to the procedure H for hydrogenolysis from previous compound (245 mg, 0.428 mmol) in a mixture EtOH/AcOH (1:1, 8.0 mL).

Estimated purity: >97% (based on LCMS and NMR)

MS (ESI+): [(M−H$_2$O)+H]+=330.2; [M+H]+=348; [(M×2)+H]+=695.4

$^1$H NMR (CD$_3$OD, 500 MHz) δ (ppm): 7.46-7.39 (m, 2H); 7.39-7.27 (m, 5H); 7.23 (td, J=7.5, 1.4 Hz, 1H); 7.15 (dd, J=7.5, 1.5 Hz, 1H); 2.93-2.84 (m, 3H); 2.45 (t, J=7.4 Hz, 2H); 2.05-1.91 (m, 1H); 1.85-1.63 (m, 3H)

$^{31}$P NMR (CD$_3$OD, 202 MHz) δ (ppm): 31.05

Example 40: 4-amino-4-{[2-(2,3-dichlorophenyl)ethyl](hydroxy)phosphoryl}butanoic acid

Step 1: 1-(2-bromoethyl)-2,3-dichlorobenzene 2-(2,3-dichlorophenyl)ethan-1-ol (1.5 g, 7.8 mmol, 1.0 eq.) and carbon tetrabromide (4.2 g, 12 mmol, 1.6 eq.) were diluted in CH$_2$Cl$_2$ (40 mL). The solution was cooled at −5° C. and triphenylphosphine (3.3 g, 12.0 mmol, 1.6 eq) was added in portions. Once the addition was completed, the yellow reaction was stirred at room temperature during 1 h. The mixture was concentrated and purified by column chromatography to afford the title compound (1.8 g, 90%) as a colorless pale yellow oil.

$^1$H NMR (CDCl$_3$, 500 MHz) δ (ppm): 7.39 (dd, J=7.1, 2.4 Hz, 1H); 7.22-7.13 (m, 2H); 3.60 (t, J=7.4 Hz, 2H); 3.33 (t, J=7.4 Hz, 2H).

Step 2: [2-(2,3-dichlorophenyl)ethyl]phosphinic acid

The title compound (690 mg, 43%) was prepared according to the procedure B from diethylchlorophosphite (1.4 mL, 6.8 mmol, 1.0 eq.) in anhydrous $Et_2O$ (6 mL) followed by addition of the freshly prepared Grignard reagent from 1-(2-bromoethyl)-2,3-dichlorobenzene in anhydrous $Et_2O$.

MS (ESI$^+$): [M+H]$^+$=240
$^1$H NMR (CD$_3$OD, 500 MHz) δ (ppm): 7.65 (t, J=1.9 Hz, 0.5H); 7.50-7.12 (m, 3H); 6.56 (t, J=1.9 Hz, 0.5H); 3.16-2.98 (m, 2H); 2.20-2.03 (m, 2H)
$^{31}$P NMR (CD$_3$OD, 202 MHz): 32.83

Step 3: [4-(benzyloxy)-1-{[(benzyloxy)carbonyl]amino}-4-oxobutyl][2-(2,3-dichlorophenyl) ethyl]phosphinic acid The title compound (1.1 g, 67%) obtained as a yellow solid was prepared according to the procedure D for multicomponent reaction from previous product (690 mg, 2.9 mmol, 1.0 eq.) and NH$_2$Cbz (479 mg, 3.17 mmol, 1.1 eq.) in AcOH (5 mL) and AcCl (0.6 mL) followed by addition of the benzyl 4-oxobutanoate (665 mg, 3.46 mmol, 1.2 eq.).

MS (ESI$^+$): [M+H]$^+$=565
$^1$H NMR (CD$_3$OD, 500 MHz) δ (ppm): 7.48-7.08 (m, 13H); 5.22-4.98 (m, 4H); 4.15-3.90 (m, 1H); 3.21-2.92 (m, 2H); 2.70-2.37 (m, 2H); 2.33-2.22 (m, 1H); 2.13-1.81 (m, 2H); 1.42-1.25 (m, 1H)
$^{31}$P NMR (CD$_3$OD, 202 MHz) δ (ppm): 48.44

Step 4: 4-{[(benzyloxy)carbonyl]amino}-4-{[2-(2,3-dichlorophenyl)ethyl](hydroxy)phosphoryl}butanoic acid The title compound (266 mg, 29%) obtained as a pale yellow solid was prepared according to the procedure F from the product obtained in the previous step (1.1 g, 1.9 mmol, 1.0 eq.) in a mixture of THF/water (3/1, 20 mL) with presence of LiOH.H$_2$O (245 mg, 5.85 mmol, 3.0 eq.).

MS (ESI$^+$): [M+H]$^+$=474.0
$^1$H NMR (CD$_3$OD, 500 MHz) δ (ppm): 7.50-7.12 (m, 8H); 5.26-5.01 (m, 2H); 4.05 (ddd, J=11.9, 8.7, 3.5 Hz, 1H); 3.16-2.97 (m, 2H); 2.55-2.36 (m, 2H); 2.34-2.17 (m, 1H); 2.02-1.68 (m, 3H)
$^{31}$P NMR (CD$_3$OD, 202 MHz) δ (ppm): 48.45

Step 5: 4-amino-4-{[2-(2,3-dichlorophenyl)ethyl](hydroxy)phosphoryl}butanoic acid The title compound (39 mg, 20%) obtained as a white solid was prepared according to the procedure G from previous product (266 mg, 561 µmol, 1.0 eq.) in TFA/anisole (1.7 mL/1.2 mL).

Estimated purity: >95% (based on LCMS and NMR)
MS (ESI$^+$): [(M−H$_2$O)+H]$^+$=323; [M+H]$^+$=341; [(M×2)+H]$^+$=681.1
$^1$H NMR (CD$_3$OD, 500 MHz) δ (ppm): 7.40 (dd, J=8.0, 1.5 Hz, 1H); 7.35 (dd, J=7.7, 1.6 Hz, 1H); 7.24 (t, J=7.8 Hz, 1H); 3.21-3.14 (m, 1H); 3.13-3.05 (m, 2H); 2.64 (t, J=7.3 Hz, 2H); 2.33-2.21 (m, 1H); 2.08-1.83 (m, 3H)
$^{31}$P NMR (CD$_3$OD, 202 MHz) δ (ppm): 30.29

Example 41: 4-amino-4-{[2-(3-chloro-2-methoxyphenyl)ethyl](hydroxy)phosphoryl}butanoic acid

Step 1: 3-chloro-2-methoxybenzaldehyde

To a solution of 3-chloro-2-hydroxy-benzaldehyde (3.0 g, 19 mmol, 1.0 eq.) in DMF (28 mL) was added K$_2$C$_{O3}$ (4.0 g, 29 mmol, 1.5 eq) and methyl iodide (1.92 mL, 30.6 mmol, 1.6 eq). The mixture took instantaneously a yellow coloration and was stirred at room temperature for 3 h. Diluted with water (140 nL) and transferred into a separatory funnel, the aqueous layer was then extracted twice with EtOAc. The organic extracts were dried over Na$_2$SO$_4$, filtered and concentrated in vacuo. The crude was purified by column chromatography to afford the title product (3 g, 92%) as a clear solid.

MS (ESI$^+$): [M+H]$^+$=171.1
$^1$H NMR (CDCl$_3$, 500 MHz) δ (ppm): 10.38 (d, J=0.8 Hz, 1H); 7.76 (dd, J=7.8, 1.7 Hz, 1H); 7.64 (dd, J=7.9, 1.7 Hz, 1H); 7.19 (dd, J=7.9, 0.8 Hz, 1H); 4.01 (s, 3H)

Step 2: 1-chloro-2-methoxy-3-[2-methoxyethenyl]benzene

To a suspension of methoxymethyltriphenylphosphonium chloride (10.5 g, 30.6 ol, 1.0 eq) in dry THF (88 mL) at 0° C., under argon atmosphere was added KOtBu (4.4 g, 39 mmol, 1.3 eq) in one portion. The suspension was stirred for a further 10 min at 0° C. The product obtained in the previous step (3.0 g, 18 mmol, 0.58 eq) was added in small portion. After 30 min, the reaction was quenched with water (50 mL) and diluted with ether (50 mL). The organic phase was separated. The aqueous phase was extracted with additional ether (2×50 mL). The combined organics layers were washed with brine and dried over Na$_2$SO$_4$, filtered and concentrated in vacuo to afford the title compound (4 g, 71%).

MS (ESI$^+$): [M+H]$^+$=199.1
$^1$H NMR (CDCl$_3$, 500 MHz) δ (ppm): 7.94 (dd, J=7.9, 1.6 Hz, 0.5H); 7.22-7.09 (m, 2H); 6.97 (dt, J=22.3, 7.9 Hz, 1H); 6.23 (d, J=7.2 Hz, 0.5H); 5.99 (d, J=13.0 Hz, 0.5H); 5.57 (d, J=7.2 Hz, 0.5H); 3.83-3.70 (m, 6H)

Step 3: 2-(3-chloro-2-methoxyphenyl)acetaldehyde

To a solution of the product obtained in the previous step (4.0 g, 20 mmol, 1 eq) in THF (110 mL) was added 10 mL of aqueous HCl 10% solution. The mixture was heated at reflux for 1 h. After 1 h, an additional 2 mL of aqueous HCl 10% solution was added and heated at reflux for 6 h. After cooling down to room temperature, the reaction mixture was treated with a saturated aqueous solution of NaHCO$_3$ until neutralization. The mixture was concentrated under reduced pressure then diluted with water and MTBE. The organic phase was separated. The aqueous phase was extracted with additional MTBE. The combined organics layers were washed with brine and dried over Na$_2$SO$_4$, filtered and concentrated in vacuo to afford the title compound (2.74 g, 74%).

MS (ESI$^+$): [M+H]$^+$=185.1
$^1$H NMR (CDCl$_3$, 500 MHz) δ (ppm): 9.74 (t, J=2.0 Hz, 1H); 7.34 (dd, J=7.8, 1.9 Hz, 1H); 7.16-6.97 (m, 3H); 3.83 (s, 3H); 3.73 (d, J=2.0 Hz, 2H)

Step 4: 2-(3-chloro-2-methoxyphenyl)ethan-1-ol

To a solution of the product obtained in the previous step (2.7 g, 15 mmol, 1.0 eq) in MeOH (75 mL) at 0° C. was added by portions NaBH$_4$ (674 mg, 17.8 µmol, 1.2 eq). The mixture was stirred at room temperature for 45 min. The mixture was concentrated under reduced pressure then diluted with water and EtOAc. The organic phase was separated. The aqueous phase was extracted with EtOAc. The combined organics layers were washed with brine and dried over Na$_2$SO$_4$, filtered and concentrated in vacuo. The residue was purified by column chromatography to afford the title compound (1.4 g, 50%) as a yellow oil.

MS (ESI$^+$): [(M−H$_2$O)+H]$^+$=169.1; [M+H]$^+$=187.1

$^1$H NMR (CDCl$_3$, 500 MHz) δ (ppm): 7.28-7.25 (m, 1H); 7.18-7.09 (m, 1H); 7.01 (t, J=7.8 Hz, 1H); 3.87 (s, 5H); 2.93 (t, J=6.5 Hz, 2H)

Step 5: 1-(2-bromoethyl)-3-chloro-2-methoxybenzene 2-(3-chloro-2-methoxyphenyl)ethan-1-ol (1.4 g, 7.5 mmol, 1.0 eq.) and carbon tetrabromide (4 g, 12 mmol, 1.6 eq.) were diluted in CH$_2$Cl$_2$ (40 mL). The solution was cooled at −5° C. and triphenylphosphine (3.2 g, 12 mmol, 1.6 eq) was added in portions. Once the addition was completed, the yellow reaction was stirred at room temperature during 45 minutes. The mixture was concentrated and purified by column chromatography to afford the title compound (1.6 g, 85%) as a pale yellow oil.

$^1$H NMR (CDCl$_3$, 500 MHz) δ (ppm): 7.29 (dd, J=8.0, 1.6 Hz, 1H); 7.13-7.10 (m, 1H); 7.01 (t, J=7.8 Hz, 1H); 3.88 (s, 3H); 3.58 (dd, J=7.9, 7.3 Hz, 2H); 3.20 (t, J=7.6 Hz, 2H)

Step 6: [2-(3-chloro-2-methoxyphenyl)ethyl]phosphinic acid

The title compound (245 mg, 17%) was prepared according to the procedure B from diethylchlorophosphite (0.67 mL, 6.1 mmol, 1.0 eq.) in anhydrous Et$_2$O (2.2 mL) followed by addition of the freshly prepared Grignard reagent from 1-(2-bromoethyl)-3-chloro-2-methoxybenzene in anhydrous Et$_2$O.

MS (ESI$^+$): [M+H]$^+$=235.1

$^1$H NMR (CD$_3$OD, 500 MHz) δ (ppm): 7.59 (t, J=1.9 Hz, 0.5H); 7.28 (dd, J=8.0, 1.6 Hz, 1H); 7.21 (dd, J=7.7, 1.6 Hz, 1H); 7.05 (t, J=7.8 Hz, 1H); 6.51 (t, J=1.9 Hz, 0.5H); 3.86 (s, 3H); 2.98-2.88 (m, 2H); 2.10-2.00 (m, 2H)

$^{31}$P NMR (CD$_3$OD, 202 MHz) δ (ppm): 33.58

Step 7: [4-(benzyloxy)-1-{[(benzyloxy)carbonyl]amino}-4-oxobutyl][2-(3-chloro-2-methoxy phenyl)ethyl]phosphinic acid The title compound (400 mg, 68%) obtained as a white solid was prepared according to the procedure D for multicomponent reaction from previous product (245 mg, 1.04 mmol, 1.0 eq.) and NH$_2$Cbz (174 mg, 1.25 mmol, 1.1 eq.) in AcOH (2 mL) and AcCl (0.9 mL) followed by addition of the benzyl 4-oxobutanoate (240 mg, 1.25 mmol, 1.2 eq.).

MS (ESI$^+$): [M+H]$^+$=560.1

$^1$H NMR (CD$_3$OD, 500 MHz) δ (ppm): 7.44-7.16 (m, 11H); 7.09 (d, J=7.5 Hz, 1H); 7.01 (t, J=7.8 Hz, 1H); 5.25-5.20 (m, 4H); 3.80 (s, 3H); 2.91 (q, J=7.9 Hz, 2H); 2.68-2.41 (m, 3H); 2.27 (m, 1H); 1.93 (m, 3H)

$^{31}$P NMR (CD$_3$OD, 202 MHz) δ (ppm): 48.66

Step 8: 4-{[(benzyloxy)carbonyl]amino}-4-{[2-(3-chloro-2-methoxyphenyl)ethyl](hydroxy)phosphoryl}butanoic acid The title compound (327 mg, 97%) was prepared according to the procedure F from the product obtained in the previous step (400 mg, 0.7 mmol, 1.0 eq.) in a mixture of THF/water (3 mL/0.5 mL) with presence of LiOH.H$_2$O (60 mg, 1.4 mmol, 2.0 eq.).

MS (ESI$^+$): [M+H]$^+$=470.1

$^1$H NMR (CD$_3$OD, 500 MHz) δ (ppm): 7.44-7.21 (m, 6H); 7.12 (dd, J=7.7, 1.6 Hz, 1H); 7.03 (t, J=7.8 Hz, 1H); 5.14 (m, 2H); 4.05 (td, J=9.2, 8.6, 5.0 Hz, 1H); 3.83 (s, 3H); 2.95 (dt, J=10.7, 7.0 Hz, 2H); 2.57-2.36 (m, 2H); 2.33-2.17 (m, 1H); 2.07-1.82 (m, 3H)

$^{31}$P NMR (CD$_3$OD, 202 MHz) δ (ppm): 51.27

Step 9: 4-amino-4-{[2-(3-chloro-2-methoxyphenyl)ethyl](hydroxy)phosphoryl}butanoic acid The title compound (69 mg, 29%) obtained as a white solid was prepared according to the procedure G from previous product (327 mg, 695 μmol, 1.0 eq.) in TFA/anisole (2.14 mL/1.5 mL).

Estimated purity: >95% (based on LCMS and NMR)

MS (ESI$^+$): [(M−H$_2$O)+H]$^+$=318.1; [M+H]$^+$=336.1; [(M×2)+H]$^+$=671.2

MS (ESI$^-$): [M−H]$^-$=334.1

$^1$H NMR (CD$_3$OD, 500 MHz) δ (ppm): 7.23 (m, 2H); 7.03 (t, J=7.8 Hz, 1H); 3.86 (s, 3H); 3.13 (td, J=8.5, 5.1 Hz, 1H); 2.95 (q, J=8.1 Hz, 2H); 2.61 (t, J=7.2 Hz, 2H); 2.30-2.20 (m, 1H); 2.03-1.79 (m, 3H)

$^{31}$P NMR (CD$_3$OD, 202 MHz) δ (ppm): 30.85

Example 42: 3-carboxy-1-{hydroxy[2-(1-methyl-1H-indol-3-yl)ethyl]phosphoryl}propan-1-aminium chloride

Step 1: methyl 2-(1-methyl-1H-indol-3-yl)acetate

To 2-(1-methyl-1H-indol-3-yl)acetic acid (3.0 g, 16 mmol, 1.0 eq.) in MeOH (30 mL) at 0° C. was added concentrated H$_2$SO$_4$ (6 drops). The reaction mixture was stirred overnight at room temperature. The mixture was concentrated under reduced pressure. The residue was diluted with EtOAc and aqueous saturated NaHCO$_3$ and transferred into a separatory funnel. The organic layer was extracted twice with EtOAc and washed with aqueous saturated NaHCO$_3$.

The organic extracts were dried over Na$_2$SO$_4$, filtered and concentrated in vacuo to afford the title product (3.17 g, 98%) as a brown oil.

MS (ESI$^+$): [M+H]$^+$=204.1

$^1$H NMR (CDCl$_3$, 500 MHz) δ (ppm): 7.60 (dt, J=7.9, 1.0 Hz, 1H); 7.30 (dt, J=8.2, 0.9 Hz, 1H); 7.24 (ddd, J=8.2, 7.0, 1.2 Hz, 1H); 7.13 (ddd, J=8.0, 7.0, 1.1 Hz, 11H); 7.05 (d, J=1.0 Hz, 1H); 3.77 (m, 5H); 3.70 (s, 3H)

Step 2: 2-(1-methyl-1H-indol-3-yl)ethan-1-ol

A solution of the compound obtained in the previous step (3.2 g, 15 ol, 1.0 eq.) in anhydrous THF (8 mL) at 0° C. was added dropwise to a lithium aluminium hydride solution (2 M solution in THF, 16 mL, 32 mmol) under argon atmosphere. The reaction was exothermic and the mixture became yellow. The reaction mixture was stirred for 40 min at room temperature, cooled to 0° C. and then quenched slowly with 1.2 mL of H$_2$O, 1.2 mL of 15% aqueous solution of NaOH and then 3.5 mL of H$_2$O. The mixture was stirred for 15 min. Anhydrous Na$_2$SO$_4$ was added and the mixture was further stirred for 15 min. The yellow mixture was filtered over a pad of celite and the filtrate was concentrated under vacuum to afford the title product (2.7 g, 99%) as a clear oil.

MS (ESI$^+$): [M+H]$^+$=176.2

$^1$H NMR (CDCl$_3$, 500 MHz) δ (ppm): 7.61 (dt, J=7.9, 1.0 Hz, 1H); 7.31 (dt, J=8.2, 0.9 Hz, 1H); 7.25-7.22 (m, 1H);

7.12 (ddd, J=8.0, 6.9, 1.1 Hz, 1H); 6.95 (s, 1H); 3.90 (t, J=6.3 Hz, 2H); 3.77 (s, 3H); 3.03 (td, J=6.4, 0.8 Hz, 2H)

Step 3: 3-(2-bromoethyl)-1-methyl-1H-indole

To a solution of the compound obtained in the previous step (1.5 g, 8.6 mmol, 1.0 eq.) in $CH_2Cl_2$ (43 mL) was added carbon tetrabromide (4.5 g, 14 mmol, 1.6 eq.). The solution was cooled in an ice/salt bath and triphenylphosphine (3.6 g, 14 mmol, 1.6 eq.) was added in portions. When the addition was completed, the yellow reaction was warmed to room temperature for 45 min. The mixture was concentrated under reduced pressure. The residue was purified by column chromatography to afford the title compound (1.6 g, 79%) as a pale yellow oil.

MS (ESI$^+$): [(M−Br]$^+$=158.2
$^1$H NMR (CDCl$_3$, 500 MHz) δ (ppm): 7.58 (dt, J=7.9, 1.0 Hz, 1H); 7.31 (dt, J=8.2, 0.9 Hz, 1H); 7.26-7.22 (m, 1H); 7.13 (ddd, J=8.0, 7.0, 1.1 Hz, 1H); 6.95 (d, J=0.9 Hz, 1H); 3.77 (s, 3H); 3.62 (dd, J=8.1, 7.3 Hz, 2H); 3.33 (td, J=7.7, 0.8 Hz, 2H)

Step 4: [2-(1-methyl-1H-indol-3-yl)ethyl]phosphinic acid

The title compound (950 mg, 65%) was prepared according to the procedure B from diethylchlorophosphite (0.71 mL, 6.5 mmol, 1.0 eq.) in anhydrous Et$_2$O (3 mL) followed by addition of the freshly prepared Grignard reagent from 3-(2-bromoethyl)-1-methyl-1H-indole in anhydrous Et$_2$O.

MS (ESI$^+$): [M+H]$^+$=224.1
$^1$H NMR (CDCl$_3$, 500 MHz) δ (ppm): 7.70 (t, J=2.1 Hz, 0.5H); 7.60 (dt, J=8.0, 1.0 Hz, 1H); 7.31 (dt, J=8.2, 0.9 Hz, 1H); 7.25 (ddd, J=8.2, 6.9, 1.1 Hz, 1H); 7.13 (ddd, J=8.0, 6.9, 1.1 Hz, 1H); 6.90 (s, 1H); 6.60 (t, J=2.1 Hz, 0.5H); 3.75 (s, 3H); 3.18-3.06 (m, 2H); 2.21 (dddd, J=15.6, 10.0, 6.1, 2.1 Hz, 2H)
$^{31}$P NMR (CDCl$_3$, 202 MHz) δ (ppm): 38.65

Step 5: benzyl [2-(1-methyl-1H-indol-3-yl)ethyl]phosphinate

To a solution of the product obtained in the previous step (450 mg, 2.02 mmol, 1.0 eq.) and benzylalcohol (241 μL, 2.32 mmol, 1.15 eq.) in $CH_2Cl_2$ (33 mL) was added EDCI (773 mg, 4.03 mmol, 2 eq.) as solid in one portion. The reaction mixture was stirred at room temperature overnight. The reaction mixture was transferred into a separatory funnel and washed with saturated aqueous solution of NaHCO$_3$ (2×), then with brine. The organic extract was dried over Na$_2$SO$_4$, filtered and concentrated in vacuo. The residue was purified by column chromatography to afford the title compound (434 mg, 78%) as a pale yellow oil.

MS (ESI$^+$): [M+H]$^+$=314.1; [(M×2)+H]$^+$=627.3
$^1$H NMR (CD$_3$OD, 500 MHz) δ (ppm): 7.59 (t, J=2.1 Hz, 0.5H); 7.51 (dt, J=7.9, 1.0 Hz, 1H); 7.40-7.29 (m, 6H); 7.16 (ddd, J=8.2, 7.0, 1.2 Hz, 1H); 7.04 (ddd, J=8.0, 7.0, 1.0 Hz, 1H); 6.97 (d, J=1.0 Hz, 1H); 6.49 (t, J=2.1 Hz, 0.5H); 5.15-4.97 (m, 2H); 3.71 (s, 3H); 3.05 (m, 2H); 2.30-2.17 (m, 2H)
$^{31}$P NMR (CD$_3$OD, 202 MHz) δ (ppm): 41.58

Step 6: benzyl 4-[(benzyloxy)[2-(1-methyl-1H-indol-3-yl)ethyl]phosphoryl]-4-[(2-methylpropane-2-sulfinyl)amino]butanoate The title compound (579 mg, 69%) was prepared according to the procedure E from previous product (434 mg, 1.39 mmol, 1.5 eq.) and cesium carbonate (753 mg, 2.31 mmol, 2.5 eq.) in $CH_2Cl_2$ (2.2 mL) followed by addition of a solution of the racemic benzyl (4E)-4-[(2-methylpropane-2-sulfinyl)imino]butanoate (273 mg, 0.924 mmol, 1.0 eq.) in $CH_2Cl_2$ (2.2 mL).

MS (ESI$^+$): [M+H]$^+$=609.3
$^1$H NMR (CD$_3$OD, 500 MHz) δ (ppm): 7.60-7.44 (m, 1H); 7.42-7.27 (m, 11H); 7.20-7.11 (m, 1H); 7.08-6.98 (m, 1H); 6.99-6.93 (m, 1H); 5.16-4.91 (m, 4H); 4.59 (s, 11H); 4.10 (q, J=7.1 Hz, 1H); 3.75-3.36 (m, 2H); 3.11-2.93 (m, 2H); 2.68-2.12 (m, 5H); 1.98-1.78 (m, 1H); 1.27-1.09 (m, 9H)
$^{31}$P NMR (CD$_3$OD, 202 MHz) δ (ppm): 57.02; 56.61; 56.31 and 56.05

Step 7: 4-{hydroxy[2-(1-methyl-JH-indol-3-yl)ethyl]phosphoryl}-4-[(2-methylpropane-2-sulfinyl)amino]butanoic acid The title compound (350 mg, 86%) was prepared according to the procedure F from the product obtained in the previous step (580 mg, 0.95 μmol, 1.0 eq.) in a mixture of THF/water (5/1, 4.7 mL) with presence of LiOH.H$_2$O (120 mg, 2.85 mmol, 3.0 eq.).

MS (ESI$^+$): [M+H]$^+$=429.1
$^1$H NMR (CD$_3$OD, 500 MHz) δ (ppm): 7.61-7.53 (m, 1H); 7.37-7.29 (m, 1H); 7.19-7.13 (m, 1H); 7.06-6.99 (m, 2H); 3.75 (s, 3H); 3.47-3.38 (m, 1H); 3.05 (m, 2H); 2.69-2.06 (m, 5H); 1.90 (m, 11H); 1.22 (m, 9H)
$^{31}$P NMR (CD$_3$OD, 202 MHz) δ (ppm): 49.53

Step 8: 3-carboxy-1-{hydroxy[2-(1-methyl-JH-indol-3-yl)ethyl]phosphoryl}propan-1-aminium chloride The title compound (122 mg, 41%) obtained as a beige powder was prepared according to the procedure G from previous product (350 mg, 0.815 mmol, 1.0 eq.) with 4.0 M HCl solution in dioxane (4.5 mL, 22 eq.).

Estimated purity: >97% (based on LCMS and NMR)
MS (ESI$^+$): [(M−H$_2$O)+H]$^+$=307.1; [M+H]$^+$=325.1; [(M×2)+H]$^+$=649.3
MS (ESI$^-$): [M−H]$^-$=323.1; [(M×2)−H]$^-$=647.3
$^1$H NMR (CD$_3$OD, 500 MHz) δ (ppm): 7.59 (dt, J=7.9, 1.0 Hz, 1H); 7.37-7.30 (m, 1H); 7.19-7.15 (m, 1H); 7.09-6.96 (m, 2H); 3.75 (s, 3H); 3.24-3.14 (m, 1H); 3.09 (dt, J=10.6, 8.1 Hz, 2H); 2.58-2.39 (m, 2H); 2.27-2.14 (m, 3H); 2.00-1.87 (m, 1H)
$^{31}$P NMR (CD$_3$OD, 202 MHz) δ (ppm): 40.27

Example 43: 3-carboxy-1-({2-[2-(cyclohexyloxy)phenyl]ethyl}(hydroxy)phosphoryl) propan-1-aminium chloride Step 1: methyl 2-[2-(cyclohexyloxy)phenyl]acetate To a solution of methyl 2-(2-hydroxyphenyl)acetate (2.0 g, 12 mmol, 1.0 eq.), cyclohexanol (1.81 g, 18.1 mmol, 1.5 eq.) and triphenylphosphine (3.79 g, 14.4 mmol, 1.2 eq.) in THF (24 mL) at 0° C., was added di-tert-butyl azodicarboxylate (3.33 g, 14.4 mmol, 1.2 eq.). The reaction mixture was stirred at room temperature for 18 h. The reaction mixture was concentrated under reduced pressure and the resulting thick syrup was triturated in pentane/Et$_2$O (1/1, 100 mL). The resulting suspension was filtered over fritted glass (pentane/Et$_2$O: 1/1 washes) and the filtrates were concentrated under reduced pressure. The residue was purified by column chromatography to afford the title compound (1.35 g 45%) as a colorless oil.

MS (ESI+): [M+H]+=249.2

1H NMR (CDCl3, 500 MHz) δ (ppm): 7.26-7.18 (m, 2H); 6.95-6.85 (m, 2H); 4.33 (m, 1H); 3.71 (s, 3H); 3.65 (s, 2H); 1.98-1.89 (m, 2H); 1.83-1.74 (m, 2H); 1.65-1.50 (m, 3H); 1.45-1.35 (m, 3H)

Step 2: 2-[2-(cyclohexyloxy)phenyl]ethan-1-ol

To a commercial solution of LiAlH4 (2.0 M in THF, 5.4 mL, 10.8 mmol, 2 eq.) at 0° C., was added dropwise a solution of the product obtained in the previous step (1.35 g, 5.42 mmol, 1 eq.) in THF (10 mL). The mixture was stirred at room temperature for 1 h. After cooling down to 0° C., water (650 µL), aqueous solution of 15% NaOH (650 µL) and water again (2 mL) were added. After stirring for 15 min, Na2SO4 was added and the suspension was filtered over celite (MTBE rinses). The filtrate was concentrated under reduced pressure. The residue was purified by column chromatography to afford the title compound (1.19 g, 100%) as a pungent colorless oil.

MS (ESI+): [M+H]+=221.2

1H NMR (CDCl3, 500 MHz) δ (ppm): 7.26-7.15 (m, 2H); 6.92-6.88 (m, 2H); 4.34 (m, 1H); 3.88 (m, 2H); 2.95 (t, J=6.3 Hz, 2H); 2.05-1.95 (m, 2H); 1.92 (br s, 1H); 1.86-1.75 (m, 2H); 1.65-1.55 (m, 3H); 1.46-1.35 (m, 3H)

Step 3: 1-(cyclohexyloxy)-2-(2-iodoethyl)benzene

To a solution of triphenylphosphine (774 mg, 2.95 mmol, 1.3 eq.) in CH2Cl2 (15 mL) at 0° C., was added I2 (749 mg, 2.95 mmol, 1.3 eq.). The mixture was stirred at 0° C. for 15 min and imidazole (201 mg, 2.95 mmol, 1.3 eq.) and a solution of the previous compound (500 mg, 2.27 mmol, 1.0 eq.) were added. The mixture was stirred at room temperature for 1 h. The reaction mixture was partitioned between EtOAc and saturated aqueous solution of Na2S2O3, triggering a decoloration. The layers were separated and the organic phase was washed with brine, dried over Na2SO4, filtered and concentrated under reduced pressure. The residue was purified by column chromatography to afford the title compound (657 mg, 88%) as a colorless oil.

MS (ESI+): [(M−I)+]=203.2

1H NMR (CDCl3, 500 MHz) δ (ppm): 7.23 (td, J=7.8, 1.8 Hz, 1H), 7.15 (dd, J=7.6, 1.8 Hz, 1H); 6.90-6.86 (m, 2H); 4.34 (m, 1H); 3.42 (t, J=7.6 Hz, 2H); 3.22 (t, J=7.6 Hz, 2H); 2.01-1.92 (m, 2H); 1.86-1.76 (m, 2H); 1.67-1.54 (m, 3H); 1.49-1.38 (m, 3H)

Step 4: phosphine-borane complex intermediate

The title compound (542 mg, 81%) obtained as a colorless oil was prepared according to the first step of the procedure C from the product obtained previously (650 mg, 1.97 mmol, 1.0 eq.) in THF (3 mL) with presence of (BH3)P(OEt)2H (321 mg, 2.36 mmol, 1.2 eq.) in THF (7 mL) and LiHMDS (1.0 M solution in THF, 2.36 mL, 2.36 mmol, 1.2 eq.).

MS (ESI+): [(M−H2)+H]+=337.2

1H NMR (CD3OD, 500 MHz) δ (ppm): 6.95-6.88 (m, 2H); 6.69 (d, J=7.9 Hz, 1H); 6.60 (td, J=7.5, 1.2 Hz, 1H); 4.18 (m, 1H); 4.90-3.75 (m, 4H); 2.60 (m, 2H); 1.82 (m, 2H); 1.77-1.68 (m, 2H); 1.65-1.55 (m, 2H); 1.45-1.30 (m, 3H); 1.28-1.16 (m, 3H); 1.07 (t, J=7.0 Hz, 6H); 0.65-0.00 (m, 3H)

Step 5: benzyl {2-[2-(cyclohexyloxy)phenyl]ethyl}phosphinate

The title compound (108 mg, 210%) obtained as a colorless oil was prepared according to a variant of the second step of the procedure C from the product obtained previously (540 mg, 1.60 mmol, 1.0 eq.) in DCM (8 mL) with presence of HBF4.Et2O (1.09 mL, 7.98 mmol, 5.0 eq.), followed by addition of BnOH (224 mg, 2.08 mmol, 1.3 eq.) and EDCI.HCl (460 mg, 2.40 mmol, 1.5 eq.).

MS (ESI+): [M+H]+=359.2; [(M×2)+H]+=717.4

1H NMR (CDCl3 500 MHz) δ (ppm): 7.45-7.35 (m, 5H); 7.21-7.16 (m, 1H); 7.16 (dm, J=533 Hz, 1H); 7.13 (dd, J=7.4, 1.7 Hz, 1H); 6.88-6.83 (m, 2H); 5.17 (dd, J=11.9, 9.8 Hz, 1H); 5.07 (dd, J=11.9, 8.3 Hz, 1H); 4.32 (m, 1H); 2.96-2.87 (m, 2H); 2.26-2.13 (m, 2H); 1.99-1.91 (m, 2H); 1.85-1.73 (m, 2H); 1.62-1.53 (m, 3H); 1.47-1.33 (m, 3H)

31P NMR (CDCl3, 202 MHz) δ (ppm): 39.02

Step 6: benzyl 4-[(benzyloxy)({2-[2-(cyclohexyloxy)phenyl]ethyl})phosphoryl]-4-[(2-methylpropane-2-sulfinyl)amino]butanoate The title compound (134 mg, 70%) obtained as a mixture of four diastereoisomers as an orange oil was prepared according to the procedure E from previous product (105 mg, 0.293 mmol, 1.0 eq.) and cesium carbonate (143 mg, 0.439 mmol, 1.5 eq.) in CH2Cl2 (1 mL) followed by addition of a solution of the racemic benzyl (4E)-4-[(2-methylpropane-2-sulfinyl) imino]butanoate (113 mg, 0.38 mmol, 1.3 eq.) in CH2Cl2 (0.5 mL).

MS (ESI+): [M+H]+=654.3

1H NMR (CD3OD, 500 MHz) δ (ppm): 7.50-7.30 (m, 10H); 7.20-7.05 (m, 2H); 6.95-6.80 (m, 2H); 5.20-5.00 (m, 4H); 4.40-4.30 (m, 1H); 3.75-3.60 (m, 1H); 2.98-2.78 (m, 2H); 2.75-2.50 (m, 2H); 2.50-2.15 (m, 3H); 2.05-1.90 (m, 3H); 1.85-1.71 (m, 2H); 1.63-1.47 (m, 3H); 1.45-1.30 (m, 3H); 1.27-1.17 (m, 9H)

31P NMR (CD3OD, 202 MHz) δ (ppm): 56.69; 56.58; 55.73; 55.49

Step 7: 4-({2-[2-(cyclohexyloxy)phenyl]ethyl}(hydroxy)phosphoryl)-4-[(2-methylpropane-2-sulfinyl)amino]butanoic acid The title compound (82 mg, 86%) obtained as a white solid was prepared according to the procedure F from the diastereomeric mixture obtained in the previous step (132 mg, 0.202 mmol, 1.0 eq.) in a mixture of THF/water (4/1, 2.0 mL) with presence of LiOH.H2O (14.5 mg, 0.606 mmol, 3.0 eq.).

MS (ESI+): [M+H]+=474.2

MS (ESI−): [M−H]−=472.2

Step 8: 3-carboxy-1-({2-[2-(cyclohexyloxy)phenyl]ethyl}(hydroxy)phosphoryl)propan-1-aminium chloride The title compound (40 mg, 57%) obtained as a white solid was prepared according to the procedure G from previous product (90 mg, 0.240 mmol, 1.0 eq.) with 4.0 M HCl solution in dioxane (1.73 mL, 6.93 mmol, 40 eq.).

Estimated purity: >95% (based on LCMS and NMR)

MS (ESI+): [(M×2)+H]+=739.4

MS (ESI−): [M−H]−=368.1; [(M×2)−H]−=737.4

1H NMR (CD3OD, 500 MHz) δ (ppm): 7.24-7.16 (m, 2H); 6.97 (d, J=7.8 Hz, 1H); 6.92 (t, J=7.4 Hz, 1H); 4.40 (m, 1H); 3.38 (m, 1H); 3.03-2.90 (m, 2H); 2.68-2.53 (m, 2H); 2.30-2.10 (m, 3H); 2.08-1.96 (m, 3H); 1.89-1.79 (m, 2H); 1.67-1.55 (m, 3H); 1.53-1.35 (m, 3H)

$^{31}$P NMR (CD$_3$OD, 202 MHz) δ (ppm): 42.40

Example 44: 3-carboxy-1-[hydroxy({2-[2-(2-methoxyethoxy)phenyl]ethyl})phosphoryl]propan-1-aminium chloride Step 1: 2-[2-(2-methoxyethoxy)phenyl]ethan-1-ol To a solution of commercially available 2-(2-hydroxyethyl)phenol (1.0 g, 7.2 mmol, 1.0 eq.) and 1-bromo-2-methoxyethane (1.09 mL, 11.6 mmol, 1.6 eq.) in DMF (7.2 mL) at room temperature, was added K$_2$CO$_3$ (2.0 g, 14.5 mmol, 2.0 eq.). The resulting suspension was stirred at 80° C. for 4 h. After cooling down to room temperature, the reaction mixture was partitioned between water and EtOAc and the layers were separated. The aqueous phase was extracted with EtOAc. The combined organic extracts were washed with water and brine, then dried over Na$_2$SO$_4$, filtered and concentrated under reduced pressure. The residue was purified by column chromatography to afford the title compound (1.25 g, 88%) as a colorless oil.

MS (ESI$^+$): [M+H]$^+$=197.2

$^1$H NMR (CDCl$_3$, 500 MHz) δ (ppm): 7.26-7.16 (m, 2H); 6.95 (td, J=7.4, 1.1 Hz, 1H); 6.89 (d, J=6.2 Hz, 1H); 4.17 (m, 2H); 3.87 (t, J=6.2 Hz, 2H); 3.79 (m, 2H); 3.47 (s, 3H); 2.96 (t, J=6.2 Hz, 2H); 2.11 (br s, 1H)

Step 2: 1-(2-iodoethyl)-2-(2-methoxyethoxy)benzene

To a solution of triphenylphosphine (768 mg, 2.93 mmol, 1.3 eq.) in DCM (15 mL) at 0° C., was added I$_2$ (743 mg, 2.93 mmol, 1.3 eq.). The mixture was stirred at 0° C. for 15 min and imidazole (199 mg, 2.93 mmol, 1.3 eq.) and the product obtained in the previous step (442 mg, 2.25 mmol, 1 eq.) were added. The mixture was stirred at room temperature for 1 h. The reaction mixture was partitioned between EtOAc and a saturated aqueous solution of Na$_2$S$_2$O$_3$, triggering a decoloration. The layers were separated and the organic phase was washed with brine, dried over Na$_2$SO$_4$, filtered and concentrated under reduced pressure. The residue was purified by column chromatography to afford the title compound (625 mg, 90%) as a colorless oil.

MS (ESI$^+$): [M−I]$^+$=179.2

$^1$H NMR (CDCl$_3$, 500 MHz) δ (ppm): 7.26 (td, J=7.8, 1.8 Hz, 1H); 7.16 (d, J=7.4 Hz, 1H); 6.93 (t, J=7.5 Hz, 1H); 6.88 (d, J=8.2 Hz, 1H); 4.16 (m, 2H); 3.79 (m, 2H); 3.49 (s, 3H); 3.43 (t, J=7.8 Hz, 2H); 3.24 (t, J=7.8 Hz)

Step 3: phosphine-borane complex intermediate

The title compound (440 mg, 69%) obtained as a colorless oil was prepared according to the first step of the procedure C from the product obtained previously (620 mg, 2.03 mmol, 1.0 eq.) in THF (3 mL) with presence of (BH$_3$)P(OEt)$_2$H (330 mg, 2.43 mmol, 1.2 eq.) in THF (7 mL) and LiHMDS (1.0 M solution in THF, 2.43 mL, 2.43 mmol, 1.2 eq.).

MS (ESI$^+$): [(M−H2)+H]$^+$=313.2

$^1$H NMR (CD$_3$OD, 500 MHz) δ (ppm): 7.06 (td, J=8.0, 1.7 Hz, 1H); 7.02 (dd, J=7.4, 2.6 Hz, 1H); 6.80 (t J=8.2 Hz, 1H); 6.88 (td, J=8.5, 1.1 Hz, 1H); 4.05-4.01 (m, 2H); 4.00-3.87 (m, 4H); 3.66 (m, 2H); 3.33 (s, 3H); 2.72 (m, 2H); 1.96 (m, 2H); 1.18 (t, J=7.0 Hz, 6H); 0.38 (br m, 3H)

Step 4: ethyl {2-[2-(2-methoxyethoxy)phenyl]ethyl}phosphinate

The title compound (382 mg, 100%) obtained as a colorless oil was prepared according to the second step of the procedure C from the product obtained previously (435 mg, 1.38 mmol, 1.0 eq.) in DCM (7 mL) with presence of HBF$_4$.Et$_2$O (942 μL, 6.92 mmol, 5.0 eq.).

MS (ESI$^+$): [M+H]$^+$=273.1

$^1$H NMR (CDCl$_3$, 500 MHz) δ (ppm): 7.22 (td, J=7.7, 1.7 Hz, 1H); 7.18 (dd, J=7.4, 1.7 Hz, 11H); 7.10 (dt, J=528, 2.1 Hz, 11H); 6.92 (t, J=7.4 Hz, 1H); 6.88 (d, J=8.2 Hz, 11H); 4.20 (m, 11H); 4.16 (m, 2H); 4.11 (m, 11H); 3.79 (m, 2H); 3.47 (s, 3H); 2.93 (m, 2H); 2.21-2.12 (m, 2H); 1.39 (t, J=7.0 Hz, 3H)

$^{31}$P NMR (CDCl$_3$, 202 MHz) δ (ppm): 38.60

Step 5: benzyl 4-{ethoxy([2-[2-(2-methoxyethoxy)phenyl]ethyl})phosphoryl]-4-[(2-methylpropane-2-sulfinyl)amino]butanoate The title compound (464 mg, 60%) obtained as a mixture of four diastereoisomers as an orange oil was prepared according to the procedure E from previous product (375 mg, 1.38 mmol, 1.0 eq.) and cesium carbonate (673 mg, 2.07 mmol, 1.5 eq.) in CH$_2$Cl$_2$ (5 mL) followed by addition of a solution of the racemic benzyl (4E)-4-[(2-methylpropane-2-sulfinyl)imino]butanoate (529 mg, 1.79 mmol, 1.3 eq.) in CH$_2$Cl$_2$ (2 mL).

MS (ESI$^+$): [M+H]$^+$=568.2

$^1$H NMR (CD$_3$OD, 500 MHz) δ (ppm): 7.44-7.30 (m, 5H); 7.25-7.14 (m, 2H); 6.99-6.87 (m, 2H); 5.20-5.11 (m, 2H); 4.24-4.04 (m, 4H); 3.84-3.74 (m, 2H); 3.70-3.54 (m, 11H); 3.46-3.41 (m, 3H); 3.00-2.80 (m, 2H); 2.80-2.53 (m, 2H); 2.54-2.10 (m, 3H); 2.06-1.86 (m, 1H); 1.38-1.30 (m, 3H); 1.28-1.22 (m, 9H)

$^{31}$P NMR (CD$_3$OD, 202 MHz) δ (ppm): 55.74; 55.38; 54.76; 54.54

Step 6: 4-[hydroxy({2-[2-(2-methoxyethoxy)phenyl]ethyl})phosphoryl]-4-[(2-methyl propane-2-sulfinyl)amino]butanoic acid The title compound (364 mg, 100%) obtained as a sticky oil was prepared according to the procedure F from the diastereomeric mixture obtained in the previous step (460 mg, 0.810 mmol, 1.0 eq.) in a mixture of THF/water (4/1, 4 mL) with presence of LiOH.H$_2$O (58 mg, 2.4 mmol, 3.0 eq.).

MS (ESI$^+$): [M+H]$^+$=450.1; [(M×2)+H]$^+$=899.5

Step 7: 3-carboxy-1-[hydroxy({2-[2-(2-methoxyethoxy)phenyl]ethyl})phosphoryl]propan-1-aminium chloride The title compound (230 mg, 74%) obtained as a white solid was prepared according to the procedure G from previous product (364 mg, 0.810 mmol, 1 eq.) with 4.0 M HCl solution in dioxane (4.05 mL, 16.2 mmol, 20 eq.).

Estimated purity: >97% (based on LCMS and NMR)

MS (ESI$^+$): [M+H]$^+$=346.1; [(M×2)+H]$^+$=691.4

MS (ESI$^-$): [M−H]$^-$=344.1; [(M×2)-H]$^-$=689.4

$^1$H NMR (CD$_3$OD, 500 MHz) δ (ppm): 7.28-7.20 (m, 2H); 6.98 (d, J=8.6 Hz, 1H); 6.92 (t, J=7.4 Hz, 1H); 4.20 (m, 2H); 3.82 (m, 2H); 3.46 (s, 3H); 3.41 (m, 1H); 3.02-2.93 (m, 2H); 2.68-2.53 (m, 2H); 2.34-2.15 (m, 3H); 2.08-1.96 (m, 1H)

$^{31}$P NMR (CD$_3$OD, 202 MHz) δ (ppm): 43.76

Example 45: 4-amino-4-{hydroxy[2-(3-phenyl-1,2-oxazol-5-yl)ethyl]phosphoryl}butanoic acid

Step 1: 2-(3-phenyl-1,2-oxazol-5-yl)ethan-1-ol

To a solution of α-chlorobenzaldoxime (2.0 g, 13 mmol, 1.0 eq.) in DCM at room temperature, were added 3-butyn-1-ol (1.35 g, 19.3 mmol, 1.5 eq.) and Et$_3$N (2.26 mL, 16.7 mmol, 1.3 eq.).

The mixture was stirred at room temperature for 16 h before being concentrated under reduced pressure. The residue was purified by column chromatography to afford the title compound (1.8 g, 65%, 4/1 mixture of isomers) as a yellow solid.

MS (ESI$^+$): [M+H]$^+$=190.2

$^1$H NMR (CDCl$_3$, 500 MHz) δ (ppm): 7.85-7. 7.70 (m, 2H); 7.50-7.35 (m, 3H); 6.46 (s, 3H); 4.05 (m, 2H); 3.10 (m, 2H)

Step 2: 5-(2-bromoethyl)-3-phenyl-1,2-oxazole

To a solution of the compound obtained in the previous step (1.7 g, 9.0 mmol, 1.0 eq.) and carbon tetrabromide (4.77 g, 14.4 mmol, 1.6 eq.) in DCM at −5° C., was added triphenylphosphine (3.77 g, 14.4 mmol, 1.6 eq.) portionwise. The reaction mixture was stirred at room temperature for 1 h before being concentrated under reduced pressure. The residue was purified by column chromatography to afford the title compound (2.2 g, 97%, 4/1 mixture of isomers) as a yellow solid.

LCMS (ESI$^+$): [M+H]$^+$=252/254

$^1$H NMR (CDCl$_3$, 500 MHz) δ (ppm): 7.86-7. 7.80 (m, 2H); 7.53-7.45 (m, 3H); 6.50 (s, 3H); 3.71 (t, J=7.0 Hz, 2H); 3.42 (t, J=7.0 Hz, 2H)

Step 3: 5-(2-iodoethyl)-3-phenyl-1,2-oxazole

To a solution of the previous compound (2.1 g, 8.8 mmol, 1.0 eq.) in acetone (220 mL) was added sodium iodide (1.87 g, 12.5 mmol, 1.5 eq.) The reaction mixture was heated at reflux overnight. The mixture was concentrated under reduced pressure then diluted with water and transferred into a separatory funnel. The aqueous layer was extracted twice with DCM. The organic extracts were dried over Na$_2$SO$_4$, filtered and concentrated in vacuo to afford the title compound (2.4 g, 96%) as a pale yellow solid.

MS (ESI$^+$): [M+H]$^+$=300.0

$^1$H NMR (CDCl$_3$, 500 MHz) δ (ppm): 7.81-7.79 (m, 2H); 7.48-7.44 (m, 3H); 6.44 (s, 1H); 3.47-3.39 (m, 4H)

Step 4: phosphine-borane complex intermediate

The title compound (697 mg, 66%) obtained as a colorless oil was prepared according to the first step of the procedure C from the product obtained previously (1.01 g, 3.37 mmol, 1.0 eq.) in THF (0.5 mL) with presence of (BH$_3$)P(OEt)$_2$H (550 mg, 4.05 mmol, 1.2 eq.) in THF (9 mL) and LiHMDS (1.0 M solution in THF, 4.05 mL, 4.05 mmol, 1.2 eq.).

MS (ESI$^+$): [(M−H2)+H]$^+$=306.2

$^1$H NMR (CD$_3$OD, 500 MHz) δ (ppm): 7.82-7.80 (m, 2H); 7.49-7.45 (m, 3H); 6.67 (s, 1H); 4.15-4.02 (m, 4H); 3.11-3.05 (m, 2H); 2.26-2.21 (m, 2H); 1.29 (t, 6H, J=7.0 Hz); 0.86-0.13 (m, 3H)

Step 5: [2-(3-phenyl-1,2-oxazol-5-yl)ethyl]phosphinic acid

The title compound (500 mg, 930%) was prepared according to a variant of the second step of the procedure C from the product obtained previously (697 mg, 2.27 mmol, 1.0 eq.) in DCM (11 mL) with presence of HBF$_4$.Et$_2$O (1.54 mL, 11.4 mmol, 5.0 eq.).

MS (ESI$^+$): [M+H]$^+$=238.1

$^1$H NMR (CD$_3$OD, 500 MHz) δ (ppm): 7.89-7.73 (m, 2H); 7.68 (t, J=1.9 Hz, 0.5H); 7.51-7.42 (m, 3H); 6.70 (s, 1H); 6.58 (t, J=1.9 Hz, 0.5H); 3.16-3.05 (m, 2H); 2.27-2.17 (m, 2H)

$^{31}$P NMR (CD$_3$OD, 202 MHz) δ (ppm): 31.74

Step 6: [4-(benzyloxy)-1-{[(benzyloxy)carbonyl]amino}-4-oxobutyl][2-(3-phenyl-1,2-oxazol-5-yl)ethyl]phosphinic acid The title compound (447 mg, 75%) obtained as a white solid was prepared according to the procedure D for multi-component reaction from previous product (250 mg, 1.05 mmol, 1.0 eq.) and NH$_2$Cbz (175 mg, 1.16 mmol, 1.1 eq.) in AcOH (2.0 mL) and AcCl (0.9 mL) followed by addition of the benzyl 4-oxobutanoate (243 mg, 1.26 mmol, 1.2 eq).

MS (ESI$^+$): [M+H]$^+$=563.2

$^1$H NMR (CD$_3$OD, 500 MHz) δ (ppm): 7.84-7.77 (m, 2H); 7.48 (dd, J=5.2, 1.9 Hz, 3H); 7.39-7.07 (m, 10H); 6.57 (s, 1H); 5.22-4.93 (m, 4H); 4.04 (ddd, J=12.0, 8.7, 3.5 Hz, 1H); 3.22-2.91 (m, 2H); 2.64-2.40 (m, 2H); 2.31-2.21 (m, 1H); 2.16-2.08 (m, 2H); 1.91 (m, 11H)

$^{31}$P NMR (CD$_3$OD, 202 MHz) δ (ppm): 47.65

Step 7: 4-{[(benzyloxy)carbonyl]amino}-4-{hydroxy[2-(3-phenyl-1,2-oxazol-5-yl)ethyl]phosphoryl}butanoic acid The title compound (134 mg, 64%) was prepared according to the procedure F from previous product (250 mg, 0.44 mmol, 1.0 eq.) in a mixture of THF/water (5/1, 2.4 mL) with presence of LiOH.H$_2$O (37 mg, 0.89 mmol, 2.0 eq.).

MS (ESI$^+$): [M+H]$^+$=473.1

$^1$H NMR (CD$_3$OD, 500 MHz) δ (ppm): 7.84-7.77 (m, 2H); 7.52-7.44 (m, 3H); 7.37-7.32 (m, 2H); 7.31-7.24 (m, 2H); 7.20 (t, J=7.4 Hz, 11H); 6.57 (s, 1H); 5.19 (d, J=12.5 Hz, 11H); 5.06 (d, J=12.5 Hz, 1H); 4.03 (ddd, J=11.8, 8.6, 3.4 Hz, 1H); 3.21-2.94 (m, 2H); 2.55-2.35 (m, 2H); 2.31-2.18 (m, 1H); 2.18-2.07 (m, 2H); 1.88 (m, 1H)

$^{31}$P NMR (CD$_3$OD, 202 MHz) δ (ppm): 47.32

Step 8: 4-amino-4-{hydroxy[2-(3-phenyl-1,2-oxazol-5-yl)ethyl]phosphoryl}butanoic acid The title compound (19.5 mg, 20%) obtained as a white solid was prepared according to the procedure G from previous product (134 mg, 284 μmol, 1.0 eq.) in TFA/anisole (1.1 mL/0.9 mL).

Estimated purity: 70% (based on LCMS) and 750% (based on NMR)

MS (ESI$^+$): [M+H]$^+$=339.1; [(M×2)+H]$^+$=677.3

MS (ESI$^-$): [M−H]$^-$=337.1; [(M×2)+H]$^+$=675.2

¹H NMR (CD₃OD, 500 MHz) δ (ppm): 7.84-7.78 (m, 2H); 7.51-7.44 (m, 3H); 6.67 (m, 1H); 3.20-3.04 (m, 3H); 2.63 (t, J=7.2 Hz, 2H); 2.39-2.20 (m, 1H); 2.10-1.91 (m, 3H)
³¹P NMR (CD₃OD, 202 MHz) δ (ppm): 29.86

Example 46: 4-amino-4-{[2-(4-fluoro-2-methoxyphenyl)ethyl](hydroxy)phosphoryl}butanoic acid Step 1: 2-(4-fluoro-2-methoxyphenyl)ethan-1-ol To a commercial solution of LiAlH₄ (2.0 M in THF, 5.43 mL, 10.9 mmol, 2.0 eq.) at 0° C., was added a solution of 2-(4-fluoro-2-methoxyphenyl)acetic acid (1.0 g, 5.4 mmol, 1.0 eq.) in THF (2.7 mL). The mixture was stirred at room temperature for 1 h. After cooling down to 0° C., water (0.5 mL), saturated aqueous solution of 15% NaOH (0.5 mL) and water again (1.5 mL) were added. After stirring for 15 min, Na₂SO₄ was added and the suspension was filtered over celite (MTBE rinses). The filtrate was concentrated under reduced pressure to afford the title compound (0.93 g, 100%) as a colorless oil.
MS (ESI⁺): [M+H]⁺=153.1
¹H NMR (CDCl₃, 500 MHz) δ (ppm): 7.15-7.11 (m, 1H); 6.97-6.60 (m, 2H); 3.83 (t, J=6.7 Hz, 2H); 2.90 (s, 3H); 2.88 (t, J=6.7 Hz, 2H)

Step 2: 1-(2-bromoethyl)-4-fluoro-2-methoxybenzene

Previous compound (0.93 g, 5.5 mmol, 1.0 eq.) and carbon tetrabromide (2.9 g, 8.7 mmol, 1.6 eq.) were diluted in CH₂Cl₂ (27 mL). The solution was cooled at −5° C. (an ice/salt bath) and triphenylphosphine (2.3 g, 8.7 mmol, 1.6 eq) was added in portions. Once the addition was completed, the yellow reaction was stirred at room temperature during 1 h. The mixture was concentrated and purified by column chromatography to afford the title compound (1.12 g, 88%) as a colorless oil.
¹H NMR (500 MHz, CDCl₃) δ (ppm): 7.17-6.97 (m, 1H); 6.73-6.52 (m, 2H); 3.84 (s, 3H); 3.56 (t, J=7.6 Hz, 2H); 3.15 (t, J=7.5 Hz, 2H)

Step 3: [2-(4-fluoro-2-methoxyphenyl)ethyl]phosphinic acid

The title compound (720 mg, 72%) was prepared according to the procedure B from diethylchlorophosphite (0.50 mL, 4.57 mmol, 1.0 eq.) in anhydrous Et₂O (3 mL) followed by addition of the freshly prepared Grignard reagent from 1-(2-bromoethyl)-4-fluoro-2-methoxybenzene in anhydrous Et₂O.
MS (ESI⁺): [M+H]⁺=219.1; [(M×2)+H]⁺=437.1
¹H NMR (500 MHz, MeOD) δ (ppm): 7.17 (dd, J=8.3, 6.7 Hz, 1H); 7.01 (dm, J¹$_{P-H}$=538 Hz, 1H); 6.76 (dd, J=11.1, 2.5 Hz, 1H); 6.62 (td, J=8.4, 2.5 Hz, 1H); 3.87 (s, 3H); 2.98-2.75 (m, 2H); 2.21-1.92 (m, 2H)
³¹P NMR (CD₃OD, 202 MHz) δ (ppm): 34.52

Step 4: [4-(benzyloxy)-1-{[(benzyloxy)carbonyl]amino}-4-oxobutyl][2-(4-fluoro-2-methoxyphenyl)ethyl]phosphinic acid The title compound (540 mg, 75%) obtained as a white solid was prepared according to the procedure D for multi-component reaction from previous product (350 mg, 1.6 mmol, 1.0 eq.) and NH₂Cbz (267 mg, 1.76 mmol, 1.1 eq.) in AcOH (5.0 mL) and AcCl (1.3 mL) followed by addition of the benzyl 4-oxobutanoate (370 mg, 1.93 mmol, 1.2 eq.).
MS (ESI⁺): [M+H]⁺=544.2
¹H NMR (CD₃OD, 500 MHz) δ (ppm): 7.45-7.17 (m, 101H); 7.07 (dd, J=8.3, 6.7 Hz, 1H); 6.72 (dd, J=11.2, 2.5 Hz, 1H); 6.58 (td, J=8.4, 2.5 Hz, 1H); 5.25-5.04 (m, 4H); 4.03 (ddd, J=12.1, 9.0, 3.4 Hz, 1H); 3.81 (s, 3H); 2.93-2.79 (m, 2H); 2.65-2.39 (m, 2H); 2.33-2.18 (m, 1H); 2.03-1.72 (m, 3H)
³¹P NMR (CD₃OD, 202 MHz) δ (ppm): 49.7

Step 5: 4-amino-4-{[2-(4-fluoro-2-methoxyphenyl)ethyl](hydroxy)phosphoryl}butanoic acid The title compound (73 mg, 42%) obtained as a white powder was prepared according to the procedure H for hydrogenolysis from previous product (300 mg, 0.55 mmol) in a mixture EtOH/AcOH (1:1, 10 mL).
Estimated purity: >97% (based on LCMS) and >950% (based on NMR)
MS (ESI⁺): [(M−H₂O)+H]⁺=302.1; [M+H]⁺=320.1; [(M×2)+H]⁺=639.2
MS (ESI⁻): [M−H]⁻=318.1; [(M×2)-H]⁻=637.2
¹H NMR (CD₃OD, 500 MHz) δ (ppm): 7.18 (dd, J=8.4, 6.7 Hz, 1H); 6.73 (dd, J=11.1, 2.5 Hz, 11H); 6.60 (td, J=8.4, 2.5 Hz, 11H); 3.85 (s, 3H), 3.16-3.05 (m, 1H); 3.01-2.74 (m, 2H); 2.70-2.48 (m, 2H); 2.37-2.19 (m, 1H); 2.07-1.92 (m, 1H); 1.92-1.76 (m, 2H)
³¹P NMR (CD₃OD, 202 MHz) δ (ppm): 31.6

Example 47: 4-amino-4-{hydroxy[2-(1H-indazol-1-yl)ethyl]phosphoryl}butanoic acid Step 1: 2-(1H-indazol-1-yl)ethan-1-ol A solution of 2-fluorobenzaldehyde (1.02 mL, 9.67 mmol, 1.0 eq.), 2-hydroxyethylhydrazine (0.79 mL, 11.6 mmol, 1.2 eq.) and DIPEA (2.47 mL, 14.5 mmol, 1.5 eq.) in NMP (9.4 mL) was stirred at 200° C. under microwave irradiations for 24 h. The reaction mixture was partitioned between saturated solution of NH₄Cl and EtOAc. The layers were separated and the organic phase was washed (water and brine), dried over Na₂SO₄, filtered and concentrated under reduced pressure. The residue was purified by column chromatography to afford the title compound (0.31 g, 20%) obtained as an orange oil.
MS (ESI⁺): [M+H]⁺=163.2
¹H NMR (CDCl₃, 500 MHz) δ (ppm): 8.06 (s, 1H); 7.78 (d, J=8.2 Hz, 1H); 7.52-7.40 (m, 2H); 7.24-7.12 (m, 1H); 4.59-4.47 (m, 2H); 4.25-4.09 (m, 2H); 2.97 (s, 1H)

Step 2: 1-(2-iodoethyl)-1H-indazole

To a solution of triphenylphosphine (0.64 g, 2.44 mmol, 1.3 eq.) in DCM (12 mL) at 0° C., was added I2 (0.62 g, 2.44 mmol, 1.3 eq.) and the mixture was stirred at 0° C. for 15 min. Imidazole (166 mg, 2.44 mmol, 1.3 eq.) and a solution of compound obtained in the previous step (305 mg, 1.88 mmol, 1.0 eq.) were added. The mixture was stirred at room temperature for 1 h. The reaction mixture was partitioned between EtOAc and saturated solution of Na₂S₂O₃, triggering a decoloration. The layers were separated and the organic phase was washed with brine, dried over Na₂SO₄, filtered and concentrated under reduced pressure. The residue was purified by column chromatography to afford the title compound (625 mg, 100%) obtained as a colorless oil.
MS (ESI⁺): [M+H]⁺=273

¹H NMR (CDCl₃, 500 MHz) δ (ppm): 8.07 (d, J=0.9 Hz, 1H); 7.77 (dt, J=8.2, 1.0 Hz, 1H); 7.50-7.42 (m, 2H); 7.20 (ddd, J=7.9, 6.4, 1.4 Hz, 1H); 4.78 (t, J=7.4 Hz, 2H); 3.63-3.57 (m, 2H)

Step 3: Phosphine-Borane Complex Intermediate

The title compound (574 mg, 92%) obtained as a colorless oil was prepared according to the first step of the procedure C from the product obtained previously (605 mg, 2.22 mmol, 1.0 eq.) in THF (10 mL) with presence of (BH₃)P(OEt)₂H (363 mg, 2.67 mmol, 1.2 eq.) in THF (8 mL) and LiHMDS (1.0 M solution in THF, 2.67 mL, 2.67 mmol, 1.2 eq.)

MS (ESI⁺): [(M−H2)+H]⁺=279.2

¹H NMR (CD₃OD, 500 MHz) δ (ppm): 7.81 (d, J=0.9 Hz, 1H); 7.53 (dt, J=8.1, 1.0 Hz, 1H); 7.32 (br d, J=8.5 Hz, 1H); 7.21 (ddd, J=8.6, 6.9, 1.1 Hz, 1H); 6.94 (ddd, J=7.9, 6.9, 0.9 Hz, 1H); 4.51-4.37 (m, 2H); 3.88-3.62 (m, 4H); 2.24-2.01 (m, 2H); 0.97 (t, J=7.0 Hz, 6H); 0.71-0.24 (m, 3H)

Step 4: ethyl [2-(1H-indazol-1-yl)ethyl]phosphinate

The title compound (355 mg, 730%) obtained as a light yellow oil was prepared according to the second step of the procedure C from the product obtained previously (570 mg, 2.03 mmol, 1.0 eq.) in DCM (10 mL) with presence of HBF₄.Et₂O (1.38 mL, 10.2 mmol, 5.0 eq.).

MS (ESI⁺): [M+H]⁺=239.1

¹H NMR (500 MHz, CD₃OD) δ (ppm): 8.12-7.99 (m, 1H); 7.78 (dt, J=8.1, 1.0 Hz, 1H); 7.67-7.60 (m, 1H); 7.51-7.37 (m, 1H); 7.34-7.02 (m, 1H); 7.05 (dm, J¹$_{P-H}$=560 Hz, 1H); 4.74 (dt, J=16.4, 7.0 Hz, 2H); 4.22-3.89 (m, 2H); 2.69-2.42 (m, 2H); 1.25 (t, J=7.0 Hz, 3H)

³¹P NMR (CD₃OD, 202 MHz) δ (ppm): 37.1

Step 5: benzyl 4-{ethoxy[2-(1H-indazol-1-yl)ethyl] phosphoryl}-4-[(2-methylpropane-2-sulfinyl)amino] butanoate The title compound (725 mg, 920%) obtained as a mixture of four diastereoisomers as a light yellow oil was prepared according to the procedure E from previous product (350 mg, 1.47 mmol, 1.0 eq.) and cesium carbonate (718 mg, 2.20 mmol, 1.5 eq.) in CH₂Cl₂ (5 mL) followed by addition of a solution of the racemic (4E)-benzyl-4-[(2-methylpropane-2-sulfinyl)imino]butanoate (564 mg, 1.91 mmol, 1.3 eq.) in CH₂C₂ (2.3 mL).

MS (ESI⁺): [M+H]⁺=534.2

¹H NMR (CD₃OD, 500 MHz) δ (ppm): 8.10-7.99 (m, 1H); 7.82-7.72 (m, 1H); 7.71-7.60 (m, 11H); 7.49-7.41 (m, 1H); 7.41-7.26 (m, 5H); 7.26-7.11 (m, 1H); 5.22-5.08 (m, 2H); 4.81-4.65 (m, 2H); 4.17-3.88 (m, 2H); 3.72-3.44 (m, 1H); 2.81-2.39 (m, 4H); 2.33-2.11 (m, 1H); 1.98-1.79 (m, 1H); 1.28-1.21 (m, 9H)

³¹P NMR (CD₃OD, 202 MHz) δ (ppm): 52.88; 52.74; 51.83; 51.73

Step 6: 4-{hydroxy[2-(]H-indazol-1-yl)ethyl]phosphoryl}-4-[(2-methylpropane-2-sulfinyl) amino] butanoic acid The title compound (520 mg, 94%) obtained as a light yellow foam was prepared according to the procedure F from the diastereomeric mixture obtained in the previous step (712 mg, 1.33 mmol, 1.0 eq.) in a mixture of THF/water (3/1, 13 mL) with presence of LiOH.H₂O (128 mg, 5.34 mmol, 3.0 eq.).

MS (ESI⁻): [M−H]⁻=414.1

Step 7: 4-amino-4-{hydroxy[2-(1H-indazol-1-yl) ethyl]phosphoryl}butanoic acid

The title compound (20 mg, 5%) obtained as a white solid was prepared according to the procedure G from previous product (520 mg, 1.25 mmol, 1 eq.) with 4.0 M HCl solution in dioxane (6.3 mL, 20 eq.).

Estimated purity: >97% (based on LCMS and NMR)

MS (ESI⁺): [(M−H₂O)+H]⁺=294.1; [M+H]⁺=312.1; [(M×2)+H]⁺=623.2

MS (ESI⁻): [M−H]⁻=310.1; [(M×2)-H]⁻=621.2

¹H NMR (CD₃OD, 500 MHz) δ (ppm): 8.05 (d, J=0.9 Hz, 1H); 7.77 (dt, J=8.2, 1.0 Hz, 1H); 7.70 (dd, J=8.5, 1.0 Hz, 1H); 7.45 (ddd, J=8.3, 6.8, 1.1 Hz, 1H); 7.18 (ddd, J=7.9, 6.9, 0.8 Hz, 1H); 4.72 (q, J=7.9 Hz, 2H); 2.99 (td, J=8.3, 5.2 Hz, 1H); 2.56 (t, J=7.3 Hz, 2H); 2.35-2.11 (m, 3H); 2.03-1.79 (m, 1H)

³¹P NMR (CD₃OD, 202 MHz) δ (ppm): 27.9

Example 48: 1-({2-[2-(benzyloxy)phenyl]ethyl} (hydroxy)phosphoryl)-3-carboxy propan-1-aminium chloride Step 1: 2-[2-(benzyloxy)phenyl]ethan-1-ol To 2-(2-hydroxyethyl)phenol (5.0 g, 36 mmol, 1.0 eq.) diluted in acetone (145 mL) were added K₂CO₃ (5.5 g, 40 mmol, 1.1 eq.) and benzyl bromide (6.8 g, 40 mmol, 1.1 eq). The mixture was stirred at room temperature overnight. The mixture was concentrated under reduced pressure then diluted with water and DCM then transferred into a separatory funnel. The aqueous layer was extracted twice with DCM. The organic extracts were dried over Na₂SO₄, filtered and concentrated in vacuo. The residue was purified by column chromatography to afford the title compound (1.67 g, 20%) as a clear oil.

MS (ESI⁺): [(M−H₂O)+H⁺]=211.2; [M+H]⁺=229.2

¹H NMR (CDCl₃, 500 MHz) δ (ppm): 7.45-7.37 (m, 4H); 7.36-7.30 (m, 1H); 7.21 (dd, J=7.9, 6.3 Hz, 2H); 6.93 (dd, J=7.8, 6.8 Hz, 2H); 5.09 (s, 2H); 3.87 (t, J=6.4 Hz, 2H); 2.97 (t, J=6.4 Hz, 2H)

Step 2: 1-(benzyloxy)-2-(2-bromoethyl)benzene

To a solution of the previous compound (1.6 g, 7.0 mmol, 1.0 eq.) in CH₂Cl₂ (35 mL) was added carbon tetrabromide (3.7 g, 11 mmol, 1.6 eq). The solution was cooled at −5° C. (ice/salt bath) and triphenylphosphine (2.9 g, 11 mmol, 1.6 eq) was added portionwise. When the addition was complete, the yellow reaction was stirred at room temperature for 1 h. The mixture was concentrated under reduced pressure. The residue was purified by column chromatography to afford the title compound (2.0 g, 98%) as a colorless oil.

¹H NMR (CDCl₃, 500 MHz) δ (ppm): 7.49-7.43 (m, 4H); 7.40-7.36 (m, 1H); 7.31-7.22 (m, 2H); 6.97 (m, 2H); 5.15 (s, 2H); 3.66 (t, J=7.6 Hz, 2H); 3.29 (t, J=7.6 Hz, 2H)

Step 3: {2-[2-(benzyloxy)phenyl]ethyl}phosphinic acid

The title compound (1.0 g, 55%) was prepared according to the procedure B from diethylchlorophosphite (0.715 mL, 6.53 mmol, 1.0 eq.) in anhydrous Et$_2$O (3 mL) followed by addition of the freshly prepared Grignard reagent from 1-(benzyloxy)-2-(2-bromoethyl)benzene in anhydrous Et$_2$O.

MS (ESI$^+$): [M+H]$^+$=277.1; [(M×2)+H]$^+$=553.1

$^1$H NMR (CD$_3$OD, 500 MHz) δ (ppm): 7.50 (t, J=2.2 Hz, 0.5H); 7.46 (d, J=7.1 Hz, 2H); 7.38 (t, J=7.5 Hz, 2H); 7.31 (t, J=7.2 Hz, 11H); 7.18 (dd, J=8.0, 6.6 Hz, 2H); 7.01 (d, J=8.2 Hz, 1H); 6.89 (td, J=7.4, 1.0 Hz, 1H); 6.42 (t, J=2.1 Hz, 0.5H); 5.12 (s, 2H); 2.99-2.82 (m, 2H); 2.04 (m, 2H)

$^{31}$P NMR (CD$_3$OD, 202 MHz) δ (ppm): 34.69

Step 4: ethyl {2-[2-(benzyloxy)phenyl]ethyl}phosphinate

To a solution of the previous compound (1.0 g, 3.6 mmol, 1.0 eq.) and ethanol (423 µL, 7.24 mmol, 2.0 eq.) in DCM (36 mL) was added EDCI (1.3 g, 4.7 mmol, 1.3 eq) in one portion. The reaction mixture was stirred at room temperature overnight. As the reaction stalled, more ethanol (1.5 eq.), EDCI (1.5 eq.) and Et$_3$N (2.5 mL, 5.0 eq.) were added. The reaction mixture was stirred at room temperature for 5 h30. The reaction mixture was transferred into a separatory funnel and washed with saturated aqueous solution of NaHCO$_3$ (2×), then with brine. The organic extract was dried over Na$_2$SO$_4$, filtered and concentrated in vacuo. The residue was purified by column chromatography to afford the title compound (548 mg, 20%) as a pale yellow oil.

MS (ESI$^+$): [M+H]$^+$=305.2; [(M×2)+H]$^+$=609.3

$^1$H NMR (CD$_3$OD, 500 MHz) δ (ppm): 7.51 (t, J=2.1 Hz, 0.5H); 7.48-7.45 (m, 2H); 7.42-7.36 (m, 2H); 7.35-7.29 (m, 1H); 7.20 (t, J=7.5 Hz, 2H); 7.05-7.01 (m, 1H); 6.89 (td, J=7.4, 1.1 Hz, 1H); 6.42 (t, J=2.1 Hz, 0.5H); 5.12 (s, 2H); 4.14-3.93 (m, 2H); 2.91 (dt, J=13.3, 8.0 Hz, 2H); 2.20-2.04 (m, 2H); 1.29 (t, J=7.1 Hz, 3H)

$^{31}$P NMR (CD$_3$OD, 202 MHz) δ (ppm): 41.26

Step 5: methyl 4-({2-[2-(benzyloxy)phenyl]ethyl}(ethoxy)phosphoryl)-4-{[(S)-2-methylpropane-2-sulfinyl]amino}butanoate The title compound (525 mg, 840%) was prepared according to the procedure E from previous product (534 mg, 1.79 mmol, 1.5 eq.) and cesium carbonate (973 mg, 2.99 mmol, 2.5 eq.) in CH$_2$Cl$_2$ (3.8 mL) followed by addition of a solution of the racemic methyl (4E)-4-{[(S)-2-methylpropane-2-sulfinyl]imino}butanoate (262 mg, 1.19 mmol, 1.0 eq.) in CH$_2$Cl$_2$ (2.5 mL).

MS (ESI$^+$): [M+H]$^+$=524.2

$^1$H NMR (CD$_3$OD, 500 MHz) δ (ppm): 7.54-7.47 (m, 2H); 7.44-7.39 (m, 2H); 7.37-7.32 (m, 1H); 7.28-7.19 (m, 2H); 7.08-7.02 (m, 1H); 6.96-6.89 (m, 1H); 5.18-5.05 (m, 2H); 4.21-3.92 (m, 2H); 3.74-3.62 (m, 3H); 2.95 (m, 2H); 2.69-2.53 (m, 11H); 2.49 (m, 1H); 2.31 (m, 2H); 2.18 (m, 2H); 2.01-1.80 (m, 1H); 1.31-1.16 (m, 12H)

$^{31}$P NMR (CD$_3$OD, 202 MHz) δ (ppm): 55.49; 55.21; 54.54; 54.37

Step 6: 4-({2-[2-(benzyloxy)phenyl]ethyl}(hydroxy)phosphoryl)-4-{[(S)-2-methyl propane-2-sulfinyl]amino}butanoic acid The title compound (470 mg, 100%) was prepared according to the procedure F from previous product (425 mg, 0.811 mmol, 1.0 eq.) in a mixture of THF/water (5/1, 4.7 mL) and LiOH.H$_2$O (68 mg, 1.6 mmol, 2.0 eq.). Additional LiOH.H$_2$O reagent (2.0 eq. then 4.0 eq.) was requested to complete the reaction.

MS (ESI$^+$): [M+H]$^+$=482.1

$^1$H NMR (CD$_3$OD, 500 MHz) δ (ppm): 7.53-7.46 (m, 2H); 7.44-7.36 (m, 2H); 7.35-7.29 (m, 1H); 7.28-7.13 (m, 2H); 7.06-6.98 (m, 1H); 6.95-6.87 (m, 1H); 5.15 (d, J=5.2 Hz, 2H); 3.55-3.42 (m, 1H); 3.13-2.88 (m, 2H); 2.60-2.39 (m, 1H); 2.31-1.84 (m, 5H); 1.39 (m, 1H); 1.26 (s, 3H); 1.22-1.14 (m, 5H)

$^{31}$P NMR (CD$_3$OD, 202 MHz) δ (ppm): 49.68; 48.99

Step 7: 1-({2-[2-(benzyloxy)phenyl]ethyl}(hydroxy)phosphoryl)-3-carboxypropan-1-aminium chloride The title compound (83 mg, 20%) obtained as a white powder was prepared according to the procedure G from previous product (470 mg, 0.98 mmol, 1.0 eq.) with 4.0 M HCl solution in dioxane (5.42 mL, 21.7 mmol, 22 eq.).

Estimated purity: >95% (based on LCMS and NMR)

MS (ESI$^+$): [M+H]$^+$=378

$^1$H NMR (CD$_3$OD, 500 MHz) δ (ppm): 7.48 (dd, J=7.3, 1.7 Hz, 2H); 7.41-7.36 (m, 2H); 7.33-7.29 (m, 1H); 7.24-7.17 (m, 2H); 7.03 (dd, J=8.2, 1.1 Hz, 1H); 6.90 (td, J=7.4, 1.1 Hz, 1H); 5.14 (s, 2H); 3.40-3.31 (m, 1H); 3.07-2.90 (m, 2H); 2.55-2.42 (m, 2H); 2.26-2.04 (m, 3H); 1.96-1.84 (m, 1H)

$^{31}$P NMR (CD$_3$OD, 202 MHz) δ (ppm): 42.08

Example 49: 5-amino-5-[hydroxy(2-phenylethyl)phosphoryl]pentanoic acid

Step 1: benzyl 5-hydroxypentanoate

To a suspension of valerolactone (5.0 g, 50 mmol, 1 eq.) in water (45 mL), was added a 32% NaOH solution in water (4.6 mL, 50 mmol, 1.0 eq.) and the mixture was stirred at 70° C. for 16 h. The reaction mixture was then concentrated in vacuo. The residue was pulverized and suspended in acetone (50 mL) at room temperature and (n-Bu)$_4$NBr (805 mg, 2.50 mmol, 0.05 eq.) and BnBr (7.1 mL, 60 mmol, 1.2 eq.) were added. The mixture was stirred at reflux for 20 h. After cooling down to room temperature, water and EtOAc were added and the layers were separated. The aqueous phase was extracted with EtOAc. The combined organic extracts were washed (water, brine), dried over Na$_2$SO$_4$, filtered and concentrated under reduced pressure to afford the crude product (12 g). The residue was purified by column chromatography to afford the title compound (4.12 g, 40%) as a colorless oil.

MS (ESI$^+$): [M+H]$^+$=209.2

$^1$H NMR (CDCl$_3$, 500 MHz) δ (ppm): 7.40-7.30 (m, 5H); 5.13 (s, 2H); 3.65 (br s, 2H); 2.42 (t, J=7.5 Hz, 2H); 1.75 (m, 2H); 1.61 (m, 2H); 1.48 (br s, 1H, OH)

Step 2: benzyl 5-oxopentanoate

To a solution of previous compound (1.0 g, 4.8 mmol, 1.0 eq.) in DCM (19 mL) at room temperature, was added Dess-Martin periodinane (3.05 g, 7.20 mmol, 1.5 eq.) and a drop of water. The mixture was stirred at room temperature for 1.5 h. The solvent was partially removed under reduced pressure and the residue was partitioned between MTBE (100 mL) and saturated solution of NaHCO$_3$ (100 mL), forming a suspension in water. The layers were separated and the organic phase was washed with saturated solution of NaHCO$_3$ and brine. The organic solution was dried over Na$_2$SO$_4$, filtered and concentrated under reduced pressure to afford 1.15 g as a turbid oil. The residue was purified by column chromatography to afford the title compound (710 mg, 72%) as a colorless oil $^1$H NMR (CDCl$_3$, 500 MHz) δ (ppm): 9.77 (t, J=1.4 Hz, 1H); 7.41-7.31 (m, 5H); 5.13 (s, 2H); 2.53 (td, J=7.2 Hz and J=1.4 Hz, 2H); 2.43 (t, J=7.3 Hz, 2H); 1.98 (m, 2H)

Step 3: [5-(benzyloxy)-1-{[(benzyloxy)carbonyl]amino}-5-oxopentyl](2-phenylethyl) phosphinic acid The title compound (528 mg) obtained as a yellow oil was prepared according to the procedure D for multi-component reaction from phenethylphosphinic acid (250 mg, 1.47 mmol, 1.0 eq.) and NH$_2$Cbz (266 mg, 1.76 mmol, 1.2 eq.) in AcOH (2 mL) and AcCl (315 L) followed by addition of the aldehyde obtained in the previous step (363 mg, 1.76 mmol, 1.2 eq.). This material was used in the next step without further purification.

MS (ESI$^+$): [M+H]$^+$=510

Step 4: 5-amino-5-[hydroxy(2-phenylethyl)phosphoryl]pentanoic acid

The title compound (20 mg) obtained as a white solid was prepared according to the procedure H for hydrogenolysis from previous product (520 mg, 1.02 mmol) in a mixture EtOH/AcOH 1/1 (10 mL).

Estimated purity: >950% (based on LCMS) and >85% (based on NMR)

MS (ESI$^+$): [(M−H$_2$O)+H]$^+$=268.2; [M+H]$^+$=286.1; [(M×2)+H]$^+$=571.2

MS (ESI$^-$): [M−H]$^-$=284.1; [(M×2)−H]$^-$=569.2

$^1$H NMR (CD$_3$OD, 500 MHz) δ (ppm): 7.31-7.21 (m, 4H); 7.20-7.12 (m, 1H); 2.98-2.83 (m, 3H); 2.40-2.34 (m, 2H); 1.99-1.76 (m, 4H), 1.75-1.64 (m, 2H)

$^{31}$P NMR (MeOD, 202 MHz) δ (ppm): 31.64

Example 50: (1R)-3-carboxy-1-[hydroxy(2-phenylethyl)phosphoryl]propan-1-aminium chloride Step 1: benzyl (2-phenylethyl)phosphinate To a solution of phenethylphosphinic acid (2.84 g, 16.69 mmol, 1.0 eq.) and benzyl alcohol (1.91 mL, 18.36 mmol, 1.1 eq.) in DCM (284 mL) was added EDCI (6.40 g, 33.38 mmol, 2 eq.) in one portion. The reaction mixture was stirred at room temperature for 6 h and then transferred into a separatory funnel, washed with saturated aqueous solution of NaHCO$_3$ (2×) and then with brine. The organic layer was dried over Na$_2$SO$_4$, filtered and concentrated in vacuo. The crude was purified by column chromatography to afford the expected compound (2.34 g, 54%) as a pale yellow oil.

MS (ESI$^+$): [M+H]$^+$=261.1

$^1$H NMR (CDCl$_3$, 500 MHz) δ (ppm): 7.40-7.34 (m, 5H); 7.30-7.28 (m, 2H); 7.23-7.17 (m, 3H); 7.14 (dt, 1H, J=535.5 and 2.0 Hz); 5.17-5.03 (m, 2H); 2.95-2.89 (m, 2H); 2.17-2.09 (m, 2H)

$^{31}$P NMR (CDCl$_3$, 202 MHz) δ (ppm): 37.11

Step 2: benzyl (4R)-4-[(benzyloxy)(2-phenylethyl)phosphoryl]-4-{[(S)-2-methylpropane-2-sulfinyl]amino}butanoate The title compound (471 mg, 33%) obtained as a mixture of 2 diastereomers as a colorless oil was prepared according to the procedure E from previous product (991 mg, 3.81 mmol, 1.5 eq.) and cesium carbonate (2.07 g, 6.35 mmol, 2.5 eq.) in CH$_2$Cl$_2$ (16.5 mL) followed by addition of a solution of the enantiopure benzyl (4E)-4-{[(S)-2-methylpropane-2-sulfinyl]imino}butanoate (750 mg, 2.54 mmol, 1.0 eq.) in CH$_2$Cl$_2$ (9 mL).

$^1$H NMR (CDCl$_3$, 500 MHz) δ (ppm): 7.39-7.15 (m, 15H); 5.14-5.00 (m, 4H); 4.16 (t, 0.4H, J=8.5 Hz); 3.87 (br s, 0.6H); 3.54-3.47 (m, 0.4H); 3.45-3.39 (m, 0.6H); 2.97-2.78 (m, 2H); 2.61-2.36 (m, 3H); 2.32-2.21 (m, 1H); 2.21-2.11 (m, 1H); 1.86-1.76 (m, 1H); 1.23 (s, 3.4H); 1.18 (s, 5.6H)

$^{31}$P NMR (CDCl$_3$, 202 MHz) δ (ppm): 54.86 (0.4P); 53.24 (0.6P)

Step 3: (4R)-4-[hydroxy(2-phenylethyl)phosphoryl]-4-{[(S)-2-methylpropane-2-sulfinyl]amino}butanoic acid The title compound (90 mg, 77%) obtained as a colorless oil was prepared according to the procedure F from the diastereomeric mixture obtained in the previous step (173 mg, 0.311 mmol, 1.0 eq.) in a mixture of THF/water (3.8 mL/1.0 mL) with presence of LiOH.H$_2$O (39 mg, 0.934 mmol, 3.0 eq.).

MS (ESI$^+$): [M+H]$^+$=376.1

$^1$H NMR (MeOD, 500 MHz) δ (ppm): 7.28-7.27 (m, 4H); 7.21-7.16 (m, 1H); 3.55-3.50 (m, 1H); 2.95-2.89 (m, 2H); 2.61-2.45 (m, 2H); 2.36-2.13 (m, 3H); 1.98-1.88 (m, 1H); 1.28 (s, 9H)

$^{31}$P NMR (MeOD, 202 MHz) δ (ppm): 48.99

Step 4: (1R)-3-carboxy-1-[hydroxy(2-phenylethyl)phosphoryl]propan-1-aminium chloride The title compound (33 mg, 450%) obtained as a white solid was prepared according to the procedure G from previous product (90 mg, 0.240 mmol, 1 eq.) with 4.0 M HCl solution in dioxane (1.3 mL, 22 eq.).

Expected purity: 95% (based on LCMS and NMR)

MS (ESI$^+$): [(M−H$_2$O)+H]$^+$=254.1; [M+H]$^+$=272.2; [(M×2)+H]$^+$=543.2; [(M×3)+H]$^+$=814.5

$^1$H NMR (MeOD, 500 MHz) δ (ppm): 7.33-7.28 (m, 4H); 7.24-7.20 (m, 1H); 3.32-3.29 (m, 1H); 2.94 (q, 2H, J=8.5 Hz); 2.59 (dt, 2H, J=7.0 and 3.5 Hz); 2.31-2.22 (m, 1H); 2.18-2.06 (m, 2H); 2.03-1.94 (m, 1H)

$^{31}$P NMR (MeOD, 202 MHz) δ (ppm): 38.88

Example 51: (1S)-3-carboxy-1-[hydroxy(2-phenylethyl)phosphoryl]propan-1-aminium chloride Step 1: benzyl (4S)-4-[(benzyloxy)(2-phenylethyl)phosphoryl]-4-{[(R)-2-methylpropane-2-sulfinyl]amino}butanoate The title compound (200 mg, 41%) obtained as a mixture of 2 of diastereomers was prepared according to the procedure E from benzyl (2-phenylethyl)phosphinate (340 mg, 1.31 mmol, 1.5 eq.) and cesium carbonate (709 mg, 2.18 mmol, 2.5 eq.) in CH$_2$Cl$_2$ (5.7 mL) followed by addition of a solution of the enantiopure benzyl (4E)-4-{[(R)-2-methylpropane-2-sulfinyl]imino}butanoate (257 mg, 0.87 mmol, 1.0 eq.) in CH$_2$Cl$_2$ (3 mL).

$^1$H NMR (CDCl$_3$, 500 MHz) δ (ppm): 7.39-7.15 (m, 15H); 5.14-5.00 (m, 4H); 4.16 (t, 0.4H, J=8.5 Hz); 3.87 (br s, 0.6H); 3.54-3.47 (m, 0.4H); 3.45-3.39 (m, 0.6H); 2.97-

2.78 (m, 2H); 2.61-2.36 (m, 3H); 2.32-2.21 (m, 1H); 2.21-2.11 (m, 1H); 1.86-1.76 (m, 1H); 1.23 (s, 3.4H); 1.18 (s, 5.6H)

$^{31}$P NMR (CDCl$_3$, 202 MHz) δ (ppm): 54.86 (0.4P); 53.24 (0.6P)

Step 2: (4S)-4-[hydroxy(2-phenylethyl)phosphoryl]-4-[[(R)-2-methylpropane-2-sulfinyl]amino]butanoic acid The title compound (164 mg, 85%) obtained as a colorless oil was prepared according to the procedure F from the diastereomeric mixture obtained in the previous step (284 mg, 0.511 mmol, 1.0 eq.) in a mixture of THF/water (6.3 mL/1.7 mL) with presence of LiOH.H$_2$O (64 mg, 1.53 mmol, 3.0 eq.).

MS (ESI$^+$): [M+H]$^+$=376.1

$^1$H NMR (MeOD, 500 MHz) δ (ppm): 7.36-7.16 (m, 5H); 3.55-3.50 (m, 1H); 2.97-2.87 (m, 2H); 2.61-2.55 (m, 1H); 2.51-2.45 (m, 1H); 2.36-2.13 (m, 3H); 1.98-1.83 (m, 1H); 1.28 (s, 9H)

$^{31}$P NMR (MeOD, 202 MHz) δ (ppm): 48.98

Step 3: (1S)-3-carboxy-1-[hydroxy(2-phenylethyl)phosphoryl]propan-1-aminium chloride The title compound (71 mg, 53%) obtained as a white powder was prepared according to the procedure G from previous product (164 mg, 0.437 mmol, 1.0 eq.) with 4.0 M HCl solution in dioxane (2.4 mL, 22 eq.).

Expected purity: 95% (based on LCMS and NMR)

MS (ESI$^+$): [(M−H$_2$O)+H]$^+$=254.1; [M+H]$^+$=272.2; [(M×2)+H]$^+$=543.2; [(M×3)+H]$^+$=814.5

$^1$H NMR (MeOD, 500 MHz) δ (ppm): 7.31-7.26 (m, 4H); 7.22-7.18 (m, 1H); 3.35-3.33 (m, 1H); 2.94 (q, 2H, J=9.0 Hz); 2.61-2.58 (m, 2I1); 2.29-2.20 (m, 1H); 2.17-2.08 (m, 2H); 2.02-1.92 (m, 1I1)

$^{31}$P NMR (MeOD, 202 MHz) δ (ppm): 39.80

Example 52: (1R)-3-carboxy-1-{hydroxy[2-(2-methoxyphenyl)ethyl]phosphoryl} propan-1-aminium chloride Step 1: benzyl [2-(2-methoxyphenyl)ethyl]phosphinate To a solution of (2-methoxyphenethyl)phosphinic acid (825 mg, 4.12 mmol, 1.0 eq.) and benzyl alcohol (0.471 mL, 4.53 mmol, 1.1 eq.) in DCM (70 mL) was added EDCI (1.58 g, 8.24 mmol, 2.0 eq.) in one portion. The reaction mixture was stirred at room temperature overnight and then transferred into a separatory funnel, washed with saturated aqueous solution of NaHCO$_3$ (2×) and then with brine. The organic layer was dried over Na$_2$SO$_4$, filtered and concentrated in vacuo. The crude was purified by column chromatography to afford the title compound (840 mg, 70%) as a colorless oil.

MS (ESI$^+$): [M+H]$^+$=291.2

$^1$H NMR (MeOD, 500 MHz) δ (ppm): 7.42-7.34 (m, 5H); 7.21-7.18 (m, 1H); 7.12 (dd, 1H, J=7.5 and 1.5 Hz); 7.04 (dt, 1H, J=547.5 and 2.0 Hz); 6.92 (dd, 1H, J=8.5 and 1.0 Hz); 6.85 (td, 1H, J=7.5 and 1.0 Hz); 5.13-5.03 (m, 2H); 3.81 (s, 3H); 2.90-2.84 (m, 2H); 2.17-2.10 (m, 2H)

$^{31}$P NMR (MeOD, 202 MHz) δ (ppm): 41.41

Step 2: benzyl (4R)-4-[(benzyloxy)[2-(2-methoxyphenyl)ethyl]phosphoryl]-4-{[(S)-2-methylpropane-2-sulfinyl]amino}butanoate The title compound (1.5 g, 40%) obtained as a mixture of 2 diastereoisomers was prepared according to the procedure E from previous product (2.28 g, 7.85 mmol, 1.5 eq.) and cesium carbonate (5.24 g, 16.08 mmol, 2.5 eq.) in CH$_2$Cl$_2$ (18.5 mL) followed by addition of a solution of the enantiopure benzyl (4E)-4-{[(S)-2-methylpropane-2-sulfinyl]imino}butanoate (1.90 g, 6.43 mmol, 1.0 eq.) in CH$_2$Cl$_2$ (10 mL).

$^1$H NMR (MeOD, 500 MHz) δ (ppm): 7.45-7.28 (m, 101H); 7.18 (td, 11H, J=8.0 and 1.5 Hz); 7.10 (dd, 1H, J=17.5, 8.0 Hz); 6.89 (dd, 1H, J=8.0 and 5.0 Hz); 6.84 (m, 1H); 5.16-4.99 (m, 4H); 3.79 (s, 1.5H); 3.78 (s, 1.5H); 3.68-3.63 (m, 0.5H); 3.60-3.55 (m, 0.5H); 2.89-2.75 (m, 2H); 2.69-2.63 (m, 1H); 2.58-2.49 (m, 1H); 2.40-2.16 (m, 3H); 2.03-1.98 (m, 1H); 1.22 (s, 4H); 1.19 (s, 5H)

$^{31}$P NMR (CDCl$_3$, 202 MHz) δ (ppm): 56.71 (0.47P); 55.80 (0.53P)

Step 3: (4R)-4-{hydroxy[2-(2-methoxyphenyl)ethyl]phosphoryl}-4-{[(S)-2-methylpropane-2-sulfinyl]amino}butanoic acid The title compound (848 mg, 82%) obtained as a white solid was prepared according to the procedure F from the diastereomeric mixture obtained in the previous step (1.5 g, 2.56 mmol, 1.0 eq.) in a mixture of THF/water (18 mL/6 mL) with presence of LiOH.H$_2$O (322 mg, 7.68 mmol, 3.0 eq.). 11H NMR (MeOD, 500 MHz) δ (ppm): 7.20-7.17 (m, 2H); 6.92 (dd, 1H, J=8.5 and 1.0 Hz); 6.86 (td, 1H, J=7.5 and 1.0 Hz); 3.84 (s, 3H); 3.53-3.48 (m, 1H); 2.97-2.84 (m, 2H); 2.62-2.56 (m, 1H); 2.50-2.44 (m, 11H); 2.36-2.14 (m, 3H); 2.00-1.90 (m, 1H); 1.27 (s, 9H)

Step 4: (1R)-3-carboxy-1-{hydroxy[2-(2-methoxyphenyl)ethyl]phosphoryl} propan-1-aminium chloride The title compound (519 mg, 73%) obtained as a white powder was prepared according to the procedure G from previous product (848 mg, 2.09 mmol, 1.0 eq.) with 4.0 M HCl solution in dioxane (11.6 mL, 22 eq.).

Estimated purity: >95% (based on LCMS and NMR)

MS (ESI$^+$): [(M−H$_2$O)+H]$^+$=284.2; [M+H]Y=302.2; [(M×2)+H]$^+$=603.3; [(M×3)+H]$^+$=904.7

$^1$H NMR (MeOD, 500 MHz) δ (ppm): 7.21-7.18 (m, 2H); 6.93 (d, 1H, J=8.0 Hz); 6.87 (td, 11H, J=8.0 and 1.0 Hz); 3.84 (s, 3H); 3.26 (td, 11H, J=8.0 and 5.0 Hz); 2.97-2.85 (m, 2H); 2.64-2.53 (m, 2H); 2.28-2.19 (m, 1H); 2.10-1.93 (m, 3H)

$^{31}$P NMR (MeOD, 202 MHz) δ (ppm): 38.10

Example 53: (4R)-4-amino-4-({2-[2-(cyclohexyloxy)phenyl]ethyl} (hydroxy) phosphoryl) butanoic acid Step 1: methyl 2-[2-(cyclohexyloxy)phenyl]acetate To a solution of methyl 2-(2-hydroxyphenyl)acetate (5.95 g, 35.82 mmol, 1.0 eq.), cyclohexanol (5.38 g, 53.7 mmol, 1.5 eq.) and triphenylphosphine (11.27 g, 43.0 mmol, 1.2 eq.) in THF (70 mL) at 0° C., was added DTAD (9.89 g, 43.0 mmol, 1.2 eq.). The reaction mixture was stirred at room temperature for 18 h. The reaction mixture was concentrated under reduced pressure and the resulting thick syrup was triturated in Pentane/Et$_2$O (75/25, 200 mL). The resulting suspension was filtered over fritted glass (pentane/Et$_2$O: 75/25) and the filtrates were concentrated under reduced pressure. The residue was purified by column chromatography to afford the title compound (4.28 g, 48%) obtained as a colorless oil.

MS (ESI$^+$): [M+H]$^+$=249.2

$^1$H NMR (CDCl$_3$, 500 MHz) δ (ppm): 7.26-7.18 (m, 2H); 6.95-6.85 (m, 2H); 4.33 (m, 1H); 3.71 (s, 3H); 3.65 (s, 2H); 1.98-1.89 (m, 2H); 1.83-1.74 (m, 2H); 1.65-1.50 (m, 3H); 1.45-1.35 (m, 3H)

Step 2: 2-[2-(cyclohexyloxy)phenyl]ethan-1-ol

To a solution of ester obtained in the previous step (4.28 g, 17.2 ol, 1.0 eq.) in THF (69 mL) at 0° C., was added dropwise a commercial solution of LiAlH$_4$ (2.0 M in THF, 17.2 mL, 34.5 mmol, 2.0 eq.). The mixture was stirred at room temperature for 1 h. After cooling down to 0° C., water, aqueous saturated solution of 15% NaOH and water again were added. After stirring for 15 min, Na$_2$SO$_4$ was added and the suspension was filtered over celite (MTBE rinses). The filtrate was concentrated under reduced pressure. The residue was purified by column chromatography to afford the title compound (3.73 g, 98%) obtained as a pungent colorless oil.

MS (ESI$^+$): [M+H]$^+$=221.2

$^1$H NMR (CDCl$_3$, 500 MHz) δ (ppm): 7.26-7.15 (m, 2H); 6.92-6.88 (m, 2H); 4.34 (m, 1H); 3.88 (in, 2H); 2.95 (t, J=6.3 Hz, 2H); 2.05-1.95 (m, 2H); 1.92 (br s, 1H); 1.86-1.75 (m, 2H); 1.65-1.55 (m, 3H); 1.46-1.35 (m, 3H)

Step 3: 1-(cyclohexyloxy)-2-(2-iodoethyl)benzene

To a solution of PPh$_3$ (3.1 g, 11.8 mmol, 1.3 eq.) in DCM (35 mL) at 0° C., was added 12 (3.0 g, 11.8 mmol, 1.3 eq.). The mixture was stirred at 0° C. for 15 min and imidazole (803 mg, 11.8 mmol, 1.3 eq.) and a solution of alcohol obtained in the previous step (2.0 g, 9.08 mmol, 1.0 eq.) were added. The mixture was stirred at room temperature for 1 h. The reaction mixture was partitioned between EtOAc and saturated solution of Na$_2$S$_2$O$_3$, triggering a decoloration. The layers were separated and the organic phase was washed with brine, dried over Na$_2$SO$_4$, filtered and concentrated under reduced pressure. The residue was purified by column chromatography to afford the title compound (2.74 g, 91%) as a colorless oil.

MS (ESI$^+$): [M−I]$^+$=203.2

$^1$H NMR (CDCl$_3$, 500 MHz) δ (ppm): 7.23 (td, J=7.8 Hz and J=1.8 Hz, 1H); 7.15 (dd, J=7.6 Hz and J=1.8 Hz, 1H); 6.90-6.86 (m, 2H); 4.34 (m, 1H); 3.42 (t, J=7.6 Hz, 2H); 3.22 (t, J=7.6 Hz, 2H); 2.01-1.92 (m, 2H); 1.86-1.76 (m, 2H); 1.67-1.54 (m, 3H); 1.49-1.38 (m, 3H)

Step 4: phosphine-borane complex intermediate

The title compound (1.97 g, 70%) obtained as a colorless oil was prepared according to the first step of the procedure C from the product obtained previously (2.73 g, 8.27 mmol, 1.0 eq.) in THF (10 mL) with presence of (BH$_3$)P(OEt)$_2$H (1.35 g, 9.92 mmol, 1.2 eq.) in THF (30 mL) and LiHMDS (1.0 M solution in THF, 9.92 mL, 9.92 mmol, 1.2 eq.).

MS (ESI$^+$): [(M−H$_2$)+H]$^+$=337.2

$^1$H NMR (CD$_3$OD, 500 MHz) δ (ppm): 6.95-6.88 (m, 2H); 6.69 (d, J=7.9 Hz, 1H); 6.60 (td, J=7.5 Hz and J=1.2 Hz, 1H); 4.18 (m, 1H); 4.90-3.75 (m, 4H); 2.60 (m, 2H); 1.82 (m, 2H); 1.77-1.68 (m, 2H); 1.65-1.55 (m, 2H); 1.45-1.30 (m, 3H); 1.28-1.16 (m, 3H); 1.07 (t, J=7.0 Hz, 6H); 0.65-0.00 (m, 3H)

Step 5: ethyl {2-[2-(cyclohexyloxy)phenyl]ethyl}phosphinate

The title compound (1.56 g) obtained as a light yellow oil was prepared according to the second step of the procedure C from the product obtained previously (1.96 g, 5.79 mmol, 1.0 eq.) in DCM (23 mL) with presence of HBF$_4$.Et$_2$O (3.94 mL, 29.0 mmol, 5.0 eq.).

MS (ESI$^+$): [M+H]$^+$=297.1; [(M×2)+H]$^+$=593.3

$^1$H NMR (CDCl$_3$ 500 MHz) δ (ppm): 7.23-7.15 (m, 2H); 7.11 (dm, J$^1$$_{P-H}$=545 Hz, 1H); 7.90-6.82 (m, 2H); 4.35 (m, 1H); 4.25-4.16 (m, 1H); 4.15-4.05 (m, 1H); 2.95-2.86 (m, 2H); 2.23-2.10 (m, 2H); 2.02-1.93 (m, 2H); 1.85-1.73 (m, 2H); 1.66-1.55 (m, 3H); 1.47-1.33 (m, 6H)

$^{31}$P NMR (CDCl$_3$, 202 MHz) δ (ppm): 38.6

Step 6: benzyl (4R)-4-({2-[2-(cyclohexyloxy)phenyl]ethyl}(ethoxy)phosphoryl)-4-{[(S)-2-methylpropane-2-sulfinyl]amino}butanoate The title compound (454 mg, 29%) obtained as a mixture of 2 diastereoisomers as a colorless oil was prepared according to the procedure E from previous product (775 mg, 2.62 mmol, 1.0 eq.) and cesium carbonate (1.28 g, 3.92 mmol, 1.5 eq.) in CH$_2$Cl$_2$ (10 mL) followed by addition of a solution of the enantiopure benzyl (4E)-4-{[(S)-2-methylpropane-2-sulfinyl]imino}butanoate (1.0 g, 3.4 mmol, 1.3 eq.) in CH$_2$Cl$_2$ (3 mL).

MS (ESI$^+$): [M+H]Y=592.2

$^1$H NMR (CD$_3$OD, 500 MHz) δ (ppm): 7.47-7.30 (m, 5H); 7.23-7.14 (m, 2H); 6.97-6.92 (m, 1H); 6.87-6.82 (m, 1H); 5.21-5.12 (m, 2H); 4.43-4.35 (m, 1H); 4.20-4.05 (m, 2H); 3.70-3.55 (m, 1H); 3.00-2.80 (m, 2H); 2.75-2.53 (m, 2H); 2.40-2.20 (m, 3H); 2.05-1.90 (m, 3H); 1.87-1.77 (m, 2H); 1.65-1.55 (m, 3H); 1.50-1.30 (m, 6H); 1.27-1.20 (m, 9H)

$^{31}$P NMR (CD$_3$OD, 202 MHz) δ (ppm): 55.74; 54.70

Step 7: (4R)-4-({2-[2-(cyclohexyloxy)phenyl]ethyl}(hydroxy)phosphoryl)-4-{[(S)-2-methyl propane-2-sulfinyl]amino}butanoic acid The title compound (500 mg, quantitative yield) obtained as a white foam was prepared according to the procedure F from previous product (445 mg, 0.752 mmol) in a mixture of THF/water (6 mL/1.5 mL) and LiOH.H$_2$O (54 mg, 2.3 mmol).

MS (ESI$^-$): [M−H]$^-$=472.1

Step 8: (4R)-4-amino-4-({2-[2-(cyclohexyloxy)phenyl]ethyl} (hydroxy) phosphoryl) butanoic acid The title compound (125 mg, 45%) obtained as an off-white solid was prepared according to the procedure G from previous product (354 mg, 0.75 mmol, 1.0 eq.) with 4.0 M HCl solution in dioxane (5.6 mL, 22.6 mmol, 30 eq.).

Estimated purity: 990% (based on LCMS) and >95% (based on NMR)

MS (ESI$^+$): [(M−H$_2$O)+H]$^+$=352.2; [M+H]$^+$=370.2; [(M×2)+H]$^+$=739.4

MS (ESI$^-$): [M−H]$^-$=368.2; [(M×2)-H]$^-$=737.4

$^1$H NMR (CD$_3$OD, 500 MHz) δ (ppm): 7.21 (d, J=4.5 Hz, 1H); 6.14 (t, J=7.8 Hz, 1H); 6.92 (d, J=8.0 Hz, 1H); 6.84 (t, J=7.4 Hz, 1H); 4.35 (m, 1H); 3.06 (m, 1H); 2.91 (m, 2H); 2.58 (m, 2H); 2.23 (m, 1H); 2.08-1.94 (m, 4H); 1.92-1.79 (m, 3H); 1.66-1.54 (m, 3H); 1.50-1.34 (m, 3H)

$^{31}$P NMR (CD$_3$OD, 202 MHz) δ (ppm): 32.0

Example 54: (1-amino-4-methoxy-4-oxobutyl)(2-phenylethyl)phosphinic acid

The title compound (44 mg, 26%) obtained as a white powder was prepared according to the procedure H for hydrogenolysis from product described in step 2 of example 22 (250 mg, 0.60 mmol, 1.0 eq.) in a mixture MeOH/AcOH (9:1, c=50 mM).

Estimated purity: 96% (based on HPLC)

MS (ESI$^+$): [(M−H$_2$O)+H]$^+$=268.1; [M+H]$^+$=286.2; [(M×2)+H]$^+$=571.3

$^1$H NMR (CD$_3$OD, 500 MHz) δ (ppm): 7.29-7.23 (m, 4H); 7.18-7.14 (m, 1H); 3.69 (s, 3H); 3.05 (td, J=8.5 and 5.5 Hz, 1H); 2.94-2.84 (m, 2H); 2.76 (t, J=7.5 Hz, 2H); 2.67-2.56 (m, 2H); 2.28-2.19 (m, 1H); 2.01-1.83 (m, 3H)

$^{31}$P NMR (CD$_3$OD, 202 MHz) δ (ppm): 31.00

Example 55: (1-amino-4-ethoxy-4-oxobutyl)(2-phenylethyl)phosphinic acid

Step 1: (1-amino-4-ethoxy-4-oxobutyl)(2-phenylethyl)phosphinic acid

The title compound (111 mg, 88%) obtained as a white powder was prepared according to the procedure H for hydrogenolysis from the 4-ethoxy analog of the product described in step 2 of example 22 (200 mg, 0.46 mmol, 1.0 eq.) in a mixture EtOH/AcOEt (9 mL/1 mL).

Estimated purity: >95% (based on HPLC)

MS (ESI$^+$): [(M−H$_2$O)+H]$^+$=282.2; [M+H]$^+$=300.2; [(M×2)+H]$^+$=599.4

$^1$H NMR (CD$_3$OD, 500 MHz) δ (ppm): 7.31-7.21 (m, 4H); 7.20-7.16 (m, 1H); 4.17 (q, J=7.0 Hz, 2H); 3.08 (td, J=8.5 and 5.5 Hz, 1H); 2.95-2.89 (m, 2H); 2.70-2.55 (m, 2H); 2.30-2.20 (m, 1H); 2.03-1.85 (m, 3H); 1.26 (t, J=7.0 Hz, 3H)

$^{31}$P NMR (CD$_3$OD, 202 MHz) δ (ppm): 31.16

Example 56: {4-ethoxy-1-[({1-[(2-methylpropanoyl)oxy]ethoxy}carbonyl)amino]-4-oxobutyl}(2-phenylethyl)phosphinic acid To a suspension of the 4-ethoxy analog of the product obtained in step 2 of example 22 (380 mg, 1.27 mmol) in DMF (4 mL), was added a solution of 1-{[(4-nitrophenoxy)carbonyl]oxy}ethyl 2-methylpropanoate as described in patent W2010/063002 (566 mg, 1.9 mmol) in DMF (4 mL). At 0° C., to this off-white suspension was added a solution of NaHCO$_3$ (533 mg, 6.37 mmol) in water (3 mL). The mixture became instantaneously yellow and was stirred at room temperature for 1 h (LCMS analysis showed an uncomplete conversion). NaHCO$_3$ (533 mg, 1.9 mmol) and 1-{[(4-nitrophenoxy)carbonyl]oxy}ethyl 2-methylpropanoate (188 mg, 0.63 mmol) were added again and the mixture was stirred overnight. The mixture was concentrated in vacuo and the residue was taken up in water and carefully acidified to pH 4 with a 2 M aqueous solution of HCl. The mixture was concentrated in vacuo and then taken up in a mixture of DCM/MeOH 90/10 and filtered on a PTFE filter to remove residual NaCl. The filtrate was concentrated in vacuo and the residue was purified by column chromatography. The fraction containing the product were concentrated in vacuo and taken up in a mixture of DCM/MeOH 95/5, filter on a PTFE filter again then concentrated to provide the title compound (231 mg, 40%) as a white foam.

Expected purity: 95% (based on HPLC and NMR)

MS (ESI$^+$): [M+H]$^+$=458.2; [(M×2)+H]$^+$=915.3

$^1$H NMR (CD$_3$OD, 500 MHz) δ (ppm): 7.29-7.19 (m, 4H); 7.33-7.26 (m, 1H); 6.80-6.75 (m, 1H); 4.14 (q, J=7.0 Hz, 2H); 3.82-3.75 (m, 1H); 2.94-2.80 (m, 2H); 2.60-2.53 (m, 0.5H); 2.52-2.36 (m, 2H); 2.34-2.24 (m, 1.5H); 1.94-1.72 (m, 3H); 1.46 (d, J=5.5 Hz, 1.5H); 1.44 (d, J=5.5 Hz, 1.5H); 1.29-1.25 (m, 3H); 1.18 (d, J=6.0 Hz, 1.5H); 1.17 (d, J=6.0 Hz, 1.5 Hz); 1.01 (d, J=5.5 Hz, 1.5H); 0.95 (d, J=6.0 Hz, 1.5H)

$^{31}$P NMR (CD$_3$OD, 202 MHz) δ (ppm): 38.42 and 38.18

Example 57: 1-[(benzyloxy)(2-phenylethyl)phosphoryl]-4-ethoxy-4-oxobutan-1-aminium chloride

Step 1: (1-{[(tert-butoxy)carbonyl]amino}-4-ethoxy-4-oxobutyl)(2-phenylethyl)phosphinic acid To a suspension of the 4-ethoxy analog of the product obtained in step 2 of example 22 (375 mg, 1.25 mmol) in DMF (2.5 mL) were successively added (Boc)$_2$O (273 mg, 1.25 mmol) and Et$_3$N (0.7 mL, 5.01 mmol) dropwise. The suspension became clear and the resulting solution was stirred at room temperature for 4 h. The mixture was concentrated in vacuo and residue was partitioned between water and DCM. The aqueous layer was extracted with DCM and the organic layer was washed with brine, dried over Na$_2$SO$_4$, filtered and concentrated in vacuo to give the title compound (193 mg, 39%) as a pale yellow oil.

MS (ESI$^+$): [M+H]$^+$=400

$^1$H NMR (CD$_3$OD, 500 MHz) δ (ppm): 7.28 (t, J=7.5 Hz, 2H); 7.24 (d, J=7.5 Hz, 2H); 7.20 (t, J=7.5 Hz, 1H); 4.16 (q, J=7.0 Hz, 2H); 3.98 (td, J=8.5 and 5.5 Hz, 1H); 2.99-2.84 (m, 2H); 2.55-2.39 (m, 2H); 2.31-2.19 (m, 2H); 2.11-1.96 (m, 2H); 1.90-1.80 (m, 1H); 1.45 (s, 9H); 1.28 (t, J=7.0 Hz, 3H)

$^{31}$P NMR (CD$_3$OD, 202 MHz) δ (ppm): 48.5

Step 2: ethyl 4-[(benzyloxy)(2-phenylethyl)phosphoryl]-4-{[(tert-butoxy)carbonyl]amino}butanoate To a solution of the product obtained in the previous step (196 mg, 0.49 mmol) in DMF (2.0 mL) was added cesium carbonate (79 mg, 0.24 mmol). To the resulting slurry was added benzyl bromide dropwise (64 µL, 0.54 mmol). The mixture was stirred at room temperature for 18 h and a white precipitate appeared. The crude was concentrated to dryness then diluted in a mixture of Et$_2$O/Water (1/1) and the aqueous layer was extracted 2 times with Et$_2$O. The combined organic layer was washed with NaHCO$_3$ (10%) and then with brine. The organic layer was dried over Na$_2$SO$_4$, filtered and then concentrated in vacuo. The residue was purified by chromatography to lead to the title product (172 mg, 72%) obtained as a transparent oil which crystallised on standing in a mixture of diastereomers (dr=50/50 according to $^{31}$P NMR).

MS (ESI$^+$): [M+H]$^+$=490

$^1$H NMR (CD$_3$OD, 500 MHz) δ (ppm): 7.44-7.30 (m, 5H); 7.27-7.21 (m, 2H); 7.20-7.11 (m, 3H); 5.11-5.04 (m, 2H); 4.17-4.07 (m, 2H); 3.98 (td, J=8.5 and 5.5 Hz, 1H); 2.99-2.75 (m, 2H); 2.52-2.35 (m, 2H); 2.28-2.03 (m, 3H); 1.89-1.73 (m, 1H); 1.45-1.44 (m, 9H); 1.27-1.23 (m, 3H)
$^{31}$P NMR (CD$_3$OD, 202 MHz) δ (ppm): 55.95 and 55.89

Step 3: 1-[(benzyloxy)(2-phenylethyl)phosphoryl]-4-ethoxy-4-oxobutan-1-aminium chloride A solution of the product obtained in the previous step (72 mg, 0.15 mmol, 1 eq.) was stirred for 4 h in pure formic acid (1 mL) and the conversion was followed by LCMS. The crude was poured into iced water and NaHCO$_3$ was added by portion (CAUTION! violent gaseous evolution). The aqueous layer (pH=7-8) was poured into a separatory funnel and extracted with Et$_2$O. LCMS of the aqueous layer showed no remaining product. The etherate layer was then acidified with 5 equivalents of 2 M HCl solution in ether while a fine milk appeared. The etherate layer was then extracted with cold water 3 times (3×5 mL) and the aqueous phase was directly frozen with dry ice and lyophilised to lead to the expected product (31 mg, 50%) obtained as a fine white cotton in a mixture of diastereomers (dr=50/50 according to $^{31}$P NMR).
Estimated purity: >95% (based on LCMS)
MS (ESI$^+$): [M+H]$^+$=390
$^1$H NMR (CD$_3$OD, 500 MHz) δ (ppm): 7.52-7.37 (m, 5H); 7.33-7.26 (m, 2H); 7.25-7.18 (m, 3H); 5.21-5.15 (m, 2H); 4.17 (q, J=7.0 Hz, 2H); 3.68-3.61 (m, 1H); 3.00-2.74 (m, 2H); 2.68-2.53 (m, 2H); 2.38-2.22 (m, 3H); 2.09-1.98 (m, 1H); 1.29-1.25 (m, 3H)
$^{31}$P NMR (CD$_3$OD, 202 MHz) δ (ppm): 51.16 and 51.09

Example 58: [1-amino-4-(benzyloxy)-4-oxobutyl](2-phenylethyl)phosphinic acid

The title compound (7 mg, 10%) was prepared according to the procedure G from (4-(benzyloxy)-1-(((benzyloxy)carbonyl)amino)-4-oxobutyl)(phenethyl) phosphinic acid (100 mg, 202 μmol, 1.0 eq.) in TFA/anisole (1.0 mL/200 μL).
Estimated purity: >95% (based on LCMS and NMR)
MS (ESI$^+$): [M+H]$^+$=362.1; [(M×2)+H]$^+$=723.3
$^1$H NMR (MeOD, 500 MHz) δ (ppm): 7.37-7.14 (m, 10H); 5.14 (s, 2H); 3.07-3.02 (m, 1H); 2.90-2.85 (m, 2H); 2.71-2.60 (m, 2H); 2.29-2.00 (m, 11H); 2.01-1.92 (m, 1H), 1.90-1.84 (m, 2H)
$^{31}$P NMR (MeOD, 202 MHz) δ (ppm): 30.93

Example 59: (4-ethoxy-4-oxo-1-{[(4R)-2-oxo-1,3-thiazolidin-4-yl]formamido} butyl)(2-phenylethyl)phosphinic acid Step 1: (4R)-2-oxo-1,3-thiazolidine-4-carboxylic acid At 0° C. (ice bath), into a 3 necked round bottom flask equipped with stirrer, inside temperature controller and dropping funnel, to a solution of NaOH (43 mL, 32% w/w 10.6 M, 459 mmol) and water (47 mL), was added by portion the L-cysteine hydrochloride monohydrate (17.6 g, 100 mmol, 1.0 eq.). The addition was slightly exothermic (the temperature dropped from 1° C. to 9° C.). After complete dissolution of the crystals, the temperature was allowed to raise at 20° C. while a solution of phenyl chloroformate (31.3 g, 200 mmol, 2 eq.) in toluene (35 mL) was added dropwise. The biphasic mixture was stirred at 25° C. for 2 h. The aqueous layer was separated, washed with toluene (35 mL) and acidified to pH=1 by addition of concentrated HCl. The aqueous layer was dried in vacuo and the residue was triturated in AcOEt, filtered and the filtrate was concentrated. The resulting solid was collected and recrystallized twice from water to afford the title compound (10.42 g, 71%) as white crystals.
MS (ESI$^+$): [M+H]$^+$=147
$^1$H NMR (DMSO-d6, 500 MHz) δ (ppm): 13.18 (brs, 1H); 8.43 (brs, 1H); 4.39 (ddd, 1H, J=8.5, 3.5, 1.5 Hz); 3.72 (dd, 1H, J=11.5, 8.5 Hz); 3.45 (dd, 1H, J=11.5, 3.5 Hz)

Step 2: (4-ethoxy-4-oxo-1-{[(4R)-2-oxo-1,3-thiazolidin-4-yl]formamido} butyl)(2-phenyl ethyl)phosphinic acid At room temperature, to a solution of the product obtained in the first step (245 mg, 1.67 mmol, 1 eq.) in THF/DMF (1/1, 10 mL) was added DCC and N-Hydroxysuccinimide (326 mg, 2.84 mmol, 1.7 eq.). After 10 min, a solid was formed. The mixture was stirred at 25° C. for 1 h (reaction was monitored by quenching an aliquot of the reaction mixture with benzylamine; the corresponding amide (m/z=236) was observed by LCMS). To the reaction mixture, a solution of the 4-ethoxy analog of the product obtained in step 2 of example 22 (500 mg, 1.67 mmol, 1.0 eq.) in a mixture of THF/DMF/EtOH (1/1/1, 5 mL) and DIPEA (2 mL, 11.69 mmol, 7.0 eq.) were then successively added dropwise. The resulting light orange solution was stirred at room temperature for 16 h. The solid formed was filtered and rinsed using AcOEt. The filtrate was concentrated and the residue was taken up in EtOAc and NH$_4$Cl saturated solution was added. The aqueous layer was separated and further extracted using EtOAc. The combined organic layers were washed with brine, dried over Na$_2$SO$_4$ and concentrated in vacuo. The crude was purified by flash chromatography to afford the expected compound (319 mg, 39%) as a white foam. A fraction of this product was repurified for analytical characterization.
Estimated purity: 87% (based on LCMS)
MS (ESI$^+$): [M+H]$^+$=429.1; [(M×2)+H]$^+$=857.3
$^1$H NMR (CD$_3$OD, 500 MHz) δ (ppm): 7.27-7.19 (m, 4H); 7.17-7.11 (m, 1H); 4.49-4.43 (m, 1H); 4.20-4.09 (m, 3H); 3.79 (dd, 1H, J=11.5, 8.5 Hz); 3.53 (dd, 1H, J=11.5, 5.0 Hz); 2.93-2.80 (m, 2H); 2.50-2.40 (m, 3H); 1.97-1.87 (m, 1H); 1.83-1.69 (m, 2H); 1.26 (t, 3H, J=7.0 Hz)
$^{31}$P NMR (CD$_3$OD, 202 MHz) δ (ppm): 36.21, 36.01

Example 60: 3-amino-3-{hydroxy[(2-methoxyphenyl)methyl]phosphoryl}propane-1-sulfonic acid Step 1: (1-{[(benzyloxy)carbonyl]amino}-3-[(2,2-dimethylpropoxy)sulfonyl]propyl)[(2-methoxyphenyl)methyl]phosphinic acid The title compound (1.2 g, 570%) obtained as a yellow solid was prepared according to the procedure D for multi-component reaction from [(2-methoxyphenyl)methyl]phosphinic acid (740 mg, 3.98 mmol, 1 eq.) and NH$_2$Cbz (661 mg, 4.37 mmol, 1.1 eq.) in AcOH (5.4 mL) and AcCl (0.7 mL) followed by addition of the 2,2-dimethylpropyl 3-oxopropane-1-sulfonate (993 mg, 4.77 mmol, 1.2 eq.).
MS (ESI$^+$): [M+H]$^+$=528.2
$^1$H NMR (MeOD, 500 MHz) δ (ppm): 7.39-7.19 (m, 7H); 6.94 (d, 1H, J=8.0 Hz); 6.87 (t, 1H, J=7.5 Hz); 5.13 (s, 2H);

4.01 (dt, 1H, J=4.0 and 10.5 Hz); 3.85 (s, 2H); 3.81 (s, 3H); 3.28-3.18 (m, 4H); 2.36-2.28 (m, 1H); 2.09-1.99 (m, 1H); 0.97 (s, 9H)

$^{31}$P NMR (MeOD, 202 MHz) δ (ppm): 44.20

Step 2: 3-amino-3-{hydroxy[(2-methoxyphenyl)methyl]phosphoryl}propane-1-sulfonic acid The title compound (105 mg, 29%) obtained as a white solid was prepared according to the procedure G from previous product (595 mg, 1.13 mmol, 1 eq.) in TFA/anisole (3.5 mL/2.5 mL).

Estimated purity: >95% (based on LCMS and NMR)

MS (ESI$^+$): [M+H]$^+$=324.1; [(M×2)+H]$^+$=647.2

$^1$H NMR (D20, 500 MHz) δ (ppm): 7.38-7.32 (m, 2H); 7.10 (d, 1H, J=8.0 Hz); 7.05 (t, 1H, J=7.5 Hz); 3.91 (s, 3H); 3.35-3.28 (m, 2H); 3.14-3.03 (m, 3H); 2.38-2.29 (m, 1H); 2.16-2.06 (m, 1H)

$^{31}$P NMR (MeOD, 202 MHz) δ (ppm): 34.57

Example 61: 3-amino-3-[hydroxy(2-phenylethyl)phosphoryl]propane-1-sulfonic acid

Step 1: 3-(acetylsulfanyl)propanal

Acrolein (900 μL, 12.8 mmol) was added dropwise to thioacetic acid (1.04 mL, 14.7 mmol) at room temperature under argon atmosphere (extremely exothermic). The mixture was stirred at room temperature for 2 h. Concentration under vacuum to remove the thioacetic acid in excess afforded the title compound (1.50 g, 88%).

$^1$H NMR (CDCl$_3$, 500 MHz) δ (ppm): 9.75 (t, 1H, J=0.9 Hz); 3.11 (t, 2H, J=6.7 Hz); 2.80 (dt, 2H, J=0.9 Hz and 6.7 Hz); 2.32 (s, 3H)

Step 2: [3-(acetylsulfanyl)-1-{[(benzyloxy)carbonyl]amino}propyl](2-phenylethyl) phosphinic acid The title compound (721 mg, 74%) obtained as a pale yellow solid was prepared according to the procedure D for multi-component reaction from (2-phenethyl)phosphinic acid (380 mg, 2.23 mmol) and NH$_2$Cbz (337 mg, 2.23 mmol) in AcOH (6 mL) and AcCl (1 mL) followed by addition of 3-(acetylsulfanyl)propanal (354 mg, 2.68 mmol). After 24 h of stirring at room temperature, additional NH$_2$Cbz (168 mg, 1.11 mmol) and 3-(acetylsulfanyl)propanal were added (147 mg, 1.11 mmol) to continue the reaction according to the procedure D. 11H NMR (DMSO-d6, 500 MHz) δ (ppm): 11 (bs, 1H); 7.58 (d, 1H, J=9.4 Hz); 7.36-7.25 (m, 7H); 7.20-7.15 (m, 3H); 5.10 (d, 11H, J=12.6 Hz); 5.02 (d, 11H, J=12.6 Hz); 3.84-3.78 (m, 1H); 3.00-2.96 (m, 1H); 2.84-2.71 (m, 3H); 2.33 (s, 3H); 2.00-1.93 (m, 1H); 1.87-1.78 (m, 3H)

Step 3: 3-{[(benzyloxy)carbonyl]amino}-3-[hydroxy(2-phenylethyl)phosphoryl] propane-1-sulfonic acid To a solution of the product obtained in the previous step (200 mg, 0.46 mmol) in AcOH (1 mL) was added dropwise aqueous hydrogene peroxyde (300%, 283 μL, 2.78 mmol). The mixture was stirred at 60° C. for 1 h and concentrated under vacuum with a rotavapor equipped with a blast shield. The crude was co-evaporated with heptane to afford the title compound (200 mg, 1000%) as a white solid.

MS (ESI$^+$): [M+H]$^+$=442.3

$^1$H NMR (DMSO-d6, 500 MHz) δ (ppm): 7.56 (d, 1H, J=9.7 Hz); 7.35-7.26 (m, 7H); 7.20-7.17 (m, 3H); 5.10 (d, 1H, J=12.6 Hz); 5.02 (d, 1H, J=12.6 Hz); 3.78-3.72 (m, 1H); 2.83-2.68 (m, 2H); 2.60-2.53 (m, 1H); 2.45-2.37 (m, 1H); 2.15-2.07 (m, 1H); 1.87-1.75 (m, 3H)

Step 4: 3-amino-3-[hydroxy(2-phenylethyl)phosphoryl]propane-1-sulfonic acid

The title compound (74 mg, 53%) obtained as a white solid was prepared according to the procedure G from previous product (200 mg, 0.45 mmol, 1 eq.) in TFA/anisole (44 mg/400 μL).

Estimated purity: 95% (based on NMR)

MS (ESI$^-$): [M–H]$^-$=306.4

$^1$H NMR (D20, 500 MHz) δ (ppm): 7.43-7.31 (m, 5H); 3.38-3.28 (m, 1H); 3.12-3.03 (m, 2H); 2.96-2.90 (m, 2H); 2.42-2.33 (m, 1H); 2.20-2.10 (m, 1H); 2.10-2.02 (m, 2H).

Example 62: 3-amino-3-{hydroxy[2-(2-methoxyphenyl)ethyl]phosphoryl}propane-1-sulfonic acid

Step 1: (1-{[(benzyloxy)carbonyl]amino}-3-[(2,2-dimethylpropoxy)sulfonyl]propyl)[2-(2-methoxyphenyl)ethyl]phosphinic acid The title compound (298 mg, 37%) obtained as a white solid was prepared according to the procedure D for multi-component reaction from [2-(2-methoxyphenyl)ethyl]phosphinic acid (300 mg, 1.50 mmol, 1 eq.) and NH$_2$Cbz (250 mg, 1.65 mmol, 1.1 eq.) in AcOH (2.0 mL) and AcCl (0.3 mL) followed by addition of the 2,2-dimethylpropyl 3-oxopropane-1-sulfonate (374 mg, 1.80 mmol, 1.2 eq.).

MS (ESI$^+$): [M+H]$^+$=542.3

$^1$H NMR (MeOD, 500 MHz) δ (ppm): 7.39-7.24 (m, 5H); 7.21-7.18 (m, 1H); 7.08 (d, 1H, J=7.5 Hz); 6.91 (d, 1H, J=8.5 Hz); 6.85 (t, 1H, J=7.5 Hz); 5.20-5.05 (m, 2H); 4.10-4.02 (m, 1H); 3.89 (s, 2H); 3.79 (s, 3H); 3.30-3.28 (m, 1H); 2.89-2.84 (m, 2H); 2.42-2.34 (m, 1H); 2.15-2.06 (m, 1H); 2.02-1.96 (m, 2H); 0.99 (s, 9H) {One H is under the MeOD peak}

$^{31}$P NMR (MeOD, 202 MHz) δ (ppm): 48.97

Step 2: 3-amino-3-{hydroxy[2-(2-methoxyphenyl)ethyl]phosphoryl}propane-1-sulfonic acid The title compound (28 mg, 15%) obtained as a white solid was prepared according to the procedure G from previous product (298 mg, 550 μmol, 1 eq.) in TFA/anisole (1.6 mL/0.385 mL).

Estimated purity: >95% (based on LCMS and NMR)

MS (ESI$^+$): [M+H]$^+$=338.1; [(M×2)+H]$^+$=675.3

$^1$H NMR (MeOD, 500 MHz) δ (ppm): 7.22-7.19 (m, 2H); 6.94 (d, 1H, J=8.0 Hz); 6.88 (t, 1H, J=7.5 Hz); 3.85 (s, 3H); 3.56-3.51 (m, 11H); 3.01 (dt, 2H, J=7.0 and 2.5 Hz); 2.96-2.90 (m, 2H); 2.47-2.37 (m, 1H); 2.21-2.06 (m, 3H)

$^{31}$P NMR (MeOD, 202 MHz) δ (ppm): 40.18

Example 63: 3-amino-3-[hydroxy(3-phenylpropyl)phosphoryl]propane-1-sulfonic acid

Step 1: (3-phenylpropyl)phosphinic acid

The preparation of (3-phenylpropyl)phosphinic acid is described originally by Smid, P. et al, PCT Int. Appl., 2008071738, 2008.

Under argon, to a previously degassed solution of hypophosphorous acid (50 wt % in water, 2.47 mL, 22.6 mmol) in EtOH (15 mL) were added allyl benzene (1 mL, 7.6 mmol) and AIBN (100 mg, 1.2 mmol). The mixture was refluxed for 6 h and LCMS revealed an uncomplete conversion. Another portion of AIBN (100 mg, 1.2 mmol) was then added and the mixture was subsequently refluxed for 18 h. The mixture is constantly colorless and transparent during the reaction. The mixture was then concentrated in vacuo and the resulting oil was cooled to 0° C. and 2 N NaOH (15 mL) was added to reach pH 14. The solution was transferred into a separatory funnel and this aqueous layer was washed with Et$_2$O (3×20 mL). The aqueous layer was acidified with 2 N HCl to reach pH 1 and then extracted with AcOEt (4×30 mL). The combined organic layers were washed with brine (100 mL), dried over Na$_2$SO$_4$ and concentrated in vacuo to provide the title compound (1.2 g, 86%) as a colorless oil contaminated by 8% of the di-addition by-product.

MS (ESI$^+$): [M+H]$^+$=185

$^1$H NMR (CDCl$_3$, 500 MHz) δ (ppm): 7.08 (dt, 1H, J=545.0 and 5.0 Hz); 7.30-7.27 (m, 2H); 7.22-7.18 (m, 1H); 7.18-7.13 (m, 2H); 2.72 (t, 2H, J=10.0 Hz); 1.97-1.88 (m, 2H); 1.78-1.72 (m, 2H)

$^{31}$P NMR (CDCl$_3$, 202 MHz) δ (ppm): 39.53

Step 2: (1-{[(benzyloxy)carbonyl]amino}-3-methanesulfinylpropyl)(3-phenylpropyl) phosphinic acid The title compound (254 mg, 690%) obtained as a fine white powder was prepared according to the procedure D for multi-component reaction from previous product (150 mg, 0.814 mmol, 1.0 eq.) and NH$_2$Cbz (135 mg, 0.895 mmol, 1.1 eq.) in AcOH (1.5 mL) and AcCl (0.4 mL) followed by addition of 3-(acetylsulfanyl)propanal prepared in step 1 of example 61 (130 mg, 0.977 mmol, 1.2 eq.) in AcOH (0.5 mL).

MS (ESI$^+$): [M+H]$^+$=450; [(M×2)+H]$^+$=899

$^1$H NMR (DMSO-d6, 500 MHz) δ (ppm): 7.51 (d, 1H, J=10.0 Hz); 7.40-7.30 (m, 5H); 7.28 (t, 2H, J=5.0 Hz); 7.21-7.13 (m, 2H); 5.09 (d, 1H, J=15.0 Hz); 5.04 (d, 1H, J=15.0 Hz); 3.74 (dtd, 1H, J=13.0, 10.0 and 3.5 Hz); 2.97 (ddd, 1H, J=13.0, 8.0 and 5.0 Hz); 2.97 (dt, 1H, J=13.0 and 8.0 Hz); 2.58 (t, 2H, 5.0 Hz); 2.32 (s, 3H); 1.95-1.85 (m, 1H); 1.84-1.65 (m, 3H), 1.57-1.47 (m, 2H)

$^{31}$P NMR (DMSO-d6, 202 MHz) δ (ppm): 46.36

Step 3: 3-{[(benzyloxy)carbonyl]amino}-3-[hydroxy(3-phenylpropyl) phosphoryl] propane-1-sulfonic acid To a solution of the product obtained in the previous step (254 mg, 0.57 mmol), in AcOH (1 mL) was added dropwise aqueous hydrogene peroxide (30%, 384 µL, 3.39 mmol). The mixture was stirred at 60° C. for 1 h and the crude was concentrated in vacuo with a rotavapor equipped with a blast shield. The crude was co-evaporated with heptane (3×) and then left at air overnight and a precipitate appeared corresponding to the title compound (254 mg, quantitative yield) as a pale yellow solid.

MS (ESI$^+$): [M+H]$^+$=456; [M+NH$_3$]$^+$=473

$^1$H NMR (DMSO-d6, 500 MHz) δ (ppm): 7.50 (d, J=9.5 Hz, 1H); 7.30-7.13 (m, 10H); 5.06 (d, J=12.5 Hz, 1H); 5.02 (d, J=12.5 Hz, 1H); 3.67 (ddd, J=20.0, 9.5 and 3.5 Hz, 1H); 2.95-2.62 (m, 2H) 2.40 (td, J=12.5 and 4.5 Hz, 1H); 2.11-2.00 (m, 1H); 1.86-1.69 (m, 3H); 1.59-1.47 (m, 2H)

$^{31}$P NMR (DMSO-d6, 202 MHz) δ (ppm): 36.07

Step 4: 3-amino-3-[hydroxy(3-phenylpropyl)phosphoryl]propane-1-sulfonic acid

The title compound (135 mg, 75%) obtained as a fine pale yellow powder was prepared according to the procedure G from previous product (252 mg, 0.55 mmol) in TFA/anisole (4 mL/1 mL).

Estimated purity: 95% (based on HPLC)

MS (ESI$^-$): [M−H]$^-$=320.2; [(M×2)-H]$^-$=641.4

$^1$H NMR (D20, 500 MHz) δ (ppm): 7.36-7.11 (m, 5H); 3.35-3.26 (m, 1H); 3.09-2.99 (m, 2H); 2.69 (t, J=7.0 Hz, 2H); 2.33-2.22 (m, 1H); 2.10-1.99 (m, 1H); 1.86-1.75 (m, 2H); 1.67-1.58 (m, 2H)

$^{31}$P NMR (D20, 202 MHz) δ (ppm): 36.27

Example 64: 3-amino-3-[({[1,1'-biphenyl]-3-yl}methyl)(hydroxy)phosphoryl]propane-1-sulfonic acid Step 1: (1-{[(benzyloxy)carbonyl]amino}-3-[(2,2-dimethylpropoxy)sulfonyl]propyl) ({[1,1'-biphenyl]-3-yl}methyl)phosphinic acid The title compound (1.15 g, estimated quantitative yield) was prepared according to the procedure D for multi-component reaction from phosphinic acid described in step 1 of example 6 (430 mg, 1.8 mmol, 1.0 eq.) and NH$_2$Cbz (308 mg, 2.04 mmol, 1.1 eq.) in AcOH (2.6 mL) and AcCl (0.3 mL) followed by addition of the 2,2-dimethylpropyl 3-oxopropane-1-sulfonate (463 mg, 2.22 mmol, 1.2 eq.).

MS (ESI$^+$): [M+H]$^+$=574.2

Step 2: 3-amino-3-[({[1,1'-biphenyl]-3-yl}methyl)(hydroxy)phosphoryl]propane-1-sulfonic acid The title compound (41 mg, 5% for two steps) obtained as a pale yellow solid was prepared according to the procedure G from previous product (1.1 g, 1.9 mmol, 1.0 eq.) in TFA/anisole (7.4 mL/6.3 mL).

Estimated purity: >95% (based on LCMS) and 95% (based on NMR)

MS (ESI$^+$): [M+H]$^+$=370.0; [(M×2)+H]$^+$=739.2

$^1$H NMR (CD$_3$OD, 500 MHz) δ (ppm): δ 7.71-7.60 (m, 3H), 7.54-7.47 (m, 1H), 7.47-7.29 (m, 5H), 3.50-3.40 (m, 1H), 3.29-3.17 (m, 2H), 3.12-2.94 (m, 2H), 2.55-2.35 (m, 1H), 2.27-2.10 (m, 1H)

$^{31}$P NMR (CD$_3$OD, 202 MHz) δ (ppm): 30.9

Example 65: 3-amino-3-{hydroxy[(3-phenyl-1,2-oxazol-5-yl)methyl]phosphoryl}propane-1-sulfonic acid Step 1: (1-{[(benzyloxy)carbonyl]amino}-3-[(2,2-dimethylpropoxy)sulfonyl]propyl)[(3-phenyl-1,2-oxazol-5-yl)methyl]phosphinic acid The title compound (950 mg, 830%) obtained as a yellow solid was prepared according to the procedure D for multi-component reaction from [(3-phenyl-1,2-oxazol-5-yl)methyl]phosphinic acid (450 mg, 2.0 mmol, 1.0 eq.) and NH$_2$Cbz (335 mg, 2.22 mmol, 1.1 eq.) in AcOH (3.5 mL)

and AcCl (0.4 mL) followed by addition of the 2,2-dimethylpropyl 3-oxopropane-1-sulfonate (504 mg, 2.42 mmol, 1.2 eq.).

MS (ESI): [M+H]$^+$=565.1

$^1$H NMR (CD$_3$OD, 500 MHz) δ (ppm): 7.92-7.78 (m, 2H); 7.57-7.45 (m, 3H); 7.41-7.24 (m, 5H); 6.76 (s, 1H); 5.26-5.02 (m, 2H); 4.24-4.13 (m, 11H); 3.90 (s, 2H); 2.54-2.29 (m, 1H); 2.27-2.06 (m, 1H); 1.44-1.23 (m, 4H); 0.98 (s, 9H)

$^{31}$P NMR (CD$_3$OD, 202 MHz) δ (ppm): 39.1

Step 2: 3-amino-3-{hydroxy[(3-phenyl-1,2-oxazol-5-yl)methyl]phosphoryl} propane-1-sulfonic acid The title compound (302 mg, 50%) obtained as a white solid was prepared according to the procedure G from previous product (915 mg, 1.68 mmol, 1.0 eq.) in TFA/anisole (6.5 mL/7.35 mL).

Estimated purity: 96% (based on LCMS) and >95% (based on NMR)

MS (ESI$^+$): [M+H]$^+$=361.0; [(M×2)+H]$^+$=721.1

MS (ESI$^-$): [M–H]-=359.0

$^1$H NMR (CD$_3$OD, 500 MHz) δ (ppm): δ 7.95-7.81 (m, 2H); 7.55-7.46 (m, 3H); 6.88 (d, J=2.8 Hz, 1H); 3.91-3.81 (m, 1H); 3.77-3.62 (m, 2H); 3.11 (t, J=6.8 Hz, 2H); 2.67-2.41 (m, 1H); 2.37-2.11 (m, 1H)

$^{31}$P NMR (CD$_3$OD, 202 MHz) δ (ppm): 32.7

Example 66: 3-amino-3-{hydroxy[(5-phenyl-1,2-oxazol-3-yl)methyl]phosphoryl}propane-1-sulfonic acid Step 1: 2,2-dimethylpropyl 3-[(benzyloxy)[(5-phenyl-1,2-oxazol-3-yl)methyl]phosphoryl]-3-[(2-methylpropane-2-sulfinyl)amino]propane-1-sulfonate The title compound (370 mg, 32%) obtained as a mixture of 4 diastereoisomers as a yellow oil was prepared according to the procedure E from benzyl [(5-phenyl-1,2-oxazol-3-yl)methyl]phosphinate obtained in step 2 of example 21 (580 mg, 1.9 mmol, 1.0 eq.) and cesium carbonate (905 mg, 2.78 mmol, 1.5 eq.) in CH$_2$Cl$_2$ (9 mL) followed by addition of a solution of the racemic 2,2-dimethylpropyl 3-[(2-methylpropane-2-sulfinyl)imino]propane-1-sulfonate (750 mg, 2.41 mmol, 1.3 eq.) in CH$_2$Cl$_2$ (0.5 mL).

MS (ESI$^+$): [M+H]$^+$=625.2

Step 2: {3-[(2,2-dimethylpropoxy)sulfonyl]-1-[(2-methylpropane-2-sulfinyl)amino]propyl}[(5-phenyl-1,2-oxazol-3-yl)methyl]phosphinic acid The title compound (164 mg, 50%) obtained as a yellow oil was prepared according to the procedure F from the diastereomeric mixture obtained in the previous step (370 mg, 0.59 mmol, 1.0 eq.) in a mixture of THF/water (4/1, 3 mL) with presence of LiOH.H$_2$O (75 mg, 1.8 mmol, 3.0 eq.).

MS (ESI$^+$): [M+H]$^+$=535.1

Step 3: 3-amino-3-{hydroxy[(5-phenyl-1,2-oxazol-3-yl)methyl]phosphoryl} propane-1-sulfonic acid The title compound (59 mg, 50%) obtained as a light yellow solid was prepared according to the procedure G from previous product (164 mg, 0.307 mmol, 1.0 eq.) with 6.0 M HCl solution in dioxane (9.0 mL, 54 mmol, 175 eq.).

Estimated purity: >95% (based on NMR & LCMS)

MS (ESI$^+$): [M+H]$^+$=361.0

MS (ESI$^-$): [M–H]-=359.0

$^1$H NMR (CD$_3$OD, 500 MHz) δ (ppm): 7.96-7.79 (m, 2H); 7.58-7.42 (m, 3H); 6.88 (s, 1H); 3.99-3.76 (m, 1H); 3.50 (d, J=16.1 Hz, 2H); 3.10 (t, J=6.9 Hz, 2H); 2.67-2.44 (m, 1H); 2.37-2.11 (m, 1H)

$^{31}$P NMR (CD$_3$OD, 202 MHz) δ (ppm): 34.5

Example 67: 4-amino-4-[hydroxy(2-phenylethyl)phosphoryl]butane-1-sulfonic acid

Step 1: 1-[(4-hydroxybutyl)sulfanyl]ethan-1-one

A mixture of 4-chlorobutanol (5.0 g, 46 mmol, 1.0 eq., mixture of monomer and polymers) and potassium thioacetate (7.9 g, 69 mmol, 1.5 eq.) in DMF (23 mL) was stirred at 50° C. for 6 h. After cooling down to room temperature, water and MTBE were added and the layers were separated. The aqueous phase was extracted with MTBE and the combined organic extracts were washed with water and brine, dried over Na$_2$SO$_4$, filtered and concentrated under reduced pressure to afford 6 g as a red oil. The residue was purified by column chromatography to afford the title compound (1.14 g, 17%) as a light orange oil.

MS (ESI$^+$): [M+H]$^+$=149.1

$^1$H NMR (CDCl$_3$, 500 MHz) δ (ppm): 3.67 (t, J=6.2 Hz, 2H); 2.91 (t, J=7.0 Hz, 2H); 2.33 (s, 3H); 1.73-1.50 (m, 4H)

Step 2: 4-(acetylsulfanyl)butanal

To a solution of DMSO (1.26 mL, 17.7 mmol, 2.3 eq.) in DCM (25 mL) at −78° C., were successively added oxalyl chloride (1.06 mL, 12.3 mmol, 1.6 eq.) and, after 15 min, a solution of alcohol obtained in the previous step (1.14 g, 7.69 mmol, 1.0 eq.) in DCM (5 mL). After stirring for 1 h at −78° C., Et$_3$N (5.4 mL, 38 mmol, 5.0 eq.) was added and the mixture was stirred 0.5 h at −78° C. and then at room temperature for 1 h. The reaction mixture was partitioned between water and MTBE. The layers were separated and the aqueous phase was extracted with MTBE. The combined organic extracts were washed with 1 M HCl solution then brine, dried over Na$_2$SO$_4$, filtered and concentrated under reduced pressure to afford the title compound (1.19 g, quantitative yield) as an orange oil.

$^1$H NMR (CDCl$_3$, 500 MHz) δ (ppm): 9.78 (t, J=1.3 Hz, 1H); 2.91 (t, J=7.2 Hz, 2H); 2.54 (td, J=7.2 Hz and J=1.4 Hz, 2H); 2.34 (s, 3H); 1.92 (tt, app q, J=7.2 Hz, 2H)

Step 3: [4-(acetylsulfanyl)-1-{[(benzyloxy)carbonyl]amino}butyl](2-phenylethyl)phosphinic acid The title compound (539 mg, 41%) obtained as a white solid was prepared according to the procedure D for multi-component reaction from phenethyl phosphinic acid (500 mg, 2.94 mmol, 1.0 eq.) and NH$_2$Cbz (533 mg, 3.53 mmol, 1.2 eq.) in AcOH (5.0 mL) and AcCl (0.63 mL) followed by addition of the aldehyde obtained in the previous step (516 mg, 3.52 mmol, 1.2 eq.).

MS (ESI$^+$): [M+H]$^+$=450.1; [(M×2)+H]$^+$=899.5

$^1$H NMR (CD$_3$OD, 500 MHz) δ (ppm): 7.40-7.33 (m, 2H); 7.33-7.24 (m, 5H); 7.23-7.12 (m, 3H); 5.20 (d, AB syst, J=12.5 Hz, 1H); 5.10 (d, AB syst, J=12.5 Hz, 1H); 3.97 (m, 1H); 3.00-2.79 (m, 4H); 2.33 (s, 3H); 2.08-1.88 (m, 3H); 1.82-1.58 (m, 3H)

$^{31}$P NMR (MeOD, 202 MHz) δ (ppm): 49.66

Step 4: 4-{[(benzyloxy)carbonyl]amino}-4-[hydroxy(2-phenylethyl)phosphoryl]butane-1-sulfonic acid To a solution of previous product (539 mg, 1.20 mmol, 1.0 eq.) in AcOH (4.8 mL) at room temperature, was added dropwise H$_2$O$_2$ (30% solution in water, 735 μL, 7.19 mmol, 6.0 eq.).

The mixture was stirred at 50° C. for 1.5 h. After cooling down to room temperature, under a blast shield, the reaction mixture was concentrated under reduced pressure and the residue was azeotropically dried with heptane to afford the title product (580 mg, quantitative yield) as a light yellow foam.

MS (ESI$^-$): [M−H]−=454.2; [(M×2)-H]$^-$=909.6

$^1$H NMR (CD$_3$OD, 500 MHz) δ (ppm): 7.40-7.33 (m, 2H); 7.33-7.24 (m, 5H); 7.23-7.12 (m, 3H); 5.21 (d, AB syst, J=12.5 Hz, 1H); 5.06 (d, AB syst, J=12.5 Hz, 1H); 3.99 (m, 1H); 3.01-2.79 (m, 4H); 2.13-1.93 (m, 4H), 1.92-1.73 (m, 2H)

$^{31}$P NMR (MeOD, 202 MHz) δ (ppm): 50.33

Step 5: 4-amino-4-[hydroxy(2-phenylethyl)phosphoryl]butane-1-sulfonic acid

The title compound (25 mg, 12%) obtained as a white solid was prepared according to a variant of the procedure G from previous product (290 mg, 0.64 mmol, 1.0 eq.) in TFA (3.2 mL).

MS (ESI$^+$): [M+H]$^+$=322.1; [(M×2)+H]$^+$=643.2
MS (ESI$^-$): [M−H]$^-$=320.0; [(M×2)-H]$^-$=641.2

$^1$H NMR (CD$_3$OD, 500 MHz) δ (ppm): 7.38-7.28 (m, 4H); 7.28-7.22 (m, 1H); 3.00 (td, J=8.6 Hz and J=3.4 Hz, 1H); 2.93-2.79 (m, 4H), 2.02-1.83 (m, 4H), 1.82-1.65 (m, 2H)

$^{31}$P NMR (MeOD, 202 MHz) δ (ppm): 35.21

Example 68: {3-amino-3-[hydroxy(2-phenylethyl) phosphoryl]propyl}phosphonic acid Step 1: dibenzyl [2-(1,3-dioxolan-2-yl)ethyl]phosphonate To a solution of dibenzylphosphonate (2.50 g, 9.53 mmol, 1.0 eq.) in DMF (19 mL) at room temperature, were added (n-Bu)$_4$NI (704 mg, 1.91 mmol, 0.2 eq.), Cs$_2$CO$_3$ (4.66 g, 14.30 mmol, 1.5 eq.) and 2-(2-bromoethyl)-1,3-dioxolane (1.34 mL, 11.4 mmol, 1.2 eq.). The reaction mixture was stirred at room temperature for 80 h. Water and MTBE were added and the layers were separated. The aqueous phase was extracted with MTBE. The combined organic extracts were washed with water and brine, dried over Na$_2$SO$_4$, filtered and concentrated under reduced pressure to afford a colorless oil. The residue was purified by column chromatography to afford the title compound (2.86 g, 83%) as a colorless oil.

MS (ESI$^+$): [M+H]$^+$=363.1

$^1$H NMR (500 MHz, CDCl$_3$) δ (ppm): 7.43-7.30 (m, 101H), 5.07 (dd, J=11.9, 8.8 Hz, 2H), 4.99 (dd, J=11.9, 7.9 Hz, 2H), 4.95-4.87 (m, 1H), 3.98-3.90 (m, 2H), 3.90-3.81 (m, 2H), 2.07-1.84 (m, 4H)

$^{31}$P NMR (CDCl$_3$, 202 MHz) δ (ppm): 33.1

Step 2: dibenzyl (3-oxopropyl)phosphonate

To a solution of acetal obtained in the previous step (1.0 g, 2.79 mmol, 1.0 eq.) in acetone (2.8 mL) at room temperature, was added 2 N HCl solution (8.28 mL, 16.7 mmol, 6.0 eq.). The mixture was stirred at 50° C. for 3 h. After cooling down to room temperature, water and MTBE were added and the layers were separated. The aqueous phase was extracted with MTBE. The combined organic extracts were washed with saturated solution of NaHCO$_3$, then brine, dried over Na$_2$SO$_4$, filtered and concentrated under reduced pressure to afford the title compound (0.82 g, 85% pure, 79%) as a light yellow oil.

MS (ESI$^+$): [M+H]$^+$=319

$^1$H NMR (500 MHz, CDCl$_3$) δ (ppm): 9.76-9.62 (m, 1H), 7.45-7.31 (m, 10H), 5.08 (dd, J=11.8, 9.0 Hz, 2H), 4.98 (dd, J=11.8, 8.4 Hz, 2H), 2.81-2.64 (m, 2H), 2.14-2.00 (m, 2H)

$^{31}$P NMR (CDCl$_3$, 202 MHz) δ (ppm): 31.8

Step 3: (1-{[(benzyloxy)carbonyl]aminol-3-[bis (benzyloxy)phosphoryl]propyl)(2-phenylethyl)phosphinic acid The title compound obtained as an oil and directly used in the following step without isolation was prepared according to the procedure D for multi-component reaction from phenethylphosphinic acid (310 mg, 1.82 mmol, 1.0 eq.) and NH$_2$Cbz (331 mg, 2.19 mmol, 1.2 eq.) in AcOH (7.3 mL) and AcCl (0.39 mL) followed by addition of dibenzyl (3-oxopropyl)phosphonate (85% pure, 819 mg, 2.19 mmol, 1.2 eq).

MS (ESI$^-$): [M−H]−=620

Step 4: {3-amino-3-[hydroxy(2-phenylethyl)phosphoryl]propyl}phosphonic acid

The title compound (80 mg, 14% over two steps) obtained as a beige solid was prepared according to the procedure G from previous product in TFA/anisole (6.96 mL/4.95 mL).

Estimated purity: >97% (based on LCMS) and >95% (based on NMR)

MS (ESI$^+$): [M+H]$^+$=308.1; [(M×2)+H]$^+$=615.1
MS (ESI$^-$): [M−H]$^-$=306.1; [(M×2)-H]$^-$=613.1

$^1$H NMR (CD$_3$OD, 500 MHz) δ (ppm): δ 7.34-7.25 (m, 4H), 7.21-7.16 (m, 1H), 3.16-3.06 (m, 1H), 2.99-2.82 (m, 2H), 2.38-2.16 (m, 1H), 2.06-1.75 (m, 5H).

$^{31}$P NMR (CD$_3$OD, 202 MHz) δ (ppm): 32.6; 24.7

Example 69: Measurement of APA Activity in Vitro

Measurement of APA activity in vitro is based on the protocol of Goldbarg adjusted to the scale of assaying on microplates (Pro Bind™ 3915) (Chauvel et al., 1994). In vitro, in the presence of calcium ions, APA hydrolyses a synthetic substrate α-L-glutamyl-β-naphthylamide (GluβNa) to glutamate and β-naphthylamine (βNa). A diazotation reaction in acidic medium makes it possible to reveal the β-naphthylamine by formation of a violet-coloured complex: spectrophotometric measurement then makes it possible to know the amount of complex formed and, by reference to a standard curve produced with increasing concentrations of β-naphthylamine, to deduce the enzymatic activity of the sample.

Reagents

The Glu-βNa substrate (Bachem) and the β-naphthylamine (Sigma) are dissolved in 50% DMSO (dimethyl sulphoxide) and 0.1 N HCl respectively, and conserved at −20° C. at a concentration of 102 M. The diazotation reaction is carried out in the presence of sodium nitrite (87 mM), ammonium sulfamate (130 mM) and N-(1-naphthyl)-ethylenediamine dihydrochloride (23 mM in 95% ethanol).

Enzymatic Reaction

The reaction takes place at pH 7.4 in 50 mM tris-HCl buffer, in the presence of calcium (4 mM $CaCl_2$)); recombinant mouse APA is incubated at 37° C. in the presence of the substrate (200 μM Glu-βNa) and in the presence or absence of various concentrations of the inhibitor to be tested, in a final volume of 100 μL. The reaction is stopped by adding 10 μL of 3N HCl. A standard curve of β-naphthylamine was prepared in parallel by diazotizing increasing concentrations (up to 0.2 mM) of 2-naphthylamine in 0.1 N HCl.

Revelation of the Formed Product

The following are added to each well: 25 μL of sodium nitrite ($NaNO_2$) (mix, wait 5 minutes at room temperature), 50 μL of ammonium sulfamate (mix, wait 5 minutes at room temperature), then add 25 μL of N-(1-naphthyl) ethylenediamine dihydrochloride (mix, wait for stabilization of the violet colour for approximately 30 minutes at 37° C.).

The absorbance is then measured at 540 nm.

The compound EC33 ((S)-3 amino-4-mercapto-butylsulfonic acid) described in application WO 99/36066 was used as a reference compound.

The results reported in Table 1. show that best compounds (classification a) exhibit the highest APA-inhibiting activity, greater than that of the reference compound by a factor of at least 20.

TABLE 1

In vitro inhibition of aminopeptidase A for exemplified inhibitors

| Activity (μM) | Classification |
|---|---|
| $IC_{50}$ < 0.030 | a |
| 0.030 ≤ $IC_{50}$ < 0.300 | b |
| 0.300 ≤ $IC_{50}$ < 10 | c |

| Examples | Results | Examples | Results | Examples | Results |
|---|---|---|---|---|---|
| 10 | a | 1 | b | 5 | c |
| 11 | a | 2 | b | 6 | c |
| 15 | a | 3 | b | 9 | c |
| 22 | a | 4 | b | 20 | c |
| 23 | a | 7 | b | 27 | c |
| 24 | a | 8 | b | 47 | c |
| 25 | a | 12 | b | 49 | c |
| 28 | a | 13 | b | 51 | c |
| 30 | a | 14 | b | 61 | c |
| 31 | a | 16 | b | 63 | c |
| 32 | a | 17 | b | 64 | c |
| 33 | a | 18 | b | 65 | c |
| 34 | a | 19 | b | 66 | c |
| 35 | a | 21 | b | 68 | c |
| 36 | a | 26 | b | EC33 | c |
| 38 | a | 29 | b | | |
| 40 | a | 37 | b | | |
| 43 | a | 39 | b | | |
| 44 | a | 41 | b | | |
| 46 | a | 42 | b | | |
| 48 | a | 45 | b | | |
| 50 | a | 60 | b | | |
| 52 | a | 62 | b | | |
| 53 | a | 67 | b | | |

Example 70: Measurement of Brain APA Activity (Ex Vivo Experiments)

Brain APA activity was determined as described above.

In vivo, in mice (male, 18-20 g Charles River), Examples 22 and 52 were administered i.v. (5 mg/kg and 4 mg/kg respectively, in a volume of 200 μL). For each condition, five mice were used. Mice were sacrified 10, 30, 60, 120 and 180 min after the injection. The brains were immediately removed and homogenized by sonication in 10 vol of ice-cold 50 mM Tris-HCl buffer (pH 7.4). APA enzymatic activity was measured on brain homogenates. For this purpose, aliquots of the tissue homogenate (16 μL) were incubated for 30 min at 37° C. with 200 μM of GluβNA, 4 mM $CaCl_2$, and 1 μM bestatin inhibitor, with or without 5 μM EC33, in a total volume of 100 μL of 50 mM Tris-HCl buffer (pH 7.4). Then the assay was pursued as described above.

FIG. 1 demonstrates the ability of Example 22 given by i.v. route to cross the blood brain barrier (BBB) and to enter the brain by measuring the inhibition of brain APA activity in conscious mice. Example 22 (5 mg/kg, i.v., 295 nmol per mouse) progressively inhibited brain APA activity that was significantly and maximally decreased by 47% from 10 min (37.5±3.3 nmol of GluNA hydrolyzed per mg of protein per h vs 70.0±4.6, P<0.001) until 60 min. A return to basal values was observed after 120 min.

Figure 2:
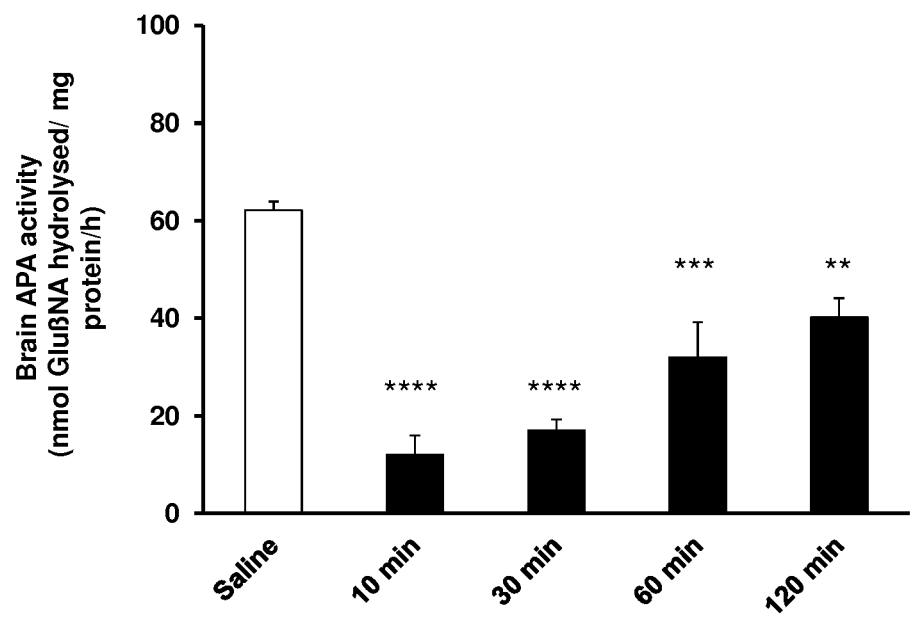
FIG. 2. describes the time course of inhibition of mouse brain APA ex vivo activity after intravenous (i.v.) administration of Example 52 (4 mg/kg).

FIG. 2 demonstrates the ability of i.v. Example 52 to cross the BBB and to enter the brain by measuring the inhibition of brain APA activity in conscious mice. Example 52 (4 mg/kg, i.v., 237 nmol per mouse) progressively inhibited brain APA activity that was maximally decreased by 810% after 10 min (12.0±4.0 nmol of GluNA hydrolyzed per mg of protein per h vs. 62.1±1.8, P<0.001) until 30 min. Brain APA activity was still significantly inhibited by 35% 120 min after the injection.

The invention claimed is:

1. A compound with the following formula (I):

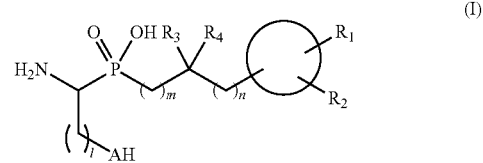

(I)

or formula (II):

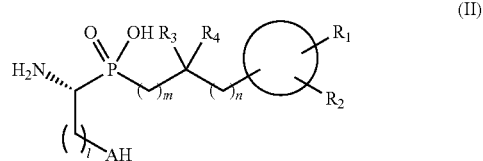

(II)

wherein

AH represents —$CO_2H$, —$SO_3H$ or —$PO_3H_2$;

l is 1, 2 or 3;

m and n are independently 0, 1 or 2;

$R_3$ and $R_4$ represent independently a hydrogen atom, a hydroxy group, a halogen atom, an alkyl or a haloalkyl group;

the ring (depicted by a circle in each formula) represents an aryl or a heterocycle;

with $R_1$ and $R_2$ representing independently a hydrogen atom, a halogen atom, a cyano group, an alkyl group, an alkoxy group, an alkylthio group, an alkylsulfoxide group, an alkylsulfonyl group, a haloalkyl group, a haloalkoxy group, a haloalkylthio group, an acyl group, an O-cycloalkyl group, a heteroalkyl group, an O-aryl group, an O-arylalkyl group, an aryl group, a heterocycle group or an arylalkyl group; and a pharmaceutical salt, solvate, zwitterionic form or prodrug thereof.

2. The compound of claim 1, wherein the compound corresponds to general formula (I) or formula (II), wherein:

l is 2 or 3; and/or m is 0 or 1; and/or n is 0 or 1; and/or

AH is $CO_2H$ or $SO_3H$ or $PO_3H_2$; and/or $R_3$ and $R_4$ are both H, or $R_3$ and $R_4$ are both methyl groups; and/or the ring is an aryl or a heterocycle group.

3. The compound of claim 1, wherein $R_1$ and $R_2$ are independently selected from the group consisting of: a hydrogen atom, a halogen atom, a cyano, an alkyl group, an alkoxy group, an alkylsulfonyl group, a haloalkyl group, a haloalkoxy group, an O-cycloalkyl group, a heteroalkyl group, an O-aryl group, an O-arylalkyl group and an aryl group.

4. The compound of claim 1, wherein the compound corresponds to general formula (I) or formula (II), wherein:

l is 2; and/or m+n=1; and/or

AH is $CO_2H$ or $SO_3H$; and/or $R_3$ and $R_4$ are H; and/or the ring is a phenyl, a naphthyl or indol group.

5. The compound of claim 1, wherein $R_1$ and $R_2$ are independently selected from the group consisting of a hydrogen atom, a halogen atom, a cyano, an alkyl group, an alkoxy group, an alkylsulfonyl group, a haloalkyl group, a haloalkoxy group, an O-cycloalkyl group, a heteroalkyl group, an O-aryl group, an O-arylalkyl group, and an aryl group.

6. A compound having the following formula (III):

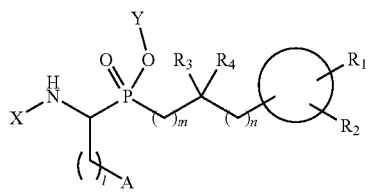

(III)

or formula (IV):

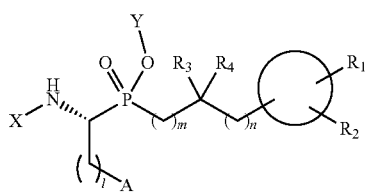

(IV)

wherein:

l, m, n, $R_1$, $R_2$, $R_3$, $R_4$, and the ring (depicted by a circle in each formula) are as defined in claim 1;

A represents —$SO_3Z$—$CO_2Z$ or —$P(O)(OZ)_2$, with Z being selected from the group consisting of a hydrogen atom, an alkyl and arylalkyl group, X represents a hydrogen atom, —(CO)-alkyl, —(CO)-alkoxy, —(CO)-benzyloxy,

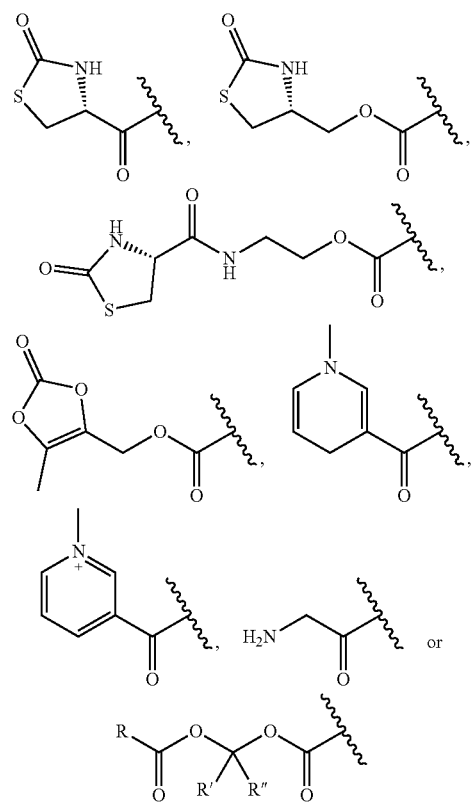

where R represents an alkyl group and, R' and R" represent independently a hydrogen atom or an alkyl group, Y represents a hydrogen atom, an alkyl, aryl, arylalkyl group or

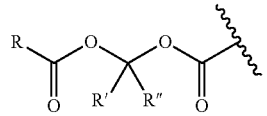

where R, R' and R", being identical or different, are as defined above, and wherein at least one of Z, X and Y is different from hydrogen atom.

7. The compound of claim 1, which is selected from the group consisting of:

4-amino-4-[benzyl(hydroxy)phosphoryl]butanoic acid;

4-amino-4-{hydroxy[(2-methylphenyl)methyl]phosphoryl}butanoic acid;

4-amino-4-{hydroxy[(3-methylphenyl)methyl]phosphoryl}butanoic acid;

4-amino-4-{hydroxy[(4-methylphenyl)methyl]phosphoryl}butanoic acid;

4-amino-4-({[3,5-bis(trifluoromethyl)phenyl]methyl}(hydroxy)phosphoryl) butanoic acid;
4-amino-4-[({[1,1'-biphenyl]-2-yl}methyl)(hydroxy)phosphoryl] butanoic acid;
4-amino-4-[hydroxy({[3-(trifluoromethoxy)phenyl]methyl})phosphoryl]butanoic acid;
4-amino-4-[hydroxy({[4-(trifluoromethoxy)phenyl]methyl})phosphoryl]butanoic acid;
4-amino-4-{hydroxy[(4-methanesulfonylphenyl)methyl]phosphoryl}butanoic acid;
4-amino-4-{hydroxy[(2-methoxyphenyl)methyl]phosphoryl} butanoic acid;
4-amino-4-{hydroxy[(3-methoxyphenyl)methyl]phosphoryl}butanoic acid;
4-amino-4-{hydroxy[(4-methoxyphenyl)methyl]phosphoryl}butanoic acid;
4-amino-4-{[(3-cyanophenyl)methyl](hydroxy)phosphoryl}butanoic acid;
4-amino-4-{[(4-cyanophenyl)methyl](hydroxy)phosphoryl}butanoic acid;
4-amino-4-{hydroxy[(naphthalen-1-yl)methyl]phosphoryl}butanoic acid;
4-amino-4-{hydroxy[(2-phenoxyphenyl)methyl]phosphoryl}butanoic acid;
4-amino-4-{hydroxy[(3-phenoxyphenyl)methyl]phosphoryl}butanoic acid;
4-amino-4-{hydroxy[(4-phenoxyphenyl)methyl]phosphoryl}butanoic acid;
4-amino-4-[({[1,1'-biphenyl]-3-yl}methyl)(hydroxy)phosphoryl]butanoic acid;
4-amino-4-{hydroxy[(3-phenyl-1,2-oxazol-5-yl)methyl]phosphoryl}butanoic acid;
4-amino-4-{hydroxy[(5-phenyl-1,2-oxazol-3-yl)methyl]phosphoryl}butanoic acid;
4-amino-4-[hydroxy(2-phenylethyl)phosphoryl]butanoic acid;
4-amino-4-{hydroxy[2-(2-methylphenyl)ethyl]phosphoryl}butanoic acid;
4-amino-4-{hydroxy[2-(3-methylphenyl)ethyl]phosphoryl}butanoic acid;
4-amino-4-{hydroxy[2-(4-methylphenyl)ethyl]phosphoryl}butanoic acid;
4-amino-4-[hydroxy({2-[3-(trifluoromethyl)phenyl]ethyl})phosphoryl]butanoic acid;
4-amino-4-[hydroxy(2-methyl-2-phenylpropyl)phosphoryl]butanoic acid;
4-amino-4-{[2-(2-chlorophenyl)ethyl](hydroxy)phosphoryl}butanoic acid;
4-amino-4-{[2-(3-chlorophenyl)ethyl](hydroxy)phosphoryl}butanoic acid;
4-amino-4-{hydroxy[2-(naphthalen-2-yl)ethyl]phosphoryl}butanoic acid;
4-amino-4-{hydroxy[2-(naphthalen-1-yl)ethyl]phosphoryl}butanoic acid;
4-amino-4-{hydroxy[2-(2-methoxyphenyl)ethyl]phosphoryl}butanoic acid;
4-amino-4-{hydroxy[2-(3-methoxyphenyl)ethyl]phosphoryl}butanoic acid;
4-amino-4-{hydroxy[2-(4-methoxyphenyl)ethyl]phosphoryl}butanoic acid;
4-amino-4-{hydroxy[2-(2-phenoxyphenyl)ethyl]phosphoryl}butanoic acid;
4-amino-4-({2-[2-(cyclopentyloxy)phenyl]ethyl}(hydroxy)phosphoryl) butanoic acid;
4-amino-4-[hydroxy(3-phenylpropyl)phosphoryl]butanoic acid;
4-amino-4-[hydroxy({2-[2-(trifluoromethoxy)phenyl]ethyl})phosphoryl] butanoic acid;
4-amino-4-[(2-{[1,1'-biphenyl]-2-yl}ethyl)(hydroxy)phosphoryl]butanoic acid;
4-amino-4-{[2-(2,3-dichlorophenyl)ethyl](hydroxy)phosphoryl}butanoic acid;
4-amino-4-{[2-(3-chloro-2-methoxyphenyl)ethyl](hydroxy)phosphoryl} butanoic acid;
3-carboxy-1-{hydroxy[2-(1-methyl-1H-indol-3-yl)ethyl]phosphoryl} propan-1-aminium chloride;
3-carboxy-1-({2-[2-(cyclohexyloxy)phenyl]ethyl}(hydroxy)phosphoryl) propan-1-aminium chloride;
3-carboxy-1-[hydroxy({2-[2-(2-methoxyethoxy)phenyl]ethyl})phosphoryl] propan-1-aminium chloride;
4-amino-4-{hydroxy[2-(3-phenyl-1,2-oxazol-5-yl)ethyl]phosphoryl}butanoic acid;
4-amino-4-{[2-(4-fluoro-2-methoxyphenyl)ethyl](hydroxy)phosphoryl}butanoic acid;
4-amino-4-{hydroxy[2-(1H-indazol-1-yl)ethyl]phosphoryl}butanoic acid;
1-({2-[2-(benzyloxy)phenyl]ethyl}(hydroxy)phosphoryl)-3-carboxy propan-1-aminium chloride;
5-amino-5-[hydroxy(2-phenylethyl)phosphoryl]pentanoic acid;
(1R)-3-carboxy-1-[hydroxy(2-phenylethyl)phosphoryl] propan-1-aminium chloride;
(1S)-3-carboxy-1-[hydroxy(2-phenylethyl)phosphoryl] propan-1-aminium chloride;
(1R)-3-carboxy-1-{hydroxy[2-(2-methoxyphenyl)ethyl]phosphoryl}propan-1-aminium chloride;
(4R)-4-amino-4-({2-[2-(cyclohexyloxy)phenyl]ethyl}(hydroxy)phosphoryl) butanoic acid;
(1-amino-4-methoxy-4-oxobutyl)(2-phenylethyl)phosphinic acid;
(1-amino-4-ethoxy-4-oxobutyl)(2-phenylethyl)phosphinic acid;
{4-ethoxy-1-[({1-[(2-methylpropanoyl)oxy]ethoxy}carbonyl)amino]-4-oxobutyl}(2-phenyl ethyl) phosphinic acid;
1-[(benzyloxy)(2-phenylethyl)phosphoryl]-4-ethoxy-4-oxobutan-1-aminium chloride;
[1-amino-4-(benzyloxy)-4-oxobutyl](2-phenylethyl) phosphinic acid;
(4-ethoxy-4-oxo-1-{[(4R)-2-oxo-1,3-thiazolidin-4-yl]formamido}butyl)(2-phenylethyl) phosphinic acid;
3-amino-3-{hydroxy[(2-methoxyphenyl)methyl]phosphoryl}propane-1-sulfonic acid;
3-amino-3-[hydroxy(2-phenylethyl)phosphoryl]propane-1-sulfonic acid;
3-amino-3-{hydroxy[2-(2-methoxyphenyl)ethyl]phosphoryl}propane-1-sulfonic acid;
3-amino-3-[hydroxy(3-phenylpropyl)phosphoryl]propane-1-sulfonic acid;
3-amino-3-[({[1,1'-biphenyl]-3-yl}methyl)(hydroxy)phosphoryl]propane-1-sulfonic acid;
3-amino-3-{hydroxy[(3-phenyl-1,2-oxazol-5-yl)methyl]phosphoryl} propane-1-sulfonic acid;
3-amino-3-{hydroxy[(5-phenyl-1,2-oxazol-3-yl)methyl]phosphoryl}propane-1-sulfonic acid;
4-amino-4-[hydroxy(2-phenylethyl)phosphoryl]butane-1-sulfonic acid;
{3-amino-3-[hydroxy(2-phenylethyl)phosphoryl]propyl}phosphonic acid;
[4-ethoxy-1-({[(5-methyl-2-oxo-2H-1,3-dioxol-4-yl)methoxy]carbonyl}amino)-4-oxobutyl] (2-phenylethyl)phosphinic acid;

ethyl 4-({[(5-methyl-2-oxo-2H-1,3-dioxol-4-yl)methoxy]carbonyl}amino)-4-({1-[(2-methyl propanoyl)oxy]ethoxy}(2-phenylethyl)phosphoryl)butanoate;

(1-{[(benzyloxy)carbonyl]amino}-4-ethoxy-4-oxobutyl)(2-phenylethyl)phosphinic acid;

3-({4-ethoxy-4-oxo-1-[(2-phenylethyl)phosphinato]butyl}carbamoyl)-1-methylpyridin-1-ium;

{4-ethoxy-4-oxo-1-[({[(4R)-2-oxo-1,3-thiazolidin-4-yl]methoxy}carbonyl)amino]butyl}(2-phenylethyl)phosphinic acid;

(4-ethoxy-4-oxo-1-{[(2-{[(4R)-2-oxo-1,3-thiazolidin-4-yl]formamido}ethoxy)carbonyl]amino}butyl)(2-phenylethyl)phosphinic acid; and

[1-(2-aminoacetamido)-4-ethoxy-4-oxobutyl](2-phenylethyl)phosphinic acid.

8. A pharmaceutical composition comprising at least one compound as defined in claim 1 and a pharmaceutically acceptable diluent or carrier.

9. The compound of claim 2, wherein the ring is a phenyl, naphthyl, indol, aza-indol or isoxazol group.

10. The compound of claim 1, wherein $R_1$ and $R_2$ are independently selected from the group consisting of a hydrogen atom, a chlorine atom, a fluorine atom, a methyl group, a methoxy group, a methanesulfonyl group, a trifluoromethyl group, a trifluoromethoxy group, an O-cyclopentyl group, an O-cyclohexyl group, a methoxyethoxy group, an O-phenyl group, an O-benzyl group and a phenyl group.

11. A method of treatment of a patient suffering from arterial hypertension or directly or indirectly related diseases, comprising the administration to such patient of a therapeutically effective amount of a compound of claim 1.

12. The method of claim 11, wherein the disorders directly or indirectly related to arterial hypertension are selected from the group consisting of heart disease, heart failure, stroke, peripheral and/or cerebral vascular system diseases, brain, eye and/or kidney diseases.

13. The method of claim 12, wherein the disorders are selected from the group consisting of primary and/or secondary arterial hypertension, an ictus, myocardial ischemia, cardiac insufficiency, renal insufficiency, myocardial infarction, a peripheral vascular disease, diabetic protinuria, syndrome X, glaucoma, neurodegenerative diseases and memory disorders.

* * * * *

UNITED STATES PATENT AND TRADEMARK OFFICE
CERTIFICATE OF CORRECTION

| | |
|---|---|
| PATENT NO. | : 11,192,907 B2 |
| APPLICATION NO. | : 17/288516 |
| DATED | : December 7, 2021 |
| INVENTOR(S) | : Fabrice Balavoine et al. |

It is certified that error appears in the above-identified patent and that said Letters Patent is hereby corrected as shown below:

In the Specification

Column 2,
Lines 31-32, "(Fournid-Zaluski" should read --(Fournié-Zaluski--.

Column 5,
Line 60, "named ($C_3$-$C_2$)" should read --named ($C_3$-$C_{12}$)--.

Column 18,
Line 50, "12: iodine" should read --$I_2$: iodine--.

Column 20,

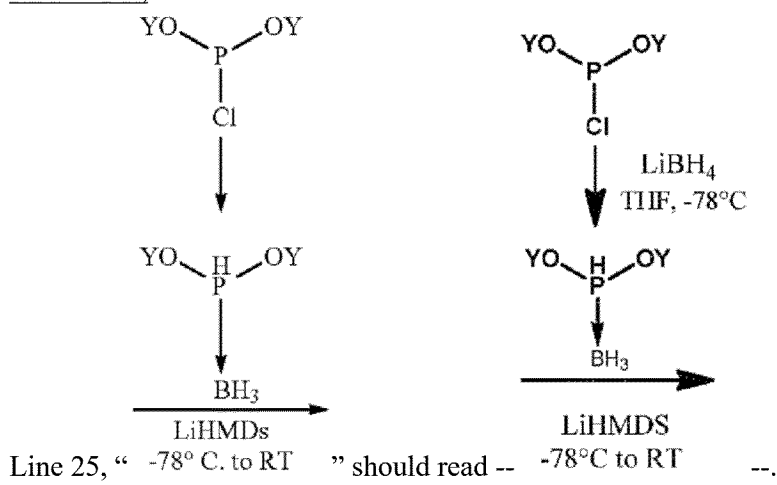

Line 25, " [left scheme with LiHMDs, -78° C. to RT] " should read -- [right scheme with LiHMDS, -78°C to RT] --.

Column 22,

Signed and Sealed this
Fifth Day of July, 2022

*Katherine Kelly Vidal*

Katherine Kelly Vidal
*Director of the United States Patent and Trademark Office*

Lines 48-50, " 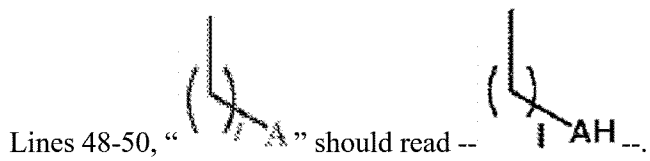 " should read -- --.

Column 24,
Line 42, "9.82 (s, 11H);" should read --9.82 (s, 1H);--.
Lines 44-46,
"2.71-2.67 (m, 2H) Preparation of methyl 4-oxobutanoate Step 1: methyl 4-hydroxybutanoate" should read
--2.71-2.67 (m, 2H)

Preparation of methyl 4-oxobutanoate
   Step 1: methyl 4-hydroxybutanoate--.

Column 25,
Lines 4-5, "(2.25 g, 380%)" should read --(2.25 g, 38%)--.
Line 19, "(4.0 g, 820%)" should read --(4.0 g, 82%)--.

Column 26,
Lines 50-51, "(3.9 g, 590%)" should read --(3.9 g, 59%)--.

Column 28,
Line 1, "(D20, 500 MHz)" should read --($D_2O$, 500 MHz)--.
Line 5, "(D20, 202 MHz)" should read --($D_2O$, 202 MHz)--.

Column 29,
Line 13, "(899 mg, 600%)" should read --(899 mg, 60%)--.
Line 41, "(m, 11H)," should read --(m, 1H),--.

Column 32,
Line 5, "(t, 11H, J=8.0 Hz);" should read --(t, 1H, J=8.0 Hz);--.
Lines 38-39,
"(m, 1H) 20 $^{31}$P NMR
(MeOD, 202 MHz)" should read
--(m, 1H)
$^{31}$P NMR (MeOD, 202 MHz)--.

Column 35,
Line 39, "MHz) S" should read --MHz) δ--.
Line 44, "MHz) S" should read --MHz) δ--.
Line 55, "MHz) S" should read --MHz) δ--.

Column 36,

Line 24, "(m, 11H);" should read --(m, 1H);--.
Line 64, "(937 mg, 700%)" should read --(937 mg, 70%)--.

Column 37,
Line 17, "(30 mg, 140%)" should read --(30 mg, 14%)--.
Line 43, "MHz) S" should read --MHz) δ--.

Column 39,
Lines 53-54, "(t, 11H, J=6.0 Hz)" should read --(t, 1H, J=6.0 Hz)--.

Column 40,
Lines 31-32, "(m, 11H);" should read --(m, 1H);--.
Line 32, "7.20-7.16 (m, 11H);" should read --7.20-7.16 (m, 1H);--.
Line 33, "(dd, 11H, J=8.5" should read --(dd, 1H, J=8.5--.

Column 41,
Line 52, "(DMSO-d6/D20," should read --(DMSO-d6/$D_2O$,--.

Column 42,
Line 37, "(in, 11H);" should read --(m, 1H);--.
Line 67, "added 12" should read --added $I_2$--.

Column 43,
Line 11, "(2.9 g, 910%)" should read --(2.9 g, 91%)--.
Line 24, "MS (ESI$^+$):" should read --MS (ESI$^-$):--.
Line 67, "MS (ESI$^-$): [M+H]$^+$=468.0; [(Mx2)+H]$^-$=935.4" should read --MS (ESI$^+$): [M+H]$^+$=468.0; [(Mx2)+H]$^+$=935.4--.

Column 45,
Line 17, "MS (ESI):" should read --MS (ESI$^+$):--.

Column 48,
Line 16, "(D20, 500" should read --($D_2O$, 500--.
Line 21, "(D20, 202" should read --($D_2O$, 202--.

Column 49,
Line 47, "(123 mg, 440%)" should read --(123 mg, 44%)--.

Column 50,
Line 14, "(1.16 g, 900%)" should read --(1.16 g, 90%)--.

Column 52,
Line 17, "(m, 11H);" should read --(m, 1H);--.

Column 55,

Line 49, "(84 mg, 480%)" should read --(84 mg, 48%)--.

Column 57,
Line 59, "(657 mg, 480%)" should read --(657 mg, 48%)--.

Column 58,
Line 64, "(1.2 g, 830%)" should read --(1.2 g, 83%)--.

Column 59,
Line 58, "in $CH_2C_{12}$" should read --in $CH_2Cl_2$--.

Column 62,
Line 16, "(50 mg, 260%)" should read --(50 mg, 26%)--.

Column 63,
Line 47, "(D20, 500" should read --($D_2O$, 500--.
Line 52, "(D20, 202" should read --($D_2O$, 202--.

Column 65,
Line 55, "(1.17 g, 590%)" should read --(1.17 g, 59%)--.
Line 66, "$CH_2C_2$" should read --$CH_2Cl_2$--.

Column 66,
Line 38, "(76 mg, 510%)" should read --(76 mg, 51%)--.

Column 68,
Line 4, "(140 nL)" should read --(140 mL)--.

Column 70,
Line 46, "11H);" should read --1H);--.
Line 52, "15 ol," should read --15 mmol,--.

Column 72,
Line 16, "4-{hydroxy[2-(1-methyl-JH-indol-3-yl)ethyl]phosphoryl}-4-[(2-methylpropane-2-sulfinyl)amino]butanoic acid" should read --4-{hydroxy[2-(1-methyl-1H-indol-3-yl)ethyl]phosphoryl}-4-[(2-methylpropane-2-sulfinyl)amino]butanoic acid--.
Line 32, "3-carboxy-1-{hydroxy[2-(1-methyl-JH-indol-3-yl)ethyl]phosphoryl}propan-1-aminium chloride" should read --3-carboxy-1-{hydroxy[2-(1-methyl-1H-indol-3-yl)ethyl]phosphoryl}propan-1-aminium chloride--.

Column 73,
Line 61, "$[(M-H2)+H]^+$" should read --$[(M-H_2)+H]^+$--.

Column 75,
Line 64, "$[(M-H2)+H]^+$" should read --$[(M-H_2)+H]^+$--.

Column 76,

CERTIFICATE OF CORRECTION (continued)
U.S. Pat. No. 11,192,907 B2

Line 15, "Hz, 11H); 6.92 (t, J=7.4 Hz, 1H); 6.88 (d, J=8.2 Hz, 11H);" should read --Hz, 1H); 6.92 (t, J=7.4 Hz, 1H); 6.88 (d, J=8.2 Hz, 1H);--.
Line 16, "(m, 11H); 4.16 (m, 2H); 4.11 (m, 11H);" should read --(m, 1H); 4.16 (m, 2H); 4.11 (m, 1H);--.

Column 77,
Line 67, "[(M-H2)+H]$^+$" should read --[(M-H$_2$)+H]$^+$--.

Column 78,
Line 9, "(500 mg, 930%)" should read --(500 mg, 93%)--.
Line 37, "(m, 11H)" should read --(m, 1H)--.
Line 51, "7.4 Hz, 11H);" should read --7.4 Hz, 1H);--.
Lines 51-52, "12.5 Hz, 11H);" should read --12.5 Hz, 1H);--.
Line 64, "and 750%" should read --and 75%--.

Column 80,
Lines 4-5, "(m, 101H);" should read --(m, 10H);--.
Line 19, "and > 950%" should read --and > 95%--.
Lines 25-26, "11H); 6.60 (td, J=8.4, 2.5 Hz, 11H);" should read --1H); 6.60 (td, J=8.4, 2.5 Hz, 1H);--.

Column 81,
Line 25, "730%)" should read --73%)--.
Line 42, "920%)" should read --92%)--.
Line 53, "11H);" should read --1H);--.

Column 83,
Line 8, "11H);" should read --1H);--.
Line 44, "840%" should read --84%--.
Line 56, "11H);" should read --1H);--.

Column 85,
Line 17, "(315 L)" should read --(315 µL)--.
Line 30, ">950%" should read -->95%--.

Column 87,
Line 41, "(m, 11H)" should read --(m, 1H)--.

Column 88,
Lines 17-18, "(m, 101H); 7.18 (td, 11H," should read --(m, 10H); 7.18 (td, 1H,--.
Lines 35-36, "7.68 mmol, 3.0 eq.). 11H NMR" should read
--7.68 mmol, 3.0 eq.).
    $^1$H NMR--.
Line 39, "(m, 11H);" should read --(m, 1H);--.
Line 51, "[M+H]Y=302.2;" should read --[M+H]$^+$=302.2;--.
Line 54, "(td, 11H," should read --(td, 1H,--.
Line 55, "(td, 11H," should read --(td, 1H,--.

Column 89,
Line 43, "added 12" should read --added I$_2$--.

Column 90,
Line 40, "[M+H]Y=592.2" should read --[M+H]$^+$=592.2--.

Column 93,
Line 47, "(m, 11H);" should read --(m, 1H);--.

Column 94,
Line 58, "(1.2 g, 570%)" should read --(1.2 g, 57%)--.

Column 95,
Line 15, "(D20," should read --(D$_2$O,--.
Line 49, "11H NMR" should read --$^1$H NMR--.
Line 51, "5.10 (d, 11H," should read --5.10 (d, 1H,--.
Line 52, "5.02 (d, 11H," should read --5.02 (d, 1H,--.
Line 62, "(300%," should read --(30%,--.
Line 66, "(200 mg, 1000%)" should read --(200 mg, 100%)--.

Column 96,
Line 16, "(D20," should read --(D$_2$O,--.
Line 56, "(m, 11H);" should read --(m, 1H);--.

Column 97,
Line 20, "(dt, 11H," should read --(dt, 1H,--.
Line 31, "(254 mg, 690%)" should read --(254 mg, 69%)--.
Line 42, "5.09 (d, I H," should read --5.09 (d, 1H,--.
Line 42, "5.04 (d, 11H," should read --5.04 (d, 1H,--.

Column 98,
Line 14, "(D20," should read --(D$_2$O,--.
Line 18, "(D20," should read --(D$_2$O,--.
Line 63, "(950 mg, 830%)" should read --(950 mg, 83%)--.

Column 99,
Line 7, "(m, 11H);" should read --(m, 1H);--.

Column 101,
Lines 66-67, "(m, 101H)," should read --(m, 10H),--.

Column 103,
Line 5, "102 M." should read --10$^{-2}$ M.--.
Line 11, "CaCl$_2$));" should read --CaCl$_2$);--.
Column 104, Line 31, "by 810%" should read --by 81%--.